(12) United States Patent
Fairhurst et al.

(10) Patent No.: US 12,226,405 B2
(45) Date of Patent: Feb. 18, 2025

(54) COMPOUNDS AND COMPOSITIONS FOR INHIBITING THE ACTIVITY OF HIF2-ALPHA AND THEIR METHODS OF USE

(71) Applicant: Novartis AG, Basel (CH)

(72) Inventors: Robin Alec Fairhurst, Allschwil (CH); Christine Fritsch, Leymen (FR); Marc Gerspacher, Hägendorf (CH); Jürgen Hans-Hermann Hinrichs, Schopfheim (DE); Jean-Baptiste Georges Armand Langlois, Schlierbach (FR); Catherine Leblanc, Basel (CH); Tengfei Li, Shanghai (CN); Edwige Liliane Jeanne Lorthiois, Niffer (FR); Christophe Mura, Rosenau (FR); Cristina Montserrat Nieto-Oberhuber, Binningen (CH); Milen Todorov, Rosenau (FR); Andrea Vaupel, Riehen (CH); Nicolas Warin, Blotzheim (FR); Rainer Wilcken, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/241,981

(22) Filed: Apr. 27, 2021

(65) Prior Publication Data
US 2022/0401422 A1 Dec. 22, 2022

(30) Foreign Application Priority Data
Apr. 29, 2020 (WO) ................ PCT/CN2020/087831

(51) Int. Cl.
| | | |
|---|---|---|
| A61K 31/437 | (2006.01) |
| A61K 31/155 | (2006.01) |
| A61K 31/436 | (2006.01) |
| A61K 31/4375 | (2006.01) |
| A61K 31/4747 | (2006.01) |
| A61K 31/519 | (2006.01) |
| A61K 31/53 | (2006.01) |
| A61K 31/5377 | (2006.01) |
| A61K 31/635 | (2006.01) |
| A61K 31/675 | (2006.01) |
| A61P 35/00 | (2006.01) |
| C07D 471/10 | (2006.01) |
| C07D 471/20 | (2006.01) |
| C07D 491/20 | (2006.01) |
| C07D 491/22 | (2006.01) |
| C07D 495/20 | (2006.01) |
| C07D 495/22 | (2006.01) |

(52) U.S. Cl.
CPC .......... *A61K 31/437* (2013.01); *A61K 31/155* (2013.01); *A61K 31/436* (2013.01); *A61K 31/4375* (2013.01); *A61K 31/4747* (2013.01); *A61K 31/519* (2013.01); *A61K 31/53* (2013.01); *A61K 31/5377* (2013.01); *A61K 31/635* (2013.01); *A61K 31/675* (2013.01); *A61P 35/00* (2018.01); *C07D 471/10* (2013.01); *C07D 471/20* (2013.01); *C07D 491/20* (2013.01); *C07D 491/22* (2013.01); *C07D 495/20* (2013.01); *C07D 495/22* (2013.01); *C07B 2200/05* (2013.01); *C07B 2200/13* (2013.01)

(58) Field of Classification Search
CPC .. C07D 471/10; C07D 471/20; C07D 491/20; C07D 491/22; C07D 495/20; C07D 495/22
See application file for complete search history.

(56) References Cited

U.S. PATENT DOCUMENTS
| | | | |
|---|---|---|---|
| 8,962,859 B2 | 2/2015 | Epstein et al. |
| 9,796,697 B2 | 10/2017 | Wehn et al. |
| 2012/0065195 A1 | 3/2012 | Clark et al. |

FOREIGN PATENT DOCUMENTS
| | | |
|---|---|---|
| CN | 101407515 A | 4/2009 |
| WO | 03064383 A2 | 8/2003 |
| WO | 2011072064 A1 | 6/2011 |
| WO | 2012143599 A1 | 10/2012 |
| WO | 2012170442 A1 | 12/2012 |
| WO | 2019191227 A1 | 10/2019 |

OTHER PUBLICATIONS

Fallah. Current Oncology Reports, 2019, 21:6, 1-10 (Year: 2019).*

* cited by examiner

*Primary Examiner* — Noble E Jarrell
(74) *Attorney, Agent, or Firm* — Derek Denhart

(57) ABSTRACT

The present invention relates to compounds of formula (I)

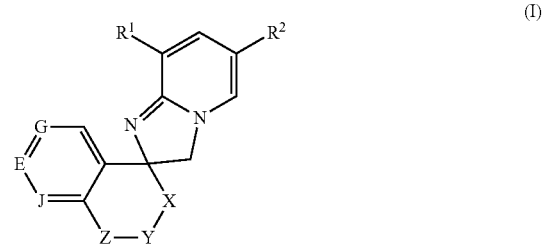

or a pharmaceutically acceptable salt form thereof, wherein the substituents are as defined in the specification; to intermediates in the preparation of the compounds, to pharmaceutical compositions comprising the compounds and to the use of the compounds in the treatment of disease.

30 Claims, 14 Drawing Sheets

Specification includes a Sequence Listing.

COMPOUNDS AND COMPOSITIONS FOR INHIBITING THE ACTIVITY OF HIF2-ALPHA AND THEIR METHODS OF USE

CROSS-REFERENCE TO RELATED APPLICATION

This application claims priority to International Application PCT/CN2020/087831 filed 29 Apr. 2020, which is incorporated in its entirety herein.

SEQUENCE LISTING

The instant application contains a Sequence Listing which has been submitted electronically in ASCII format and is hereby incorporated by reference in its entirety. Said ASCII copy, created on Jul. 13, 2021, is named PAT058789-US-PCT_SL.txt and is 3,279 bytes in size.

FIELD OF THE INVENTION

The invention provides spiro[imidazo[1,2-a]pyridine type compounds, the use thereof for inhibiting or modulating HIF2α and methods of treating disease using same.

BACKGROUND OF THE INVENTION

Hypoxia-inducible factors (HIFs) such as HIF1α and HIF2α are transcription factors well known as master regulators of oxygen homeostasis that control transcriptional responses to reduced $O_2$ availability (hypoxia). HIFs are heterodimeric proteins composed of an $O_2$-regulated HIF-α subunit and a constitutively expressed HIF-1β subunit also known as ARNT. Under well-oxygenated or normoxic conditions, HIF-α is bound by the von Hippel-Lindau (VHL) protein, which recruits a ubiquitin ligase that targets HIF-α for proteasomal degradation (Kaelin and Ratcliffe, 2008). VHL binding is dependent upon hydroxylation of a specific proline residue in HIF-α by the prolyl hydroxylases PHD, which use $O_2$ as a substrate such that its activity is inhibited under hypoxic conditions. HIF1α and HIF2α are transcription factors that regulate the expression of many genes involved in critical physiological functions such as development, metabolism, angiogenesis, cell proliferation and cell survival. While HIF1α is broadly expressed, HIF2α transcripts are restricted to particular cell types, including vascular endothelial cells, neural crest cell derivatives, lung type II pneumocytes, liver parenchyma, and interstitial cells in the kidney. HIF2α is described as a key mediator of the cellular adaptation to oxygen deprivation (hypoxia), playing important roles in physiological processes, such as erythropoiesis and vascularization. HIF2α is required for normal embryonic development, and postnatal ablation leads to severe anemia and impaired erythroid development. Consistent with these findings, erythropoietin (EPO) is reported to be predominantly controlled by HIF2α while some others HIFs-dependent genes can be regulated by both HIF-α isoforms.

Hypoxia plays a critical role in the progression of many common disorders, and evidence have been generated that modulation of HIFs transcriptional programs may be a beneficial therapeutic strategy in a wide variety of diseases like ischemia, inflammation, chronic lung disease and cancer (Semenza, 2011). In cancer in particular, intratumoral hypoxia is associated with poor patient prognosis and resistance to radiation and chemotherapy treatments.

HIFs activation is reported in many advanced human cancers such as cancers of the brain, breast, colon, lung and renal cell carcinoma. Independently of oxygen levels in clear cell renal cell carcinoma (ccRCC), frequently reported genetic alterations in the VHL gene (e.g. mutation or silencing) leads to the accumulation of HIF-α in the tumor. While HIF2α is expressed in most ccRCC tumor samples, only a subset accumulates HIF1α (Gordan, 2008). Furthermore, in ccRCC, HIF2α is described to be the key oncogenic event while HIF1α displays tumor suppressor properties (Shen and Kaelin, 2013, Gordan 2008). For example, overexpression of HIF2α leads to an increase in the in vivo growth of the VHL-deficient 786-0 RCC tumor xenografts. In contrast, down regulation of HIF2α by inducible shRNA or pharmacological inhibition seems sufficient to suppress tumor growth in VHL-defective 786-0 and A498 RCC models (Kondo et al., 2002; Kondo et al., 2003; Zimmer et al., 2004; Cho et al., 2016). These results support HIF2α as an attractive target for anti-cancer therapy.

SUMMARY OF THE INVENTION

The present invention provides compounds of formula (I), or pharmaceutically acceptable salts thereof, as defined below. The compounds of formula (I) are HIF2α inhibitors or modulators and are therefore potentially useful in the treatment of conditions, disease and disorders mediated by HIF2α.

In one aspect of the present invention, a compound of formula (I) is provided,

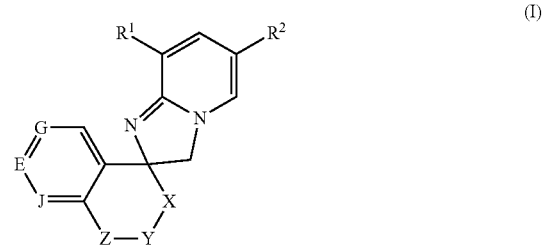

(I)

or a pharmaceutically acceptable salt thereof,
wherein:
$R^1$ is F, Cl, Br, $OCH_3$, $OCH_2F$, $OCHF_2$, or $OCF_3$;
$R^2$ is F, Cl, $CF_3$, or CN;
X is $(CH_2)_{1-2}$, CHF, CHD, $CD_2$ or $CF_2$;
Y is $(CH_2)_{0-2}$, CHF, CHD, $CD_2$, O, S, $OCH_2$, or $CF_2$;
Z is $CH_2$, $CD_2$, CHF, CDF, $CF_2$, CH(OH), CO, $CH(CH_3)$, O or S,
  wherein, when Y is O, $OCH_2$, or S, then Z is $CH_2$;
  wherein, when Z is O, S, or $NCH_3$, then Y is $(CH_2)_{0-2}$, or $CF_2$;
  wherein, when Z is CH(OH), then Y is CHF or $CF_2$;
J is $CR^J$;
  wherein $R^J$ is H, F, Cl, Br, $CH_3$, $CD_3$, $CF_3$, $CHF_2$, $CDF_2$, or CN;
E is $CR^E$ or N;
  wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD_3)F_2$, $CF_3$, cyclopropyl, $OCH_3$, $OCH_2CH_2OH$, $OCF_3$, $SCH_3$ or $SCHF_2$; and
G is CH or N;
in free form or in pharmaceutically acceptable salt form.

In another aspect, the invention provides a pharmaceutical composition comprising a compound of formula (I), or subformulae thereof, or a pharmaceutically acceptable salt thereof, and one or more pharmaceutically acceptable carriers.

In another aspect, the invention provides a combination, in particular a pharmaceutical combination comprising a compound of formula (I), or subformulae thereof, or a pharmaceutically acceptable salt thereof, and one or more therapeutic agents. In certain instances, compounds of the present invention are combined with other therapeutic agents, such as other anti-cancer agents (in particular, mTOR inhibitors such as everolimus), anti-nausea agents (or anti-emetics), a chemotherapy, pain relievers, cytoprotective agents, and combinations thereof.

The mTOR inhibitors include Temsirolimus (Torisel®); Ridaforolimus (formally known as deferolimus, (1R,2R,4S)-4-[(2R)-2 [(1R,9S,12S,15R,16E,18R,19R,21R, 23S, 24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ. ID NO: 1), inner salt (SF1126, CAS 936487-67-1); and N-[4-[[[3-[(3,5-dimethoxyphenyl)amino]-2-quinoxalinyl]amino]sulfonyl]phenyl]-3-methoxy-4-methyl-benzamide (XL765, also known as SAR245409); and (1r,4r)-4-(4-amino-5-(7-methoxy-1H-indol-2-yl)imidazo[1,5-f][1,2,4]triazin-7-yl)cyclohexanecarboxylic acid (OSI-027).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In another aspect, the invention provides a method of inhibiting or modulating HIF2α activity in a subject in need thereof, the method comprises administering to the subject in need thereof a compound of formula (I), or subformulae thereof, or a pharmaceutically acceptable salt thereof.

In another aspect, the invention provides a compound of formula (I), or subformulae thereof, or a pharmaceutically acceptable salt thereof, for use in the treatment, or prevention of cancer, wherein the cancer is selected from adrenocortical carcinoma, breast cancer, clear cell renal cell carcinoma (ccRCC), colorectal cancer (may include colon cancer), germ cell tumor (e.g. cranial and extracranial germ cell tumor, gonadal and extragonadal germ cell tumor), glioblastoma multiforme (GBM), glioma, head and neck cancer (may include lip, oral cavity, mouth cancer), hepatocellular carcinoma, kidney cancer, lung cancer, malignant glioma, ocular cancer, pancreatic cancer, paraganglioma, pheochromocytoma, prostate cancer, and renal cell carcinoma.

In another aspect, the present invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form.

In another aspect, the present invention provides a crystalline form of the fumarate salt of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline].

In another aspect, the present invention provides a process for formula (I),

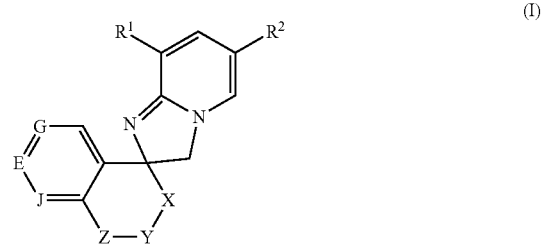

or a pharmaceutically acceptable salt thereof, comprising the step of reacting the compound of formula (IV),

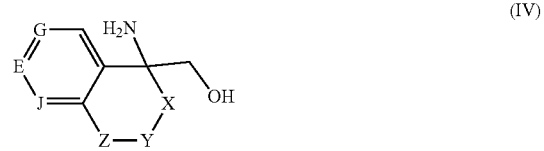

or a salt, solvate, stereoisomer, complex, co-crystal, ester, or oxazoline thereof,
and the compound of formula (II),

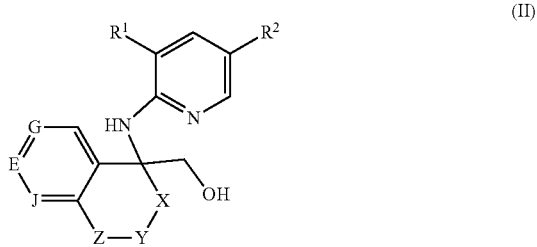

or a salt, solvate, stereoisomer, complex, co-crystal, ester, or oxazoline thereof,
with a compound of formula (III)

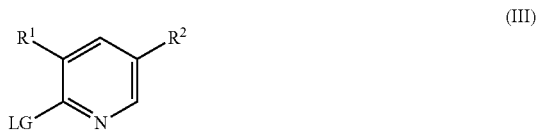

or a salt, solvate, stereoisomer, complex, co-crystal, ester, or oxazoline thereof,
wherein
$R^1$ is F, Cl, Br, $OCH_3$, $OCH_2F$, $OCHF_2$, or $OCF_3$;
$R^2$ is F, Cl, $CF_3$, or CN;
X is $CH_2$, CHF, or $CF_2$;
Y is $CH_2$, CHF, O, S, a single bond, $CH_2CH_2$, $OCH_2$, or $CF_2$;
Z is $CH_2$, $CD_2$, CHF, CDF, $CF_2$, CH(OH), CO, $CH(CH_3)$, O or S;
  wherein, when Y is O, $OCH_2$, or S, then Z is $CH_2$;
  wherein, when Z is O, S, or $NCH_3$, then Y is $CH_2$, a single bond, $CH_2CH_2$, or $CF_2$;
  wherein, when Z is CH(OH), then Y is CHF or $CF_2$;
J is $CR^J$;
  wherein $R^J$ is H, F, Cl, Br, $CH_3$, $CD_3$, $CF_3$, $CHF_2$, $CDF_2$, CN;
E is $CR^E$ or N;
  wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD_3)F_2$, $CF_3$, cyclopropyl, $OCH_3$, $OCH_2CH_2OH$, $OCF_3$, $SCH_3$, or $SCHF_2$;
G is CH or N; and
LG is a leaving group selected from F, Cl, or Br;
  optionally in the presence of base selected from $K_2CO_3$ or $Et_3N$,
to obtain the compound of formula (1) or a pharmaceutically acceptable salt thereof.

DETAILED DESCRIPTION OF THE INVENTION

Figure 1:
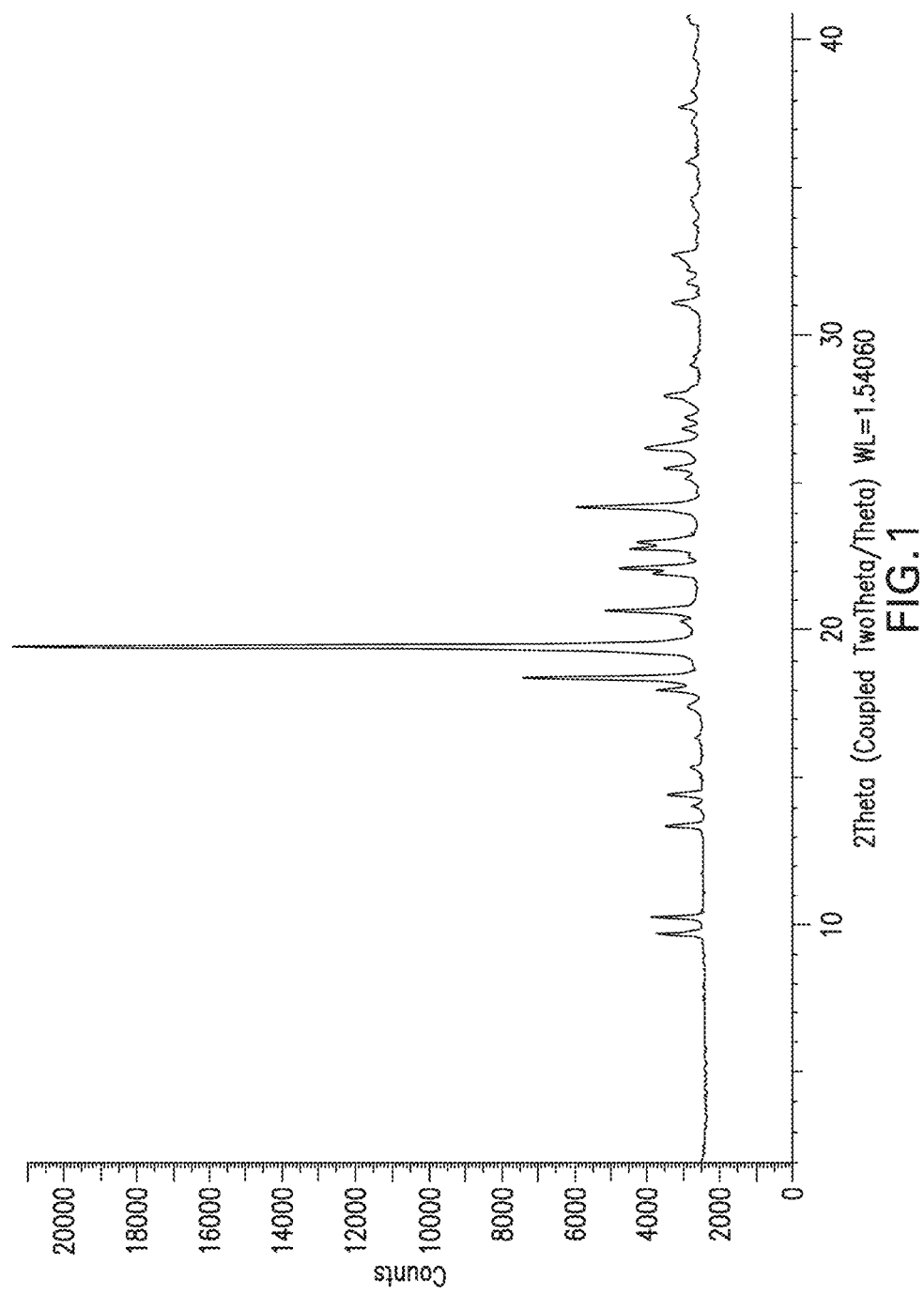
FIG. 1: illustrates a representative X-ray powder diffraction (XRPD) of Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention. The x-axis shows the scattering angle in ° 2-Theta, the y-axis shows the intensity of the scattered X-ray beam in counts of detected photons.

The invention provides a compound of formula (I)

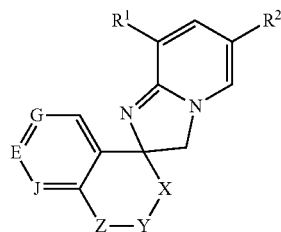

(I)

or a pharmaceutically acceptable salt thereof, wherein $R^1$ is F, Cl, Br, $OCH_3$, $OCH_2F$, $OCHF_2$, or $OCF_3$;

$R^2$ is F, Cl, $CF_3$, or CN;

X is $(CH_2)_{1-2}$, CHF, CHD, $CD_2$ or $CF_2$;

Y is $(CH_2)_{0-2}$, CHF, CHD, $CD_2$, O, S, $OCH_2$ or $CF_2$;

Z is $CH_2$, $CD_2$, CHF, CDF, $CF_2$, CH(OH), CO, $CH(CH_3)$, O, or S, wherein, when Y is O, $OCH_2$, or S, then Z is $CH_2$;

wherein, when Z is O, S, or $NCH_3$, then Y is $(CH_2)_{0-2}$, or $CF_2$;

wherein, when Z is CH(OH), then Y is CHF or $CF_2$;

J is $CR^J$;

wherein $R^J$ is H, F, Cl, Br, $CH_3$, $CD_3$, $CF_3$, $CHF_2$, $CDF_2$, OCH3 or CN;

E is $CR^E$ or N;

wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD_3)F_2$, $CF_3$, cyclopropyl, $OCH_3$, $OCH_2CH_2OH$, $OCF_3$, $SCH_3$ or $SCHF_2$; and G is CH or N;

in free form or in pharmaceutically acceptable salt form.

Various embodiments of the invention are described herein, it will be recognized that features specified in each embodiment may be combined with other specified features to further embodiments of the present invention.

In embodiment 1, the invention provides a compound of formula (I), or a pharmaceutically acceptable salt thereof, as described above.

In embodiment 2, the invention provides a compound of formula (I), or a pharmaceutically acceptable salt thereof, according to embodiment 1, wherein $R^1$ is F, Cl or $OCHF_2$;

$R^2$ is $CF_3$ or CN;

X is $CH_2$ or CHF;

Y is a $(CH_2)_{0-2}$ or CHF;

Z is CHF, CDF, $CF_2$, O, or S;

J is $CR^J$;

wherein $R^J$ is H, F, Cl, $CH_3$ or $CD_3$;

E is $CR^E$ or N;

wherein $R^E$ is H, F, Br, or $CF_3$; and

G is CH.

In embodiment 3, the invention provides a compound of formula (I), or a pharmaceutically acceptable salt thereof, according to embodiment 1 or 2, wherein $R^1$ is $OCHF_2$;

$R^2$ is $CF_3$;

X is $CH_2$ or CHF;

Y is $(CH)_{0-2}$;

Z is $CF_2$, or O;

J is $CR^J$;

wherein $R^J$ is H, F, Cl, $CH_3$ or $CD_3$;

E is $CR^E$ or N;

wherein $R^E$ is H, F, Br or $CF_3$; and

G is CH.

In embodiment 4, the invention provides a compound of formula (I) in free form or in pharmaceutically acceptable salt form according to embodiment 1 to 3, wherein the stereochemistry is defined as shown in formula (Ia)

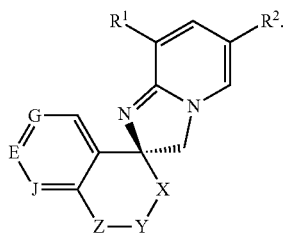

(Ia)

In embodiment 5, the invention provides a compound of formula (I) in free form or a pharmaceutically acceptable salt form according to any one of claims from 1 to 4, wherein the stereochemistry is defined as shown in formula (Ib)

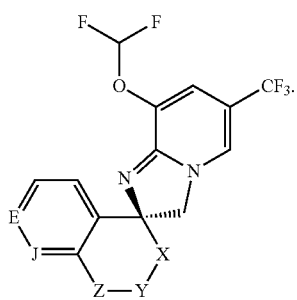

(Ib)

In embodiment 6, the invention provides a compound of formula (I), or a pharmaceutically acceptable salt thereof, according to embodiment 5,
wherein
X is $CH_2$ or CHF;
Y is $(CH_2)_{0-2}$;
Z is O, S or $CF_2$;
E is $CR^E$ or N;
  wherein $R^E$ is H, F, Br or $CF_3$; and
J is $CR^J$;
  wherein $R^J$ is H, F, Cl, $CH_3$ or $CD_3$.

In embodiment 7, the invention provides a compound of formula (I), or a pharmaceutically acceptable salt thereof, according to embodiment 1 which is selected from the group consisting of:
(S)-5'-bromo-8-(difluoromethoxy)-4'-fluoro-6-(trifluoromethyl)-2',3'-dihydro-3H-spiro[imidazo[1,2-a]pyridine-2,1'-indene];
(S)-8-(difluoromethoxy)-4',5'-difluoro-6-(trifluoromethyl)-2',3'-dihydro-3H-spiro[imidazo[1,2-a]pyridine-2,1'-indene];
(S)-8'-(difluoromethoxy)-3,6'-bis(trifluoromethyl)-5,6-dihydro-3'H-spiro[cyclopenta[c]pyridine-7,2'-imidazo[1,2-a]pyridine];
(S)-5'-bromo-8-(difluoromethoxy)-4'-fluoro-2',3'-dihydro-3H-spiro[imidazo[1,2-a]pyridine-2,1'-indene]-6-carbonitrile;
(S)-5'-bromo-4'-fluoro-8-(fluoromethoxy)-6-(trifluoromethyl)-2',3'-dihydro-3H-spiro[imidazo[1,2-a]pyridine-2,1'-indene];
(S)-8-(difluoromethoxy)-5',6-bis(trifluoromethyl)-2',3'-dihydro-3H-spiro[imidazo[1,2-a]pyridine-2,1'-indene];
(S)-6'-bromo-8-(difluoromethoxy)-5'-fluoro-6-(trifluoromethyl)-3',4'-dihydro-2'H,3H-spiro[imidazo[1,2-a]pyridine-2,1'-naphthalene];
(S)-6'-bromo-8-(difluoromethoxy)-5'-fluoro-6-(trifluoromethyl)-2'H,3H-spiro[imidazo[1,2-a]pyridine-2,1'-naphthalen]-4'(3R)-one;
(1'S,3'R)-6'-bromo-8-(difluoromethoxy)-3',5'-difluoro-6-(trifluoromethyl)-2'H,3H-spiro[imidazo[1,2-a]pyridine-2,1'-naphthalen]-4'(3'H)-one;
(1'S,3'R,4'S)-6'-bromo-8-(difluoromethoxy)-3',5'-difluoro-6-(trifluoromethyl)-3',4'-dihydro-2'H,3H-spiro[imidazo[1,2-a]pyridine-2,1'-naphthalen]-4'-ol;
(S)-6'-bromo-8-(difluoromethoxy)-6-(trifluoromethyl)-3',4'-dihydro-2'H,3H-spiro[imidazo[1,2-a]pyridine-2,1'-naphthalene];
(S)-8-(difluoromethoxy)-6-(trifluoromethyl)-3',4'-dihydro-2'H,3H-spiro[imidazo[1,2-a]pyridine-2,1'-naphthalene];
(S)-6'-bromo-8-(difluoromethoxy)-5'-fluoro-3',4'-dihydro-2'H,3H-spiro[imidazo[1,2-a]pyridine-2,1'-naphthalene]-6-carbonitrile;
(S)-6'-bromo-8-(difluoromethoxy)-4',4',5'-trifluoro-6-(trifluoromethyl)-3',4'-dihydro-2'H,3H-spiro[imidazo[1,2-a]pyridine-2,1'-naphthalene];
(S)-8-(difluoromethoxy)-4',4',5'-trifluoro-6-(trifluoromethyl)-3',4'-dihydro-2'H,3H-spiro[imidazo[1,2-a]pyridine-2,1'-naphthalene]-6'-carbonitrile;
(S)-6'-bromo-8-chloro-5'-fluoro-6-(trifluoromethyl)-3',4'-dihydro-2'H,3H-spiro[imidazo[1,2-a]pyridine-2,1'-naphthalene];
(S)-6'-bromo-8-(difluoromethoxy)-3',3',5'-trifluoro-6-(trifluoromethyl)-2'H,3H-spiro[imidazo[1,2-a]pyridine-2,1'-naphthalen]-4'(3M-one;
(1'S,4'S)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol;
(1'S,4'R)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol;
(1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one;
(1'S,3'R)-8-(difluoromethoxy)-3',5'-difluoro-6-(trifluoromethyl)-2'H,3H-spiro[imidazo[1,2-a]pyridine-2,1'-naphthalen]-4'(3M-one;
(S)-8-(difluoromethoxy)-5'-fluoro-6-(trifluoromethyl)-3',4'-dihydro-2'H,3H-spiro[imidazo[1,2-a]pyridine-2,1'-naphthalene]-6'-carbonitrile;
(S)-8-(difluoromethoxy)-4',4',5'-trifluoro-6-(trifluoromethyl)-3',4'-dihydro-2'H,3H-spiro[imidazo[1,2-a]pyridine-2,1'-naphthalene];
(2S,4'S)-6'-bromo-8-(difluoromethoxy)-4',5'-difluoro-3',4'-dihydro-2'H,3H-spiro[imidazo[1,2-a]pyridine-2,1'-naphthalene]-6-carbonitrile;
(1'S,4'S)-8-(difluoromethoxy)-4',5'-difluoro-6-(trifluoromethyl)-3',4'-dihydro-2'H,3H-spiro[imidazo[1,2-a]pyridine-2,1'-naphthalene]-6'-carbonitrile;
(S)-8-(difluoromethoxy)-5'-fluoro-3',4'-dihydro-2'H,3H-spiro[imidazo[1,2-a]pyridine-2,1'-naphthalene]-6-carbonitrile;
$d_2$-(S)-8-(difluoromethoxy)-5'-fluoro-3',4'-dihydro-2'H,3H-spiro[imidazo[1,2-a]pyridine-2,1'-naphthalene]-6-carbonitrile;
(S)-8-(difluoromethoxy)-5'-fluoro-6-(trifluoromethyl)-3',4'-dihydro-2'H,3H-spiro[imidazo[1,2-a]pyridine-2,1'-naphthalene];
(S)-5',6',8-trifluoro-6-(trifluoromethyl)-3',4'-dihydro-2'H,3H-spiro[imidazo[1,2-a]pyridine-2,1'-naphthalene];
(S)-1'-chloro-8',8'-difluoro-8-methoxy-6-(trifluoromethyl)-7',8'-dihydro-3H,6'H-spiro[imidazo[1,2-a]pyridine-2,5'-isoquinoline];

(S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-(methyl-d3)-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-methoxy-6-(trifluoromethyl)-7',8'-dihydro-3H,6'H-spiro[imidazo[1,2-a]pyridine-2,5'-isoquinoline];

(S)-8-(difluoromethoxy)-6'-fluoro-3',4'-dihydro-2'H,3H-spiro[imidazo[1,2-a]pyridine-2,1'-naphthalene]-6-carbonitrile;

(S)-1'-chloro-8-(difluoromethoxy)-6-(trifluoromethyl)-7',8'-dihydro-3H,6'H-spiro[imidazo[1,2-a]pyridine-2,5'-isoquinoline];

(S)-3'-chloro-8-(difluoromethoxy)-6-(trifluoromethyl)-6',7'-dihydro-3H,5'H-spiro[imidazo[1,2-a]pyridine-2,8'-isoquinoline];

(S)-8-(difluoromethoxy)-6-(trifluoromethyl)-3',4'-dihydro-2'H,3H-spiro[imidazo[1,2-a]pyridine-2,1'-naphthalene]-6'-carbonitrile;

(S)-7-bromo-8'-(difluoromethoxy)-8-fluoro-6'-(trifluoromethyl)-3'H-spiro[chroman-4,2'-imidazo[1,2-a]pyridine];

(S)-8'-(difluoromethoxy)-8-fluoro-6',7-bis(trifloromethyl)-3'H-spiro[chroman-4,2'-imidazo[1,2-a]pyridine];

(S)-7-chloro-8'-(difluoromethoxy)-6'-(trifluoromethyl)-3'H-spiro[chroman-4,2'-imidazo[1,2-a]pyridine]; (S)-7-bromo-8-fluoro-8'-(fluoromethoxy)-6'-(trifluoromethyl)-3'H-spiro[chroman-4,2'-imidazo[1,2-a]pyridine];

(S)-7-chloro-8'-(difluoromethoxy)-8-fluoro-6'-(trifluoromethyl)-3'H-spiro[chroman-4,2'-imidazo[1,2-a]pyridine];

(S)-8'-(difluoromethoxy)-6',7-bis(trifluoromethyl)-3'H-spiro[chroman-4,2'-imidazo[1,2-a]pyridine];

(S)-8'-(difluoromethoxy)-7,8-difluoro-6'-(trifluoromethyl)-3'H-spiro[chroman-4,2'-imidazo[1,2-a]pyridine];

(S)-8'-(difluoromethoxy)-8-fluoro-7-methyl-6'-(trifluoromethyl)-3'H-spiro[chroman-4,2'-imidazo[1,2-a]pyridine];

(S)-8'-(difluoromethoxy)-8-fluoro-6'-(trifluoromethyl)-3'H-spiro[chroman-4,2'-imidazo[1,2-a]pyridine]; (S)-8-chloro-8'-(difluoromethoxy)-6'-(trifluoromethyl)-3'H-spiro[chroman-4,2'-imidazo[1,2-a]pyridine]; (S)-7-bromo-8'-(difluoromethoxy)-8-fluoro-3'H-spiro[chroman-4,2'-imidazo[1,2-a]pyridine]-6'-carbonitrile;

(S)-7-bromo-8'-(difluoromethoxy)-6'-(trifluoromethyl)-3'H-spiro[chroman-4,2'-imidazo[1,2-a]pyridine]; (S)-8'-(difluoromethoxy)-8-fluoro-7-iodo-3'H-spiro[chroman-4,2'-imidazo[1,2-a]pyridine]-6'-carbonitrile; (S)-7-bromo-6'-chloro-8'-(difluoromethoxy)-8-fluoro-3'H-spiro[chroman-4,2'-imidazo[1,2-a]pyridine]; (S)-8'-chloro-6',7-bis(trifluoromethyl)-3'H-spiro[chroman-4,2'-imidazo[1,2-a]pyridine];

(S)-7,8'-bis(difluoromethoxy)-8-fluoro-6'-(trifluoromethyl)-3'H-spiro[chroman-4,2'-imidazo[1,2-a]pyridine];

(S)-8'-(difluoromethoxy)-8-(difluoromethyl)-6'-(trifluoromethyl)-3'H-spiro[chroman-4,2'-imidazo[1,2-a]pyridine];

(S)-8'-chloro-8-(difluoromethoxy)-6-(trifluoromethyl)-2',3'-dihydro-3H-spiro[imidazo[1,2-a]pyridine-2,4'-pyrano[2,3-a]pyridine];

(2'S,3R)-7-bromo-8'-(difluoromethoxy)-3,8-difluoro-6'-(trifluoromethyl)-3'H-spiro[chroman-4,2'-imidazo[1,2-a]pyridine];

(2'S,3S)-7-bromo-8'-(difluoromethoxy)-3,8-difluoro-6'-(trifluoromethyl)-3'H-spiro[chroman-4,2'-imidazo[1,2-a]pyridine];

(2'S,3R)-7-bromo-8'-(difluoromethoxy)-3-fluoro-6'-(trifluoromethyl)-3'H-spiro[chroman-4,2'-imidazo[1,2-a]pyridine];

(2'S,3R)-8'-(difluoromethoxy)-3-fluoro-7-iodo-6'-(trifluoromethyl)-3'H-spiro[chroman-4,2'-imidazo[1,2-a]pyridine];

(2'S,3R)-8'-(difluoromethoxy)-3-fluoro-6',7-bis(trifluoromethyl)-3'H-spiro[chroman-4,2'-imidazo[1,2-a]pyridine];

(2'S,3R)-8'-(difluoromethoxy)-3,8-difluoro-6'-(trifluoromethyl)-3'H-spiro[chroman-4,2'-imidazo[1,2-a]pyridine];

(S)-8-(difluoromethoxy)-8'-fluoro-6-(trifluoromethyl)-3H-spiro[imidazo[1,2-a]pyridine-2,4'-isochroman]; (S)-7'-chloro-8-(difluoromethoxy)-8'-fluoro-3H-spiro[imidazo[1,2-a]pyridine-2,4'-thiochroman]-6-carbonitrile;

(S)-8-(difluoromethoxy)-8'-fluoro-6-(trifluoromethyl)-3H-spiro[imidazo[1,2-a]pyridine-2,4'-thiochroman];

(S)-8-(difluoromethoxy)-8'-fluoro-3H-spiro[imidazo[1,2-a]pyridine-2,4'-thiochroman]-6-carbonitrile;

(S)-8-(difluoromethoxy)-8'-fluoro-6,7'-bis(trifluoromethyl)-2',3'-dihydro-3H-spiro[imidazo[1,2-a]pyridine-2,4'-thiopyrano[3,2-c]pyridine];

(S)-8-(difluoromethoxy)-8'-fluoro-3H-spiro[imidazo[1,2-a]pyridine-2,4'-isothiochroman]-6-carbonitrile; (S)-8'-(difluoromethoxy)-9-fluoro-6'-(trifluoromethyl)-3,4-dihydro-2H,3'H-spiro[benzo[b]oxepine-5,2'-imidazo[1,2-a]pyridine];

(S)-8-(difluoromethoxy)-1'-(difluoromethyl)-8',8'-difluoro-6-(trifluoromethyl)-7',8'-dihydro-3H,6'H-spiro[imidazo[1,2-a]pyridine-2,5'-isoquinoline];

(S)-5'-bromo-4',8-dichloro-6-(trifluoromethyl)-2',3'-dihydro-3H-spiro[imidazo[1,2-a]pyridine-2,1'-indene];

(S)-5'-bromo-8-(difluoromethoxy)-6-(trifluoromethyl)-2',3'-dihydro-3H-spiro[imidazo[1,2-a]pyridine-2,1'-indene];

(S)-8-(difluoromethoxy)-5'-iodo-2',3'-dihydro-3H-spiro[imidazo[1,2-a]pyridine-2,1'-indene]-6-carbonitrile;

(S)-8-(difluoromethoxy)-4'-fluoro-5',6-bis(trifluoromethyl)-2',3'-dihydro-3H-spiro[imidazo[1,2-a]pyridine-2,1'-indene];

(S)-8-(difluoromethoxy)-6-(trifluoromethyl)-2',3'-dihydro-3H-spiro[imidazo[1,2-a]pyridine-2,1'-indene]; (S)-5',8-difluoro-6'-methoxy-6-(trifluoromethyl)-3',4'-dihydro-2'H,3H-spiro[imidazo[1,2-a]pyridine-2,1'-naphthalene];

(S)-8-fluoro-6,6'-bis(trifluoromethyl)-3',4'-dihydro-2'H,3H-spiro[imidazo[1,2-a]pyridine-2,1'-naphthalene];

rac-5',6',8-trifluoro-6-(trifluoromethyl)-3',4'-dihydro-2'H,3H-spiro[imidazo[1,2-a]pyridine-2,1'-naphthalene];

(S)-8-chloro-5'-fluoro-6-(trifluoromethyl)-3',4'-dihydro-2'H,3H-spiro[imidazo[1,2-a]pyridine-2,1'-naphthalene];

(S)-6'-bromo-5'-fluoro-8-methoxy-6-(trifluoromethyl)-3',4'-dihydro-2'H,3H-spiro[imidazo[1,2-a]pyridine-2,1'-naphthalene];

rac-5'-bromo-8-(difluoromethoxy)-6-(trifluoromethyl)-3',4'-dihydro-2'H,3H-spiro[imidazo[1,2-a]pyridine-2,1'-naphthalene];

(S)-5'-chloro-8-(difluoromethoxy)-6'-fluoro-6-(trifluoromethyl)-3',4'-dihydro-2'H,3H-spiro[imidazo[1,2-a]pyridine-2,1'-naphthalene];

(2S,3'R,4'R)-6'-bromo-8-(difluoromethoxy)-3',4',5'-trifluoro-6-(trifluoromethyl)-3',4'-dihydro-2'H,3H-spiro[imidazo[1,2-a]pyridine-2,1'-naphthalene];

(S)-8-(difluoromethoxy)-5'-fluoro-6'-methoxy-6-(trifluoromethyl)-3',4'-dihydro-2'H,3H-spiro[imidazo[1,2-a]pyridine-2,1'-naphthalene];

(S)-8-(difluoromethoxy)-5',6'-difluoro-6-(trifluoromethyl)-3',4'-dihydro-2'H,3H-spiro[imidazo[1,2-a]pyridine-2,1'-naphthalene];

(S)-8-(difluoromethoxy)-6,6'-bis(trifluoromethyl)-3',4'-dihydro-2'H,3H-spiro[imidazo[1,2-a]pyridine-2,1'-naphthalene];

rac-8-(difluoromethoxy)-5',6-bis(trifluoromethyl)-3',4'-dihydro-2'H,3H-spiro[imidazo[1,2-a]pyridine-2,1'-naphthalene];

(S)-5'-chloro-8-(difluoromethoxy)-6-(trifluoromethyl)-3',4'-dihydro-2'H,3H-spiro[imidazo[1,2-a]pyridine-2,1'-naphthalene];

(S)-6'-bromo-6-chloro-8-(difluoromethoxy)-5'-fluoro-3',4'-dihydro-2'H,3H-spiro[imidazo[1,2-a]pyridine-2,1'-naphthalene];

(S)-6'-bromo-8-(difluoromethoxy)-6-(trifluoromethyl)-2',3'-dihydro-3H,4'H-spiro[imidazo[1,2-a]pyridine-2,1'-naphthalen]-4'-one;

(S)-8-(difluoromethoxy)-5',6'-difluoro-3',4'-dihydro-2'H,3H-spiro[imidazo[1,2-a]pyridine-2,1'-naphthalene]-6-carbonitrile;

(S)-6'-bromo-8-(difluoromethoxy)-4',4',5'-trifluoro-3',4'-dihydro-2'H,3H-spiro[imidazo[1,2-a]pyridine-2,1'-naphthalene]-6-carbonitrile;

rac-8-(difluoromethoxy)-6-(trifluoromethyl)-7',8'-dihydro-3H,6'H-spiro[imidazo[1,2-a]pyridine-2,5'4 soquinoline];

(S)-1'-chloro-8-(difluoromethoxy)-7',8'-dihydro-3H,6'H-spiro[imidazo[1,2-a]pyridine-2,5'-isoquinoline]-6-carbonitrile;

(S)-8-chloro-8'-(fluoromethoxy)-6'-(trifluoromethyl)-3'H-spiro[chromane-4,2'-imidazo[1,2-a]pyridine]; (S)-8-chloro-8'-(difluoromethoxy)-6'-(trifluoromethyl)-3'H-spiro[chromane-4,2'-imidazo[1,2-a]pyridine]-7-carbonitrile;

(3R,4S)-7-chloro-8'-(difluoromethoxy)-3,8-difluoro-6'-(trifluoromethyl)-3'H-spiro[chromane-4,2'-imidazo[1,2-a]pyridine];

(3R,4S)-8'-(difluoromethoxy)-3,7,8-trifluoro-6'-(trifluoromethyl)-3'H-spiro[chromane-4,2'-imidazo[1,2-a]pyridine];

(S)-8'-(difluoromethoxy)-8-fluoro-7-(methylthio)-6'-(trifluoromethyl)-3'H-spiro[chromane-4,2'-imidazo[1,2-a]pyridine];

(S)-7-bromo-8-chloro-8'-(difluoromethoxy)-6'-(trifluoromethyl)-3'H-spiro[chromane-4,2'-imidazo[1,2-a]pyridine];

rac-8'-(difluoromethoxy)-3,8-difluoro-6'-(trifluoromethyl)-3'H-spiro[chromane-4,2'-imidazo[1,2-a]pyridine];

(S)-7,8-dibromo-8'-(difluoromethoxy)-6'-(trifluoromethyl)-3'H-spiro[chromane-4,2'-imidazo[1,2-a]pyridine];

(S)-8'-(difluoromethoxy)-8-fluoro-7-methoxy-6'-(trifluoromethyl)-3'H-spiro[chromane-4,2'-imidazo[1,2-a]pyridine];

(S)-8'-(difluoromethoxy)-6',8-bis(trifluoromethyl)-3'H-spiro[chromane-4,2'-imidazo[1,2-a]pyridine];

(S)-8'-(difluoromethoxy)-8-fluoro-7-(trifluoromethoxy)-6'-(trifluoromethyl)-3'H-spiro[chromane-4,2'-imidazo[1,2-a]pyridine];

(S)-8'-(difluoromethoxy)-7-((difluoromethyl)thio)-8-fluoro-6'-(trifluoromethyl)-3'H-spiro[chromane-4,2'-imidazo[1,2-a]pyridine];

(S)-8-bromo-8'-(difluoromethoxy)-6'-(trifluoromethyl)-3'H-spiro[chromane-4,2'-imidazo[1,2-a]pyridine]; rac-8-(difluoromethoxy)-8'-fluoro-6,7'-bis(trifluoromethyl)-3H-spiro[imidazo[1,2-a]pyridine-2,4'-isochroman];

(2S)-8-(difluoromethoxy)-8'-fluoro-3H-spiro[imidazo[1,2-a]pyridine-2,4'-thiochromane]-6-carbonitrile-2',2',3'-d3;

(S)-7'-bromo-8-(difluoromethoxy)-8'-fluoro-3H-spiro[imidazo[1,2-a]pyridine-2,4'-thiochromane]-6-carbonitrile;

(S)-8-(difluoromethoxy)-8'-fluoro-6-(trifluoromethyl)-3H-spiro[imidazo[1,2-a]pyridine-2,4'-thiochromane]-7'-carbonitrile;

(S)-8-(difluoromethoxy)-7',8'-difluoro-3H-spiro[imidazo[1,2-a]pyridine-2,4'-thiochromane]-6-carbonitrile;

(S)-8-(difluoromethoxy)-7',8'-difluoro-6-(trifluoromethyl)-3H-spiro[imidazo[1,2-a]pyridine-2,4'-thiochromane];

(S)-8'-fluoro-8-(fluoromethoxy)-6,7'-bis(trifluoromethyl)-2',3'-dihydro-3H-spiro[imidazo[1,2-a]pyridine-2,4'-thiopyrano[3,2-c]pyridine];

(S)-8-(difluoromethoxy)-8'-fluoro-6-(trifluoromethyl)-3H-spiro[imidazo[1,2-a]pyridine-2,4'-isothiochromane];

(S)-8-(difluoromethoxy)-7'-fluoro-6-(trifluoromethyl)-3H-spiro[imidazo[1,2-a]pyridine-2,4'-isothiochromane];

(S)-8'-(difluoromethoxy)-8,9-difluoro-6'-(trifluoromethyl)-3,4-dihydro-2H,3'H-spiro[benzo[b]oxepine-5,2'-imidazo[1,2-a]pyridine];

rac-9-chloro-8'-(difluoromethoxy)-6'-(trifluoromethyl)-3,4-dihydro-2H,3'H-spiro[benzo[b]oxepine-5,2'-imidazo[1,2-a]pyridine]; and (S)-8-chloro-8'-(difluoromethoxy)-9-fluoro-6'-(trifluoromethyl)-3,4-dihydro-1H,3'H-spiro[benzo[c]oxepine-5,2'-imidazo[1,2-a]pyridine].

In embodiment 8, the invention provides for a compound of formula (I), or a pharmaceutically acceptable salt thereof, according to embodiment 1 which is selected from the group consisting of:

(S)-8-(difluoromethoxy)-8'-fluoro-3H-spiro[imidazo[1,2-a]pyridine-2,4'-thiochroman]-6-carbonitrile;

(S)-8'-(difluoromethoxy)-9-fluoro-6'-(trifluoromethyl)-3,4-dihydro-2H,3'H-spiro[benzo[b]oxepine-5,2'-imidazo[1,2-a]pyridine];

(S)-8'-(difluoromethoxy)-6',7-bis(trifluoromethyl)-3'H-spiro[chroman-4,2'-imidazo[1,2-a]pyridine];

(S)-7-bromo-8'-(difluoromethoxy)-8-fluoro-6'-(trifluoromethyl)-3'H-spiro[chroman-4,2'-imidazo[1,2-a]pyridine];

(2'S,3R)-8'-(difluoromethoxy)-3,8-difluoro-6'-(trifluoromethyl)-3'H-spiro[chroman-4,2'-imidazo[1,2-a]pyridine];

(S)-8'-(difluoromethoxy)-7,8-difluoro-6'-(trifluoromethyl)-3'H-spiro[chroman-4,2'-imidazo[1,2-a]pyridine];

(S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-(methyl-d$_3$)-6-(trifluoromethyl)-7',8'-dihydro-3H,6'H-spiro[imidazo[1,2-a]pyridine-2,5'-isoquinoline]; and (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline].

In embodiment 9 the invention provides a compound or pharmaceutically acceptable salt form selected from the group consisting of:

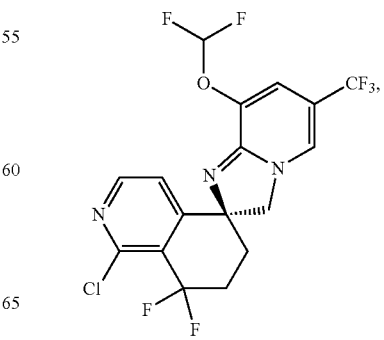

-continued

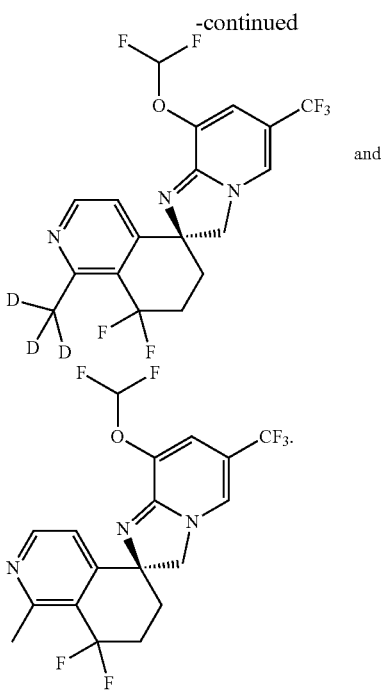

and

In embodiment 10, the invention provides a compound or a pharmaceutically acceptable salt thereof, that is:

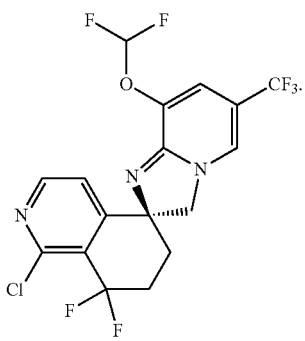 [SMILES: FC(F)OC1=CC(C(F)(F)F)=CN2C[C@@]3(CCC(F)(F)c4c3ccnc4Cl)N=C12]

In embodiment 11, the invention provides a pharmaceutical composition comprising a therapeutically effective amount of a compound according to any one of embodiments 1 to 10 or a pharmaceutically acceptable salt thereof and one or more pharmaceutically acceptable carriers.

In embodiment 12, the invention provides a combination comprising a therapeutically effective amount of a compound according to any one of embodiments 1 to 10 or a pharmaceutically acceptable salt thereof and one or more therapeutically active agents.

In embodiment 13, the invention provides a combination according to embodiment 8, wherein said therapeutic agent is selected from a mTOR inhibitor selected from Temsirolimus; Ridaforolimus; Everolimus (RAD001); Rapamycin; Simapimod; (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one; $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 1); N-[4-[[[3-[(3,5-dimethoxyphenyl)amino]-2-quinoxalinyl]amino]sulfonyl]phenyl]-3-methoxy-4-methyl-benzamide; or (1r,4r)-4-(4-amino-5-(7-methoxy-1H-indol-2-yl)imidazo[1,5-f][1,2,4]triazin-7-yl)cyclohexanecarboxylic acid.

In embodiment 14, the invention provides a combination according to embodiment 9, wherein said mTOR inhibitor is everolimus.

In embodiment 15, the invention provides a method or use of modulating HiF2alpha activity in a subject, wherein the method comprises administering to the subject a therapeutically effective amount of the compound according to any one of embodiments 1 to 10 or a pharmaceutically acceptable salt thereof.

In embodiment 16, the invention provides a method or use of treating a disorder or disease, which is a cancer, comprising administering to the subject a therapeutically effective amount of the compound according to any one of embodiments 1 to 10 or a pharmaceutically acceptable salt thereof.

In embodiment 17, the invention provides a method or use of treating according to embodiment 12 wherein the cancer is selected from adrenocortical carcinoma, breast cancer, clear cell renal cell carcinoma (ccRCC), colorectal cancer, germ cell tumor, glioblastoma multiforme (GBM), glioma, head and neck cancer, hepatocellular carcinoma, kidney cancer, lung cancer, malignant glioma, ocular cancer, pancreatic cancer, paraganglioma, pheochromocytoma, prostate cancer, and renal cell carcinoma, comprising administering to the subject a therapeutically effective amount of the compound according to any one of embodiments 1 to 10 or a pharmaceutically acceptable salt thereof.

In embodiment 18, the invention provides a compound according to any one of embodiments 1 to 10 or a pharmaceutically acceptable salt thereof, for use as a medicament.

In embodiment 19, the invention provides a compound according to any one of embodiments 1 to 10 or a pharmaceutically acceptable salt thereof, for use in the treatment of a disorder or disease is a cancer.

In embodiment 20, the invention provides a compound according to any one of embodiments 1 to 10 or a pharmaceutically acceptable salt thereof, for use in the treatment of a disorder or disease selected from adrenocortical carcinoma, breast cancer, clear cell renal cell carcinoma (ccRCC), colorectal cancer, germ cell tumor, glioblastoma multiforme (GBM), glioma, head and neck cancer, hepatocellular carcinoma, kidney cancer, lung cancer, malignant glioma, ocular cancer, pancreatic cancer, paraganglioma, pheochromocytoma, prostate cancer, and renal cell carcinoma.

In embodiment 21, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate characterized by having a powder X-ray diffractogram comprising reflections at 2-Theta angles of (24.9±0.2)°, (6.2±0.2)° and (20.9±0.2)°, when measured at a temperature in the range of from 20 to 30° C. with Cu-Kalpha1,2 radiation having a wavelength of 0.15406 nm.

In embodiment 22, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate characterized by having a powder X-ray diffractogram comprising reflections at 2-Theta angles of (24.9±0.2)°, (6.2±0.2)°, (20.9±0.2)°, (10.9±0.2)° and (18.5±0.2)°, when measured at a temperature in the range of from 20 to 30° C. with Cu-Kalpha1,2 radiation having a wavelength of 0.15406 nm.

In embodiment 23, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate characterized by having a powder X-ray diffractogram comprising reflections at 2-Theta angles of (24.9±0.2)°, (6.2±0.2)°, (20.9±0.2)°, (10.9±0.2)°, (18.5±0.2)°, (22.8±0.2)°, (12.9±0.2)° and (16.1±0.2)°, when measured at a temperature in the range of from 20 to 30° C. with Cu-Kalpha1,2 radiation having a wavelength of 0.15406 nm.

In embodiment 24, the invention provides a crystalline form according to any one of embodiments 21-23 characterized by having a thermogravimetric analysis curve showing a mass loss of not more than 0.4 weight % based on the weight of the crystalline form, when heated from 10 to 250° C. at a rate of 10 K/min.

In embodiment 25, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form characterized by having a powder X-ray diffractogram comprising reflections at 2-Theta angles of (9.7±0.2)°, (18.4±0.2)° and (19.4±0.2)°, when measured at a temperature in the range of from 20 to 30° C. with Cu-Kalpha1,2 radiation having a wavelength of 0.15406 nm.

In embodiment 26, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form characterized by having a powder X-ray diffractogram comprising reflections at 2-Theta angles of (9.7±0.2)°, (18.4±0.2)°, (19.4±0.2)°, (13.4±0.2)° and (20.7±0.2)°, when measured at a temperature in the range of from 20 to 30° C. with Cu-Kalpha1,2 radiation having a wavelength of 0.15406 nm.

In embodiment 27, the invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form characterized by having a powder X-ray diffractogram comprising reflections at 2-Theta angles of (9.7±0.2)°, (18.4±0.2)°, (19.4±0.2)°, (13.4±0.2)°, (20.7±0.2)°, (24.2±0.2)°, (22.1±0.2)° and (10.3±0.2)°, when measured at a temperature in the range of from 20 to 30° C. with Cu-Kalpha1,2 radiation having a wavelength of 0.15406 nm.

In embodiment 28, the invention provides a crystalline form according to any one of embodiments 25-27 characterized by having a thermogravimetric analysis curve showing a mass loss of not more than 0.2 weight % based on the weight of the crystalline form, when heated from 10 to 250° C. at a rate of 10 K/min.

In embodiment 29, the invention provides a compound according to any one of embodiments 21 to 28 or a pharmaceutically acceptable salt thereof, for use as a medicament.

In embodiment 30, the invention provides a compound according to embodiment 29 or a pharmaceutically acceptable salt thereof, for use in the treatment of a disorder or disease is a cancer.

In embodiment 31, the invention provides a compound according to embodiment 30 or a pharmaceutically acceptable salt thereof, for use in the treatment of a disorder or disease selected from adrenocortical carcinoma, breast cancer, clear cell renal cell carcinoma (ccRCC), colorectal cancer, germ cell tumor, glioblastoma multiforme (GBM), glioma, head and neck cancer, hepatocellular carcinoma, kidney cancer, lung cancer, malignant glioma, ocular cancer, pancreatic cancer, paraganglioma, pheochromocytoma, prostate cancer, and renal cell carcinoma.

In embodiment 32, the invention provides a process for producing the compound of formula (I)

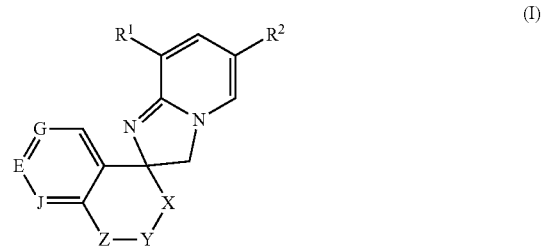

or a pharmaceutically acceptable salt thereof,
comprising the step of reacting the compound of formula (IV),

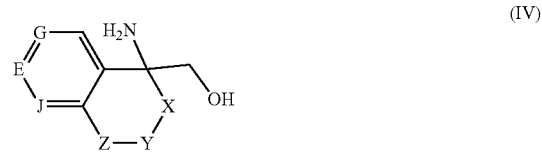

or a salt, solvate, stereoisomer, complex, co-crystal, ester, or oxazoline thereof, and the compound of formula (II),

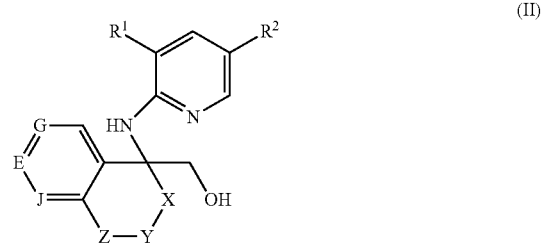

or a salt, solvate, stereoisomer, complex, co-crystal, ester, or oxazoline thereof, with a compound of formula (III)

or a salt, solvate, stereoisomer, complex, co-crystal, ester, or oxazoline thereof, wherein
$R^1$ is F, Cl, Br, $OCH_3$, $OCH_2F$, $OCHF_2$ or $OCF_3$;
$R^2$ is F, Cl, $CF_3$ or CN;
X is $(CH_2)_{1-2}$, CHF, CHD, $CD_2$ or $CF_2$;
Y is $(CH_2)_{0-2}$, CHF, CHD, $CD_2$, O, S, $OCH_2$ or $CF_2$;
Z is $CH_2$, $CD_2$, CHF, CDF, $CF_2$, CH(OH), CO, $CH(CH_3)$, O or S,
wherein, when Y is O, $OCH_2$, or S, then Z is $CH_2$;
wherein, when Z is O, S, or $NCH_3$, then Y is $(CH_2)_{0-2}$, or $CF_2$;

wherein, when Z is CH(OH), then Y is CHF or $CF_2$;
J is $CR^J$;
   wherein $R^J$ is H, F, Cl, Br, $CH_3$, $CD_3$, $CF_3$, $CHF_2$, $CDF_2$, $OCH_3$ or CN;
E is $CR^E$ or N;
   wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD_3)F_2$, $CF_3$, cyclopropyl, $OCH_3$, $OCH_2CH_2OH$, $OCF_3$, $SCH_3$, $SCHF_2$,
G is CH or N; and
LG is a leaving group selected from F, Cl, or Br;
   optionally in the presence of base selected from $K_2CO_3$ or $Et_3N$,
to obtain the compound of formula (1) or a pharmaceutically acceptable salt thereof.

In embodiment 33, the invention provides a process according to embodiment 32, wherein the compound of formula (II) is cyclised with reagents selected from $SOCl_2$ in toluene, toluene sulfonyl chloride, or methanesulfonyl chloride, in the presence of a base selected from pyridine or $Et_3N$ to give a compound of formula (I).

Definitions

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. Accordingly, it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagents in place of the non-labeled reagent previously employed.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the present invention that, when administered to a subject, is effective to (1) at least partially alleviate, prevent and/or ameliorate a condition, or a disorder or a disease (i) mediated by HIF2α, or (ii) associated with HIF2α activity, or (iii) characterized by activity (normal or abnormal) of HIF2α; or (2) reduce or inhibit the activity of HIF2α; or (3) reduce or inhibit the expression of HIF2α. In another embodiment, the term "a therapeutically effective amount" refers to the amount of the compound of the present invention that, when administered to a cell, or a tissue, or a non-cellular biological material, or a medium, is effective to at least partially reducing or inhibiting the activity of HIF2α; or at least partially reducing or inhibiting the expression of HIF2α.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

The stereochemistry of the spirocyclic center has been assigned by single-crystal X-ray structural analysis for a subset of the Examples either alone, or bound within the PAS-B domain of HIF2α, or from the Intermediates used to prepare the Examples. The stereochemistry of the remaining Examples has been assigned by analogy based upon their HIF2α affinities: eg the IC$_{50}$ determined in the Hif2α SPA assay for Example 44 was found to be greater than 700-fold lower than for the corresponding enantiomer (R)-8'-(difluoromethoxy)-6',7-bis(trifluoromethyl)-3'H-spiro[chroman-4, 2'-imidazo[1,2-a]pyridine] (HIF2α SPA IC$_{50}$>10000 nM).

General Conditions:

Typically, the compounds of formula (I) can be prepared according to the schemes provided infra.

The schemes provided infra are intended to represent single diastereoisomers/enantiomers as well as their isomeric mixtures. Separation of diastereoisomers/enantiomers may be performed according to techniques described herein.

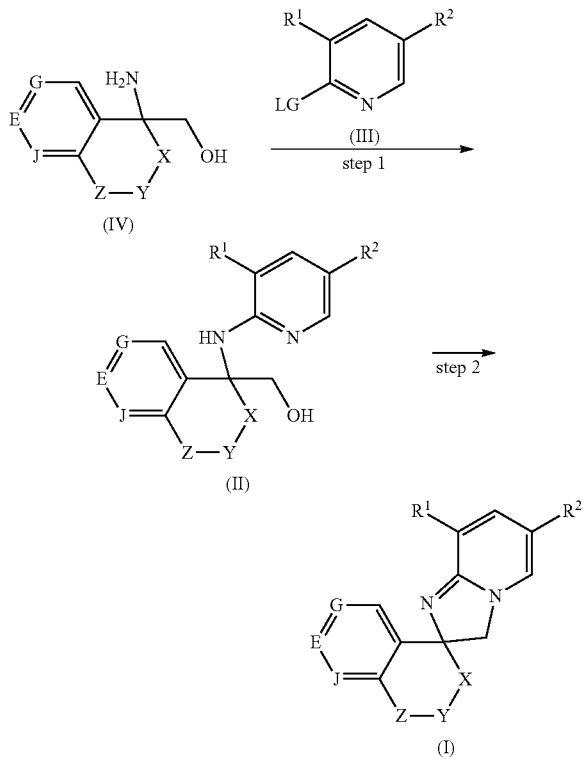

Scheme 1: General synthesis of compounds of formula (I)

Step 1:

The compound of formula (IV) is arylated with a pyridine of formula (III), where LG is a leaving group, to give a compound of formula (II). The arylation reaction can be a nucleophilic aromatic substitution reaction where the LG is a group such as fluoro, chloro or bromo, and the reaction maybe carried out in the presence of a base, such as $K_2CO_3$ or $Et_3N$, with heating. Alternatively, the reaction can be a transition metal catalysed coupling reaction, for example a Buchwald reaction, or an Ullmann-type amination reaction where the LG is a group such as chloro, bromo or iodo, using for example a Pd catalyst, or a Cu catalyst, such as CuI, CuBr, or copper(I) thiophene-2-carboxylate, in the presence of a base, such as KOtBu, or $K_3PO_4$.

Step 2:

The compound of formula (II) is cyclised to give a compound of formula (I). The alcohol group can be activated to become a leaving group by heating with reagents such as $SOCl_2$ in toluene, or with toluene sulfonyl chloride, or methanesulfonyl chloride, in the presence of a base, such as pyridine or $Et_3N$, with, or without heating.

In some instances both step 1 and step 2 can be carried out in a one-pot reaction by performing step 1 with two or more equivalents the pyridine (III), in a reaction in which the alcohol is also arylated by the pyridine to provide the leaving group for the cyclisation reaction.

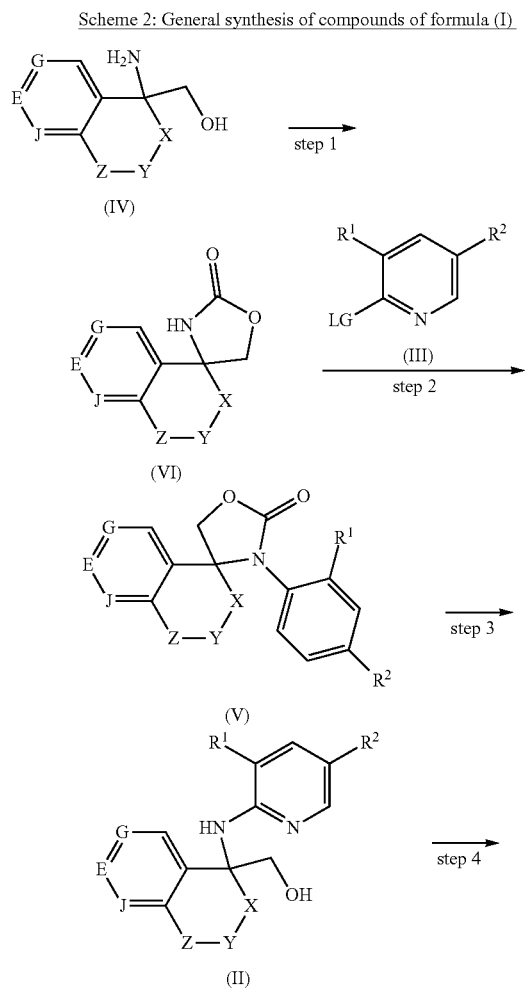

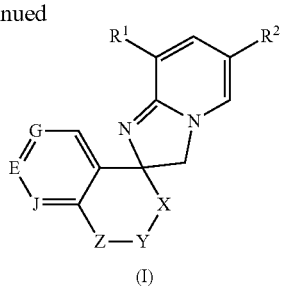

(I)

Step 1:

In some instances the arylation reaction is carried out with the amino alcohol protected. A suitable protected form of the amino alcohol (IV) is the oxazolidinone (VI) which be prepared by reaction with phosgene, or a phosgene equivalent, such as carbonyl diimidazole, or triphosgene, and the reaction maybe carried out in the presence of a base.

Step 2:

The compound of formula (VI) is arylated with a pyridine (III), where LG is a leaving group, to give a compound of formula (II). The arylation reaction can be a transition metal catalysed coupling reaction, using for example a Pd catalyst in the presence of a base, such as KOtBu. Alternatively, the arylation reaction can be an Ullmann-type amination reaction, using for example a Cu catalyst, such as CuI, CuBr, or copper(I) thiophene-2-carboxylate, in the presence of a base, such as KOtBu, or $K_3PO_4$.

Step 3: The oxazolidinone of formula (V) is deprotected in a hydrolysis reaction to give the amino alcohol of formula (II) in aqueous acid, or base, such as NaOH in EtOH, $Cs_2CO_3$ in MeOH, such hydrolysis reactions can be carried out in the presence of an additional solvent, such as THF.

Step 4:

The cyclisation reaction can be carried out in an analogous manner to that described for step 2 of scheme 1.

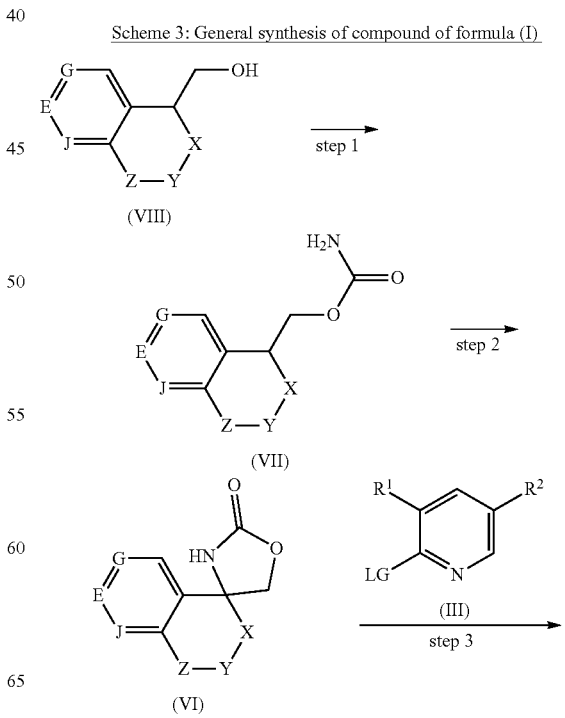

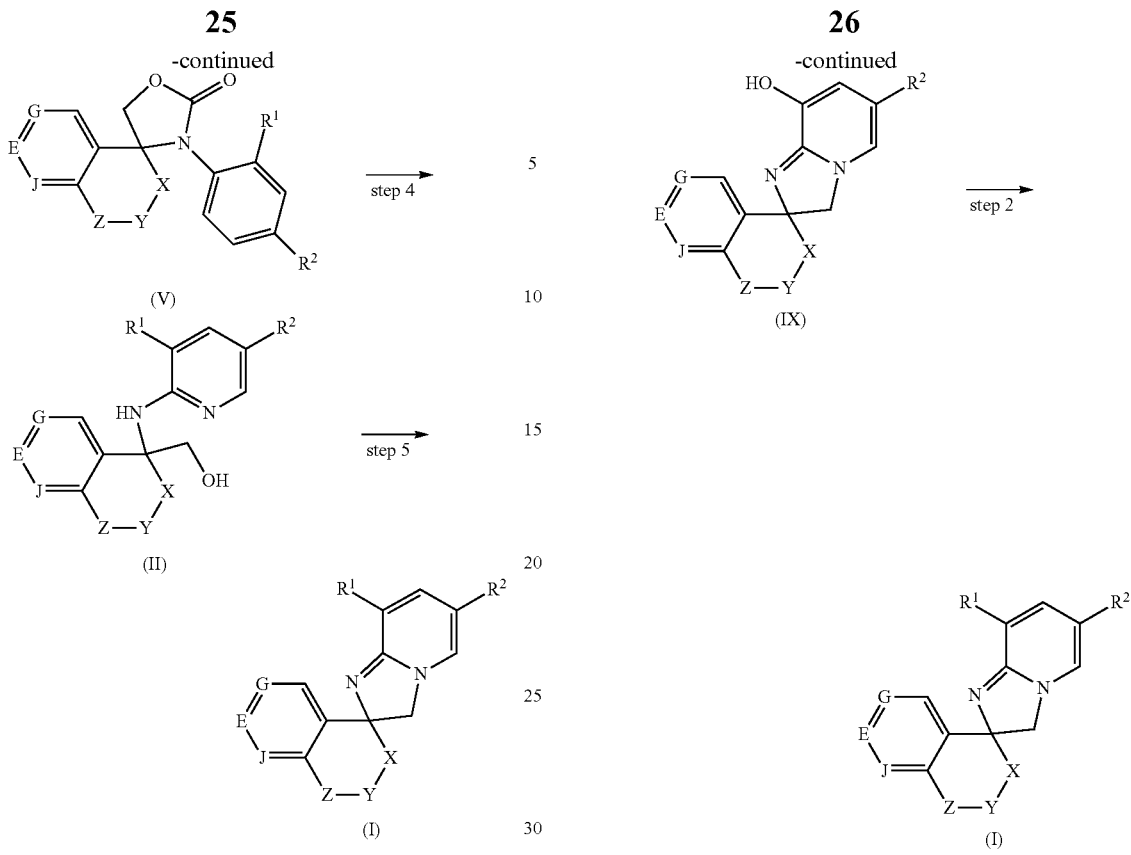

Step 1:

The alcohol of formula (VIII) is converted to the carbamate of formula (VII) in an acylation reaction. The reaction can be carried out with an acylating agent, such as trichloroacetyl isocyanate, which is then hydrolysed in a second step under basic conditions, such as $K_2CO_3$ in MeOH, or NaOH in aqueous EtOH.

Step 2:

The carbamate of formula (VII) is cyclised to the oxazolidinone of the formula (VI) in a nitrene insertion reaction. The niterene intermediate can be formed by an oxidative process, using an oxidant such as iodosobenzene diacetate, and stabilised to react in the insertion step through the addition of a catalyst, such $Rh_2(OAc)_4$, $Rh_2[OC(O)Ph]_4$, $Rh_2(esp)_2$, and with an additive, such as MgO.

Steps 3-5:

The conversion of the oxazolidinone (VI) to compounds of formula (I) can be carried out in an analogous manner to that described for the equivalent steps of scheme 2.

Step 1:

Compounds of formula (I), where $R^1$ is F, Cl, or Br, can undergo a nucleophilic aromatic nucleophilic substitution reaction with a sodium or potassium alkoxide, to give intermediates where $R^1$ is an ether group that can be further deprotected to the corresponding phenols of formula (IX). When the alkoxide is derived from 2-(methylsulfonyl)ethanol and NaH in DMF the ether is deprotected in situ to give directly compounds of formula (IX).

Step 2:

The phenol group of compounds of formula (IX) can be alkylated to give compounds of the formula (I), where $R^1$ is $OCH_2F$, $OCHF_2$. The alkylation reaction can be carried out with reagents such as bromodifluoromethyl)trimethylsilane and KOH, or dibromodifluoromethane and NaH, followed by $AgBF_4$ in DCM.

Compounds of formula (I), where $R^1$ is OMe can be obtained directly by reaction of a compound of formula (I), where $R^1$ is F, Cl, or Br, with MeOH and NaOtBu.

Scheme 4: General synthesis of compounds of formula (I)

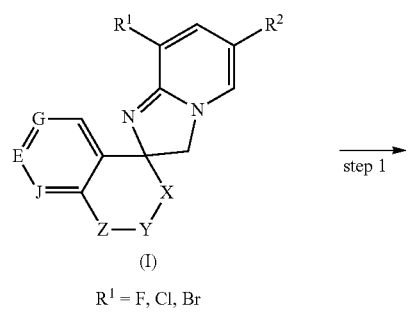

Scheme 5: General synthesis of compounds of formula (I)

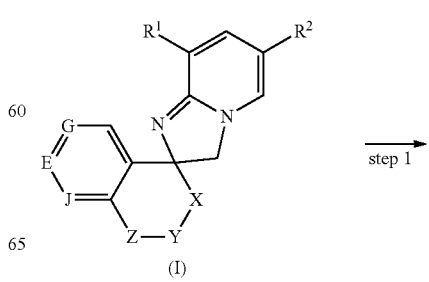

-continued

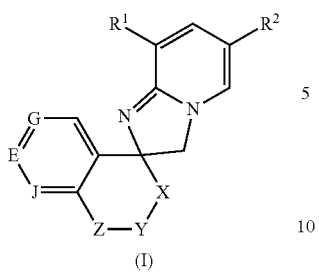

(I)

Step 1:

Compounds of formula (I), where E or J are CR$^J$ or CR$^E$ wherein R$^J$ and R$^E$ are independently Cl, Br, or I and can be converted with transition metal catalysed coupling reactions into compounds of formula (I), where R$^J$ or R$^E$ are Cl, H, CN, Me, d$_3$-Me, SCF$_3$, CHF$_2$, CF$_2$Me, MeO. The transition metal catalysed coupling reaction can be an ether formation, such as with tButylBrettPhos-Pd-G3, NaOtBu and MeOH in 1,4-dioxane, a thiol formation, such as with 2-ethylhexyl 3-mercaptopropanoate, Pd$_2$(dba)$_3$, xantphos, and iPr$_2$NEt in 1,4-dioxane, the free thiol is then formed in a reaction with NaOEt in EtOH, a difluoromethylation reaction, such as with 2,2-difluoro-1-phenylethanone, Pd(dba)$_2$, SPhos, and Cs$_2$CO$_3$ in toluene, the intermediate is then deacylated with reagents such as aqueous KOH in toluene, a thiomethylation, such as with DMSO, CuI and DABCO, a hydrogenation reaction, such as with a Pd on carbon catalyst with hydrogen in MeOH and THF, a cyanation reaction, such as with potassium hexacyanoferrate(II), XPhos, XPhos Pd G3 and KOAc in water and 1,4-dioxane, a trifluoromethylation reaction, such as with diphenyl(trifluoromethyl)sulfonium trifluoromethanesulfonate and Cu powder in DMF, a borylation reaction, such as with bis(pinacolato)diboron, PdCl$_2$(dppf).CH$_2$Cl$_2$ adduct and KOAc in 1,4-dioxane, the boronic esters can then be further converted to the corresponding chloro derivatives by treatment with reagents such as CuCl$_2$ in MeOH and water.

The products of the transition metal catalysed coupling reaction of formula (I) can be converted to further derivatives of the formula (I) using reactions such as triflouromethylation to convert a thiol into a trifluoromethylthiol using diethyl (bromodifluoromethyl)phosphonate and KOH in AcCN.

Scheme 6: General synthesis of compounds of formula (I)

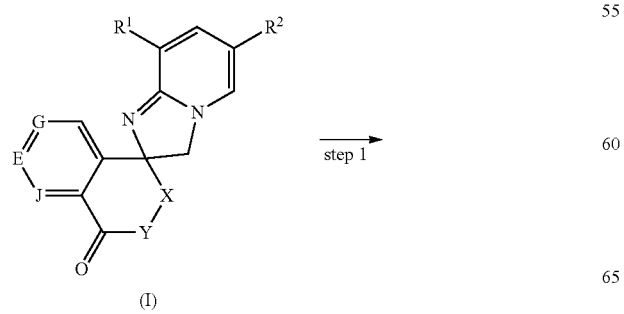

(I)

step 1

-continued

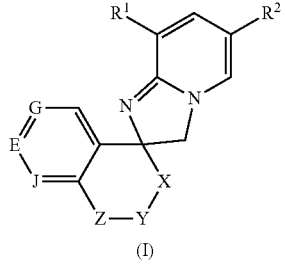

(I)

Step 1:

Compounds of formula (I), where Z=C=O, can be converted to compounds of formula (I), where Z=C=O and Y=CHF, using a fluorination reaction, such as reacting a silyl enol ether intermediate with Selectfluor in AcCN, the silyl enol ether intermediate can be prepared from a compound of formula (I), where Z=C=O, by a silylation reaction, such as with tert-butyldimethylsilyl trifluoromethanesulfonate, and Et$_3$N in DCM, the sequence can be repeated to give compounds of the formula (I) where Z=C=O and Y=CF$_2$, where Z=CH(OH), using a reduction reaction, such as with NaBH$_4$ in EtOH, the alcohol can be further converted to compounds of formula (I), where Z=CHF, using a fluorination reaction, such as with DAST in DCM.

Compounds of formula (I), where Z=C=O, can be prepared by the oxidation of compounds of formula (I), where Z=CH$_2$, by oxidation, such as with oxygen, N-hydroxyphthalimide and iron(III) nitrate in AcCN, or from compounds of formula (I), where Z=a thioketal by a deprotection reaction, such as with N-bromosuccinimide in aqueous acetone.

Scheme 7: General synthesis of compounds of formula (I)

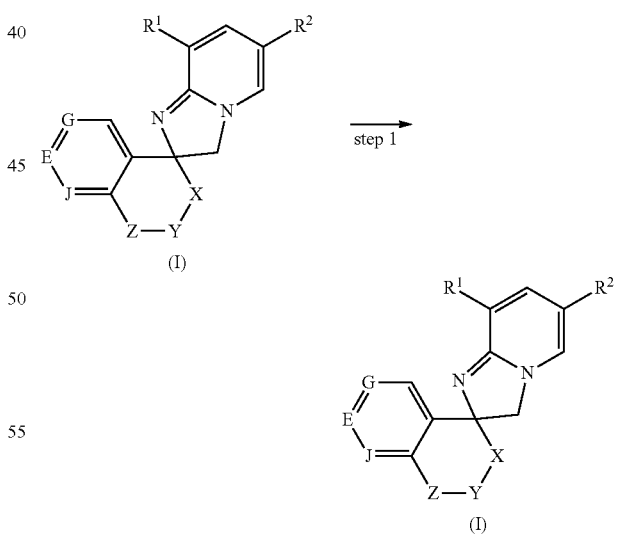

Step 1:

Compounds of formula (I), where CR$^J$ or CR$^E$ are Br or I can be converted by a lithiation reaction and addition of the resulting organo lithium intermediate to a carbonyl compound followed by a fluorination reaction into compounds of formula (I), where CR$^J$ or CR$^E$ are CHF$_2$, such as with nBuLi in THF followed by the addition of DMF, the formylated intermediate is then fluorinated in a fluorination reaction, such as with DAST in DCM.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Method of Use of the Invention

The compounds of any one of formulae (I) and (Ia) in free form or in pharmaceutically acceptable salt form, exhibit valuable pharmacological properties, e.g. inhibiting or modulating HIF2α, e.g. as indicated in in vitro and in vivo tests as provided in the next sections, and are therefore indicated for therapy or for use as research chemicals, e.g. as tool compounds.

Compounds of the invention may be useful in the treatment or prevention of cancer, wherein the cancer is selected from adrenocortical carcinoma, breast cancer, clear cell renal cell carcinoma (ccRCC), colorectal cancer (may include colon cancer), germ cell tumor (e.g. cranial and extracranial germ cell tumor, gonadal and extragonadal germ cell tumor), glioblastoma multiforme (GBM), glioma, head and neck cancer (may include lip, oral cavity, mouth cancer), hepatocellular carcinoma, kidney cancer, lung cancer, malignant glioma, ocular cancer, pancreatic cancer, paraganglioma, pheochromocytoma, prostate cancer, and renal cell carcinoma.

Thus, as a further aspect, the present invention provides the use of a compound of formula (I) or (Ia), or a compound according to any of the preceding embodiments or a pharmaceutically acceptable salt thereof, in therapy. In a further embodiment, the therapy is selected from a disease, which may be treated by inhibiting or modulating HIF2α. In another embodiment, the disease is selected from adrenocortical carcinoma, breast cancer, clear cell renal cell carcinoma (ccRCC), colorectal cancer (may include colon cancer), germ cell tumor (e.g. cranial and extracranial germ cell tumor, gonadal and extragonadal germ cell tumor), glioblastoma multiforme (GBM), glioma, head and neck cancer (may include lip, oral cavity, mouth cancer), hepatocellular carcinoma, kidney cancer, lung cancer, malignant glioma, ocular cancer, pancreatic cancer, paraganglioma, pheochromocytoma, prostate cancer, and renal cell carcinoma.

Thus, as a further aspect, the present invention provides a compound of any one of formulae (I) or (Ia), or a compound according to any one of the preceding embodiments, or a pharmaceutically acceptable salt thereof, for use in therapy. In a further embodiment, the therapy is selected from a disease, which may be treated by inhibiting or modulating HIF2α. In another embodiment, the disease is selected from the afore-mentioned list, suitably from cancer, in particular.

Thus, as a further aspect, the present invention provides the use of a compound of any one of formulae (I) or (Ia), or a compound according to any one of the preceding embodiment, or a pharmaceutically acceptable salt thereof, for the manufacture of a medicament. In a further embodiment, the medicament is for treatment, or prevention of a disease, which may be treated by inhibiting or modulating HIF2α. In another embodiment, the disease is selected from the afore-mentioned list, suitably from cancer in particular.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable using in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g.

powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g. tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before, or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) or (Ia), or a compound according to any one of the preceding embodiments, or a pharmaceutically acceptable salt thereof, and at least one other therapeutic agent as a combined preparation for simultaneous, separate or sequential use in therapy.

In one embodiment, the therapy is the treatment, or prevention of a disease or condition mediated by inhibiting or modulating HIF2α. Products provided as a combined preparation include a composition comprising the compound of any one of formulae (I) or (Ia), or a pharmaceutically acceptable salt thereof, and the other therapeutic agent(s) together in the same pharmaceutical composition, or the compound of any one of formulae (I) or (Ia), or a pharmaceutically acceptable salt thereof, and the other therapeutic agent(s) in separate form, e.g. in the form of a kit.

In one embodiment, the invention provides a pharmaceutical combination comprising a compound of any one of formulae (I) or (Ia), or a compound according to any one of the preceding embodiments, or a pharmaceutically acceptable salt thereof, and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any one of formulae (I) or (Ia), or a compound according to any one of the preceding embodiments, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formulae (I) or (Ia), or a compound according to any one of the preceding embodiments, or a pharmaceutically acceptable salt thereof, for treating, or preventing a disease or condition mediated by inhibiting or modulating HIF2α, wherein the medicament is prepared for administration with another therapeutic agent. The invention also provides the use of another therapeutic agent for treating, or preventing a disease or condition mediated by inhibiting or modulating HIF2α wherein the medicament is administered with a compound of any one of formulae (I) or (Ia), or a pharmaceutically acceptable salt thereof.

The invention also provides a compound of any one of formulae (I) or (Ia), or a compound according to any one of the preceding embodiments, or a pharmaceutically acceptable salt thereof, for use in a method of treating, or preventing a disease or condition mediated by inhibiting or modulating HIF2α, wherein the compound of formula (I) or (Ia), or a compound according to any one of the preceding embodiments, or a pharmaceutically acceptable salt thereof, is prepared for administration with another therapeutic agent. The invention also provides another therapeutic agent for use in a method of treating, or preventing a disease or condition mediated by inhibiting or modulating HIF2α, wherein the other therapeutic agent is prepared for administration with a compound of formula (I) or (Ia), or a compound according to any one of the preceding embodiments, or a pharmaceutically acceptable salt thereof. The invention also provides a compound of formula (I) or (Ia), or a compound according to any one of the preceding embodiments, or a pharmaceutically acceptable salt thereof, for use in a method of treating, or preventing a disease or condition mediated by inhibiting or modulating HIF2α, wherein the compound of formula (I) or (Ia), or a compound according to any one of the preceding embodiments, or a pharmaceutically acceptable salt thereof, is administered with another therapeutic agent. The invention also provides another therapeutic agent for use in a method of treating, or preventing a disease or condition mediated by inhibiting or modulating HIF2α, wherein the other therapeutic agent is administered with a compound of formula (I) or (Ia), or a compound according to any one of the preceding embodiments or a pharmaceutically acceptable salt thereof.

Mass spectra were acquired on LC-MS, SFC-MS, or GC-MS systems using electrospray, chemical and electron impact ionization methods with a range of instruments of the following configurations: Waters Acquity UPLC with Waters SQ detector, [M+H]$^+$ refers to the protonated molecular ion of the chemical species, and [M−H]$^-$ refers to the deprotonated molecular ion of the chemical species.

NMR spectra were run with Bruker Ultrashield™400 (400 MHz) and Bruker Ultrashield™600 (600 MHz) spectrometers, both with and without tetramethylsilane as an internal standard. Chemical shifts (δ-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses.

Celite: Celite® (the Celite corporation)=filtering aid based on diatomaceous earth Phase separator: Biotage Isolute phase separator (Part number: 120-1908-F for 70 mL and part number: 120-1909-J for 150 mL)

Instrumentation

Microwave: All microwave reactions were conducted in a Biotage Initiator, irradiating at 0-400 W from a magnetron at 2.45 GHz with Robot Eight/Robot Sixty processing capacity, unless otherwise stated.

UPLC-MS Methods: Using Waters Acquity UPLC with Waters SQ detector.

General

| Column | Acquity HSS T3, 1.8 µm, 2.1 × 50 mm, |
| Column Temperature | 60° C. |
| Eluents | A: water + 0.05% formic acid + 3.75 mM ammonium acetate (pH 3.8), B: acetonitrile + 0.04% formic acid |
| Flow Rate | 1.0 mL/min |

Methods

| | Initial | Gradient | Hold/Plateau |
| --- | --- | --- | --- |
| UPLC-MS 1 | 5% B | 5% to 98% B in 1.40 min | 98% B for 0.40 min |
| UPLC-MS 2 | 5% B | 5% to 98% B in 1.40 min | 98% B for 0.40 min |
| UPLC-MS 3 | 1% B | 1% to 98% B in 1.40 min | 98% B for 0.40 min |
| UPLC-MS 4 | 5% B | 5% to 98% B in 9.40 min | 98% B for 0.40 min |
| UPLC-MS 5 | 5% B | 5% to 98% B in 2.40 min | 98% B for 0.40 min |

UPLC-MS 6

| Column | Acquity HSS T3, 1.8 µm, 2.1 × 100 mm |
| Column Temperature | 60° C. |
| Eluents | A: water + 0.05% formic acid + 3.75 mM ammonium acetate (pH 3.8), B: acetonitrile + 0.04% formic acid |
| Gradient | 5% to 98% B in 9.4 min |
| Flow Rate | 0.8 mL/min |

UPLC-MS 7

| Column | Acquity UPLC BEH C18, 1.7 µm, 2.1 × 50 mm |
| Column Temperature | 80° C. |
| Eluents | A: water + 0.05% formic acid + 3.75 mM ammonium acetate, B: iPrOH + 0.05% formic acid |
| Gradient | 5% to 98% B in 1.7 min |
| Flow Rate | 0.6 mL/min |

Chiral HPLC/SFC Methods:
C-HPLC 1
Instrument: Agilent 1200 HPLC system
Injection: 10 µL
Mobile phase: heptane:EtOH:[MeOH+0.05% Et$_2$NH] 80:10:10
Flow rate: 1 mL/min
Column: Chiralcel OZ-I 20 µm 4.6×250 mm
Detection UV: 220, or 260 nm
C-HPLC 7
Instrument: Agilent 1200 HPLC system
Injection: 10 µL
Mobile phase: heptane:TBME:EtOH+0.05% Et$_2$NH 80:10:10
Flow rate: 1 mL/min
Column: Chiralcel ID 5 µm 4.6×250 mm
Detection UV: 230 nm
C-SFC 8
Instrument: Water UPC2 analytical SFC
Mobile phase: CO$_2$:MeOH with 0.05% Et$_2$NH
Flow rate: 2.5 mL/min
Column: ChiralPak AD 3 µm 4.6×150 mm
Temperature: 35° C.
Back pressure: 100 bar
Detection UV: 220 nm
C-HPLC 9
Instrument: Agilent 1100 HPLC system
Injection: 5 µL
Mobile phase: heptane:DCM:MeOH 80:10:10
Flow rate: 1 mL/min
Column: Chiralcel IC 5 µm 4.6×250 mm
Detection UV: 270 nm
C-SFC 10
Instrument: Water UPC$^2$ analytical SFC
Mobile phase: CO$_2$: [MeOH+0.05% Et$_2$NH]
Gradient: 5-40% B
Flow rate: 2.5 mL/min
Column: Chiralpak AD, 150×4.6 mm I.D., 3 µm, 35° C.

BPR: 100 bar
Detection UV: 220 nm
C-HPLC 12
Instrument: Agilent 1100 HPLC system
Injection: 10 μL
Mobile phase: heptane:MeOH:EtOH+0.1% Et$_2$NH 80:10:10
Flow rate: 1 mL/min
Column: Chiralcel AD-H 5 μm 4.6×250 mm
Detection UV: 220 nm
C-HPLC 15
Instrument: Agilent 1100 HPLC system
Injection: 10 μL
Mobile phase: heptane:iPrOH+0.05% Et$_2$NH 60:40
Flow rate: 1 mL/min
Column: Chiralpak IC 5 μm 4.6×250 mm
Detection UV: 280 nm
C-HPLC 16
Instrument: Agilent 1100 HPLC system
Injection: 10 μL
Mobile phase: heptane:MeOH:EtOH+0.1% Et$_2$NH 80:10:10
Flow rate: 1 mL/min
Column: Chiralcel AD-H 5 μm 4.6×250 mm
Detection UV: 230 nm
C-HPLC 17
Instrument: Shimadzu prominence HPLC system
Injection: 5 μL
Mobile phase: heptane:MeOH:EtOH:Et$_2$NH 90:5:5:0.1
Flow rate: 1 mL/min
Column: Chiralpak OZ-H 5 μm 4.6×250 mm
Detection UV: 225 nm
C-SFC 19
Instrument: Thar analytical SFC (SFC-A)
Mobile phase: CO$_2$:[MeOH+0.05% Et$_2$NH]
Gradient: 5-40% B
Flow rate: 2.4 mL/min
Column: Chiralpak AD, 150×4.6 mm I.D., 3 μm, 35° C.
BPR: 100 bar
Detection UV: 220 nm
C-SFC 20
Instrument: Water ACQUITY UPLC system
Mobile phase: CO$_2$:iPrOH with 0.1% Et$_2$NH
Flow rate: 2.5 mL/min
Column: Chiralpak IG 5 μm 4.6×100 mm
Temperature: 35° C.
Back pressure: 100 bar
Detection UV: DAD 190-400 nm
HPLC 22
Mobile phase: isocratic using solvents A: water 0.05% TFA, B: acetonitrile 0.05% TFA; gradient: 0 min 56% B; 13 min 56% B; 13.5 min 100% B; 21.5 min 100% B; 22 min 56% B; 254 nm
Flow rate: 1.0 mL/min
Column: Macherey+Nagel Nucleodur Sphinx RP 5 μm, 4.6×250 mm
Temperature: 30° C.
C-HPLC 28
Instrumentation: Shimadzu SCL-10A prominence HPLC system
Injection: 10 μL
Mobile phase: heptane:EtOH 80:20+0.1% Et$_2$NH, RT
Flow rate: 1 mL/min
Column: Chiralpak ID 5 μm 4.6×250 mm
Detection UV: 250 nm
C-HPLC 29
Instrumentation: Shimadzu Prominence HPLC system
Injection: 10 μL
Mobile phase: n-heptane:iPrOH+0.1% Et$_2$NH 90:10
Flow rate: 1 mL/min
Column: Chiralcel AD-H 5 μm 4.6×250 mm, RT
Detection UV: 230 nm
C-SFC 30
Instrumentation: Waters UPC$^2$ analytical SFC (SFC-H)
Column: Chiralpak AD, 150×4.6 mm I.D., 3 μm
Mobile phase: A for CO$_2$ and B for Ethanol+0.05% Et$_2$NH
Gradient: B 5-40%
Flow rate: 2.5 mL/min
Column temperature: 35° C.
Wavelength: 220 nm
C-HPLC 31
Instrumentation: Shimadzu Prominence HPLC system
Injection: 10 μL
Mobile phase: heptane:iPrOH+0.1% Et$_2$NH 80:20
Flow rate: 1 mL/min
Column: Chiralcel OD-H 5 μm 4.6×250 mm, RT
Detection UV: 250 nm
C-HPLC 33
Instrumentation: Gilson PLC2020 HPLC system
Mobile phase: heptane:EtOH+0.1% Et$_2$NH 80:20
Flow rate: 1 mL/min
Column: Chiralpak ID 5 μm 250×20 mm, 25° C.
Detection UV: 220 nm
C-HPLC 37
Instrument: Ultimate 3000
Injection: 0.5 μL
Mobile phase: heptane:EtOH+0.1% Et$_2$NH 70:30
Flow rate: 0.42 mL/min
Column: Chiralpak OJ-3 3 μm 3.0×100 mm, 30° C.
Detection UV: 265 nm
C-SFC 42
Instrumentation: Waters UPC$^2$ analytical SFC (SFC-H)
Mobile phase: CO$_2$: [EtOH+0.05% Et$_2$NH]
Gradient: 5-40% B
Flow rate: 2.5 mL/min
Column: Chiralpak IC 3 μm 150×4.6 mm, 35° C.
Detection UV: 220 nm
C-SFC 43
Instrumentation: Waters UPC$^2$ analytical SFC (SFC-H)
Mobile phase: CO$_2$: [MeOH+0.05% Et$_2$NH]
Gradient: 5-40% B
Flow rate: 2.5 mL/min
Column: Chiralpak IC 3 μm 150×4.6 mm, 35° C.
BPR: 100 bar
Detection UV: 220 nm
C-HPLC 44
Instrumentation: Agilent 1200 HPLC system
Injection: 10 μL
Mobile phase: heptane:EtOH:[MeOH+0.1% Et$_2$NH] 80:10:10
Flow rate: 1 mL/min
Column: Chiralpak AD 20 μm 4.6×250 mm, RT
Detection UV: 225 nm
C-HPLC 45
Instrumentation: Agilent 1200 DAD
Mobile phase: heptane:MeOH (+0.1% Et$_2$NH)
Eluent: isocratic 80:20
Flow rate: 1.0 mL/min
Column: Chiralpak AD-H
Detection UV: 220 nm
C-HPLC 47
Instrumentation: Agilent 1200 DAD Magellan system
Injection: 5 μL
Mobile phase: heptane:EtOH:MeOH+0.1% Et$_2$NH 90:5:5

Flow rate: 1 mL/min
Column: Chiralcel OD-H 5 μm 4.6×250 mm, RT
Detection UV: 225 nm
C-HPLC 49
Mobile phase: heptane:EtOH:MeOH
Eluent: isocratic 70:15:15
Flow rate: 1.0 mL/min
Column: Chiralpak IC
Detection UV: 225 nm
C-SFC 50
Mobile phase: $CO_2$:EtOH (1% $iPrNH_2$)
Gradient: 70:30 isocratic
Flow rate: 4 mL/min
Column: Chiralcel ID 4.6 μm 250×4.6 mm, 40° C.
Detection UV: 220 nm Preparative Methods:
Normal Phase Chromatography:
Normal phase chromatography was run on silica gel using prepacked columns, as detailed below, or using glass columns following standard flash chromatography methodology, unless otherwise stated.

| | |
|---|---|
| System 1 | Teledyne ISCO, CombiFlash Rf |
| System 2 | Biotage Isolera |
| Column | pre-packed RediSep Rf cartridges, or SNAP cartridges |
| Sample adsorption | onto Isolute, or on silica gel, or applied as solutions |

Supercritical Fluid Chromatography SFC 1:
Purifications were achieved on a Waters Preparative SFC-100-MS system with a Waters 2998 Photodiode Array Detector and a Waters MS Single Quadrupole Detector.

| Modifier | Methanol |
|---|---|
| Pressure | 120 bar |
| Column temperature | 40° C. |
| Flow rate | 100 g/min |

Reversed Phase HPLC:

| RP-HPLC 1 | |
|---|---|
| System | Gilson PLC 2020 |
| Column | Dr. Maisch Reprosil 100 C18 5 um; 250 × 30 mm |
| Column Temperature | RT |
| Eluents | A: water + 0.1% TFA, B: acetonitrile |
| RP-HPLC 2 | |
| System | Waters |
| Column | Waters Sunfire C18, OBD 5 um; 100 × 30 mm |
| Column Temperature | RT |
| Eluents | A: water + 0.1% TFA, B: acetonitrile |
| Flow rate | 40 mL/ min |
| Standard Gradient | 5 to 100% B in 20 min with a plateau at 100% for 1 min |
| RP-HPLC 3 | |
| System | Waters |
| Column | Waters X-Bridge C18, OBD 5 um; 100 × 30 mm |
| Column Temperature | RT |
| Eluents | A: water + 7.3 mM $NH_4OH$, B: acetonitrile + 7.3 mM $NH_4OH$ |
| Flow rate | 40 mL/ min |
| Standard Gradient | 5 to 100% B in 20 min with a plateau at 100% for 1 min |
| RP-HPLC 6 | |
| System | Macherey + Nagel Nucleodur Sphinx RP (5 μm, 10 × 250 mm) |
| Column Temperature | 20° C. |
| Eluents | isocratic using solvents A: water 0.1% TFA; B: acetonitrile 0.1% TFA; 0 min 57% B; 13 min 57% B; 13.5 min 100% B; 21 min 100% B; 21.5 min 57% B |
| Flow rate | 4.7 ml/min |
| Detection UV | 254 nm and 240 nm |

Solid samples: solids were analysed using the following instrumentation and methods.

| TGA method | |
|---|---|
| Instrument | TA Discovery/Q5000 |
| Temperature range | Equilibrate at 30° C.; Ramp 10° C./min to 300° C. |
| Scan rate | 10° C./min |
| Nitrogen flow | 20 mL/min |
| Sample mass | ~2 mg |
| DSC method | |
| Instrument | TA Q2000 |
| Temperature range | Equilibrate at 30° C.; Ramp 10° C./min to 300° C. |
| Scan rate | 10° C./min |
| Nitrogen flow | 50 mL/min |
| Sample mass | ~2 mg |
| XRPD method (CPP) | |
| Instrument | Bruker D8 Advance |
| Detector | VANTEC −500 (1D mode) |
| Radiation | CuKα (0.15406 nm) |
| X-ray generator power | 40 kV, 40 mA |
| Step size, resolution | 0.02 degrees |
| Scan range | 3° to 45° (2 theta value) |
| Scan time | 4.50 min |
| Source slit | primary slit: 0.6 mm, secondary slit: 5 mm, axial soller: 2.5° |
| DVS | |
| Instrument | Intrinsic/Advantage/SPS100n |
| Sample mass | 2-5 mg |
| Temperature | 25° C. |
| Method | 2 cycles, dm/dt = 0.005, from 50% RH to 90% RH, from 90% RH to 0% RH, from 0% RH to 90% RH, from 90% RH to 50% RH. |
| NMR | |
| Instrument | Bruker AVANCE III 400 MHZ |
| Probe | 5 mm PABBO BB-1H/D Z-GRD Z108618/0226 |
| Temperature | 295.7 K |
| Relaxation time | 1 second |
| Instrument | 600 MHz Brucker Ultrashield instrument |
| UPLC Method | |
| Instrument | Waters Acquity UPLC |
| Column Chemistry | ACQUITY UPLC BEH C18 |
| Column Manufacturer | Waters |
| Particle Size (um) | 1.7 |
| Dimensions (mm) | 2.1 × 100 |
| Column Temperature (° C.) | 30 |
| Flow Rate (mL/minute) | 0.50 |
| Injection Volume (uL) | 1 |
| Sample Solvent | Acetonitrile/Water (80:20) |
| Sample Concentration (μg/mL) | 300 |

| | |
|---|---|
| Wavelength(nm) | 248 |
| Mobile Phase A | 0.05% TFA in 95% Water/5% Acetonitrile |
| Mobile Phase B | 0.05% TFA in 95% Acetonitrile/5% Water |
| Run Time (minutes) | 12 |

| Gradient | % B | Minutes |
|---|---|---|
| | 5 | Initial |
| | 95 | 9.0 |
| | 95 | 10.0 |
| | 5 | 10.1 |
| | 5 | 12.0 |

Abbreviations

| Abbreviation | Description |
|---|---|
| AcCN | acetonitrile |
| aq | aqueous |
| Ar | argon |
| BPR | Back pressure |
| brine | Saturated aqueous Sodium chloride |
| cataCXium a Pd G3 | [(Di(1-adamantyl)-butylphosphine)-2-(2'-amino-1,1'-biphenyl)] palladium(II) methanesulfonate |
| (S,R,R)-Chenphos | 1-Dicyclohexylphosphino-1'-{(R)-{($R_P$)-2-[(S)-1-(dimethylamino)ethyl] ferrocenyl}phenylphosphino}ferrocene |
| conc | concentrated |
| C-Phos | 2-Dicyclohexylphosphino-2',6'-bis (N,N-dimethylamino)biphenyl |
| DAST | (Diethylamino)sulfur trifluoride |
| dba | Dibenzylideneacetone |
| DCM | Dichloromethane |
| DEA | Diethanolamine |
| DIPEA | N,N-Diisopropylethylamine, N-Ethyl-N-isopropylpropan-2-amine |
| DMA | N,N-Dimethylacetamide |
| DMAP | 4-Dimethylaminopyridine |
| DMF | N,N-Dimethylformamide |
| DMSO | dimethylsulfoxide |
| DMSO-$d_6$ | Hexadeuterodimethyl sulfoxide |
| dppf | 1,1'-bis(diphenylphosphino)ferrocene |
| DSC | Differential scanning calorimetry |
| ee | Enantiomeric excess |
| ESI-MS | Electrospray ionization mass spectroscopy |
| h, hr | hour |
| HPLC | High-performance liquid chromatography |
| IPA | 2-Propanol |
| IPAC | isopropyl acetate |
| L/mL | litre/millilitre |
| LDA | Lithium diisopropylamide |
| LC-MS | liquid chromatography and mass spectroscopy |
| LHMDS | Lithium hexamethyldisilazide |
| M | molar |
| min | minutes |
| mp | melting point |
| MTBE | methyl tert-butyl ether |
| MW, mw | microwave |
| m/z | mass to charge ratio |
| NaOtBu | Sodium tert-butoxide |
| NBS | N-Bromosuccinimide |
| ORTEP | Oak Ridge Thermal Ellipsoid Plot |
| n-BuLi | n-Butyllithium |
| NEt$_3$, Et$_3$N | Triethylamine |
| NMP | N-methylpyrrolidinone |
| NMR | Nuclear magnetic resonance |
| org | organic |
| Rh$_2$(esp)$_2$ | Bis[rhodium(α,α,α',α'-tetramethyl-1,3-benzenedipropionic acid)] |

| Abbreviation | Description |
|---|---|
| Rh(NBD)$_2$BF$_4$ | Bis(norbornadiene)rhodium(I) tetrafluoroborate |
| RM or rm | Reaction mixture |
| RP | Reversed phase |
| RPM | Revolutions per minute |
| RT | Room temperature |
| sat | saturated |
| SFC | Supercritical fluid chromatography |
| TBAF | Tetrabutylammonium fluoride |
| TBME | 2-Methoxy-2-methylpropane |
| TFA | Trifluoroacetic acid |
| THF | Tetrahydrofuran |
| TPGS-750-M | DL-α-Tocopherol methoxypolyethylene glycol succinate solution 2 wt % in H2O |
| Rt | Retention time (if not indicated, in minutes) |
| UPLC | Ultra-performance liquid chromatography |
| XRPD | X-Ray Powder Diffraction |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Preparation of Final Compounds

Example 1: (5)-5'-bromo-8-(difluoromethoxy)-4'-fluoro-6-(trifluoromethyl)-2',3'-dihydro-3H-spiro[imidazo[1,2-a]pyridine-2,1'-indene]

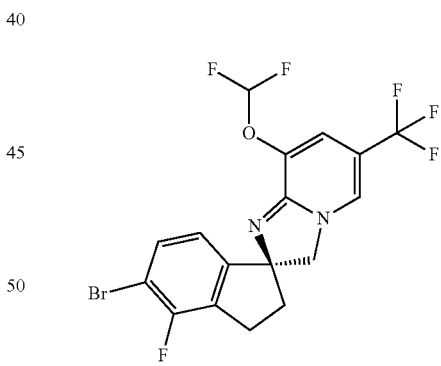

(S)-5'-bromo-8-(difluoromethoxy)-4'-fluoro-6-(trifluoromethyl)-2',3'-dihydro-3H-spiro[imidazo[1,2-a]pyridine-2,1'-indene] (Intermediate G, 12.5 g, 21.5 mmol) was dissolved in toluene (100 mL) in an Ar-flushed flask. SOCl$_2$ (9.89 mL, 135 mmol) in toluene (10 mL) was added dropwise and the RM was heated to 80° C. for 2 hr. The RM was partitioned between TBME (100 mL), EtOAc (100 mL), MeOH (100 mL) and saturated aq NaHCO$_3$(200 mL). The aq layer was extracted with EtOAc, the combined organic layers were then washed with brine, dried over Na$_2$SO$_4$ and evaporated. The crude product was adsorbed onto Isolute and purified by normal phase chromatography (2×120 g SiO$_2$-column; eluent hexane:[DCM:MeOH 5:1] 100:0 to 50:50), followed by reversed phase chromatography (RP-HPLC 1). Product containing fractions were combined and the AcCN removed by evaporation. The remaining predominantly aq solution was treated with solid NaHCO$_3$ until basic and then extracted 3× with DCM. Organic layers were combined, dried over Na$_2$SO$_4$, and evaporated to give the title compound as a yellow solid.

$^1$H NMR (400 MHz, DMSO-d$_6$) δ 7.97 (s, 1H), 7.57-7.12 (m, 2H), 7.07 (d, 1H), 6.98 (s, 1H), 4.27 (q, 2H), 3.06-2.88 (m, 2H), 2.29-2.19 (m, 2H).

LC-MS: Rt=0.91 min; MS m/z [M+H]$^+$ 453/455; UPLC-MS 1.

Example 2: (S)-8-(difluoromethoxy)-4',5'-difluoro-6-(trifluoromethyl)-2',3'-dihydro-3H-spiro[imidazo[1,2-a]pyridine-2,1'-indene]

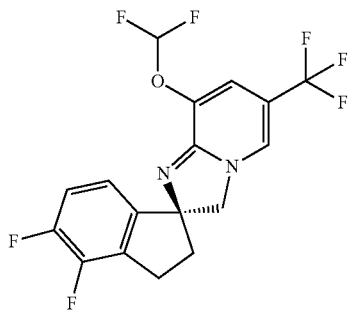 [SMILES: Fc1ccc2c(c1F)CC[C@@]21CN2C=C(C(F)(F)F)C=C(OC(F)F)C2=N1]

A mixture of (S)-(1-amino-4,5-difluoro-2,3-dihydro-1H-inden-1-yl)methanol (Intermediate K, 504 mg, 2.53 mmol), 2-chloro-3-(difluoromethoxy)-5-(trifluoromethyl)pyridine (Intermediate A, 1.38 g, 5.56 mmol), CuI (337 mg, 1.77 mmol), K$_3$PO$_4$ (1.01 g, 5.06 mmol) and DMF (1.8 mL) was heated in a microwave at 160° C. for 1 hr. The RM was cooled and additional CuI (337 mg, 1.77 mmol) added before heating for a further 1 hr at 160° C. Toluene (1.8 mL) and SOCl$_2$ (922 μL, 12.64 mmol) were added to the cooled RM which was then heated for 40 min at 80° C. The cooled RM was then diluted with EtOAc, the organic phase washed with saturated aq NaHCO$_3$ and brine, and the organic layer evaporated and maintained under high vacuum for 1 hr. The residue was then taken up into DCM and the organic phase washed with saturated aq NaHCO$_3$ and brine (phase separator cartridge), and then evaporated. Purification of the crude product by normal phase chromatography (25 g SiO$_2$ SNAP column, eluent hexane:EtOAc 100:0 to 75:25) followed by reversed phase chromatography (RP-HPLC 3, gradient: 30% to 70% B over 20 min) and crystallisation from MeOH gave the title compound as a yellow powder.

$^1$H NMR (400 MHz, MeOH-d$_4$) δ 7.81 (s, 1H), 7.00-7.08 (m, 1H), 6.97 (s, 1H), 6.67-7.24 (m, 2H), 4.22-4.45 (m, 2H), 3.08-3.19 (m, 1H), 2.88-3.05 (m, 1H), 2.23-2.51 (m, 2H).

LC-MS: Rt=0.71 min; MS m/z [M+H]$^+$ 393.0; UPLC-MS 1.

Example 3: (S)-8'-(difluoromethoxy)-3,6'-bis(trifluoromethyl)-5,6-dihydro-3'H-spiro[cyclopenta[c]pyridine-7,2'-imidazo[1,2-a]pyridine]

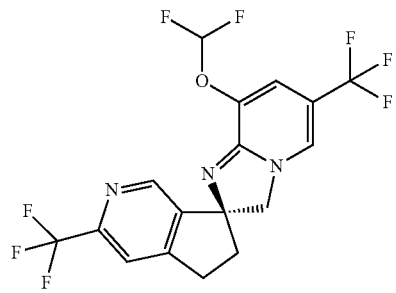 [SMILES: FC(F)OC1=CC(C(F)(F)F)=CN2C[C@@]3(CCc4cc(C(F)(F)F)ncc43)N=C12]

Into a 50 mL flask were charged (S)-3,6'-bis(trifluoromethyl)-5,6-dihydro-3'H-spiro[cyclopenta[c]pyridine-7,2'-imidazo[1,2-a]pyridin]-8'-ol (Intermediate M, 50 mg, 133 μmol), an aq solution of KOH (4.1 M, 114 μL, 466 μmol) and DCM (6 mL). The RM was cooled down to 0° C. using an ice bath and (bromodifluoromethyl)trimethylsilane (27 μL, 173 μmol) was added dropwise. The RM was stirred at 0° C. for 5 min, then quenched with water and extracted with ethyl acetate. The organic layer was successively washed with brine, dried over a phase separator and concentrated in vacuo. The crude mixture was purified by reverse phase chromatography (RP HPLC 3). The fractions containing the product were pooled and lyophilized to afford the title compound.

$^1$H-NMR (400 MHz, DMSO-d$_6$): δ 8.69 (s, 1H), 8.02 (s, 1H), 7.85 (s, 1H), 7.52-7.15 (t, 1H), 7.03 (s, 1H), 4.44-4.35 (q, 2H), 3.13-2.98 (m, 2H), 2.31-2.28 (t, 2H).

LC-MS: Rt=2.95 min; MS (m/z)=[M+H]$^+$ 426.2; UPLC-MS 4.

Example 4: (S)-5'-bromo-8-(difluoromethoxy)-4'-fluoro-2',3'-dihydro-3H-spiro[imidazo[1,2-a]pyridine-2,1'-indene]-6-carbonitrile

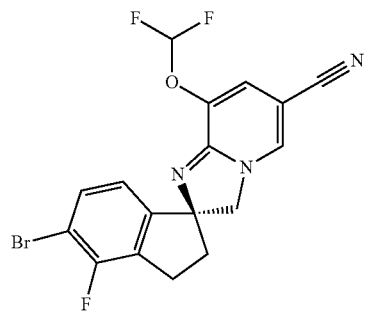 [SMILES: N#CC1=CN2C[C@@]3(CCc4c3ccc(Br)c4F)N=C2C(OC(F)F)=C1]

To a solution of (S)-(1-amino-5-bromo-4-fluoro-2,3-dihydro-1H-inden-1-yl)methanol (Intermediate J, 50.0 mg, 0.19 mmol) in DMF (1.80 mL) was added 6-chloro-5-(difluoromethoxy)nicotinonitrile (Intermediate B, 89.0 mg, 0.30 mmol), K$_3$PO$_4$ (81.0 mg, 0.38 mmol) and CuBr (8.19 mg, 0.06 mmol), and the RM was stirred for 2.5 hr at 120° C. in a microwave. The RM was partitioned between TBME and H$_2$O and the layers were separated. The aqueous layer was washed with TBME, the combined organic layers were then washed with brine, dried with Na$_2$SO$_4$, filtered and evaporated. The residue was dissolved in MeOH and purified by SFC (SFC 1). Product containing fractions were combined and evaporated to give the title compound as a yellow foam.

¹H NMR (600 MHz, DMSO-d₆) δ 8.21 (d, 1H), 7.58-7.53 (m, 1H), 7.32 (t, 1H), 7.11-7.05 (m, 2H), 4.36-4.25 (m, 2H), 3.07-2.92 (m, 2H), 2.34-2.22 (m, 2H).

LC-MS: Rt=0.76 min; MS m/z [M+H]⁺ 409.9/411.9; UPLC-MS 1.

Example 5: (5)-5'-bromo-4'-fluoro-8-(fluoromethoxy)-6-(trifluoromethyl)-2',3'-dihydro-3H-spiro[imidazo[1,2-a]pyridine-2,1'-indene]

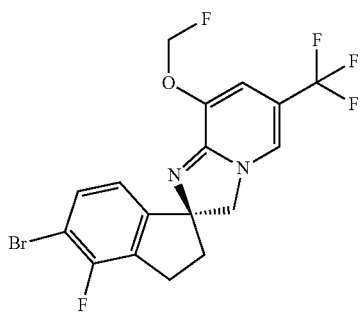 [SMILES: FCOC1=CC(C(F)(F)F)=CN2C[C@@]3(CCc4c3ccc(Br)c4F)N=C12]

A solution of (5)-5-bromo-4-fluoro-3'-(3-(fluoromethoxy)-5-(trifluoromethyl)pyridin-2-yl)-2,3-dihydrospiro[indene-1,4'-oxazolidin]-2'-one (Intermediate N, 40 mg, 62 µmol) in 4M aq NaOH (0.154 mL, 618 µmol) and EtOH (2 mL) was stirred for 20 min at 80° C. The cooled RM was diluted with EtOAc, and the organic layer washed with saturated aq NaHCO₃, the layers separated using a phase separator and concentrated. The residue was redissolved in toluene (2 mL) and SOCl₂ (6.76 µl, 0.093 mmol) was added, and the RM heated for 20 min at 80° C. After cooling the RM was quenched with MeOH, concentrated, partitioned between EtOAc and saturated aq NaHCO₃, the organic layer was dried and concentrated. The residue was purified by reversed phase chromatography (RP-HPLC 3) and the product containing fractions were combined and evaporated to give the title compound as a yellow solid.

¹H NMR (400 MHz, DMSO-d₆) δ 7.90 (s, 1H), 7.55 (t, 1H), 7.07 (d, 1H), 6.78 (s, br, 1H), 5.89 (d, 2H), 4.34-4.35 (m, 2H), 3.09-2.91 (m, 2H), 2.32-2.22 (m, 2H).

LC-MS: Rt=3.25 min; MS m/z [M+H]⁺ 435.1/437.1; UPLC-MS 4.

Example 6: (S)-8-(difluoromethoxy)-5',6-bis(trifluoromethyl)-2',3'-dihydro-3H-spiro[imidazo[1,2-a]pyridine-2,1'-indene]

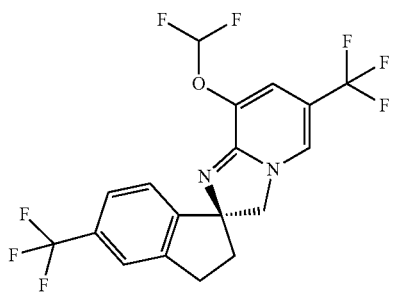 [SMILES: FC(F)OC1=CC(C(F)(F)F)=CN2C[C@@]3(CCc4cc(C(F)(F)F)ccc43)N=C12]

To a solution of (S)-5',6-bis(trifluoromethyl)-2',3'-dihydro-3H-spiro[imidazo[1,2-a]pyridine-2,1'-inden]-8-ol (Intermediate Q, 138 mg, 369 µmol) in DCM (1 mL), cooled with an ice bath, was added KOH (20% in water, 352 µL, 1.25 mmol) and (bromodifluoromethyl)trimethylsilane (82 mg, 396 µmol). The RM was stirred at 0° C. for 30 min, diluted with DCM, the organic phase washed with H₂O and then brine, separated by passing through a phase separator cartridge and concentrated. Purification by reversed phase chromatography (RP-HPLC 3) was followed by lyophilizing the product containing fractions, diluting with MeOH and evaporating to give the title compound as a yellow solid.

¹H NMR (400 MHz, MeOH-d₄) δ 7.82 (s, 1H), 7.49-7.66 (m, 2H), 7.43 (d, 1H), 6.99 (s, 1H), 6.95 (br t, 1H), 4.22-4.51 (m, 2H), 3.08-3.22 (m, 1H), 2.93-3.07 (m, 1H), 2.24-2.52 (m, 2H).

LC-MS: Rt=3.66 min; MS m/z [M+H]⁺ 424.2; UPLC-MS 4.

Example 7: (S)-6'-bromo-8-(difluoromethoxy)-5'-fluoro-6-(trifluoromethyl)-3',4'-dihydro-2'H,3H-spiro[imidazo[1,2-a]pyridine-2,1'-naphthalene]

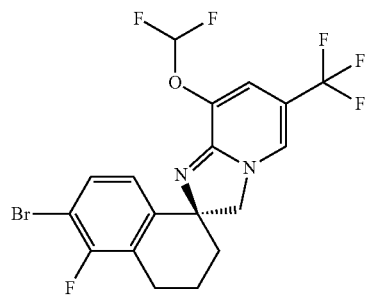

A mixture of (S)-(1-amino-6-bromo-5-fluoro-1,2,3,4-tetrahydronaphthalen-1-yl)methanol (Intermediate R, 1.0 g, 3.61 mmol), 2-chloro-3-(difluoromethoxy)-5-(trifluoromethyl)pyridine (Intermediate A, 1.81 g, 7.22 mmol), CuBr (264 mg, 1.81 mmol), K₃PO₄ (1.53 g, 7.22 mmol), and DMF (12 mL) was heated in a microwave at 140° C. for 7 hr under argon. The cooled RM was diluted with saturated aq NaHCO₃, and extracted with EtOAc. The combined organic layers were washed with brine, dried over Na₂SO₄, filtered and evaporated. The residue was absorbed onto Isolute and purified by normal phase chromatography (120 g SiO₂-column; eluent heptane:EtOAc 100:0 to 75:25). Product containing fractions were combined and evaporated to give a brown solid, which was dissolved in toluene (10.5 mL) and SOCl₂ (0.17 mL, 2.33 mmol) was added. The RM was heated to 70° C. for 45 min. The RM was quenched with saturated aq NaHCO₃, and extracted with EtOAc. The combined organic layers were washed with brine, dried over Na₂SO₄, and evaporated. The residue was absorbed onto Isolute and purified by normal phase chromatography (80 g SiO₂-column, eluent heptane:EtOAc 100:0 to 75:25). Product containing fractions were combined, evaporated and dried to give the title compound as a yellow solid.

¹H NMR (600 MHz, DMSO-d₆) δ 7.93 (s, 1H), 7.53-7.45 (m, 1H), 7.32 (d, 1H), 7.07 (d, 1H), 7.01 (s, 1H), 4.22 (d, 1H), 4.07 (d, 1H), 2.83-2.75 (m, 1H), 2.75-2.67 (m, 1H), 1.96 (s, 1H), 1.85 (dd, 2H), 1.72 (s, 1H).

LC-MS: Rt=0.87 min; MS m/z [M+H]⁺ 467.1/469.1; UPLC-MS 1.

Example 8: (S)-6'-bromo-8-(difluoromethoxy)-5'-fluoro-6-(trifluoromethyl)-2'H,3H-spiro[imidazo[1,2-a]pyridine-2,1'-naphthalen]-4'(3'H)-one

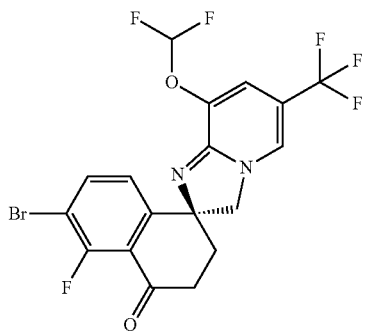 [SMILES: O=C1CC[C@@]2(CN3C=C(C(F)(F)F)C=C(OC(F)F)C3=N2)c2ccc(Br)c(F)c21]

Water (6 mL) was added to a solution of (S)-6'-bromo-8-(difluoromethoxy)-5'-fluoro-6-(trifluoromethyl)-2',3'-dihydro-3H,4'H-spiro[imidazo[1,2-a]pyridine-2,1'-naphthalen]-4'-one (Intermediate S, 2.66 g, 4.58 mmol) in acetone (60 mL) and the RM cooled to 0° C. NBS (6.52 g, 36.7 mmol) was added and the RM stirred at 0° C. for 5 min then quenched with saturated aq. sodium thiosulfate, then basified with saturated aq NaHCO₃ and extracted 2× with EtOAc. The combined organic layers were washed with brine, dried over Na₂SO₄ and evaporated. The residue was absorbed onto Isolute and purified by normal phase chromatography (80 g SiO₂-column, eluent DCM:MeOH 100:0 to 95:5). Product containing fractions were combined and evaporated to give the title compound as orange solid.

¹H NMR (600 MHz, DMSO-d₆) δ 8.03-7.88 (m, 2H), 7.54-7.23 (m, 2H), 7.07 (s, 1H), 4.44 (d, 1H), 4.18 (d, 1H), 2.77 (dtq, 2H), 2.24 (dtd, 2H).

LC-MS: Rt=0.76 min; MS m/z [M+H]⁺ 480.9/482.9; UPLC-MS 1.

Example 9: (1'S,3'R)-6'-bromo-8-(difluoromethoxy)-3',5'-difluoro-6-(trifluoromethyl)-2'H,3H-spiro[imidazo[1,2-a]pyridine-2,1'-naphthalen]-4'(3H')-one

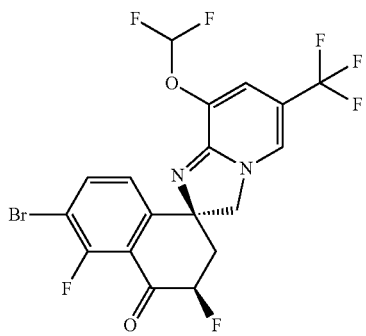 [SMILES: O=C1c2c(ccc(Br)c2F)[C@@]2(C[C@H]1F)CN1C=C(C(F)(F)F)C=C(OC(F)F)C1=N2]

(S)-6'-bromo-4'-((tert-butyldimethylsilyl)oxy)-8-(difluoromethoxy)-5'-fluoro-6-(trifluoromethyl)-2'H,3H-spiro[imidazo[1,2-a]pyridine-2,1'-naphthalene] (Intermediate U, 137 mg, 228 µmol) was dissolved in AcCN (2 mL) under argon. The RM was cooled to 0° C. and Selectfluor® (89 mg, 251 µmol) added. The RM was stirred at 0° C. for 30 min then at RT for 1.3 hr. The RM was quenched with saturated aq NaHCO₃ and extracted with EtOAc. The combined organic layers were washed with brine, dried over Na₂SO₄ and evaporated. The residue was absorbed onto Isolute and purified by normal phase chromatography (40 g SiO₂-column, eluent heptane:EtOAc 100:0 to 75:25). Product containing fractions were combined, evaporated and subjected to SFC (SFC 1). The product containing fractions were evaporated to give (1'S,3'S)-6'-bromo-8-(difluoromethoxy)-3',5'-difluoro-6-(trifluoromethyl)-2'H,3H-spiro[imidazo[1,2-a]pyridine-2,1'-naphthalen]-4'(3'H)-one as the first eluting peak, Rt 5.86 min (SFC 1).

¹H NMR (600 MHz, DMSO-d₆) δ 8.03-7.97 (m, 2H), 7.36 (t, 1H), 7.26 (d, 1H), 7.13 (s, 1H), 5.61 (ddd, 1H), 4.69 (d, 1H), 4.03 (d, 1H), 2.75-2.67 (m, 1H), 2.49-2.41 (m, 1H).

LC-MS: Rt=0.98 min; MS m/z [M+H]⁺ 499.0/500.9; UPLC-MS 1.

(1'S,3'R)-6'-bromo-8-(difluoromethoxy)-3',5'-difluoro-6-(trifluoromethyl)-2'H,3H-spiro[imidazo[1,2-a]pyridine-2,1'-naphthalen]-4'(3'H)-one was obtained as the second eluting peak, Rt 8.32 min (SFC 1).

¹H NMR (400 MHz, DMSO-d₆) δ 8.07 (d, 1H), 7.99-7.95 (m 1H), 7.32 (t, 1H), 7.28 (d, 1H), 7.06 (d, 1H), 5.86-5.63 (m, 1H), 4.61 (d, 1H), 4.28 (d, 1H), 2.72-2.54 (m, 2H).

LC-MS: Rt=0.89 min; MS m/z [M+H]⁺ 499.0/500.9; UPLC-MS 1.

Example 10 (1'S,3'R,4'S)-6'-bromo-8-(difluoromethoxy)-3',5'-difluoro-6-(trifluoromethyl)-3',4'-dihydro-2'H,3H-spiro[imidazo[1,2-a]pyridine-2,1'-naphthalen]-4'-ol

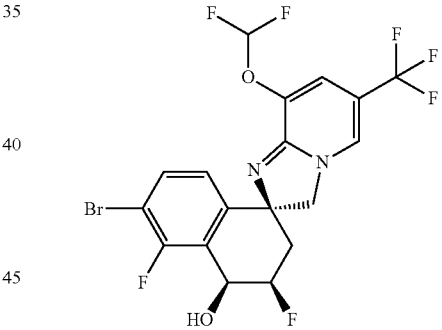

(1'S,3'R)-6'-bromo-8-(difluoromethoxy)-3',5'-difluoro-6-(trifluoromethyl)-2'H,3H-spiro[imidazo[1,2-a]pyridine-2,1'-naphthalen]-4'(3'H)-one (Example 9, 60 mg, 118 µmol) was dissolved in EtOH (2 mL). The RM was cooled to 0° C. and sodium tetrahydroborate (5.11 mg, 0.13 mmol) was added. The RM was stirred at 0° C. for 30 min. The RM was quenched with 2M aq HCl and stirred at RT for 5 min, basified with saturated aq NaHCO₃ and extracted with EtOAc. The combined organic layers were washed with brine, dried over Na₂SO₄ and evaporated. The residue was purified by SFC (SFC 1) and the product containing fractions evaporated to give (1'S,3'R,4'R)-6'-bromo-8-(difluoromethoxy)-3',5'-difluoro-6-(trifluoromethyl)-3',4'-dihydro-2'H,3H-spiro[imidazo[1,2-a]pyridine-2,1'-naphthalen]-4'-ol as the first eluting peak, Rt 6.06 min. (SFC 3).

¹H NMR (400 MHz, DMSO-d₆) δ 7.93 (s, 1H), 7.63 (t, 1H), 7.36 (t, 1H), 7.05 (d, 2H), 6.07 (d, 1H), 4.96 (dt, 2H), 4.83 (d, 1H), 4.39 (d, 1H), 4.03 (d, 1H), 2.39 (d, 1H), 2.15 (q, 1H).

LC-MS: Rt=0.74 min; MS m/z [M+H]⁺ 501.1/503.1; UPLC-MS 1.

(1'S,3'R,4'S)-6'-bromo-8-(difluoromethoxy)-3',5'-difluoro-6-(trifluoromethyl)-3',4'-dihydro-2'H,3H-spiro[imidazo[1,2-a]pyridine-2,1'-naphthalen]-4'-ol was obtained as the second eluting peak, Rt 7.79 min. (SFC 3).

¹H NMR (400 MHz, DMSO-d₆) δ 7.91 (s, 1H), 7.66 (t, 1H), 7.36 (t, 1H), 7.14-6.95 (m, 2H), 5.79 (d, 1H), 5.06 (s, 1H), 4.88 (dd, 1H), 4.42 (d, 1H), 3.84 (d, 1H), 2.09 (t, 1H).

LC-MS: Rt=0.74 min; MS m/z [M+H]⁺ 501.0/503.0; UPLC-MS 1.

Example 11: (S)-6'-bromo-8-(difluoromethoxy)-6-(trifluoromethyl)-3',4'-dihydro-2'H,3H-spiro[imidazo[1,2-a]pyridine-2,1'-naphthalene]

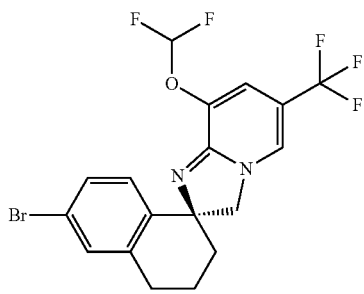

(S)-6'-bromo-6-(trifluoromethyl)-3',4'-dihydro-2'H,3H-spiro[imidazo[1,2-a]pyridine-2,1'-naphthalen]-8-ol (Intermediate W, 305 mg, 764 μmol) was dissolved in DCM (7 mL) and cooled to 0° C. Aq KOH (20%, 0.4 mL, 1.64 mmol) was added to the RM followed by (bromodifluoromethyl)trimethylsilane (127 μL, 802 μmol). The RM was stirred at 0° C. for 10 min, then diluted with DCM and washed with brine, dried over Na₂SO₄ and evaporated. The residue was absorbed onto Isolute and purified by normal phase chromatography (40 g SiO₂-column, eluent heptane:EtOAc 100:0 to 75:25). Product containing fractions were combined and evaporated to give the title compound.

¹H NMR (400 MHz, DMSO-d₆) δ 8.05-7.80 (br, m, 1H), 7.34-6.90 (br, m, 4H), 7.32 (t, 1H), 4.30-3.96 (br, m, 2H), 2.79-2.72 (m, 2H), 1.98-1.62 (br, m, 4H).

LC-MS: Rt=0.85 min; MS m/z [M+H]⁺ 449.1/451.1; UPLC-MS 1.

Example 12: (S)-8-(difluoromethoxy)-6-(trifluoromethyl)-3',4'-dihydro-2'H,3H-spiro[imidazo[1,2-a]pyridine-2,1'-naphthalene]

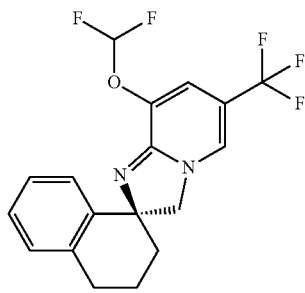 [SMILES: FC(F)OC1=CC(C(F)(F)F)=CN2C[C@@]3(CCCc4ccccc43)N=C12]

(S)-6'-bromo-8-(difluoromethoxy)-6-(trifluoromethyl)-3',4'-dihydro-2'H,3H-spiro[imidazo[1,2-a]pyridine-2,1'-naphthalene] (Example 11, 43 mg, 85 μmol) was dissolved in a MeOH:THF (1:1) solution and 5% Pd/C (20 mg) was added. The RM was stirred under a positive pressure of hydrogen (0.1 bar) at RT for 10.5 hr. After flushing with N2 the RM was filtered through a celite pad, washing with MeOH, and the filtrate evaporated. The residue was absorbed onto Isolute and purified by normal phase chromatography (24 g SiO₂-column, eluent heptane:EtOAc 100:0 to 75:25). Product containing fractions were combined and evaporated to give the title compound as yellow film.

¹H NMR (400 MHz, DMSO-d₆) δ 7.91 (s, 1H), 7.59-7.98 (m, 6H), 4.30-3.98 (m, 2H), 2.77 (t, 2H), 1.97-1.83 (m, 3H), 1.73 (dt, 1H).

LC-MS: Rt=0.76 min; MS m/z [M+H]⁺ 371.2; UPLC-MS 1.

Example 13: (S)-6'-bromo-8-(difluoromethoxy)-5'-fluoro-3',4'-dihydro-2'H,3H-spiro[imidazo[1,2-a]pyridine-2,1'-naphthalene]-6-carbonitrile

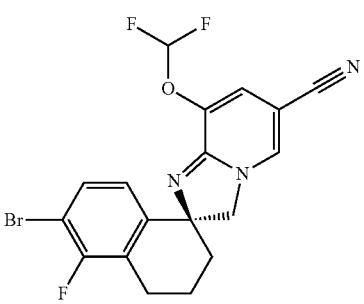

A microwave vial was charged with (S)-(1-amino-6-bromo-5-fluoro-1,2,3,4-tetrahydronaphthalen-1-yl)methanol (Intermediate R, 1.5 g, 5.42 mmol), 6-chloro-5-(difluoromethoxy)nicotinonitrile (Intermediate B, 2.22 g, 10.8 mmol), K₃PO₄ (2.3 g, 10.8 mmol), CuBr (0.389 g, 2.65 mmol) and DMF (15 mL) under Ar. The RM was heated in a microwave at 120° C. for 145 min, diluted with saturated aq NaHCO₃ solution and extracted with EtOAc. The combined organic layers were washed with brine, dried over Na₂SO₄, filtered and evaporated. The residue was absorbed onto Isolute and purified by normal phase chromatography (120 g SiO₂-column, eluent heptane:EtOAc 100:0 to 70:30). Product containing fractions were combined and evaporated to give the title compound as yellow solid.

¹H NMR (400 MHz, DMSO-d₆) δ 8.12 (s, 1H), 7.57-6.97 (m, 4H), 4.35-3.92 (m, 2H), 2.72 (dt, 2H), 1.84 (dt, 4H).

LC-MS: Rt=0.82 min; MS m/z [M+H]⁺ 424.2/426.2; UPLC-MS 1.

Example 14: (S)-6'-bromo-8-(difluoromethoxy)-4',4',5'-trifluoro-6-(trifluoromethyl)-3',4'-dihydro-2'H,3H-spiro[imidazo[1,2-a]pyridine-2,1'-naphthalene]

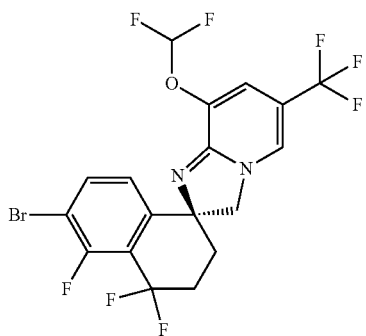 [SMILES: Fc1c(Br)ccc2c1C(F)(F)CC[C@@]21CN2C=C(C(F)(F)F)C=C(OC(F)F)C2=N1]

NIS (194 mg, 861 µmol) was suspended in DCM (3 mL) under Ar and cooled to −78° C. To the RM was added dropwise pyridine hydrofluoride (107 µL, 861 µmol; 70%) followed by a solution of (S)-6'-bromo-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane] (Intermediate S, 120 mg, 215 µmol) in DCM (5 mL). The RM was stirred at −78° C. for 4.5 hr, then diluted with EtOAc and quenched with saturated aq sodium thiosulfate, and extracted 2× with EtOAc. The combined organic layers were washed with brine, dried over Na$_2$SO$_4$, filtered and evaporated. The residue was absorbed onto Isolute and purified by normal phase chromatography (40 g SiO$_2$-column; eluent heptane:EtOAc 100:0 to 50:50). Product containing fractions were combined and evaporated and further purified by SFC (SFC 1), and the product containing fractions evaporated and dried to give the title compound.

$^1$H NMR (600 MHz, DMSO-d$_6$) δ 7.97 (s, 1H), 7.87 (t, 1H), 7.49-7.21 (m, 2H), 7.06 (s, 1H), 4.36 (d, 1H), 4.21 (d, 1H), 2.58 (d, 1H), 2.38 (s, 1H), 2.09 (s, 1H), 2.03 (t, 1H).

LC-MS: Rt=0.94 min; MS m/z [M+H]$^+$ 503.0/505.0; UPLC-MS 1.

Example 15: (S)-8-(difluoromethoxy)-4',4',5'-trifluoro-6-(trifluoromethyl)-3',4'-dihydro-2'H,3H-spiro[imidazo[1,2-a]pyridine-2,1'-naphthalene]-6'-carbonitrile

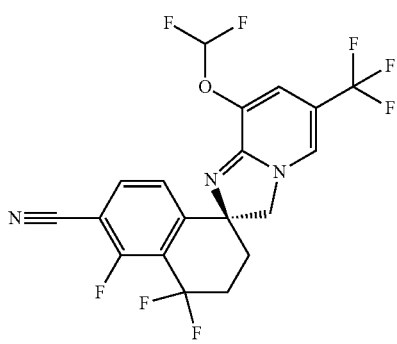 [SMILES: N#Cc1ccc2c(c1F)C(F)(F)CC[C@@]21CN2C=C(C(F)(F)F)C=C(OC(F)F)C2=N1]

A microwave vial was charged with (S)-6'-bromo-8-(difluoromethoxy)-4',4',5'-trifluoro-6-(trifluoromethyl)-3',4'-dihydro-2'H,3H-spiro[imidazo[1,2-a]pyridine-2,1'-naphthalene] (Example 14, 160 mg, 312 µmol), XPhos Pd G3 (26.4 mg, 31 µmol), XPhos (30.3 mg, 62 µmol), potassium hexacyanoferrate(II) (65.8 mg, 156 µmol), potassium acetate (6.12 mg, 62 µmol) and 1,4-dioxane (1.5 mL) and water (1.5 mL) under Ar. The RM was heated in a microwave at 100° C. for 1.5 hr, then diluted with saturated aq NaHCO$_3$ and extracted 2× with EtOAc. The combined organic layers were washed with brine, dried over Na$_2$SO$_4$, filtered and evaporated. The residue was diluted with THF and SiliaMetS® Thiol (0.212 mmol, 150 mg, Particle Size: 40-63 µm, loading 1.41 mmol/g, Silicycle) added, and the RM stirred at 40° C. for 1 hr. The RM was filtered, washed with THF and the filtrate evaporated. The residue was absorbed onto Isolute and purified by normal phase chromatography (SiO$_2$-column; eluent heptane:EtOAc 100:0 to 75:25). Product containing fractions were combined and evaporated. The residue was triturated with hexane, filtered, and dried to give the title compound as yellow solid.

$^1$H NMR (400 MHz, DMSO-d$_6$) δ 8.08 (t, 1H), 7.99 (s, 1H), 7.56-7.13 (m, 2H), 7.08 (s, 1H), 4.38 (d, 1H), 4.25 (d, 1H), 2.60 (s, 2H), 2.13 (d, 1H), 2.05 (d, 1H).

LC-MS: Rt=0.87 min; MS m/z [M+H]$^+$ 450.1; UPLC-MS 1.

Example 16: (S)-6'-bromo-8-chloro-5'-fluoro-6-(trifluoromethyl)-3',4'-dihydro-2'H,3H-spiro[imidazo[1,2-a]pyridine-2,1'-naphthalene]

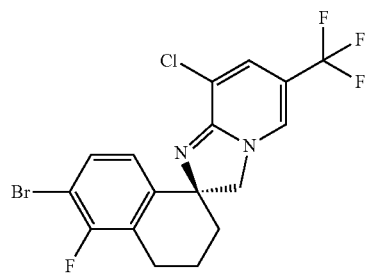 [SMILES: Fc1c(Br)ccc2c1CCC[C@@]21CN2C=C(C(F)(F)F)C=C(Cl)C2=N1]

(S)-(6-bromo-1-((3-chloro-5-(trifluoromethyl)pyridin-2-yl)amino)-5-fluoro-1,2,3,4-tetrahydronaphthalen-1-yl)methanol (Intermediate P1, 215 mg, 427 µmol) was dissolved in toluene (2 mL) under Ar and SOCl$_2$ (0.05 mL, 685 µmol) was added. The RM was heated to 80° C. for 1 hr, cooled, then quenched with saturated aq NaHCO$_3$ and extracted with EtOAc. The combined organic layers were washed with brine, dried over Na$_2$SO$_4$, filtered and evaporated. The residue was absorbed onto Isolute and purified by normal phase chromatography (40 g SiO$_2$-column; eluent heptane:EtOAc 100:0 to 70:30). Product containing fractions were combined and evaporated. The residue was dissolved in Et$_2$O with a few drops of EtOAc, then heptane was added. The resulting solution was kept in a fridge at 4° C. for 18 hr. The precipitated impurities were removed by filtration. The mother liquor was evaporated and the remaining solid dried to give the title compound as yellow foam.

$^1$H NMR (400 MHz, DMSO-d$_6$) δ 8.00 (s, 1H), 7.57-7.39 (m, 2H), 7.05 (d, 1H), 4.20 (dd, 2H), 2.86-2.63 (m, 2H), 2.05-1.92 (m, 1H), 1.92-1.77 (m, 2H), 1.77-1.63 (m, 1H).

LC-MS: Rt=0.82 min; MS m/z [M+H]$^+$ 435.1/437.1; UPLC-MS 1.

Example 17: (S)-6'-bromo-8-(difluoromethoxy)-3',3',5'-trifluoro-6-(trifluoromethyl)-2'H,3H-spiro[imidazo[1,2-a]pyridine-2,1'-naphthalen]-4'(3'H)-one

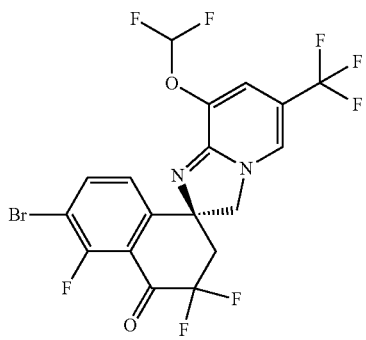 [SMILES: O=C1c2c(ccc(Br)c2F)[C@]2(CN3C=C(C(F)(F)F)C=C(OC(F)F)C3=N2)CC1(F)F]

(S)-6'-bromo-4'-((tert-butyldimethylsilyl)oxy)-8-(difluoromethoxy)-3',5'-difluoro-6-(trifluoromethyl)-2'H,3H-spiro[imidazo[1,2-a]pyridine-2,1'-naphthalene] (Intermediate X, 177 mg, 274 µmol) was dissolved in AcCN (5 mL) under Ar. The RM was cooled to 0° C. and Selectfluor® (126 mg, 356 µmol) was added. The RM was stirred at RT for 5 hr, then quenched with saturated aq NaHCO₃ and extracted with EtOAc. The combined organic layers were washed with brine, dried over Na₂SO₄, filtered and evaporated. The residue was absorbed onto Isolute and purified by normal phase chromatography (24 g SiO₂-column; eluent heptane:EtOAc 100:0 to 75:25). Product containing fractions were combined and evaporated and dried to give the title compound.

¹H NMR (600 MHz, DMSO-d₆) δ 8.11 (dd, 1H), 8.04 (s, 1H), 7.49-7.21 (m, 2H), 7.15 (d, 1H), 4.54 (d, 1H), 4.21 (d, 1H), 3.10-2.95 (m, 2H).

LC-MS: Rt=1.08 min broad peak; MS m/z [M+H]⁺ 516.9/518.9; UPLC-MS 1.

Examples 18 and 19: (1'S,4'S)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol and (1'S,4'R)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol

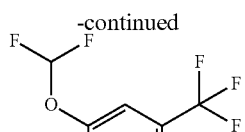

(S)-6'-bromo-8-(difluoromethoxy)-3',3',5'-trifluoro-6-(trifluoromethyl)-2'H,3H-spiro[imidazo[1,2-a]pyridine-2,1'-naphthalen]-4'(3M-one (Example 17, 116 mg, 213 µmol) was dissolved in EtOH (5 mL) under Ar. The RM was cooled to 0° C. and sodium borohydride (9.2 mg, 234 µmol) was added. The RM was stirred at 0° C. for 1 hr, then quenched with 4 drops of 2 M aq HCl and the RM stirred at RT for 5 min. The RM was diluted with saturated aq NaHCO₃ and extracted 2× with EtOAc. The combined organic layers were washed with brine, dried over Na₂SO₄, filtered and evaporated. The residue was purified by SFC (SFC 1) and the product containing fractions were combined and evaporated to give (1'S,4'S)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol as the first eluting peak, Rt 7.54 min (SFC 1)

¹H NMR (600 MHz, DMSO-d₆) δ 7.97 (q, 1H), 7.73 (dd, 1H), 7.35 (t, 1H), 7.15 (dd, 1H), 7.11 (d, 1H), 6.69 (d, 1H), 4.87-4.81 (m, 1H), 4.46 (d, 1H), 3.95 (d, 1H), 2.69-2.53 (m, 2H). LC-MS: Rt=0.86 min; MS m/z [M+H]⁺ 518.9/520.9; UPLC-MS 1.

(1'S,4'R)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol was obtained as the second eluting peak, Rt 8.80 min (SFC 1).

¹H NMR (600 MHz, DMSO-d₆) δ 8.01 (q, 1H), 7.70 (dd, 1H), 7.34 (t, 1H), 7.12 (dd, 1H), 7.06 (d, 1H), 6.54 (d, 1H), 4.99-4.93 (m, 1H), 4.41 (d, 1H), 4.25 (d, 1H), 2.76-2.66 (m, 1H), 2.53-2.43 (m, 1H).

LC-MS: Rt=0.77 min; MS m/z [M+H]⁺ 519.0/521.0; UPLC-MS 1.

Examples 20 and 21: (1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one and (1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one

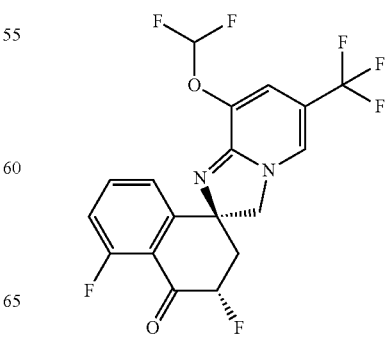

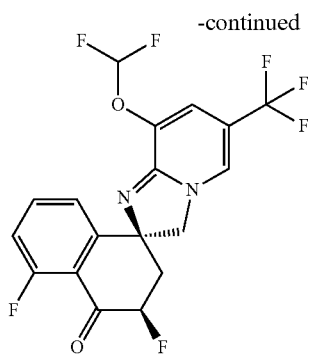

Selectfluor® (1.64 g, 4.62 mmol) was added to (S)-4'-((tert-butyldimethylsilyl)oxy)-8-(difluoromethoxy)-5'-fluoro-6-(trifluoromethyl)-2'H,3H-spiro[imidazo[1,2-a]pyridine-2,1'-naphthalene] (Intermediate AB, 2.05 g, 3.85 mmol) in AcCN (40 mL) under Ar and cooled to 0° C. The RM was stirred at 0° C. for 3.5 hr, then quenched with saturated aq NaHCO₃ and extracted with EtOAc. The combined organic layers were washed with brine, dried over Na₂SO₄, filtered and evaporated. The residue was absorbed onto Isolute and purified by normal phase chromatography (120 g SiO₂-column; eluent heptane:EtOAc 100:0 to 70:30). Product containing fractions were combined and evaporated to give the title compounds. The diastereoisomers were separated by chiral HPLC: (instrument: Gilson Trilution I System; column: Lux Cellulose-5, 5 μM 250×30 mm, 25° C.; eluent: n-heptane (saturated with MeOH)/iPrOH 8:2: detection: UV 230 nm; flow rate 20 mL/min; injection volume 1.0 mL) to give (1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one as the second eluting peak, Rt 8.8 min (C-HPLC-18).

¹H NMR (600 MHz, DMSO-d₆) δ 7.99 (s, 1H), 7.71 (m, 1H), 7.57-7.22 (m, 3H), 7.12 (s, 1H), 5.61 (m, 1H), 4.69 (d, 1H), 4.03 (d, 1H), 2.71 (m, 1H), 2.47-2.38 (m, 1H).

LC-MS: Rt=0.68 min; MS m/z [M+H]⁺ 421.0; UPLC-MS 1.

(1'S,3'S)-8-(difluoromethoxy)-3',5'-difluoro-6-(trifluoromethyl)-2'H,3H-spiro[imidazo[1,2-a]pyridine-2,1'-naphthalen]-4'(3M-one was obtained as the first eluting peak, Rt 4.9 min (C-HPLC-18).

¹H NMR (400 MHz, DMSO-d₆) δ 8.08 (s, 1H), 7.70 (td, 1H), 7.58-7.17 (m, 3H), 7.06 (s, 1H), 5.69 (m, 1H), 4.64 (d, 1H), 4.29 (d, 1H), 2H unassigned due to solvent peaks.

LC-MS: Rt=0.77 min; MS m/z [M+H]⁺ 421.0; UPLC-MS 1.

Example 22: (S)-8-(difluoromethoxy)-5'-fluoro-6-(trifluoromethyl)-3',4'-dihydro-2'H,3H-spiro[imidazo[1,2-a]pyridine-2,1'-naphthalene]-6'-carbonitrile

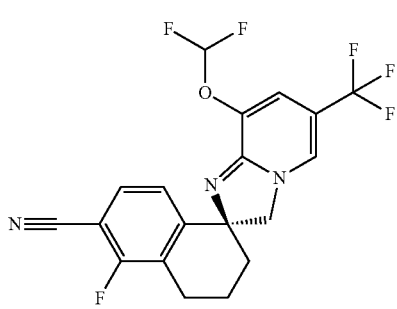

A microwave vial was charged with (S)-6'-bromo-8-(difluoromethoxy)-5'-fluoro-6-(trifluoromethyl)-3',4'-dihydro-2'H,3H-spiro[imidazo[1,2-a]pyridine-2,1'-naphthalene] (Example 7, 245 mg, 524 μmol), XPhos Pd G3 (44.4 mg, 52 XPhos (51 mg, 105 μmol), potassium hexacyanoferrate(II) (111 mg, 262 μmol), potassium acetate (6.4 mg, 66 μmol),1,4-dioxane (2 mL) and water (1 mL) under Ar. The RM was heated in a microwave at 100° C. for 1.5 hr. The RM was diluted with saturated aq NaHCO₃ solution and extracted with EtOAc. The combined organic layers were washed with brine, dried over Na₂SO₄, filtered and evaporated. The residue was absorbed onto Isolute and purified by normal phase chromatography (80 g SiO₂ column; eluent heptane:EtOAc 100:0 to 75:25). Product containing fractions were combined and evaporated. The residue was dissolved in MeOH (4 mL) and filtered through a Stratosphere SPE PL-Thiol cartridge (500 mg/6 mL; Agilent Technologies) and the filtrate was evaporated. The residue was repurified by reverse phase chromatography (RP-HPLC 2). Product containing fractions were combined and partitioned between DCM and saturated aq. NaHCO₃ solution. The combined organic layers were dried over Na₂SO₄, filtered and evaporated to give the title compound as yellow foam.

¹H NMR (600 MHz, DMSO-d₆, with TFA additive) δ 8.76 (s, 1H), 8.22 (d, 1H), 7.90 (dd, 1H), 7.77 (d, 1H), 7.51 (t, 1H), 4.93 (d, 1H), 4.71 (d, 1H), 2.87-2.79 (m, 1H), 2.78-2.71 (m, 1H), 2.35-2.28 (m, 1H), 2.09-1.98 (m, 2H), 1.86-1.76 (m, 1H).

LC-MS: Rt=0.77 min; MS m/z [M+H]⁺ 414.2; UPLC-MS 1.

Example 23: (S)-8-(difluoromethoxy)-4',4',5'-trifluoro-6-(trifluoromethyl)-3',4'-dihydro-2'H,3H-spiro[imidazo[1,2-a]pyridine-2,1'-naphthalene]

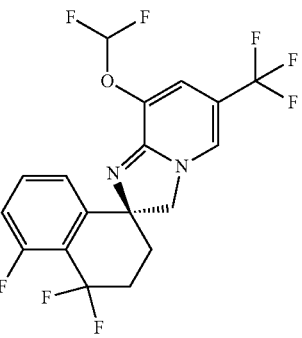

NIS (261 mg, 1.16 mmol) was suspended in DCM (5 ml) under Ar and cooled to −78° C. To the RM was added dropwise pyridine hydrofluoride (0.144 mL, 1.16 mmol) followed by a solution of (S)-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane] (Intermediate Y, 140 mg, 0.29 mmol) in DCM (10 mL). The RM was stirred at −78° C. for 4 hr. The RM was diluted with EtOAc and saturated aq. sodium thiosulfate solution, and extracted with EtOAc. The combined organic layers were washed with brine, dried over Na₂SO₄, filtered and evaporated. The residue was absorbed onto Isolute and purified by normal phase chromatography (40 g SiO₂-column; eluent heptane:

EtOAc 100:0 to 80:20). Product containing fractions were combined and evaporated and dried to give the title compound as yellow solid.

$^1$H NMR (400 MHz, DMSO-d$_6$) δ 7.96 (s, 1H), 7.62-7.13 (m, 4H), 7.04 (s, 1H), 4.36 (d, 1H), 4.22 (d, 1H), 2.64-2.27 (m, 2H), 2.10-1.95 (m, 2H).

LC-MS: Rt=0.78 min; MS m/z [M+H]$^+$ 425.0; UPLC-MS 1.

Examples 24: (2S,4'S)-6'-bromo-8-(difluoromethoxy)-4',5'-difluoro-3',4'-dihydro-2'H,3H-spiro[imidazo[1,2-a]pyridine-2,1'-naphthalene]-6-carbonitrile and (2S,4'R)-6'-bromo-8-(difluoromethoxy)-4',5'-difluoro-3',4'-dihydro-2'H,3H-spiro[imidazo[1,2-a]pyridine-2,1'-naphthalene]-6-carbonitrile

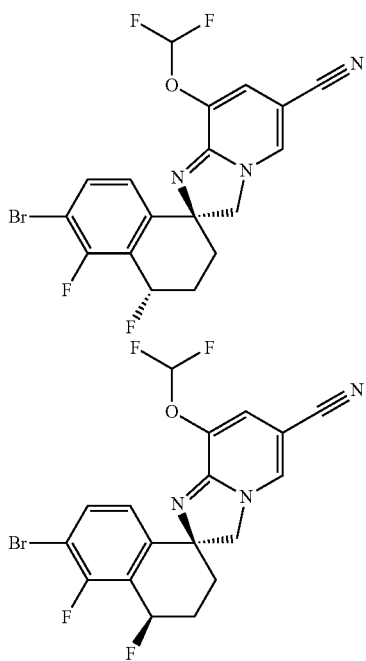

DAST (6.5 μL, 48 μmol) was added to (1'S)-6'-bromo-8-(difluoromethoxy)-5'-fluoro-4'-hydroxy-3',4'-dihydro-2'H,3H-spiro[imidazo[1,2-a]pyridine-2,1'-naphthalene]-6-carbonitrile (Intermediate AC and AD, 11 mg, 24 μmol) in DCM (0.5 mL) cooled to −78° C. under Ar. The RM was stirred at RT for 1 hr, then additional DAST (6.5 μL, 48 μmol) was added and the RM was stirred for another 45 min at RT. The RM was quenched with saturated aq NaHCO$_3$ and extracted with EtOAc. The combined organic layers were washed with brine, dried over Na$_2$SO$_4$, filtered and evaporated. The residue was purified by SFC (SFC 1) and the product containing fractions evaporated to give the first eluting diastereomer with the highest affinity for the HIF2 PAS-B domain for which the data are included in the table of activities.

LC-MS: Rt=0.82 min; MS m/z [M+H]$^+$ 442.0/444.0; UPLC-MS 1.

The second eluting diastereomer was absorbed onto Isolute and repurified by normal phase chromatography (12 g SiO$_2$-column; eluent heptane:EtOAc 100:0 to 30:70). Product containing fractions were combined and evaporated.

$^1$H NMR (400 MHz, DMSO-d$_6$) δ 8.13 (d, 1H), 7.79-7.72 (m, 1H), 7.31 (t, 1H), 7.14-7.09 (m, 2H), 5.86 (d, 1H), 4.33 (d, 1H), 3.85 (d, 1H), 2.26-1.95 (m, 3H), 1.88-1.80 (m, 1H).

LC-MS: Rt=0.78 min; MS m/z [M+H]$^+$ 442.0/444.0; UPLC-MS 1.

Example 25: (1'S,4'S)-8-(difluoromethoxy)-4',5'-difluoro-6-(trifluoromethyl)-3',4'-dihydro-2'H,3H-spiro[imidazo[1,2-a]pyridine-2,1'-naphthalene]-6'-carbonitrile

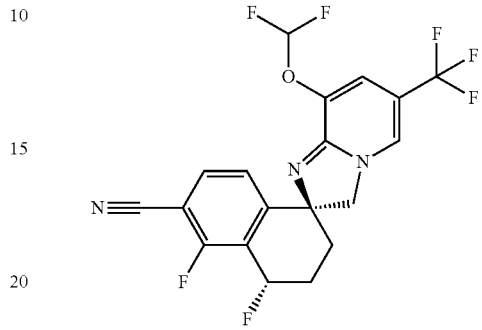

DAST (0.02 ml, 151 μmol) was added to the first eluting diastereoisomer from the reduction of (S)-8-(difluoromethoxy)-5'-fluoro-4'-oxo-6-(trifluoromethyl)-3',4'-dihydro-2'H,3H-spiro[imidazo[1,2-a]pyridine-2,1'-naphthalene]-6'-carbonitrile (Intermediates AE/AF, 30 mg, 68 μmol) in DCM (2 mL) cooled to −78° C. under Ar. The RM was stirred at 0° C. for 2.5 hr, then quenched with saturated aq NaHCO$_3$ and extracted with EtOAc. Product containing fractions were combined and evaporated and the diastereoisomers separated by SFC (SFC-1) to give the title compound as the first eluting peak as a yellow solid, Rt=5.7 min.

$^1$H NMR (600 MHz, DMSO-d$_6$) δ 7.99-7.91 (m, 2H), 7.44 (d, 1H), 7.31 (t, 1H), 7.07 (d, 1H), 5.89 (dd, 1H), 4.36 (d, 1H), 3.88 (d, 1H), 2.31-2.20 (m, 1H), 2.18-1.98 (m, 2H), 1.94-1.87 (m, 1H). LC-MS: Rt=0.79 min; MS m/z [M+H]$^+$ 432.1; UPLC-MS 1.

(1'S,4'R)-8-(difluoromethoxy)-4',5'-difluoro-6-(trifluoromethyl)-3',4'-dihydro-2'H,3H-spiro[imidazo[1,2-a]pyridine-2,1'-naphthalene]-6'-carbonitrile was obtained as the second eluting peak as a yellow solid, Rt=8.1 min.

$^1$H NMR (600 MHz, DMSO-d$_6$) δ 8.02-7.99 (m, 1H), 7.97-7.93 (m, 1H), 7.48 (d, 1H), 7.29 (t, 1H), 7.02 (d, 1H), 5.96 (d, 1H), 4.53 (d, 1H), 4.26 (d, 1H), 2.46-2.32 (m, 1H), 2.17-2.08 (m, 2H), 1.94-1.89 (m, 1H).

LC-MS: Rt=0.74 min; MS m/z [M+H]$^+$ 432.1; UPLC-MS 1.

Example 26: (S)-8-(difluoromethoxy)-5'-fluoro-3',4'-dihydro-2'H,3H-spiro[imidazo[1,2-a]pyridine-2,1'-naphthalene]-6-carbonitrile

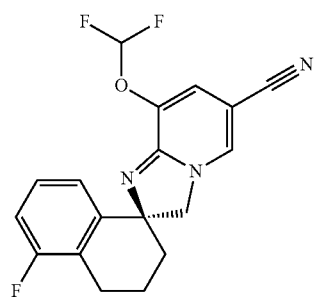 [SMILES: N#CC1=CN2C[C@@]3(CCCc4c(F)cccc43)N=C2C(OC(F)F)=C1]

A solution of (S)-(1-amino-5-fluoro-1,2,3,4-tetrahydronaphthalen-1-yl)methanol (Intermediate AA, 700 mg, 3.59 mmol), 6-chloro-5-(difluoromethoxy)nicotinonitrile (Intermediate B, 1.47 g, 7.17 mmol), copper iodide (205 mg, 1.08 mmol) and potassium phosphate (1.52 g, 7.17 mmol) in DMF (18 mL) was heated at 140° C. in a microwave for 1.5 hr. The RM was poured into saturated aq NaHCO₃ and extracted 3× with EtOAc. The combined organic extracts were washed with 2× water, dried (phase separator) and evaporated. The crude material was dissolved in THF (20 mL), SiliaMetS® Thiol (Particle Size: 40-63 μm, loading 1.35 mmol/g, 6.45 mmol, 4.78 g) was added and the mixture swirled for 1 hr at 40° C. The mixture was filtered and the filtrate was evaporated. The crude residue was purified by normal phase flash chromatography (120 g SiO₂ column, eluent EtOAc:c-hexane 0:100 to 25:75) to give the title compound as a yellow foam.

¹H NMR (400 MHz, DMSO-d₆) δ 8.14 (d, 1H), 7.30 (t, 1H), 7.22 (m, 1H), 7.07-7.03 (m, 2H), 7.06 (d, 1H), 4.22 (d, 1H), 4.09 (d, 1H), 2.77-2.72 (m, 1H), 2.69-2.64 (m, 1H), 1.97 (m, 1H), 1.90-1.82 (m, 2H), 1.73 (m, 1H).

LC-MS: Rt=2.51 min; MS m/z [M+H]⁺ 346.2; UPLC-MS 6.

Example 27: d2-(S)-8-(difluoromethoxy)-5'-fluoro-3',4'-dihydro-2'H,3H-spiro[imidazo[1,2-a]pyridine-2,1'-naphthalene]-6-carbonitrile

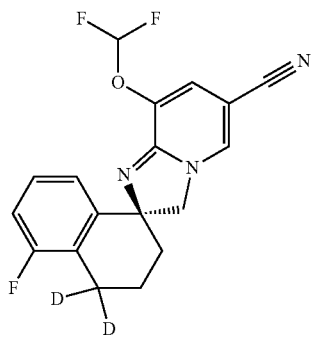 [SMILES: [2H]C1([2H])CC[C@@]2(CN3C=C(C#N)C=C(OC(F)F)C3=N2)c2cccc(F)c21]

A solution of (S)-(1-amino-5-fluoro-1,2,3,4-tetrahydronaphthalen-1-yl-4,4-d₂)methanol (Intermediate AG, 22 mg, 0.10 mmol), 6-chloro-5-(difluoromethoxy)nicotinonitrile (Intermediate B, 39.7 mg, 0.19 mmol), copper iodide (5.54 mg, 0.03 mmol) and potassium phosphate (41.2 mg, 0.19 mmol) in DMF (0.5 mL) was heated at 140° C. in a microwave for 1.5 hr. The RM was poured into saturated aq NaHCO₃ and extracted with 3× EtOAc. The combined organic extracts were washed 2× with water, dried (phase separator) and evaporated. The crude residue was dissolved in THF (2 mL) SiliaMetS® Thiol (Particle Size: 40-63 μm, loading 1.35 mmol/g, 0.09 mmol, 64 mg) was added and the mixture swirled for 1 hr at 40° C. The mixture was filtered, washed with THF and the filtrate evaporated. The crude product was purified by reverse phase preparative HPLC (RP-HPLC 2), the product containing fractions were neutralized with saturated aq NaHCO₃, extracted with DCM and evaporated. The residue was again purified by reverse phase preparative HPLC (RP-HPLC 3), the product containing fractions were extracted with DCM and evaporated to give the title compound as a yellow foam.

¹H NMR (400 MHz, DMSO-d₆) δ 8.14 (s, 1H), 7.30 (t, 1H), 7.23 (m, 1H), 7.09-7.02 (m, 3H), 4.24 (d, 1H), 4.10 (d, 1H), 2.00-1.94 (m, 1H), 1.91-1.82 (m, 2H), 1.76-1.68 (m, 1H).

LC-MS: Rt=2.52 min; MS m/z [M+H]⁺ 348.2; UPLC-MS 6.

Example 28: (S)-8-(difluoromethoxy)-5'-fluoro-6-(trifluoromethyl)-3',4'-dihydro-2'H,3H-spiro[imidazo[1,2-a]pyridine-2,1'-naphthalene]

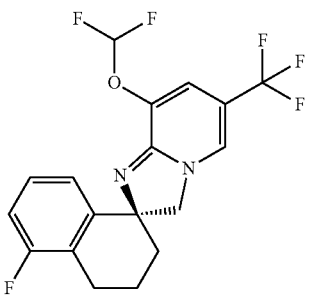

SOCl₂ (0.07 mL, 0.959 mmol) was added to (S)-(1-((3-(difluoromethoxy)-5-(trifluoromethyl)pyridin-2-yl)amino)-5-fluoro-1,2,3,4-tetrahydronaphthalen-1-yl)methanol (Intermediate CK, 290 mg, 607 μmol) was dissolved in toluene (6 mL) under Ar. The RM was heated to 80° C. for 45 min, cooled, then quenched with saturated aq NaHCO₃ solution and extracted with EtOAc. The combined organic layers were washed with brine, dried over Na₂SO₄, filtered and evaporated. The residue was dissolved in MeOH and filtered through a Stratosphere SPE PL-Thiol cartridge (500 mg/6 mL; Agilent Technologies) and the filtrate evaporated. The residue was absorbed onto Isolute and purified by normal phase chromatography (80 g SiO₂-column; eluent heptane:EtOAc 100:0 to 80:20). Product containing fractions were combined and evaporated and dried to give the title compound.

¹H NMR (600 MHz, DMSO-d₆) δ 7.92 (s, 1H), 7.37 (t, 1H), 7.20 (dt, 1H), 7.08 (dd, 1H), 7.03 (ddd, 1H), 6.99 (d, 1H), 4.21 (d, 1H), 4.07 (d, 1H), 2.78-2.70 (m, 1H), 2.70-2.59 (m, 1H), 2.00-1.92 (m, 1H), 1.91-1.80 (m, 2H), 1.76-1.65 (m, 1H).

LC-MS: Rt=0.78 min; MS m/z [M+H]⁺ 389.2; UPLC-MS 1.

Example 29: (S)-5',6',8-trifluoro-6-(trifluoromethyl)-3',4'-dihydro-2'H,3H-spiro[imidazo[1,2-a]pyridine-2,1'-naphthalene]

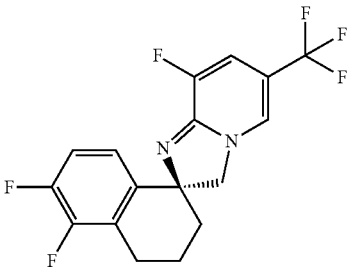 [SMILES: FC1=CC(C(F)(F)F)=CN2C[C@@]3(CCCc4c3ccc(F)c4F)N=C12]

To a solution of (S)-(5,6-difluoro-1-((3-fluoro-5-(trifluoromethyl)pyridin-2-yl)amino)-1,2,3,4-tetrahydronaphthalen-1-yl)methanol (Intermediate OI, 90 mg, 167 µmol) in toluene (5 mL) was added SOCl$_2$ (122 µL, 1.67 mmol). The vial was sealed and stirred at 80° C. for 5 min, cooled to RT and diluted with EtOAc. This mixture was washed 2× with saturated aq Na$_2$SO$_4$. The aq layer was extracted with EtOAc, the combined organic phases washed with brine, dried over Na$_2$SO$_4$, filtered and concentrated in vacuo. The residue was purified by normal phase chromatography (silica gel, eluent heptane:EtOAc containing 1% 7M NH$_3$ in MeOH) to afford the title compound as a light brown solid.

$^1$H NMR (600 MHz, DMSO-d$_6$) δ 7.90 (s, 1H), 7.32-7.18 (m, 2H), 7.13-7.09 (m, 1H), 4.22 (d, 1H), 4.09 (d, 1H), 2.82-2.69 (m, 2H), 2.01-1.94 (m, 1H), 1.93-1.80 (m, 2H), 1.77-1.70 (m, 1H). LC-MS: Rt=0.74 min; MS m/z [M+H]$^+$ 359.2; UPLC-MS 1.

Example 30: (S)-1'-chloro-8',8'-difluoro-8-methoxy-6-(trifluoromethyl)-7',8'-dihydro-3H,6'H-spiro[imidazo[1,2-a]pyridine-2,5'-isoquinoline]

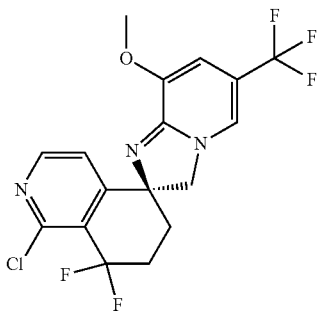 [SMILES: COC1=CC(C(F)(F)F)=CN2C[C@@]3(CCC(F)(F)c4c3ccnc4Cl)N=C12]

MeOH (41 µL, 1.006 mmol) was added to a mixture (S)-1'-chloro-8,8',8'-trifluoro-6-(trifluoromethyl)-7',8'-dihydro-3H,6'H-spiro[imidazo[1,2-a]pyridine-2,5'-isoquinoline] (Intermediate AH, 80 mg, 201 µmol) and NaOtBu (26 mg, 262 µmol) in 1,4-dioxane (2 mL) at RT under an argon atmosphere. The RM was heated at 50° C. for 18 hr, cooled and diluted with saturated aq NaHCO$_3$. The mixture was extracted 3× with DCM, the combined organic layers were dried by passing through a phase separator and concentrated. The residue was purified by normal phase column chromatography (silica gel, eluent heptane:EtOAc 100:0 to 0:100) followed by chiral SFC (column: Chiralpak IC, 5 µm, 250×30 mm; eluent: 40% iPrOH+0.1% aq. NH$_4$OH; temperature: 40° C.; flow rate: 80 mL/min; pressure: 120 bar) to give the title compound as a white powder.

$^1$H NMR (400 MHz, DMSO-d$_6$) δ 8.47 (d, 1H), 7.69 (s, 1H), 7.38 (d, 1H), 6.50 (s, 1H), 4.31 (q, 2H), 3.77 (s, 3H), 2.69-2.31 (m, 2H), 2.18-1.91 (m, 2H).

LC-MS: Rt=0.64 min; MS m/z [M+H]$^+$ 406.1/408.0; UPLC-MS 1.

Example 31: (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline]

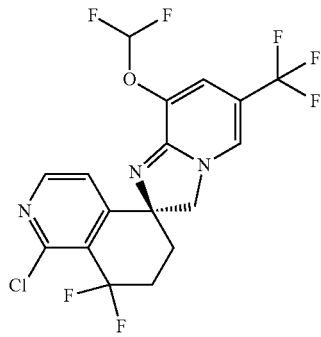 [SMILES: FC(F)OC1=CC(C(F)(F)F)=CN2C[C@@]3(CCC(F)(F)c4c3ccnc4Cl)N=C12]

SOCl$_2$ (3.87 ml, 53.1 mmol) was added dropwise to a solution of (S)-(1-chloro-5-((3-(difluoromethoxy)-5-(trifluoromethyl)pyridin-2-yl)amino)-8,8-difluoro-5,6,7,8-tetrahydroisoquinolin-5-yl)methanol (Intermediate AJ, 12.84 g, 26.5 mmol) in toluene (160 mL) at RT under an atmosphere of argon. The RM was then heated for 30 min at 80° C., cooled to 0° C., MeOH was added and evaporated. The residue was partitioned between EtOAc and saturated aq NaHCO$_3$, extracted with EtOAc, the combined organic layers dried over Na$_2$SO$_4$ and concentrated. The residue was purified by normal phase chromatography (330 g silica gel, eluent heptane:EtOAc 100:0 to 70:30) and the product containing fractions evaporated and taken up into the minimum volume of MeOH and stood at RT for 18 hr. The title compound was obtained as a yellow solid by filtration after drying under vacuum. A second crop of the title compound could be obtained from the filtrate following normal phase chromatography and crystallisation from MeOH.

$^1$H NMR (600 MHz, DMSO-d$_6$) δ 8.49 (d, 1H), 8.00 (s, 1H), 7.51 (d, 1H), 7.33 (t, 1H), 7.09 (d, 1H), 4.37 (d, 1H), 4.27 (d, 1H), 2.68-2.54 (m, 1H), 2.47-2.33 (m, 1H), 2.17-2.10 (m, 1H), 2.06-1.97 (m, 1H).

LC-MS: Rt=0.80 min; MS m/z [M+H]$^+$ 442.4/444.4; UPLC-MS 1.

The following salts were prepared from the above free base form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] by precipitation with the appropriate counter ions.

Fumarate with 1:1 stoichiometry (mw 557.77), mp (DSC) 171.9 and 179.8° C. (onset): The free base (76.0 mg, 172 µmol) was placed in a 2 mL glass vial and iPrOH (500 µL) was added and the yellow suspension stirred at 55° C. After stirring for 4 hr at 55° C., fumaric acid (19.95 mg, 172 µmol) was added, the RM remained as a slurry. The heating was stopped and the slurry stirred at RT for 18 hr, the solid separated by centrifugation, and the powder dried under vacuum at 40° C. to give the title compound.

Sulfate with 1:1 stoichiometry (mw 539.78), mp (DSC) 135.8° C. (onset): The free base (56.67 mg, 128 µmol) was placed in a 2 mL glass vial and iPrOH (400 µL) was added and the yellow suspension stirred at RT. Aq H$_2$SO$_4$ (1N, 128 µL) was then added, transforming the RM into an off-white slurry within approximately 10 min. The slurry was stirred at RT for 18 hr, the solid separated by centrifugation, and the powder dried under vacuum at 40° C. for 18 hr to give the title compound.

Examples 32: (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline]

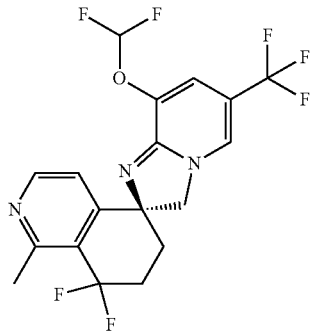

A mixture of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Example 31, 50 mg, 112 µmol), trimethylboroxine (13 µL, 90 µmol), $Cs_2CO_3$ (73 mg, 224 µmol) and $PdCl_2(dppf).CH_2Cl_2$ complex (9.2 mg, 11 µmol) in 1,4-dioxane (0.9 mL) and water (0.1 mL) was heated under an argon atmosphere at 100° C. for 20 hr and then 120° C. for 4 hr. The cooled RM was partitioned between saturated aq $NaHCO_3$ and DCM, extracted 2× with DCM, the combined organic layers dried by passing through a phase separator cartridge and evaporated. The residue taken up into MeOH and swirled with Biotage SPE-PL thiol resin followed by SFC purification (SFC 1 with a Princeton 4-EP 60 A 5 µm 250×30 mm column, eluent 2-22% MeOH) to give (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline] as the first eluting peak, Rt 6.73 min.

$^1$H NMR (600 MHz, DMSO-$d_6$) δ 8.51 (d, 1H), 7.97 (m, 1H), 7.34 (t, 1H), 7.26 (d, 1H), 7.06 (s, 1H), 4.36 (d, 1H), 4.21 (d, 1H), 2.67 (s, 3H), 2.61-2.36 (m, 2H), 2.11-1.98 (m, 2H).

LC-MS: Rt=0.68 min; MS m/z [M+H]$^+$ 422.1; UPLC-MS 1.

(S)-8-(difluoromethoxy)-8',8'-difluoro-6-(trifluoromethyl)-7',8'-dihydro-3H,6'H-spiro[imidazo[1,2-a]pyridine-2,5'-isoquinoline] was obtained as the second eluting peak, Rt 7.36 min.

$^1$H NMR (400 MHz, chloroform-d) δ 8.97 (s, 1H), 8.72 (d, 1H), 7.47 (s, 1H), 7.28-7.22 (m, 1H), 7.06 (s, 1H), 7.03 (t, 1H), 4.39 (d, 1H), 4.27 (d, 1H), 2.78-2.69 (m, 1H), 2.51-2.27 (m, 2H), 2.25-2.19 (m, 1H).

LC-MS: Rt=0.64 min; MS m/z [M+H]$^+$ 408.1; UPLC-MS 1.

Example 32 can also be synthesized via the following alternative procedure:

A solution of trimethylboroxine (5.1 g, 40.7 mmol) in iPrOAc (10 mL) was added to a mixture of (S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] (Example 31, 18.0 g, 40.7 mmol) and $Cs_2CO_3$ (26.6 g, 81.5 mmol) in iPrOAc (290 mL) under a N2 atmosphere. $PdCl_2(dppf)$ (298 mg, 0.4 mmol) was then added under N2 protection and the mixture purged with N2 for 10 min. The reactor was transferred to a pre-heated oil batch and stirred at 100° C. for 24 hr. Additional $PdCl_2(dppf)$ (298 mg, 0.4 mmol) and trimethylboroxine (1.4 g, 11.2 mmol) were added under N2 protection, and the RM refluxed for an additional 17 hr. The cooled RM was filtered and washed with iPrOAc (150 mL), and the filtrate then washed with water (250 mL). The separated aqueous phase was extracted with iPrOAc (200 mL). The combined organic phases were washed with 10% aq NaCl (200 mL), dried over anhydrous $MgSO_4$, filtered and concentrated. The residue was purified by normal phase chromatography (200-300 mesh silica gel, eluent heptane:EtOAc 77:34 to 50:50) to give an off-white solid. MTBE/heptane 1:5 (240 mL) was added and the mixture agitated on a rotavap without vacuum and a bath temperature of 60° C. After dissolving to become a bright red/yellow solution a solid precipitated from the mixture which was allowed to cool to RT. The solid was collected by filtration, and heptane (120 mL) was added to the mother liquor to give a second crop of material. The title compound was obtained after further recrystallisation from MTBE:heptane 1:5 and drying.

The following crystalline forms and salts were prepared from the above free base form of (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline] by seeding and by precipitation with the appropriate counter ions.

Crystalline modification A mp (DSC) 129.9° C. (onset): The free base (3.13 g, 7.06 mmol, assay 95.5%) and iPrOH (3 mL) were added into a 100 mL vessel and the mixture heated to 65° C. (jacket temperature) with mechanical agitation at 250 RPM. n-Heptane (9 mL) was added to the mixture over 1 hr, followed by the addition of seed crystals of modification A (30 mg) at 65° C. The resulting mixture became cloudy, and was maintained at 65° C. for 1 hr. Further n-heptane (51 mL) was added over 10 hr, the temperature was maintained at 65° C. for a further 1 hr, and the mixture then cool to 4° C. over 4 hr. After maintaining the slurry at 4° C. for 2.5 hr the solid was collected by filtration at 25° C. using a glass filter, and washed with a mixture of iPrOH and n-heptane (v/v=1:20, 4.2 mL). The solid was dried under vacuum at 60° C. for 3.5 hr, to give the title compound as a powder (2.46 g).

Fumarate with 1:1 stoichiometry (mw 537.37), mp (DSC) 172.3 (onset): The free base (2.0 g) was placed in a 100 mL EasyMax Reactor and a mixture of iPrOH and heptane (80:20, 40 mL) was added. Fumaric acid (1.73 mg) was added, and the RM heated to 50° C., and then maintained at 50° C. for 18-24 hr. The mixture was cooled to 25° C. over 4 hr, and then stirred at 25° C. for 4-6 hr. The resulting solid was collected by filtration at 25° C. using a glass filter, and washed with a mixture of iPrOH and n-heptane (4:1, 10 mL). The solid was dried under vacuum at 40° C. for 12 hr, to give the title compound as an off-white powder.

Example 33: (S)-8-(difluoromethoxy)-8',8'-difluoro-1'-(methyl-d₃)-6-(trifluoromethyl)-7',8'-dihydro-3H,6'H-spiro[imidazo[1,2-a]pyridine-2,5'-isoquinoline]

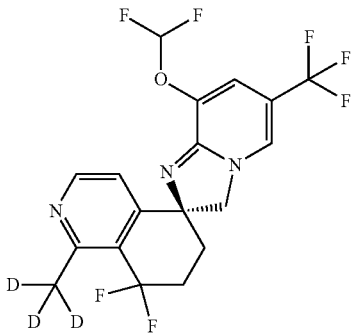 [SMILES: [2H]C([2H])([2H])c1nccc2c1C(F)(F)CC[C@@]21CN2C=C(C(F)(F)F)C=C(OC(F)F)C2=N1]

2-(methyl-d₃)-1,3,2-dioxaborinane (Intermediate AV, 127 mg, 1.11 mmol) was added to a mixture of (S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] (Example 31, 200 mg, 444 µmol), K₂CO₃ (153 mg, 1.11 mmol) and tetrakis(triphenylphosphine)palladium (51 mg, 44 µmol) in 1,4-dioxane (1.5 mL), THF (1.5 mL) and water (1.5 mL) under argon. The RM was stirred for 48 hr at 90° C. and additional d₃-2-(methyl-d₃)-1,3,2-dioxaborinane (23 mg, 222 µmol), K₂CO₃ (31 mg, 222 µmol) and tetrakis(triphenylphosphine)palladium (26 mg, 22 µmol) were added, and the RM stirred for a further 5 hr at 90° C. The cooled RM was partitioned between EtOAc and saturated aq NaHCO₃, the aq layer further extracted with EtOAc, the combined organic layers were washed with brine, dried by passing through a phase separator and evaporated. The residue was dissolved in MeOH and treated with 2.0 g of SPE-PL thiol resin from Biotage and swirled for 1 hr at 40° C. then filtered, washing with MeOH, and the filtrate evaporated. The crude product was adsorbed on Isolute and purified by normal phase chromatography (40 g SiO₂-cartridge, eluent heptane/EtOAc 10:90 to 50:50) followed by chiral SFC: (column: Chiralcel OD-H, 250×30 mm I.D., 5 µm, 40° C.; eluent: CO₂/iPrOH (+0.1% NH₃) 94:6; flow rate: 80 mL/min; detection: DAD 190-400 nm) to give the title compound as the first eluting peak (RT 10.5 min). (S)-8-(difluoromethoxy)-8',8'-difluoro-6-(trifluoromethyl)-7',8'-dihydro-3H,6'H-spiro[imidazo[1,2-a]pyridine-2,5'-isoquinoline] eluted with a RT of 16.7 min. The desired product (360 mg) was dissolved in EtOH (1.5 mL), and H₂O (1.5 mL) was added followed by a seed crystal of (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline]. The resulting suspension was sonicated for 5 min and the solid collected by filtration, washing with H₂O, then dried, to give the title compound as yellow crystals.

Example 33 can also be synthesized via the following alternative procedure:

In glovebox, to a round bottom flask was charged with Ni(glyme)Br₂ (6.46 g, 20.9 mmol), 1,10-phenanthroline (7.54 g, 41.8 mmol) and DMF (300 mL). The reaction mixture was allowed to stir in the glovebox at room temperature for 30 min to form a dark green suspension. To the above mixture was added Co(salen) (3.40 g, 10.5 mmol), and the mixture stirred in the glovebox for 10 min to form a dark brown solution. In parallel, to a second round bottom flask was charged with (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Example 31, 61.6 g, 139.5 mmol), Mn (38.31 g, 697.3 mmol), DMF (300 mL) and TsOCD₃ (84.0 g, 94.3% assay, 418.6 mmol). In the glovebox, the first Ni catalyst-containing solution was transferred into the second reaction mixture, the flask sealed with a rubber stopper and stirred at 40-45° C. for 16 hours under N2. The reaction mixture was then cooled to room temperature, the solid material removed by filtration, washing with EtOH. The filtrates were combined and concentrated at 50° C., then EtOAc (1.0 L) was added with vigorous agitation. A precipitate formed and the suspension was filtered through a silica gel pad (100 g), washing with EtOAc (1.5 L). The filtrate was concentrated to form a dark green oil, and then again filtered through a silica gel pad (200 g) with heptane/EtOAc=2:1, 3 L). The filtrate was concentrated and IPA (60 mL) and water (300 mL) were added. The crude product was obtained as a light yellow solid by filtration. The crude product was slurried with IPA (240 mL) and H₂O (480 mL), filtered and dried in vacuo at 40° C. to give the title compound as a yellow solid.

¹H NMR (600 MHz, DMSO-d₆) δ 8.52 (d, 1H), 7.98 (d, 1H), 7.49-7.19 (m, 2H), 7.08 (d, 1H), 4.29 (dd, 2H), 2.58 (dd, 1H), 2.43-2.39 (m, 1H), 2.17-1.95 (m, 2H).

LC-MS: Rt=0.59 min; MS m/z [M+H]⁺ 425.2; UPLC-MS 7.

Example 34: (S)-8-(difluoromethoxy)-8',8'-difluoro-1'-methoxy-6-(trifluoromethyl)-7',8'-dihydro-3H, 6'H-spiro[imidazo[1,2-a]pyridine-2,5'-isoquinoline]

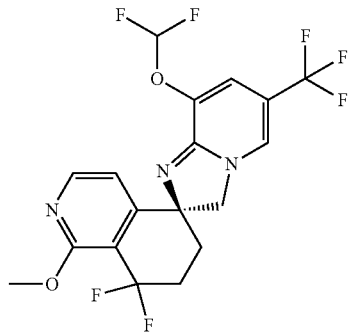 [SMILES: COc1nccc2c1C(F)(F)CC[C@@]21CN2C=C(C(F)(F)F)C=C(OC(F)F)C2=N1]

From the purification of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Example 31, 1.99 g, 4.37 mmol) by normal phase chromatography (220 g RediSep Gold column, eluent c-hexane/EtOAc 100-0 to 73-27) a minor component eluted prior to the desired product. Further purification of the minor component by normal phase chromatography (4 g RediSep Gold column, eluent c-hexane:EtOAc 100:0 to 81:19) gave the title compound as a yellow solid.

¹H NMR (600 MHz, DMSO-d₆) δ 8.24 (d, 1H), 7.97 (s, 1H), 7.34 (t, 1H), 7.07 (s, 1H), 6.98 (d, 1H), 4.34 (d, 1H), 4.20 (d, 1H), 3.92 (s, 3H), 2.60-2.49 (m, 1H), 2.37-2.26 (m, 1H), 2.10-1.94 (m, 2H).

LC-MS: Rt=3.11 min; MS m/z [M+H]⁺ 438.0; UPLC-MS 6.

Example 35: (S)-8-(difluoromethoxy)-6'-fluoro-3',4'-dihydro-2'H,3H-spiro[imidazo[1,2-a]pyridine-2,1'-naphthalene]-6-carbonitrile

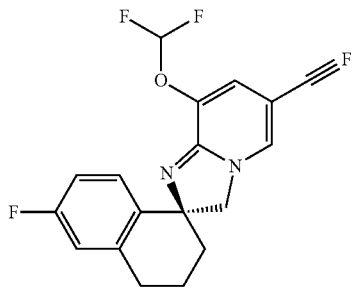

A mixture of (S)-(1-amino-6-fluoro-1,2,3,4-tetrahydronaphthalen-1-yl)methanol free base (Intermediate AO, 100 mg, 461 µmol), 6-chloro-5-(difluoromethoxy)nicotinonitrile (Intermediate B, 277 mg, 1.01 mmol), $K_3PO_4$ (196 mg, 922 µmol) and CuI (62 mg, 323 µmol) in DMF (3 mL) was heated at 160° C. for 30 min in a microwave under an atmosphere of argon. The RM was partitioned between TBME (20 mL) and $H_2O$ (20 mL) the aq layer extracted with TBME, and the combined organic layers washed with brine, dried over $Na_2SO_4$ and evaporated. The residue was purified by normal phase chromatography (12 g $SiO_2$ column, eluent hexane:TBME from 0-50%) followed by reversed phase chromatography (RP-HPLC 1). Product containing fractions were combined, AcCN removed under vacuum, the predominantly aq phase basified with $Na_2CO_3$ and extracted 3× with DCM, the combined organic layers dried over $Na_2SO_4$, and evaporated to give the title compound as a yellow solid.

$^1$H NMR (400 MHz, DMSO-$d_6$) δ 8.10 (s, 1H), 7.27 (t, 1H), 7.25-7.20 (m, 1H), 7.03-6.89 (m, 3H), 4.19 (d, 1H), 4.02 (d, 1H), 2.79-2.73 (m, 2H), 1.95-1.62 (m, 4H).

LC-MS: Rt=0.62 min; MS m/z [M+H]$^+$ 346.1; UPLC-MS 1.

Chiral HPLC (C-HPLC 9) indicated the sample to have an ee of 72%: title compound eluting with Rt=17.8 minutes, and (R)-8-(difluoromethoxy)-6'-fluoro-3',4'-dihydro-2'H,3H-spiro[imidazo[1,2-a]pyridine-2,1'-naphthalene]-6-carbonitrile eluting with Rt=15.7 minutes.

Example 36: (S)-1'-chloro-8-(difluoromethoxy)-6-(trifluoromethyl)-7',8'-dihydro-3H,6'H-spiro[imidazo[1,2-a]pyridine-2,5'-isoquinoline]

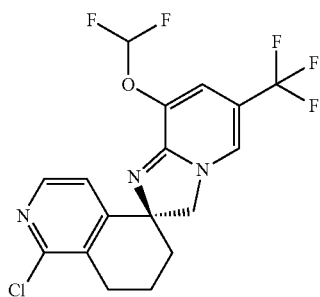 [SMILES: FC(F)OC1=CC(C(F)(F)F)=CN2C[C@@]3(CCCc4c3ccnc4Cl)N=C12]

To a solution of (S)-(1-chloro-5-((3-(difluoromethoxy)-5-(trifluoromethyl)pyridin-2-yl)amino)-5,6,7,8-tetrahydroisoquinolin-5-yl)methanol (Intermediate AP, 330 mg, 0.78 mmol) in toluene (4.8 mL) was added thionyl chloride (0.11 mL, 1.56 mmol) and the reaction mixture was stirred at 80° C. for 45 min. The cooled RM was poured into saturated aq $NaHCO_3$ and extracted 2× with DCM. The combined organic extracts were dried (phase separator) and evaporated. The crude compound was purified by normal phase flash chromatography (12 g $SiO_2$ column, eluent EtOAc:c-hexane 0:100 to 23:77) to give the title compound as a yellow foam.

$^1$H NMR (600 MHz, DMSO-$d_6$) δ 8.20 (d, 1H), 7.96 (m, 1H), 7.36 (t, 1H), 7.34 (d, 1H), 7.05 (d, 1H), 4.25 (d, 1H), 4.13 (d, 1H), 2.80-2.68 (m, 2H), 2.01 (m, 1H), 1.91 (m, 1H), 1.84 (td, 1H), 1.78 (m, 1H).

LC-MS: Rt=2.64 min; MS m/z [M+H]$^+$ 406.2/408.2; UPLC-MS 6.

Example 37: (S)-3'-chloro-8-(difluoromethoxy)-6-(trifluoromethyl)-6',7'-dihydro-3H,5'H-spiro[imidazo[1,2-a]pyridine-2,8'-isoquinoline]

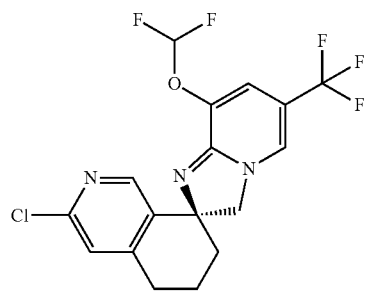 [SMILES: FC(F)OC1=CC(C(F)(F)F)=CN2C[C@@]3(CCCc4cc(Cl)ncc43)N=C12]

$SOCl_2$ (0.04 mL, 548 µmol) was added to (3-chloro-8-((3-(difluoromethoxy)-5-(trifluoromethyl)pyridin-2-yl)amino)-5,6,7,8-tetrahydroisoquinolin-8-yl)methanol (Intermediate AQ, 130 mg, 279 µmol) in toluene (2 mL) under Ar. The RM was heated to 80° C. for 45 min, cooled, then quenched with saturated aq $NaHCO_3$ solution and extracted with EtOAc. The combined organic layers were washed with brine, dried over $Na_2SO_4$, filtered and evaporated. The residue was absorbed onto Isolute and purified by normal phase chromatography (40 g $SiO_2$-column; eluent heptane:EtOAc 100:0 to 70:30). Product containing fractions were combined, evaporated and dried to give the title compound as yellow solid.

$^1$H NMR (400 MHz, DMSO-$d_6$) δ 8.30 (s, 1H), 7.93 (s, 1H), 7.30 (t, 1H), 7.27 (s, 1H), 7.02 (d, 1H), 4.24 (d, 1H), 4.14 (d, 1H), 2.79 (t, 2H), 1.95-1.66 (m, 4H).

LC-MS: Rt=0.68 min; MS m/z [M+H]$^+$ 406.1/408.1; UPLC-MS 1.

Example 38: (S)-8-(difluoromethoxy)-6-(trifluoromethyl)-3',4'-dihydro-2'H,3H-spiro[imidazo[1,2-a]pyridine-2,1'-naphthalene]-6'-carbonitrile

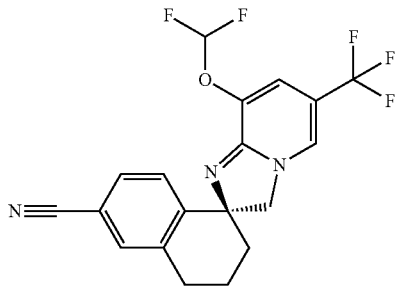 [SMILES: N#Cc1ccc2c(c1)CCC[C@@]21CN2C=C(C(F)(F)F)C=C(OC(F)F)C2=N1]

A microwave vial was charged with (S)-6'-bromo-8-(difluoromethoxy)-6-(trifluoromethyl)-3',4'-dihydro-2'H,3H-spiro[imidazo[1,2-a]pyridine-2,1'-naphthalene] (Example 11, 223 mg, 402 µmol), XPhos Pd G3 (34 mg, 40 µmol), XPhos (39.1 mg, 80 µmol), potassium hexacyanoferrate(II) (85 mg, 201 µmol), potassium acetate (4.93 mg, 50 µmol), 1,4-dioxane (2 mL) and water (1 mL) under Ar. The RM was heated in a microwave at 100° C. for 1.5 hr. The cooled RM was diluted with saturated aq NaHCO$_3$ and extracted with EtOAc. The combined organic layers were washed with brine, dried over Na$_2$SO$_4$, filtered and evaporated. The residue was absorbed onto Isolute and purified by normal phase chromatography (80 g SiO$_2$-column; eluent heptane:EtOAc 100:0 to 70:30). Product containing fractions were combined and evaporated. The residue was dissolved in MeOH (4 mL) and filtered through a Stratosphere SPE PL-Thiol cartridge (500 mg/6 mL; Agilent Technologies) and the filtrate was evaporated and dried to give the title compound as yellow foam.

$^1$H NMR (600 MHz, DMSO-d$_6$, with TFA additive) δ 8.75 (t, 1H), 8.21 (d, 1H), 7.90 (d, 1H), 7.78 (dd, 1H), 7.75 (d, 1H), 7.51 (t, 1H), 4.93 (d, 1H), 4.72 (d, 1H), 2.87 (d, 2H), 2.36-2.29 (m, 1H), 2.13-2.05 (m, 1H), 1.99 (td, 1H), 1.86-1.76 (m, 1H).

LC-MS: Rt=0.71 min; MS m/z [M+H]$^+$ 396.2; UPLC-MS 1.

Example 39: (S)-7-bromo-8'-(difluoromethoxy)-8-fluoro-6'-(trifluoromethyl)-3'H-spiro[chroman-4,2'-imidazo[1,2-a]pyridine]

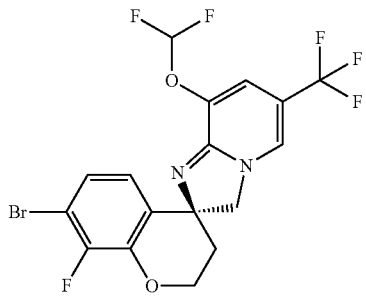

To a solution of (S)-(7-bromo-4-((3-(difluoromethoxy)-5-(trifluoromethyl)pyridin-2-yl)amino)-8-fluorochroman-4-yl)methanol (Intermediate AR, 5.32 g, 10.9 mmol) in toluene (43 mL) was added thionyl chloride (1.59 mL, 21.8 mmol) and the RM stirred for 15 min at 80° C. The cooled RM was quenched with MeOH and evaporated. The residue was dissolved in DCM and poured into saturated aq NaHCO$_3$. The layers were separated and the aqueous layer was back-extracted 2× with DCM. The combined organic extracts were dried (phase separator) and evaporated. The crude material was purified by normal phase flash chromatography (120 g SiO$_2$ column, eluent EtOAc:c-hexane 0:100 to 20:80 then switched to MeOH:CH$_2$Cl$_2$ 0:100 to 40:60) to give the title compound as a yellow foam.

$^1$H NMR (400 MHz, DMSO-d$_6$) δ 7.98 (br s, 1H), 7.36 (t, 1H), 7.16 (dd, 1H), 7.06 (dd, 1H), 7.03 (d, 1H), 4.46 (m, 1H), 4.49 (m, 1H), 4.27 (s, 2H), 2.17-2.04 (m, 2H).

LC-MS: Rt=3.70 min; MS m/z [M+H]$^+$ 469.0/471.0; UPLC-MS 6.

Example 40: (S)-8'-(difluoromethoxy)-8-fluoro-6',7-bis(trifluromethyl)-3'H-spiro[chroman-4,2'-imidazo[1,2-a]pyridine]

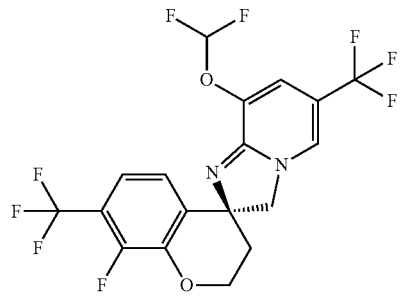 [SMILES: Fc1c(C(F)(F)F)ccc2c1OCC[C@@]21CN2C=C(C(F)(F)F)C=C(OC(F)F)C2=N1]

A mixture of (S)-8'-(difluoromethoxy)-8-fluoro-7-iodo-6'-(trifluoromethyl)-3'H-spiro[chroman-4,2'-imidazo[1,2-a]pyridine] (Intermediate AW, 147 mg, 285 µmol), diphenyl(trifluoromethyl)sulfonium trifluoromethanesulfonate (173 mg, 427 µmol) and Cu powder (54 mg, 854 µmol) in DMF (2.5 mL) was heated in a sealed tube at 60° C. for 18 hr. The cooled RM was partitioned between EtOAc and saturated aq NaHCO$_3$, the aq phase extracted with EtOAc, the combined organic layers washed with brine, dried and concentrated. The residue was purified by reversed phase chromatography (RP-HPLC 2) and the product containing fractions were neutralised with saturated aq NaHCO$_3$, extracted with DCM, the combined organic phases dried by passing through a phase separator cartridge and concentrated to give the title compound as a yellow solid.

$^1$H NMR (400 MHz, DMSO-d$_6$) δ 8.00 (s, 1H), 7.33-7.25 (m, 1H), 7.25-7.18 (m, 1H), 7.62-7.11 (m, 1H), 7.05 (s, 1H), 4.58-4.43 (m, 1H), 4.40-4.19 (m, 2H), 4.27 (br s, 1H), 2.24-1.98 (m, 2H).

LC-MS: Rt=4.09 min; MS m/z [M+H]$^+$ 459.2; UPLC-MS 4.

Example 41: (S)-7-chloro-8'-(difluoromethoxy)-6'-(trifluoromethyl)-3'H-spiro[chroman-4,2'-imidazo[1,2-a]pyridine]

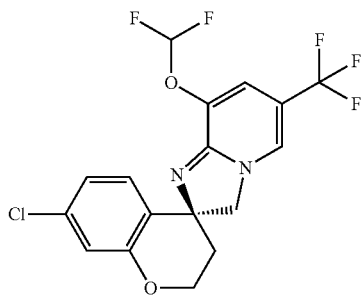 [SMILES: FC(F)OC1=CC(C(F)(F)F)=CN2C[C@@]3(CCOc4cc(Cl)ccc43)N=C12]

To a solution of (S)-(7-chloro-4-((3-(difluoromethoxy)-5-(trifluoromethyl)pyridin-2-yl)amino)chroman-4-yl)methanol (Intermediate AX, 4.79 g, 11.3 mmol) in toluene (75 mL) was added thionyl chloride (1.65 mL, 22.6 mmol) and the reaction mixture was stirred at 80° C. for 1 hr. The cooled RM was quenched by the addition of saturated aq NaHCO$_3$. EtOAc was added and the layers were separated. The aq layer was back-extracted 2× with EtOAc and the combined organic extracts dried (phase separator) and evaporated. The crude material was purified by normal phase chromatography (220 g RediSep Gold column, eluent: c-hexane:EtOAc 70:30) to give the title compound.

TLC, Rf (Cyclohexane/EtOAc 1:1): 0.55

$^1$H NMR (400 MHz, DMSO-d$_6$) δ 7.96 (br s, 1H), 7.36 (t, 1H), 7.27 (d, 1H), 7.02 (br s, 1H), 7.94 (dd, 1H), 6.87 (d, 1H), 4.37 (m, 1H), 4.25 (s, 2H), 4.19 (m, 1H), 2.06 (m, 2H).

LC-MS: Rt=3.49 min; MS m/z [M+H]$^+$ 407.1/409.1; UPLC-MS 6.

Example 42: (S)-7-bromo-8-fluoro-8'-(fluoromethoxy)-6'-(trifluoromethyl)-3'H-spiro[chroman-4,2'-imidazo[1,2-a]pyridine]

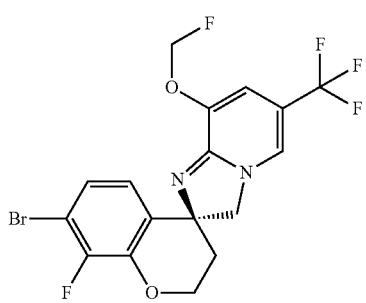

A solution of (S)-7-bromo-8-fluoro-3'-(3-(fluoromethoxy)-5-(trifluoromethyl)pyridin-2-yl)spiro[chroman-4,4'-oxazolidin]-2'-one (Intermediate AY, 70 mg, 117 μmol) in aq NaOH (2M, 293 μL, 1.17 mmol) and EtOH (3 mL) was stirred for 20 min at 80° C. The RM was diluted with EtOAc, washed with saturated aq NaHCO$_3$, dried and concentrated. The residue was dissolved in toluene (3 mL) and SOCl$_2$ (13 μL, 176 μmol) added and the RM stirred for 20 min at 80° C. MeOH was added to the cooled RM which was then concentrated, partitioned between EtOAc and saturated aq NaHCO$_3$, dried and concentrated. The residue was purified by normal phase chromatography (silica gel, eluent c-hexane:EtOAc 100:0 to 50:50) to give the title compound as a yellow solid.

$^1$H NMR (400 MHz, DMSO-d$_6$) δ 7.87 (s, br, 1H), 7.15 (t, 1H), 7.02 (d, 1H), 6.79 (s, br, 1H), 5.90 (d, 2H), 4.52-4.40 (m, 1H), 4.31-4.18 (m, 3H), 2.20-2.05 (m, 2H).

LC-MS: Rt=0.79 min; MS m/z [M+H]$^+$ 451.2/453.2; UPLC-MS 1.

Example 43: (S)-7-chloro-8'-(difluoromethoxy)-8-fluoro-6'-(trifluoromethyl)-3'H-spiro[chroman-4,2'-imidazo[1,2-a]pyridine]

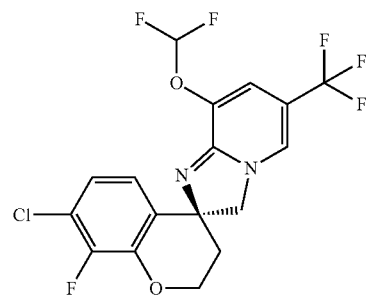 [SMILES: Fc1c(Cl)ccc2c1OCC[C@@]21CN2C=C(C(F)(F)F)C=C(OC(F)F)C2=N1]

A solution of (S)-8'-(difluoromethoxy)-8-fluoro-7-(4,4,5,5-tetramethyl-1,3,2-dioxaborolan-2-yl)-6'-(trifluoromethyl)-3'H-spiro[chroman-4,2'-imidazo[1,2-a]pyridine] (Intermediate AZ, 550 mg, 1.07 mmol) and copper(II) chloride (430 mg, 3.20 mmol) in a mixture of MeOH (5 mL) and Water (5 mL) was stirred at 100° C. for 8 hr. The RM was poured into saturated aq NaHCO$_3$ and extracted 2× with EtOAc. To the combined organic extracts was added saturated aq NH$_4$Cl and the mixture was stirred at RT for 1 hr. The organic layer was separated, washed with saturated aq NH$_4$Cl, dried (phase separator) and evaporated. The crude material was dissolved in THF (10 mL), SiliaMetS® Thiol (Particle Size: 40-63 μm, loading 1.39 mmol/g, 13 mmol, 9.86 g) was added and the mixture swirled for 1 hr at 40° C. The mixture was filtered and the filtrate evaporated. The crude residue was purified by reverse phase preparative HPLC (RP HPLC 3), the product containing fractions were extracted with DCM and evaporated to give the title compound as a yellow solid.

$^1$H NMR (400 MHz, DMSO-d$_6$) δ 7.94 (s, br, 1H), 7.33 (t, 1H), 7.12 (m, 1H), 7.02 (m, 2H), 4.50 (m, 1H), 4.34-4.29 (m, 3H), 2.16 (m, 2H).

LC-MS: Rt=3.65 min; MS m/z [M+H]$^+$ 425.1/427.1; UPLC-MS 6.

Example 44: (S)-8'-(difluoromethoxy)-6',7-bis(trifluoromethyl)-3'H-spiro[chroman-4,2'-imidazo[1,2-a]pyridine]

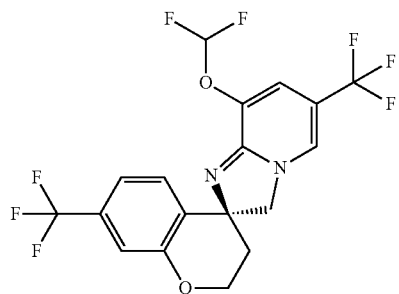 [SMILES: FC(F)OC1=CC(C(F)(F)F)=CN2C[C@@]3(CCOc4cc(C(F)(F)F)ccc43)N=C12]

To a solution of (S)-(4-((3-(difluoromethoxy)-5-(trifluoromethyl)pyridin-2-yl)amino)-7-(trifluoromethyl)chroman-4-yl)methanol (Intermediate BA, 3.18 g, 6.24 mmol) in toluene (40 mL) was added thionyl chloride (0.91 mL, 12.5 mmol) and the yellow suspension was stirred at 80° C. for 1 hr. The cooled RM was quenched by the addition of saturated aq NaHCO$_3$ and extracted 2× with EtOAc. The combined organic extracts were dried (phase separator) and evaporated. The residue was purified by normal flash chromatography (120 g SiO$_2$ column; eluent c-hexane:EtOAc 100:0 to 70:30) to give the title compound as a yellow solid.

$^1$H NMR (400 MHz, DMSO-d$_6$) δ 7.98 (br, s, 1H), 7.49 (d, 1H), 7.37 (t, 1H), 7.22 (d, 1H), 7.10 (s, 1H), 7.04 (s, 1H), 4.41 (m, 1H), 4.29 (s, 2H), 4.23 (m, 1H), 2.16-2.03 (m, 2H).

LC-MS: Rt=3.92 min; MS m/z [M+H]$^+$ 441.1; UPLC-MS 6.

The following salts were prepared from the above free base form of (S)-8'-(difluoromethoxy)-6',7-bis(trifluoromethyl)-3'H-spiro[chroman-4,2'-imidazo[1,2-a]pyridine] by precipitation with the appropriate counter ions.

Hydrochloride with 1:1 stoichiometry (mw 476.76), mp (DSC) 58.3° C. (onset): The free base (50.12 mg, 114 μmol) was placed in a 2 mL glass vial and EtOAc (100 μL) was added and the clear yellow solution stirred at RT. Hydrochloric acid (1N, 114 μL) was then added at RT and the solution stirred for 18 hr at RT. Heptane (500 μL) was then added to the solution at RT leading to precipitation within 10 min of the addition. The suspension was stirred for 2 hr at RT, the solid separated by centrifugation, and the powder dried under vacuum at 40° C. for 18 hr to give the title compound.

Example 45: (S)-8'-(difluoromethoxy)-7,8-difluoro-6'-(trifluoromethyl)-3'H-spiro[chroman-4,2'-imidazo[1,2-a]pyridine]

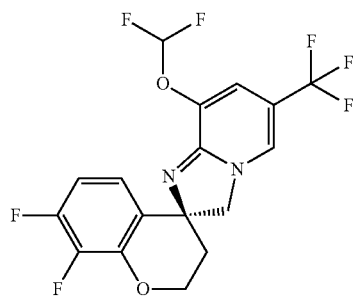

A solution of (S)-(4-((3-(difluoromethoxy)-5-(trifluoromethyl)pyridin-2-yl)amino)-7,8-difluorochroman-4-yl)methanol (Intermediate BC, 2.7 g, 6.33 mmol) and thionyl chloride (0.93 mL, 12.7 mmol) in toluene (38 mL) was stirred at 80° C. for 1 hr. The cooled RM was quenched by the addition of MeOH and evaporated. The residue was diluted with DCM, washed with saturated aq NaHCO$_3$, dried (phase separator) and evaporated. The crude residue was purified by normal phase flash chromatography (120 g SiO$_2$ column; eluent c-hexane:EtOAc 100:0 to 75:25) to give the title compound as a yellow foam.

$^1$H NMR (600 MHz, DMSO-d$_6$) δ 7.99 (br, s, 1H), 7.37 (t, 1H), 7.15-7.09 (m, 1H), 7.04 (d, 1H), 6.97-6.89 (m, 1H), 4.49-4.45 (m, 1H), 4.34-4.27 (m, 1H), 4.26 (s, 2H), 2.16-2.04 (m, 2H).

LC-MS: Rt=3.12 min; MS m/z [M+H]$^+$ 409.2; UPLC-MS 6.

The following salts were prepared from the above free base form of (S)-8'-(difluoromethoxy)-7,8-difluoro-6'-(trifluoromethyl)-3'H-spiro[chroman-4,2'-imidazo[1,2-a]pyridine] by precipitation with the appropriate counter ions.

Hydrochloride with 1:1 stoichiometry (mw 444.76), mp (DSC) 67° C. (onset): The free base (44.24 mg, 108 μmol) was placed in a 2 mL glass vial, tBuOMe (500 μL) was added, and the mixture stirred at 55° C. to give a clear yellow solution. Hydrochloric acid (1N, 108 μL) was added at 55° C. and the solution stirred for 4 hr at 55° C., followed by 18 hr at RT. Heptane (200 μL) was then added, and the clear solution evaporated to give a glass. Heptane (200 μL) was again added to the glass and the mixture stirred for 24 hr at RT, leading to the formation of a slurry. The slurry was centrifuged, and the solid dried under vacuum at 40° C. for 18 hr to give the title compound.

Example 46: (S)-8'-(difluoromethoxy)-8-fluoro-7-methyl-6'-(trifluoromethyl)-3'H-spiro[chroman-4,2'-imidazo[1,2-a]pyridine]

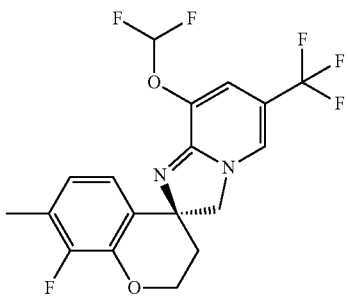 [SMILES: Cc1ccc2c(c1F)OCC[C@@]21CN2C=C(C(F)(F)F)C=C(OC(F)F)C2=N1]

(S)-7-bromo-8'-(difluoromethoxy)-8-fluoro-6'-(trifluoromethyl)-3'H-spiro[chroman-4,2'-imidazo[1,2-a]pyridine] (Example 39, 100 mg, 0.21 mmol), trimethylboroxine (26.8 mg, 0.21 mmol), tBuOK (71.8 mg, 0.64 mmol), XPhos-Pd-G3 (18.0 mg, 0.021 mmol), THF (2 mL) and water (1 mL) were added to a microwave vial, purged with argon, sealed and stirred under microwave heating at 100° C. for 1.5 hr. The RM was poured into saturated aq NaHCO$_3$ and extracted 2× with EtOAc. The combined organic extracts were dried (phase separator) and evaporated. The crude material was dissolved in THF (3 mL), SiliaMetS® Thiol (Particle Size: 40-63 μm, loading 1.39 mmol/g, 0.085 mmol, 64 mg) was added and the mixture swirled for 1 hr at 40° C. The mixture was filtered and the filtrate evaporated. The crude residue was purified by reverse phase preparative HPLC (RP-HPLC 3) and the product containing fractions were lyophilized to give the title compound.

¹H NMR (400 MHz, DMSO-d₆) δ 7.97 (br, s, 1H), 7.37 (t, 1H), 7.01 (br s, 1H), 6.93 (d, 1H), 6.75 (t, 1H), 4.40 (m, 1H), 4.24 (s, 2H), 4.22 (m, 1H), 2.19 (s, 3H), 2.09-2.05 (m, 2H).

LC-MS: Rt=3.37 min; MS m/z [M+H]⁺ 405.1; UPLC-MS 6.

Example 47: (S)-8'-(difluoromethoxy)-8-fluoro-6'-(trifluoromethyl)-3'H-spiro[chroman-4,2'-imidazo[1,2-a]pyridine]

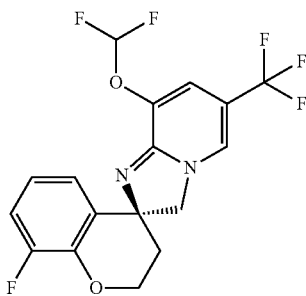

Pd—C (5%, 75 mg, 0.71 mmol) was added to a solution of (S)-7-bromo-8'-(difluoromethoxy)-8-fluoro-6'-(trifluoromethyl)-3'H-spiro[chroman-4,2'-imidazo[1,2-a]pyridine] (Example 39, 600 mg, 1.28 mmol) in THF (15 mL) and MeOH (15 mL), and the mixture shaken under a hydrogen atmosphere for 3 hr at RT. The RM was filtered through a pad of Celite, washing with MeOH, the filtrate evaporated, and the crude residue purified by normal phase chromatography (80 g SiO₂ column, eluent DCM:MeOH 100:0 to 70:30) followed by reverse phase preparative HPLC (RP-HPLC 3). The product containing fractions were extracted with DCM and evaporated to give the title compound as a yellow solid.

¹H NMR (400 MHz, DMSO-d₆) δ 7.97 (br, s, 1H), 7.37 (t, 1H), 7.13-7.05 (m, 2H), 7.02 (d, 1H), 6.89-6.81 (m, 1H), 4.45-4.37 (m, 1H), 4.30-4.19 (m, 3H), 2.14-2.06 (m, 2H).

LC-MS: Rt=2.85 min; MS m/z [M+H]⁺ 391.1; UPLC-MS 6.

Example 48: (S)-8-chloro-8'-(difluoromethoxy)-6'-(trifluoromethyl)-3'H-spiro[chroman-4,2'-imidazo[1,2-a]pyridine]

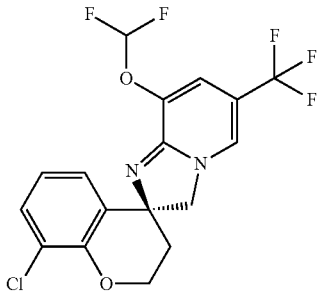

A mixture of (S)-(4-amino-8-chlorochroman-4-yl)methanol (Intermediate BE, 423 mg, 1.98 mmol), 2-chloro-3-(difluoromethoxy)-5-(trifluoromethyl)pyridine (Intermediate A, 1.00 g, 4.05 mmol), CuBr (113 mg, 791 μmol) and K₃PO₄ (839 mg, 3.95 mmol) in DMF (5 mL) was heated in a sealed vial at 140° C. for 90 min under a N2 atmosphere. To the cooled RM was added additional 2-chloro-3-(difluoromethoxy)-5-(trifluoromethyl)pyridine (1.00 g, 4.05 mmol), CuBr (113 mg, 791 μmol) and K₃PO₄ (839 mg, 3.95 mmol) and the heating continued at 140° C. for a further 90 min. The RM was partitioned between EtOAc and saturated aq NaHCO₃, extracted 2× with EtOAc, dried and evaporated. The residue was purified by normal phase chromatography (50 g SNAP SiO₂ cartridge, eluent hexane:EtOAc 100:0 to 65:35) followed by reversed phase chromatography (RP-HPLC 2), and the product containing fractions evaporated to leave a predominantly aq phase which was basified with saturated aq NaHCO₃, extracted with DCM, the organic layers dried and evaporated to give the title compound as a yellow foam.

¹H NMR (400 MHz, DMSO-d₆) δ 7.97 (s, 1H), 7.34-7.19 (m, 2H), 7.61-7.14 (m, 1H), 7.02 (d, 1H), 6.90 (t, 1H), 4.55-4.38 (m, 1H), 4.35-4.20 (m, 3H), 2.17-2.00 (m, 2H).

LC-MS: Rt=3.10 min; MS m/z [M+H]⁺ 407.2/409.2; UPLC-MS 4.

Example 49: (S)-7-bromo-8'-(difluoromethoxy)-8-fluoro-3'H-spiro[chroman-4,2'-imidazo[1,2-a]pyridine]-6'-carbonitrile

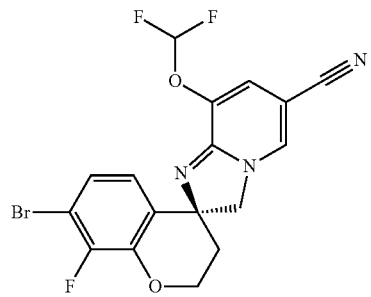 [SMILES: N#CC1=CN2C[C@@]3(CCOc4c3ccc(Br)c4F)N=C2C(OC(F)F)=C1]

A solution of (S)-(4-amino-7-bromo-8-fluorochroman-4-yl)methanol (Intermediate AT, 200 mg, 0.72 mmol), 6-chloro-5-(difluoromethoxy)nicotinonitrile (Intermediate B, 326 mg, 1.59 mmol), copper(I) bromide (31.2 mg, 0.22 mmol) and potassium phosphate (308 mg, 1.45 mmol) in DMF (4.8 mL) was heated at 120° C. in a microwave 1.5 hr. The RM was poured into saturated aq NaHCO₃ and extracted 3× with EtOAc. The combined organic extracts were washed 2× with water, dried (phase separator) and concentrated. The residue was dissolved in THF (3 mL), SiliaMetS® Thiol (Particle Size: 40-63 μm, loading 1.35 mmol/g, 0.087 mmol, 64 mg) was added and the mixture swirled for 1 hr at 40° C. The mixture was filtered and the filtrate was evaporated. The crude residue was purified by normal phase flash chromatography (40 g SiO₂ column, eluent EtOAc:c-hexane 0:100 to 50:50) to give the title compound as a yellow foam.

¹H NMR (600 MHz, DMSO-d₆) δ 8.21 (d, 1H), 7.28 (t, 1H), 7.19-7.15 (m, 1H), 7.11 (d, 1H), 7.05 (dd, 1H), 4.48-4.43 (m, 1H), 4.33-4.27 (m, 1H), 4.27 (s, 2H), 2.19-2.05 (m, 2H).

LC-MS: Rt=3.34 min; MS m/z [M+H]⁺ 426.1/428.1; UPLC-MS 6.

Example 50: (S)-7-bromo-8'-(difluoromethoxy)-6'-(trifluoromethyl)-3'H-spiro[chroman-4,2'-imidazo[1,2-a]pyridine]

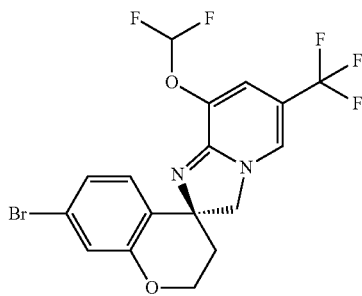

SOCl$_2$ (0.15 mL, 2.06 mmol) was added to (S)-(7-bromo-4-((3-(difluoromethoxy)-5-(trifluoromethyl)pyridin-2-yl)amino)chroman-4-yl)methanol (Intermediate BF, 615 mg, 1.11 mmol) in toluene (10 mL) under Ar. The RM was heated to 80° C. for 1 hr, cooled, then quenched with saturated aq NaHCO$_3$ and extracted with EtOAc. The combined organic layers were washed with brine, dried over Na$_2$SO$_4$, filtered and evaporated. The residue was absorbed onto Isolute and purified by normal phase chromatography (80 g SiO$_2$-column; eluent heptane:EtOAc 100:0 to 70:30). Product containing fractions were combined and evaporated to give a yellow foam. The product was dissolved in iPrOH (12 mL) and stirred at 80° C. for 5 min, then the solution was allowed to cool to RT and stirred for 5 days to recrystallize. The crystals were isolated by filtration, washing with iPrOH, and then dried to give the title compound as yellow crystals.

$^1$H NMR (400 MHz, DMSO-d$_6$) δ 7.96 (s, 1H), 7.36 (t, 2H), 7.20 (d, 1H), 7.07 (dd, 1H), 7.04-6.97 (m, 2H), 4.44-4.31 (m, 1H), 4.23 (s, 2H), 4.21-4.13 (m, 1H), 2.11-1.98 (m, 2H).

LC-MS: Rt=0.79 min; MS m/z [M+H]$^+$ 451.1/453.1; UPLC-MS 1.

Example 51: (S)-8'-(difluoromethoxy)-8-fluoro-7-iodo-3'H-spiro[chroman-4,2'-imidazo[1,2-a]pyridine]-6'-carbonitrile

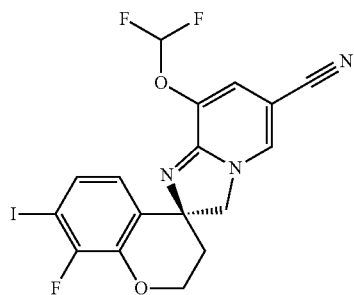 [SMILES: N#CC1=CN2C[C@@]3(CCOc4c3ccc(I)c4F)N=C2C(OC(F)F)=C1]

A mixture of (S)-7-bromo-8'-(difluoromethoxy)-8-fluoro-3'H-spiro[chroman-4,2'-imidazo[1,2-a]pyridine]-6'-carbonitrile (Example 49, 232 mg, 544 µmol), CuI (52 mg, 272 mmol), NaI (163 mg, 1.09 mmol) and trans-N,N-dimethyl-1,2-cyclohexanediamine (8.6 µL, 54 µmol) in 1,4-dioxane (2 mL) was heated in a sealed tube at 110° C. under an atmosphere of nitrogen for 18 hr. The cooled RM was partitioned between DCM and 30% aq NH$_3$, the aq phase extracted 3× with DCM, the combined organic phases were dried by passing through a separator phase cartridge and concentrated. The residue was purified by reversed phase chromatography (RP-HPLC 2), the product containing fractions were lyophilized and then triturated with MeOH to give the title compound as a yellow powder.

$^1$H NMR (400 MHz, MeOH-d$_4$) δ 7.95 (s, 1H), 7.29 (dd, 1H), 7.01 (s, 1H), 6.86 (d, 1H), 7.20-6.71 (m, 1H), 4.56-4.42 (m, 1H), 4.41-4.22 (m, 3H), 2.33-2.06 (m, 2H).

LC-MS: Rt=3.45 min; MS m/z [M+H]$^+$ 474.1; UPLC-MS 4.

Example 52: (S)-7-bromo-6'-chloro-8'-(difluoromethoxy)-8-fluoro-3'H-spiro[chroman-4,2'-imidazo[1,2-a]pyridine]

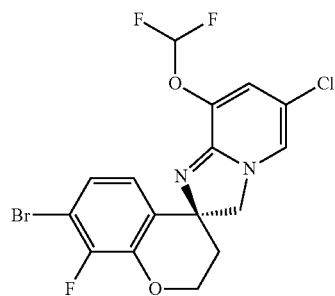

A mixture of (S)-(4-amino-7-bromo-8-fluorochroman-4-yl)methanol (Intermediate AT, 100 mg, 0.36 mmol), 2-bromo-5-chloro-3-(difluoromethoxy)pyridine (Intermediate F, 186 mg, 0.72 mmol), CuBr (15.6 mg, 0.11 mmol) and potassium phosphate (154 mg, 0.72 mmol) in DMF (3.6 mL) was heated at 140° C. in a microwave for 4 hr. The RM was poured into saturated aq NaHCO$_3$, extracted 3× with EtOAc. The combined organic extracts were dried (phase separator) and concentrated. The crude material was dissolved in THF (5 mL), SiliaMetS®Thiol (Particle Size: 40-63 µm, loading 1.35 mmol/g, 0.44 mmol, 323 mg) was added, the mixture swirled for 1 hr at 40° C., filtered and the filtrate was evaporated. The crude residue was purified by normal phase flash chromatography (12 g SiO$_2$ column, eluent c-hexane:EtOAc 100:0 to 50:50), then by reverse phase preparative HPLC (RP-HPLC 2) and the product containing fractions basified with saturated aq. NaHCO$_3$, extracted with DCM, the organic layers dried and evaporated to give the title compound as a yellow solid.

$^1$H NMR (600 MHz, DMSO-d$_6$) δ 7.60 (br, s, 1H), 7.36 (t, 1H), 7.16 (dd, 1H), 7.04 (d, 1H), 6.98 (br, s, 1H), 4.45 (m, 1H), 4.29 (m, 1H), 4.20 (s, 2H), 2.12-2.03 (m, 2H).

LC-MS: Rt=3.20 min; MS m/z [M+H]$^+$ 435.1/437.1; UPLC-MS 6.

Example 53: (S)-8'-chloro-6',7-bis(trifluoromethyl)-3'H-spiro[chroman-4,2'-imidazo[1,2-a]pyridine]

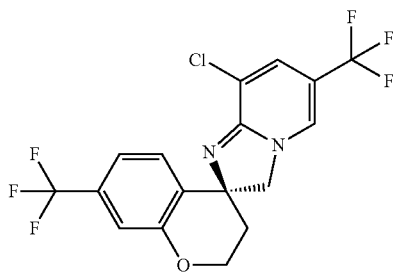 [SMILES: FC(F)(F)C1=CN2C[C@@]3(CCOc4cc(C(F)(F)F)ccc43)N=C2C(Cl)=C1]

To a solution of (4-((3-chloro-5-(trifluoromethyl)pyridin-2-yl)amino)-7-(trifluoromethyl)chroman-4-yl)methanol (Intermediate P2, 57 mg, 135 µmol) in toluene (2 mL) was added thionyl chloride (0.05 mL, 0.67 mmol) and the RM was stirred at 80° C. for 2.5 hr. The RM was allowed to cool to RT, poured into saturated aq NaHCO$_3$ and extracted 3× with DCM. The combined organic extracts were dried (phase separator) and concentrated. The crude residue was purified by reverse phase preparative HPLC (RP-HPLC 2) and the product containing fractions basified with saturated aq NaHCO$_3$, extracted with DCM, the organic layers dried (phase separator) and evaporated to give the racemic title compound. The enantiomers were separated by preparative chiral HPLC (instrument: Gilson PLC2020; column: Chiralpak ID; 5 µm, 250×20 mm, RT; eluent: heptane/EtOH 80/20+0.1% Et$_2$NH; flow rate: 10 mL/min; detection: 250 nm; injection volume: 1.5 mL) to give the title compound as the second eluting peak (yellow solid).

$^1$H NMR (600 MHz, DMSO-d$_6$) δ 8.08 (br, s, 1H), 7.53 (d, 1H), 7.48 (d, 1H), 7.24 (dd, 1H), 7.12 (d, 1H), 4.44-4.39 (m, 1H), 4.37 (d, 1H), 4.33 (d, 1H), 4.27-4.22 (m, 1H), 2.18-2.05 (m, 2H).

LC-MS: Rt=3.68 min; MS m/z [M+H]$^+$ 409.2/411.2; UPLC-MS 6.

Chiral-HPLC: Rt=9.99 min; with (R)-8'-chloro-6',7-bis(trifluoromethyl)-3'H-spiro[chroman-4,2'-imidazo[1,2-a]pyridine] eluting as the first peak Chiral-HPLC: Rt=3.95 min; (C-HPLC 28).

Example 54: (S)-7,8'-bis(difluoromethoxy)-8-fluoro-6'-(trifluoromethyl)-3'H-spiro[chroman-4,2'-imidazo[1,2-a]pyridine]

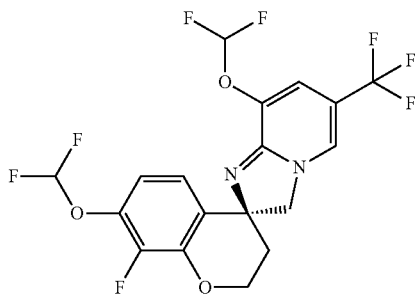

To a solution of (S)-8'-(difluoromethoxy)-8-fluoro-6'-(trifluoromethyl)-3'H-spiro[chroman-4,2'-imidazo[1,2-a]pyridin]-7-ol (Intermediate BI, 20 mg, 46 µmol) and KOH (52 mg, 925 µmol) in a mixture of AcCN (1 mL) and water (1 mL) was added diethyl (bromodifluoromethyl)phosphonate (37.1 mg, 139 µmol) and the RM stirred at RT for 30 min. The RM was then extracted with EtOAc and the combined organic layers washed with brine, filtered through a phase separator and the filtrate evaporated. The residue was purified by reverse phase chromatography (RP-HPLC 2). Product containing fractions were combined and partitioned between DCM and saturated aq NaHCO$_3$. The combined organic layers were filtered through a phase separator and the filtrate evaporated. The residue was absorbed onto Isolute and repurified by normal phase chromatography (4 g SiO$_2$-column; eluent DCM:MeOH 100:0 to 80:20). Product containing fractions were combined, evaporated and dried to give the title compound.

$^1$H NMR (600 MHz, DMSO-d$_6$) δ 7.99 (s, 1H), 7.52-7.32 (m, 1H), 7.24 (d, 1H), 7.17-7.08 (m, 1H), 7.05 (d, 1H), 6.88 (t, 1H), 4.47 (ddd, 1H), 4.33-4.23 (m, 3H), 2.18-2.05 (m, 2H).

LC-MS: Rt=0.84 min; MS m/z [M+H]$^+$ 457.2; UPLC-MS 1.

Example 55: (S)-8'-(difluoromethoxy)-8-(difluoromethyl)-6'-(trifluoromethyl)-3'H-spiro[chroman-4,2'-imidazo[1,2-a]pyridine]

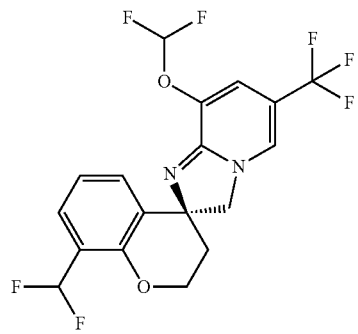 [SMILES: FC(F)OC1=CC(C(F)(F)F)=CN2C[C@@]3(CCOc4c(C(F)F)cccc43)N=C12]

DAST (20 µL, 148 µmol) was added to a solution of (S)-8'-(difluoromethoxy)-6'-(trifluoromethyl)-3'H-spiro[chroman-4,2'-imidazo[1,2-a]pyridine]-8-carbaldehyde (Intermediate BJ, 40 mg, 74 µmol) in DCM (1 mL) at RT and stirred for 16 hr. Additional DAST (10 µL, 74 µmol) was added and the RM was stirred for 5 days at RT. The RM was then partitioned between DCM (20 mL) and saturated aq NaHCO$_3$ (20 mL), extracted 2× with DCM (5 mL), the combined organic layers dried by passing through a phase separator cartridge and evaporated. The residue was purified by normal phase chromatography (4 g SiO$_2$ column, eluent hexane:TBME 90:10 to 10:90) to give the title compound as a beige solid.

$^1$H NMR (400 MHz, chloroform-d) δ 7.52-7.42 (m, 2H), 7.30-7.21 (m, 1H), 7.04-6.72 (m, 4H), 4.61-4.56 (m, 1H), 4.40-4.21 (m, 3H), 2.45-2.36 (m, 1H), 2.21-2.08 (m, 1H).

LC-MS: Rt=0.78 min; MS m/z [M+H]$^+$ 423.2; UPLC-MS 1.

Example 56: (S)-8'-chloro-8-(difluoromethoxy)-6-(trifluoromethyl)-2',3'-dihydro-3H-spiro[imidazo[1,2-a]pyridine-2,4'-pyrano[2,3-c]pyridine]

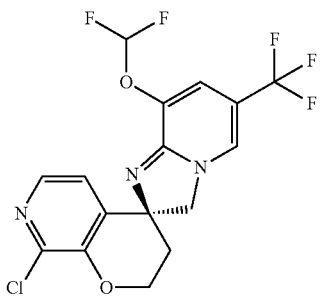 [SMILES: FC(F)OC1=CC(C(F)(F)F)=CN2C[C@@]3(CCOc4c3ccnc4Cl)N=C12]

A mixture of (S)-8'-chloro-3-(3-(difluoromethoxy)-5-(trifluoromethyl)pyridin-2-yl)-2',3'-dihydrospiro[oxazolidine-4,4'-pyrano[2,3-c]pyridin]-2-one (Intermediate BK, 408 mg, 813 µmol), aq NaOH (4M, 2.03 mL, 8.13 mmol) and EtOH (10 mL) was stirred for 20 min at 80° C. The cooled RM was extracted with EtOAc, washed with saturated aq NaHCO₃, dried and concentrated. The residue was taken up into toluene (10 mL) and SOCl₂ (89 µL, 1.22 mmol) added and the RM stirred for 20 min at 80° C. MeOH was added to the cooled RM which was concentrated, partitioned between EtOAc and saturated aq NaHCO₃, the combined organic layers dried and concentrated. The residue was purified by reversed phase chromatography (RP-HPLC 2) and product containing fractions were combined and evaporated. The residue was partitioned between DCM and saturated aq NaHCO₃, the combined organic layers dried and concentrated to give the title compound as a yellow solid.

¹H NMR (400 MHz, DMSO-d₆) δ 8.03 (s, br, 1H), 7.93 (d, 1H), 7.61-6.96 (m, 3H), 4.56-4.46 (m, 1H), 4.39-4.20 (m, 3H), 2.24-2.05 (m, br, 2H).

LC-MS: Rt=2.42 min; MS m/z [M+H]⁺ 408.1/410.1; UPLC-MS 4.

Example 57: (2'S,3R)-7-bromo-8'-(difluoromethoxy)-3,8-difluoro-6'-(trifluoromethyl)-3'H-spiro[chroman-4,2'-imidazo[1,2-a]pyridine]

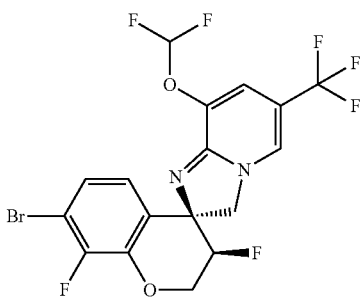

A mixture of ((3R,4S)-4-amino-7-bromo-3,8-difluorochroman-4-yl)methanol (Intermediate BO, 273 mg, 928 µmol), 2-chloro-3-(difluoromethoxy)-5-(trifluoromethyl)pyridine (Intermediate A, 306 mg, 1.11 mmol), CuBr (53 mg, 371 µmol), K₃PO₄ (394 mg, 1.86 mmol) and DMF (1.5 mL) was sealed in a vial under a N2 atmosphere and heated in a microwave for 90 min at 140° C. The cooled RM was partitioned between saturated aq NaHCO₃ and EtOAc, the combined organic layers dried and concentrated. Additional 2-chloro-3-(difluoromethoxy)-5-(trifluoromethyl)pyridine (306 mg, 1.11 mmol), CuBr (53 mg, 371 µmol), K₃PO₄ (394 mg, 1.86 mmol) and DMF (1.5 mL) were added and the mixture sealed in a vial under a N2 atmosphere and heated in a microwave for a further 90 min at 140° C. The cooled RM was partitioned between saturated aq NaHCO₃ and EtOAc, the combined organic layers dried and concentrated. The residue was purified by normal phase chromatography (50 g SiO₂ SNAP cartridge, eluent hexane:(95:5 TBME:MeOH) 100:0 to 65:35) followed by reversed phase chromatography (RP-HPLC 3) and the product containing fractions extracted with DCM, the combined organic layers dried and concentrated. The residue was taken up into MeOH and the volume reduced to enable the title compound to crystallise as a yellow solid which was collected by filtration.

¹H NMR (400 MHz, DMSO-d₆) δ 7.98 (s, 1H), 7.63-7.17 (m, 2H), 7.16-6.97 (m, 2H), 5.23-4.93 (m, 1H), 4.73-4.53 (m, 1H), 4.51-4.33 (m, 1H), 4.33-4.08 (m, 2H).

LC-MS: Rt=3.83 min; MS m/z [M+H]⁺ 487.1/489.0; UPLC-MS 4.

Example 58: (2'S,3S)-7-bromo-8'-(difluoromethoxy)-3,8-difluoro-6'-(trifluoromethyl)-3'H-spiro[chroman-4,2'-imidazo[1,2-a]pyridine]

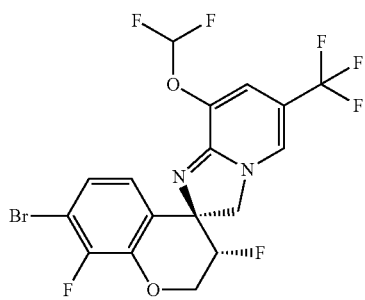

The title compound was prepared by a method similar to that of Example 57 by replacing ((3R,4S)-4-amino-7-bromo-3,8-difluorochroman-4-yl)methanol (Intermediate BO) with ((3S,4S)-4-amino-7-bromo-3,8-difluorochroman-4-yl)methanol (Intermediate BU). The title compound was obtained as a pale-orange powder after normal phase chromatography (25 g SiO₂ SNAP cartridge, eluent hexane:EtOAc 100:0 to 80:20).

¹H NMR (400 MHz, DMSO-d₆) δ 8.10 (br, s, 1H), 7.57-7.11 (m, 4H), 5.12-4.85 (m, 1H), 4.69-4.35 (m, 4H).
LC-MS: Rt=5.20 min; MS m/z [M+H]⁺ 487.1/489.0; UPLC-MS 4.

Example 59: (2'S,3R)-7-bromo-8'-(difluoromethoxy)-3-fluoro-6'-(trifluoromethyl)-3'H-spiro[chroman-4,2'-imidazo[1,2-a]pyridine]

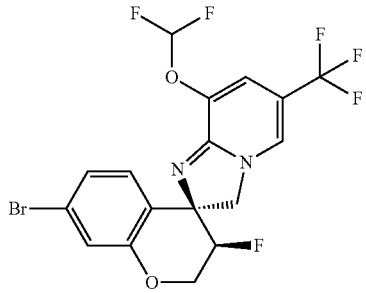

The title compound was prepared by a method similar to that of Example 57 by replacing ((3R,4S)-4-amino-7-bromo-3,8-difluorochroman-4-yl)methanol (Intermediate BO) with ((3R,4S)-4-amino-7-bromo-3-fluorochroman-4-yl)methanol (Intermediate BV). The title compound was obtained as a pale-yellow solid after normal phase chromatography (50 g silica SNAP column, eluent hexane:EtOAc 100:0 to 80:20).

$^1$H NMR (400 MHz, DMSO-$d_6$) δ 7.97 (s, 1H), 7.63-7.17 (m, 2H), 7.16-7.11 (m, 1H), 7.08 (dd, 2H), 5.14-4.89 (m, 1H), 4.59-4.42 (m, 1H), 4.40-4.14 (m, 3H).

LC-MS: Rt=3.42 min; MS m/z [M+H]$^+$ 469.0/471.0; UPLC-MS 4.

Example 60: (2'S,3R)-8'-(difluoromethoxy)-3-fluoro-7-iodo-6'-(trifluoromethyl)-3'H-spiro[chroman-4,2'-imidazo[1,2-a]pyridine]

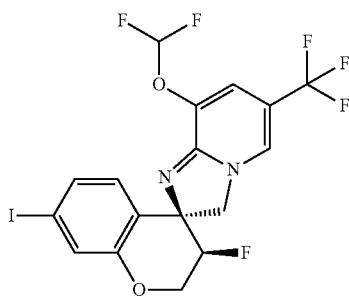 [SMILES: FC(F)OC1=CC(C(F)(F)F)=CN2C[C@@]3(N=C12)c1ccc(I)cc1OC[C@@H]3F]

The title compound was prepared by a method similar to that of Example 51 by replacing (S)-7-bromo-8'-(difluoromethoxy)-8-fluoro-3'H-spiro[chroman-4,2'-imidazo[1,2-a]pyridine]-6'-carbonitrile (Example 49) with (2'S,3R)-7-bromo-8'-(difluoromethoxy)-3-fluoro-6'-(trifluoromethyl)-3'H-spiro[chroman-4,2'-imidazo[1,2-a]pyridine] (Example 59). The title compound was obtained as a yellow powder after trituration with MeOH.

$^1$H NMR (400 MHz, DMSO-$d_6$) δ 7.96 (br, s, 1H), 7.66-7.14 (m, 3H), 7.12-6.92 (m, 2H), 5.14-4.85 (m, 1H), 4.47-4.34 (m, 1H), 4.38-4.10 (m, 3H).

LC-MS: Rt=3.69 min; MS m/z [M+H]$^+$ 517.0; UPLC-MS 4.

Example 61: (2'S,3R)-8'-(difluoromethoxy)-3-fluoro-6',7-bis(trifluoromethyl)-3'H-spiro[chroman-4,2'-imidazo[1,2-a]pyridine]

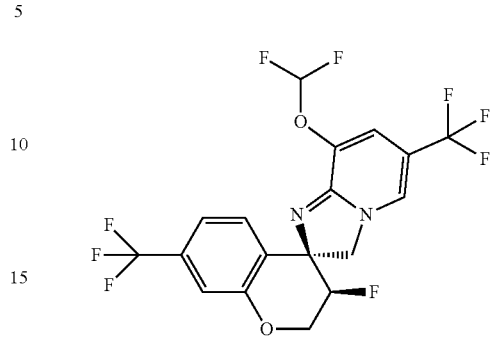

The title compound was prepared by a method similar to that of Example 40 by replacing (S)-8'-(difluoromethoxy)-8-fluoro-7-iodo-6'-(trifluoromethyl)-3'H-spiro[chroman-4,2'-imidazo[1,2-a]pyridine] (Intermediate AW) with (2'S,3R)-8'-(difluoromethoxy)-3-fluoro-7-iodo-6'-(trifluoromethyl)-3'H-spiro[chroman-4,2'-imidazo[1,2-a]pyridine] (Example 60). The title compound was obtained as yellow needles after normal phase chromatography (40 g SiO$_2$ Redisep cartridge, eluent hexane:TBME 100:0 to 0:100) followed by reversed phase chromatography (RP-HPLC 2) and partitioning of the product containing fractions between DCM and saturated aq NaHCO$_3$, extracting 2× with DCM, drying the combined organic layers by passing through a phase separator cartridge and evaporation.

$^1$H NMR (400 MHz, DMSO-$d_6$) δ 7.98 (s, 1H), 7.61-7.21 (m, 4H), 7.12 (s, 1H), 5.21-4.93 (m, 1H), 4.65-4.48 (m, 1H), 4.46-4.15 (m, 3H).

LC-MS: Rt=4.06 min; MS m/z [M+H]$^+$ 459.1; UPLC-MS 4.

Example 62: (2'S,3R)-8'-(difluoromethoxy)-3,8-difluoro-6'-(trifluoromethyl)-3'H-spiro[chroman-4,2'-imidazo[1,2-a]pyridine]

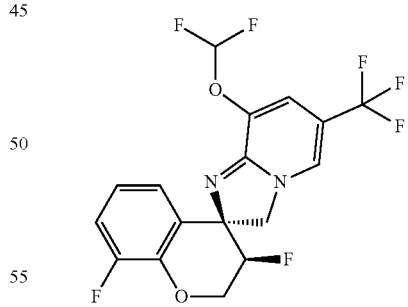

A mixture of ((3R,4S)-4-amino-3,8-difluorochroman-4-yl)methanol (Intermediate BW, 5.0 g, 22.77 mmol), 2-chloro-3-(difluoromethoxy)-5-(trifluoromethyl)pyridine (Intermediate A, 11.27 g, 45.5 mmol), CuBr (1.31 g, 9.11 mmol) and K$_2$PO$_4$ (9.67 g, 45.5 mmol) in DMF (24 mL) was heated at 140° C. for 1.5 hr in a sealed vial under an argon atmosphere. The cooled RM was filtered washing with EtOAc (150 mL), the filtrate washed with saturated aq NaHCO$_3$, dried and concentrated. Additional 2-chloro-3-

(difluoromethoxy)-5-(trifluoromethyl)pyridine (11.27 g, 45.5 mmol), CuBr (1.31 g, 9.11 mmol), K$_2$PO$_4$ (9.67 g, 45.5 mmol) and DMF (5 mL) were added to the residue and the mixture heated at 140° C. for 1.5 hr in a sealed vial under an argon atmosphere. The cooled RM was filtered, washing with EtOAc (150 mL), the filtrate washed with saturated aq NaHCO$_3$, dried and concentrated. The residue was purified by normal phase chromatography (340 g silica gel, eluent c-hexane:EtOAc 100:0 to 70:30). Product containing fractions were combined and evaporated, the residue taken up into 1N aq HCl and the aq layer washed with EtOAc, and washed a further 3× with EtOAc. The acidic aq layer was made basic with saturated aq NaHCO$_3$ (pH 8), extracted with 3× with DCM, the combined DCM layers dried and evaporated. The residue was then taken up into the minimum volume of MeOH and the solution slowly evaporated on a rotavapor until the first solid material precipitated. The solution was then allowed to stand at RT for 3 hr and the formed precipitate collected by filtration and dried to give the title compound as a pale yellow powder.

$^1$H NMR (400 MHz, DMSO-d$_6$) δ 7.98 (s, 1H), 7.40 (t, 1H), 7.19 (t, 1H), 7.11 (s, 1H), 7.07 (d, 1H), 6.97-6.89 (m, 1H), 5.08 (dd, 1H), 4.62-4.53 (m, 1H), 4.42-4.22 (m, 3H).

LC-MS: Rt=0.67 min; MS m/z [M+H]$^+$ 409.0; UPLC-MS 1.

The following salts were prepared from the above free base form of (2'S,3R)-8'-(difluoromethoxy)-3,8-difluoro-6'-(trifluoromethyl)-3'H-spiro[chroman-4,2'-imidazo[1,2-a]pyridine] by precipitation with the appropriate counter ions.

Hydrochloride with 1:1 stoichiometry (mw 444.76): The free base (50.8 mg, 124 μmol) was placed in a 2 mL glass vial and tBuOMe (1 mL) was added and the clear solution stirred at 55° C.

Hydrochloric acid (1N, 124 μL) was then slowly added at 55° C., and the solution slowly becomes a suspension. Stirring was continued at 55° C. for 4 hr, then for 18 hr at RT, the solid was separated by centrifugation, and the powder dried under vacuum at 40° C. for 18 hr to give the title compound.

Sulfate with 1:1 stoichiometry iPrOH solvate (1:1) (mw 506.38), mp (DSC) broad endothermic transition 147° C., and 206° C. (onset): The free base (50.74 mg, 124 μmol) was placed in a 2 mL glass vial and iPrOH (1.2 mL) was added. Hydrochloric acid (1N, 124 μL) was then added at 55° C. and the solution stirred for 4 hr at 55° C., and then for 18 hr at RT leading to precipitation. The solid was separated by centrifugation, and the powder dried under vacuum at 40° C. for 18 hr to give the title compound.

Citrate with 1:1 stoichiometry AcCN solvate (1:1) (mw 600.42), mp (DSC) broad endothermic transition 140° C., and 176° C. (onset): The free base (51.84 mg, 126 μmol) was placed in a 2 mL glass vial and AcCN (0.6 mL) was added. Citric acid (24.4 mg, 127 μmol) was then added at 55° C. and the slurry stirred for 4 hr at 55° C., and then for 18 hr at RT. The solid was separated by centrifugation, and the powder dried under vacuum at 40° C. for 18 hr to give the title compound.

Example 63: (S)-8-(difluoromethoxy)-8'-fluoro-6-(trifluoromethyl)-3H-spiro[imidazo[1,2-a]pyridine-2,4'-isochroman]

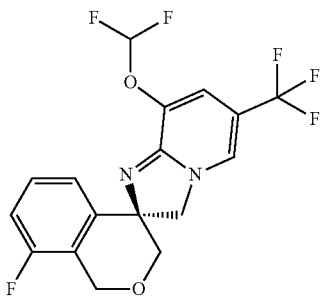 [SMILES: Fc1cccc2c1COC[C@@]21CN2C=C(C(F)(F)F)C=C(OC(F)F)C2=N1]

To a solution of rac-(4-((3-(difluoromethoxy)-5-(trifluoromethyl)pyridin-2-yl)amino)-8-fluoroisochroman-4-yl)methanol (Intermediate BZ, 598 mg, 1.39 mmol) in toluene (9 mL) was added thionyl chloride (0.20 mL, 2.78 mmol) and the RM was stirred at 80° C. for 1 hr. The RM was quenched by addition of saturated aq NaHCO$_3$ and extracted 2× with EtOAc. The combined organic extracts were dried (phase separator), evaporated, and the crude residue was purified by normal phase flash chromatography (80 g silica column, eluent c-hexane:EtOAc 100:0 to 50:50) to give the racemic title compound. The enantiomers were separated by preparative chiral HPLC (instrument: Gilson Trilution HPLC system; column: Chiralcel OJ-H; 5 μm, 250×30 mm, RT; eluent: heptane/iPrOH 70/30+0.1% Et$_2$NH; flow rate: 20 mL/min; detection: 230 nm; injection volume: 1.5 mL) to give the title compound as the second eluting peak (yellow solid).

$^1$H NMR (600 MHz, DMSO-d$_6$) δ 7.97 (br s, 1H), 7.36 (t, 1H), 7.33 (m, 1H), 7.21 (d, 1H), 7.11 (t, 1H), 7.07 (br s, 1H), 4.75 (d, 1H), 4.87 (d, 1H), 4.43 (d, 1H), 4.00 (d, 1H), 3.86 (d, 1H), 3.58 (d, 1H).

LC-MS: Rt=2.85 min; MS m/z [M+H]$^+$ 391.1; UPLC-MS 6.

Chiral-HPLC: Rt=7.37 min; with ((R)-8-(difluoromethoxy)-8'-fluoro-6-(trifluoromethyl)-3H-spiro[imidazo[1,2-a]pyridine-2,4'-isochroman] obtained as the first eluting peak, Rt=5.89 min; (C-HPLC 29).

Example 64: (S)-7'-chloro-8-(difluoromethoxy)-8'-fluoro-3H-spiro[imidazo[1,2-a]pyridine-2,4'-thiochroman]-6-carbonitrile

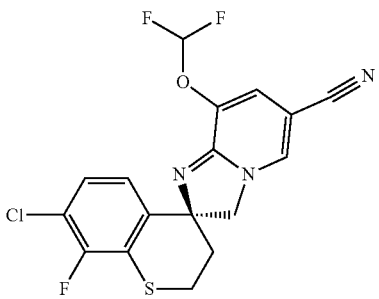 [SMILES: N#CC1=CN2C[C@@]3(CCSc4c3ccc(Cl)c4F)N=C2C(OC(F)F)=C1]

Cs$_2$CO$_3$ (1.15 g, 3.54 mmol) was added to a suspension of 6-(7'-chloro-8'-fluoro-2-oxospiro[oxazolidine-4,4'-thiochroman]-3-yl)-5-(difluoromethoxy)nicotino-nitrile (Intermediate CA, 3.43 g, 5.90 mmol) in MeOH (113 mL) and the RM was stirred at 90° C. for 2 hr. The RM was allowed to cool to RT and extracted with EtOAc. The organic phase was washed with saturated aq NaHCO$_3$, dried over a phase separator and concentrated in vacuo. The residue was dissolved in toluene (113 mL) and SOCl$_2$ (1.29 mL, 17.70 mmol) added, and the resulting mixture was stirred for 1 hr at 90° C. The RM was cooled to RT, MeOH was slowly added, and the resulting mixture concentrated in vacuo. The residue was taken up into EtOAc, washed with saturated aq NaHCO$_3$, dried over a phase separator and concentrated. The residue was purified by flash column chromatography (silica gel, eluent heptane:EtOAc 100:0 to 30:70) to give the racemic title compound. The enantiomers were separated by chiral SFC: (instrument: MG II preparative SFC; column: Chiralpak AD, 250×30 mm 5 μm at 38° C.; eluent: CO$_2$: EtOH containing 0.1% aq. NH$_3$; Gradient: 35% EtOH containing 0.1% aq. NH$_3$; flow rate: 50 mL/min; Detection: 220 nm) to give the title compound as the second eluting peak.

$^1$H NMR (400 MHz, DMSO-d$_6$) δ 8.16 (s, 1H), 7.50-7.15 (m, 3H), 7.10 (s, 1H), 4.36-4.08 (m, 2H), 3.26-3.08 (m, 2H), 2.30-2.01 (m, 2H).

LC-MS: Rt=3.78 min; MS m/z [M+H]$^+$ 398.0; UPLC-MS 4.

Chiral-SFC: Rt=5.28 min; with (R)-7'-chloro-8-(difluoromethoxy)-8'-fluoro-3H-spiro[imidazo[1,2-a]pyridine-2,4'-thiochroman]-6-carbonitrile as the first eluting peak, Rt=4.83 min; C-SFC 30.

Example 65: (S)-8-(difluoromethoxy)-8'-fluoro-6-(trifluoromethyl)-3H-spiro[imidazo[1,2-a]pyridine-2,4'-thiochroman]

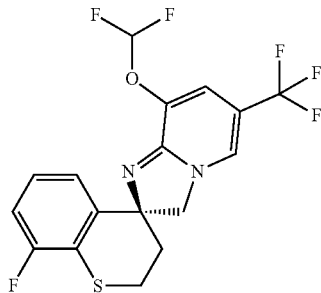 [SMILES: Fc1cccc2c1SCC[C@@]21CN2C=C(C(F)(F)F)C=C(OC(F)F)C2=N1]

(4-Amino-8-fluorothiochroman-4-yl)methanol (Intermediate CE, 100 mg, 445 μmol), 2-bromo-3-(difluoromethoxy)-5-(trifluoromethyl)pyridine (Intermediate CC, 199 mg, 668 μmol), K$_2$CO$_3$ (123 mg, 891 μmol) and CuI (8.48 mg, 45 μmol) were dissolved in DMF (2.6 mL). The resulting green suspension was irradiated for 30 min at 160° C. in a microwave oven. The cooled RM was diluted with EtOAc, the organic phase washed with saturated aq NaHCO$_3$ and brine, filtered through a phase separator and concentrated. The residue was purified by normal phase chromatography on (silica gel, eluent heptane:EtOAc) to give the racemic title compound. The enantiomers were separated by chiral HPLC: (instrument: Gilson PLC2020 HPLC system; column: Chiralcel OD-H; 5 μm 250×20 mm at 25° C.; eluent: heptane:isopropanol=80:20+0.1% Et$_2$NH;

flow rate: 10 mL/min; Detection: 250 nm) to give the title compound as a yellow powder as the second eluting peak.

$^1$H NMR (600 MHz, DMSO-d$_6$) δ 7.94 (d, 1H), 7.38 (ddd, 1H), 7.17 (d, 1H), 7.14-7.06 (m, 2H), 7.04 (d, 1H), 4.30-4.12 (m, 2H), 3.25-3.01 (m, 2H), 2.25-2.05 (m, 2H).

LC-MS: Rt=3.20 min; MS m/z [M+H]$^+$ 407.1; UPLC-MS 4.

Chiral-HPLC: Rt=11.52 min; with (R)-8-(difluoromethoxy)-8'-fluoro-6-(trifluoromethyl)-3H-spiro[imidazo[1,2-a]pyridine-2,4'-thiochroman as the first eluting peak, Rt=6.10 min; C-HPLC 31.

Example 66: (S)-8-(difluoromethoxy)-8'-fluoro-3H-spiro[imidazo[1,2-a]pyridine-2,4'-thiochroman]-6-carbonitrile

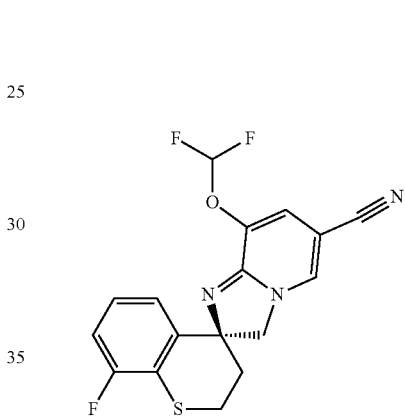

(S)-5-(Difluoromethoxy)-6-(8'-fluoro-2-oxospiro[oxazolidine-4,4'-thiochroman]-3-yl)nicotinonitrile (Intermediate CD, 4.11 g, 9.99 mmol) was dissolved in MeOH (75 mL) to give a clear yellow solution which was placed in two microwave vials. To each vial Cs$_2$CO$_3$ (976 mg, 2×2.99 mmol) was added. The vials were sealed, heated to 90° C. and stirred for 60 min at this temperature. The RM was cooled to RT, diluted with EtOAc (300 mL) and water (100 mL), and the phases separated. The aq phase was extracted with EtOAc (2×200 mL), the combined organic phases were washed with brine, dried over Na$_2$SO$_4$, filtered and concentrated in vacuo. The residue was dissolved in toluene (75 mL) and SOCl$_2$ (2.5 mL, 35.0 mmol) was added resulting in a yellow slurry which was stirred for 15 min at 90° C. The cooled RM was quenched by the addition of saturated aq NaHCO$_3$. The mixture was then extracted 2× with EtOAc, the combined organic phases were washed with brine, dried over Na$_2$SO$_4$, filtered and concentrated. The residue was purified by normal phase chromatography on (silica gel, eluent heptane:EtOAc) to provide the title compound.

$^1$H NMR (400 MHz, DMSO-d$_6$) δ 8.14 (d, 1H), 7.28 (t, 1H), 7.17-7.02 (m, 4H), 4.25 (d, 1H), 4.16 (d, 1H), 3.21-3.13 (m, 1H), 3.12-3.03 (m, 1H), 2.21-2.15 (m, 1H), 2.14-2.07 (m, 1H). LC-MS: Rt=0.72 min; MS m/z [M+H]$^+$ 364.2; UPLC-MS 1.

Example 67: (S)-8-(difluoromethoxy)-8'-fluoro-6,7'-bis(trifluoromethyl)-2',3'-dihydro-3H-spiro[imidazo[1,2-a]pyridine-2,4'-thiopyrano[3,2-c]pyridine]

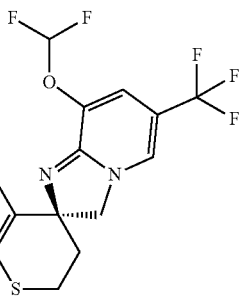

SOCl$_2$ (88 µL, 1.20 mmol) was added to a solution of (S)-(4-((3-(difluoromethoxy)-5-(trifluoromethyl)pyridin-2-yl)amino)-8-fluoro-7-(trifluoromethyl)-3,4-dihydro-2H-thiopyrano[3,2-c]pyridin-4-yl)methanol (Intermediate CF, 66 mg, 120 µmol) in toluene (2 mL) and the RM was stirred for 1 hr at 80° C. The cooled RM was partitioned between saturated aq Na$_2$CO$_3$ (20 mL) and DCM (20 mL), extracted with DCM (20 mL), the combined organic layers washed with brine (20 mL), dried and evaporated. The residue was dissolved into EtOAc and adsorbed on Isolute for normal phase purification (12 g SiO$_2$ column, eluent hexane: (TBME:MeOH 95:5) from 90:10 to 50:50) to give the title compound as a yellow solid.

$^1$H NMR (400 MHz, DMSO-d$_6$) δ 8.47 (s, 1H), 7.97 (s, 1H), 7.34 (t, 1H), 7.08 (s, 1H), 4.31 (dd, 2H), 3.34-3.26 (m, 1H), 3.23-3.16 (m, 1H), 2.24-2.17 (m, 1H), 2.16-2.09 (m, 1H).

LC-MS: Rt=0.97 min; MS m/z [M+H]$^+$ 476.1; UPLC-MS 1.

Example 68: (S)-8-(difluoromethoxy)-8'-fluoro-3H-spiro[imidazo[1,2-a]pyridine-2,4'-isothiochroman]-6-carbonitrile

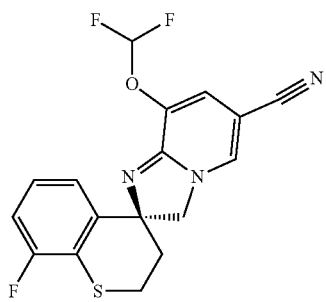 [SMILES: N#CC1=CN2C[C@@]3(CCSc4c(F)cccc43)N=C2C(OC(F)F)=C1]

(4-Amino-8-fluoroisothiochroman-4-yl)methanol (Intermediate CG, 50 mg, 232 µmol), 6-chloro-5-(difluoromethoxy)nicotinonitrile (Intermediate B, 99 mg, 348 µmol), K$_3$PO$_4$ (99 mg, 464 µmol) and CuI (4.42 mg, 23 µmol) were suspended in DMF (1.37 mL). The brown suspension was then irradiated for 30 min at 160° C. in a microwave oven. EtOAc was added to the cooled RM, the organic phase was washed with saturated aq NaHCO$_3$ and brine, filtered over a phase separator and concentrated. The residue was purified by normal phase chromatography (silica gel, eluent heptane:EtOAc 100:0 to 30:70, followed by a second purification with DCM:MeOH 100:0 to 90:10) to afford the racemic title compound. The enantiomers were separated by chiral HPLC: (instrument: Gilson PLC2020 HPLC system; column: Chiralcel ID; 5 µm 250×20 mm at 25° C.; eluent: heptane:EtOH 80:20+0.1% Et$_2$NH; flow rate: 10 mL/min; Detection: 220 nm) to give the title compound as a yellow powder as the second eluting peak.

$^1$H NMR (600 MHz, DMSO-d$_6$) δ 8.18 (d, 1H), 7.44-7.07 (m, 5H), 4.54 (d, 1H), 4.04 (d, 1H), 3.95 (d, 1H), 3.65 (d, 1H), 2.98 (dd, 1H), 2.80 (dd, 1H).

LC-MS: Rt=2.84 min; MS m/z [M+H]$^+$ 364.1; UPLC-MS 4.

Chiral-HPLC: Rt=10.82 min; with (R)-8-(difluoromethoxy)-8'-fluoro-3H-spiro[imidazo[1,2-a]pyridine-2,4'-isothiochroman]-6-carbonitrile as the first eluting peak, Rt=7.04 min; C-HPLC 33.

Example 69: (S)-8'-(difluoromethoxy)-9-fluoro-6'-(trifluoromethyl)-3,4-dihydro-2H,3'H-spiro[benzo[b]oxepine-5,2'-imidazo[1,2-a]pyridine]

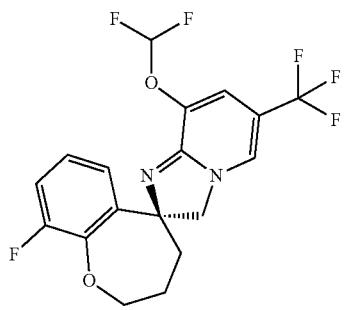 [SMILES: Fc1cccc2c1OCCC[C@@]21CN2C=C(C(F)(F)F)C=C(OC(F)F)C2=N1]

Aq NaOH (2M, 20.18 mL, 40.4 mmol) was added to a solution of 3'-(3-(difluoromethoxy)-5-(trifluoro-methyl)pyridin-2-yl)-9-fluoro-3,4-dihydro-2H-spiro[benzo[b]oxepine-5,4'-oxazolidin]-2'-one (Intermediate CH, 2.08 g, 4.04 mmol) in EtOH (42.9 mL), and the RM stirred for 1 hr at 80° C. LC-MS analysis showed the formation of the intermediate (5-((3-(difluoromethoxy)-5-(trifluoromethyl)pyridin-2-yl)amino)-9-fluoro-2,3,4,5-tetrahydrobenzo[b]oxepin-5-yl)methanol. The RM was allowed to cool to RT and diluted with EtOAc phase, the organic layer was washed with saturated aq NaHCO$_3$, dried over a phase separator and concentrated. Toluene (43 mL) was added to the residue followed by addition of SOCl$_2$ (2.95 mL, 40.4 mmol) and heating for 15 min at 90° C. The cooled RM was quenched by addition of MeOH and concentrated. The residue was taken up into EtOAc and washed with saturated aq NaHCO$_3$, dried over a phase separator and concentrated. The residue was purified by normal phase chromatography (silica gel, eluent heptane:EtOAc=100:0 to 60:40) to afford the racemic title compound. The enantiomers were separated by chiral HPLC: (instrument: Gilson Trilution I system; column: Chiralpak AD-H; 5 250×30 mm at 25° C.; eluent: n-heptane (saturated with MeOH):EtOH 80:20+0.1% Et$_2$NH; flow rate: 20 mL/min; Detection: 265 nm) to give the title compound as a yellow powder as the first eluting peak.

$^1$H NMR (400 MHz, DMSO-d$_6$) δ 7.88 (s, 1H), 7.48 (t, 1H), 7.24 (d, 1H), 7.15-7.11 (m, 1H), 7.09-7.02 (m, 1H), 7.01 (s, 1H), 4.59 (d, 1H), 4.47-4.41 (m, 1H), 3.96 (d, 1H), 3.60-3.53 (m, 1H), 2.26-2.18 (m, 1H), 1.96-1.92 (m, 2H), 1.82-1.76 (m, 1H).

LC-MS: Rt=3.15 min broad peak; MS m/z [M+H]+ 405.1; UPLC-MS 4.

Chiral-HPLC: Rt=3.06 min; with (R)-8'-(difluoromethoxy)-9-fluoro-6'-(trifluoromethyl)-3,4-dihydro-2H,3'H-spiro[benzo[b]oxepine-5,2'-imidazo[1,2-a]pyridine] as the second eluting peak, Rt=5.23 min; C-HPLC 37.

Example 70: (S)-8-(difluoromethoxy)-1'-(difluoromethyl)-8',8'-difluoro-6-(trifluoromethyl)-7',8'-dihydro-3H,6'H-spiro[imidazo[1,2-a]pyridine-2,5'-isoquinoline]

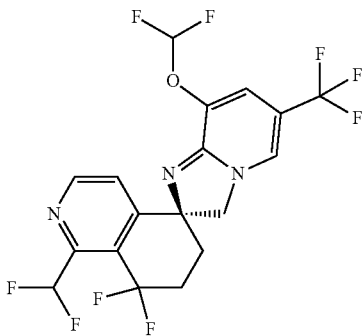 [SMILES: FC(F)OC1=CC(C(F)(F)F)=CN2C[C@@]3(CCC(F)(F)c4c3ccnc4C(F)F)N=C12]

DAST (58 μL, 436 μmol) was added to a stirred solution of (S)-8-(difluoromethoxy)-8',8'-difluoro-6-(trifluoromethyl)-7',8'-dihydro-3H,6'H-spiro[imidazo[1,2-a]pyridine-2,5'-isoquinoline]-1'-carbaldehyde (Intermediate CI, 80 mg, 175 μmol) in DCM (1 mL) cooled with an ice bath, under a positive pressure of Ar. After 1 hr at 0° C. additional DAST (58 μL, 436 μmol) was added and the RM stirred for 1 hr at 0° C., followed by 1 hr at rt. The RM was partitioned between DCM and saturated aq NaHCO₃, the aq layer extracted with DCM, dried by passing through a phase separator and evaporated. The residue was purified by normal phase chromatography (12 g SiO₂ cartridge, eluent heptane:EtOAc 90:10 to 0:100) to give the title compound as a yellow foam.

¹H NMR (400 MHz, DMSO-d₆) δ 8.83 (d, 1H), 8.01 (s, 1H), 7.70 (d, 1H), 7.32 (t, 1H), 7.24 (t, 1H), 7.09 (d, 1H), 4.35 (dd, 2H), 2.73-2.40 (m, 2H), 2.22-2.02 (m, 2H).

LC-MS: Rt=0.83 min; MS m/z [M+H]+ 458.3; UPLC-MS 1.

The following examples were prepared using analogous methods to those used in the preparation of Examples 1 to 70.

Example 71: (S)-5'-bromo-4',8-dichloro-6-(trifluoromethyl)-2',3'-dihydro-3H-spiro[imidazo[1,2-a]pyridine-2,1'-indene]

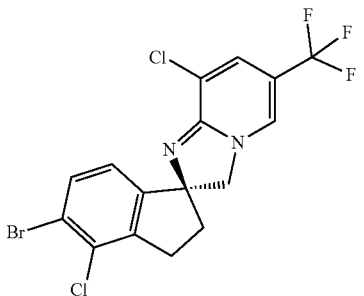 [SMILES: FC(F)(F)C1=CN2C[C@@]3(CCc4c3ccc(Br)c4Cl)N=C2C(Cl)=C1]

Prepared following analogous procedures to those described for the preparation of Intermediates J step 4A, K, P and Example 28. LC-MS: Rt=0.89 min; MS m/z [M+H]+ 437.0/439.0/441.0; UPLC-MS 1.

Example 72: (S)-5'-bromo-8-(difluoromethoxy)-6-(trifluoromethyl)-2',3'-dihydro-3H-spiro[imidazo[1,2-a]pyridine-2,1'-indene]

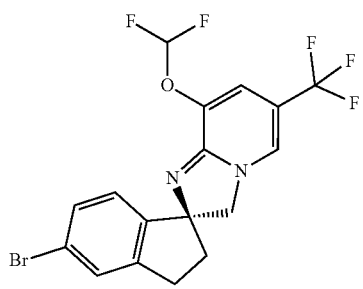 [SMILES: FC(F)OC1=CC(C(F)(F)F)=CN2C[C@@]3(CCc4cc(Br)ccc43)N=C12]

Prepared following analogous procedures to those described for the preparation of Intermediates A, AT step 2 and Example 4. LC-MS: Rt=0.83 min; MS m/z [M+H]+ 434.9/436.9; UPLC-MS 1.

Example 73: (S)-8-(difluoromethoxy)-5'-iodo-2',3'-dihydro-3H-spiro[imidazo[1,2-a]pyridine-2,1'-indene]-6-carbonitrile

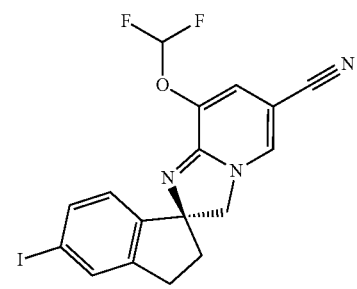 [SMILES: N#CC1=CN2C[C@@]3(CCc4cc(I)ccc43)N=C2C(OC(F)F)=C1]

Prepared following analogous procedures to those described for the preparation of Intermediate AT step 2B and Example 2. LC-MS: Rt=3.18 min; MS m/z [M+H]+ 440.1; UPLC-MS 4.

Example 74: (S)-8-(difluoromethoxy)-4'-fluoro-5',6-bis(trifluoromethyl)-2',3'-dihydro-3H-spiro[imidazo[1,2-a]pyridine-2,1'-indene]

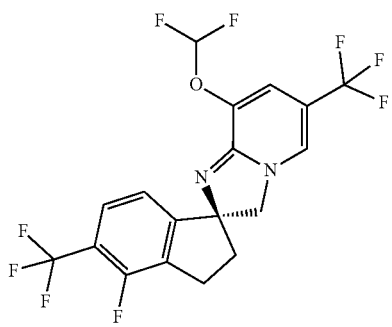 [SMILES: Fc1c(C(F)(F)F)ccc2c1CC[C@@]21CN2C=C(C(F)(F)F)C=C(OC(F)F)C2=N1]

Prepared following analogous procedures to those described for the preparation of Intermediates J step 4A and 5A, Intermediates P, Q, AW and Example 28, 40 and 3. LC-MS: Rt=0.87 min; MS m/z [M+H]⁺ 443.2; UPLC-MS 1.

Example 75: (S)-8-(difluoromethoxy)-6-(trifluoromethyl)-2',3'-dihydro-3H-spiro[imidazo[1,2-a]pyridine-2,1'-indene]

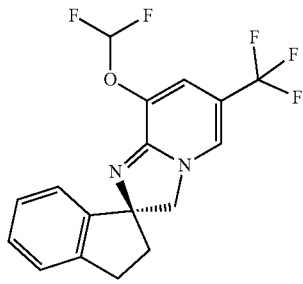 [SMILES: FC(F)OC1=CC(C(F)(F)F)=CN2C[C@@]3(CCc4ccccc43)N=C12]

Prepared following analogous procedures to those described for the preparation of Intermediates A, AT step 2 and Example 4. LC-MS: Rt=0.71 min; MS m/z [M+H]⁺ 357.0; UPLC-MS 1.

Example 76: (S)-5',8-difluoro-6'-methoxy-6-(trifluoromethyl)-3',4'-dihydro-2'H,3H-spiro[imidazo[1,2-a]pyridine-2,1'-naphthalene]

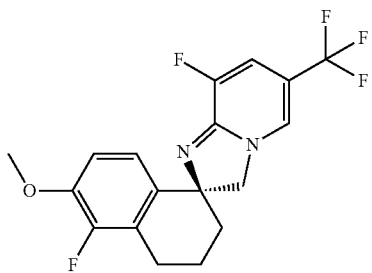 [SMILES: COc1ccc2c(c1F)CCC[C@@]21CN2C=C(C(F)(F)F)C=C(F)C2=N1]

Prepared following analogous procedures to those described for the preparation of Intermediates K, P, Example 28 and general procedure Scheme 5. LC-MS: Rt=0.72 min; MS m/z [M+H]⁺ 371.2; UPLC-MS 1.

Example 77: (S)-8-fluoro-6,6'-bis(trifluoromethyl)-3',4'-dihydro-2'H,3H-spiro[imidazo[1,2-a]pyridine-2,1'-naphthalene]

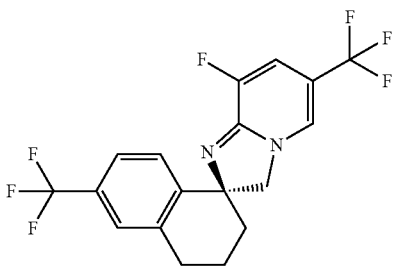 [SMILES: FC1=CC(C(F)(F)F)=CN2C[C@@]3(CCCc4cc(C(F)(F)F)ccc43)N=C12]

Prepared following analogous procedures to those described for the preparation of Intermediate J steps 1 and 2, Intermediates K, P and Example 16. LC-MS: Rt=0.83 min; MS m/z [M+H]⁺ 391.2; UPLC-MS 1.

Example 78: rac-5',6',8-trifluoro-6-(trifluoromethyl)-3',4'-dihydro-2'H,3H-spiro[imidazo[1,2-a]pyridine-2,1'-naphthalene]

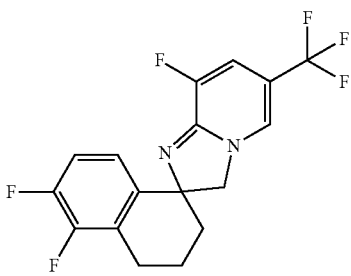 [SMILES: FC1=CC(C(F)(F)F)=CN2CC3(CCCc4c3ccc(F)c4F)N=C12]

Prepared following analogous procedures to those described for the preparation of Intermediate J steps 1 and 2, Intermediate K, P and Example 16. LC-MS: Rt=0.74 min; MS m/z [M+H]⁺ 359.2; UPLC-MS 1.

Example 79: (S)-8-chloro-5'-fluoro-6-(trifluoromethyl)-3',4'-dihydro-2'H,3H-spiro[imidazo[1,2-a]pyridine-2,1'-naphthalene]

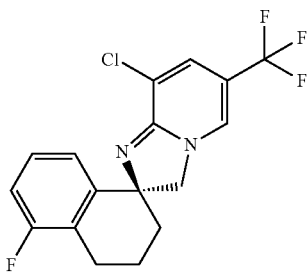 [SMILES: Fc1cccc2c1CCC[C@@]21CN2C=C(C(F)(F)F)C=C(Cl)C2=N1]

Prepared following analogous procedures to those described for the preparation of Intermediate AT steps 1 and 2, Intermediate P and Example 28. LC-MS: Rt=0.72 min; MS m/z [M+H]+ 357.2/359.1; UPLC-MS 1.

Example 80: (S)-6'-bromo-5'-fluoro-8-methoxy-6-(trifluoromethyl)-3',4'-dihydro-2'H,3H-spiro[imidazo[1,2-a]pyridine-2,1'-naphthalene]

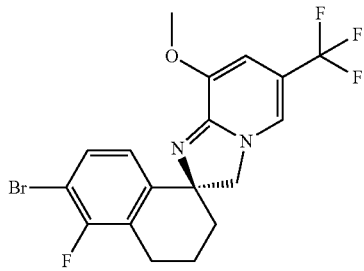 [SMILES: COC1=CC(C(F)(F)F)=CN2C[C@@]3(CCCc4c3ccc(Br)c4F)N=C12]

Prepared following analogous procedures to those described for the preparation of Intermediates K, P, Example 28 and general procedures Scheme 5. LC-MS: Rt=0.84 min; MS m/z [M+H]+ 431.2/433.2 UPLC-MS 2.

Example 81: rac-5'-bromo-8-(difluoromethoxy)-6-(trifluoromethyl)-3',4'-dihydro-2'H,3H-spiro[imidazo[1,2-a]pyridine-2,1'-naphthalene]

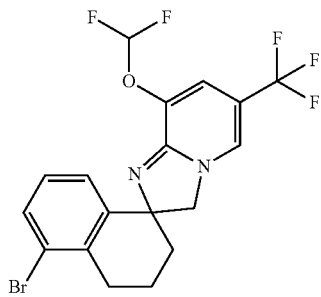 [SMILES: FC(F)OC1=CC(C(F)(F)F)=CN2CC3(CCCc4c(Br)cccc43)N=C12]

Prepared following analogous procedures to those described for the preparation of Intermediates A, J steps 1 and 2, Intermediates K, P and Example 28. LC-MS: Rt=0.84 min; MS m/z [M+H]+ 449.1/451.1; UPLC-MS 1.

Example 82: (5)-5'-chloro-8-(difluoromethoxy)-6'-fluoro-6-(trifluoromethyl)-3',4'-dihydro-2'H,3H-spiro[imidazo[1,2-a]pyridine-2,1'-naphthalene]

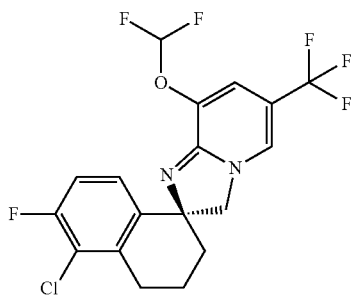

Prepared following analogous procedures to those described for the preparation of Intermediates A, J steps 1 and 2, Intermediates K, P and Example 28. LC-MS: Rt=0.89 min; MS m/z [M+H]+ 423.2/425.2; UPLC-MS 1.

Example 83: (2S,3'R,4'R)-6'-bromo-8-(difluoromethoxy)-3',4',5'-trifluoro-6-(trifluoromethyl)-3',4'-dihydro-2'H,3H-spiro[imidazo[1,2-a]pyridine-2,1'-naphthalene]

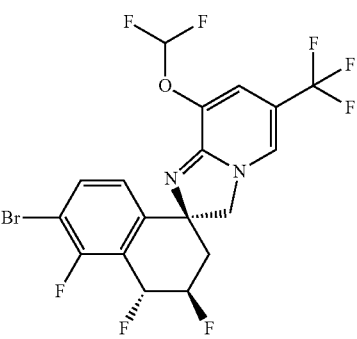 [SMILES: Fc1c(Br)ccc2c1[C@@H](F)[C@H](F)C[C@@]21CN2C=C(C(F)(F)F)C=C(OC(F)F)C2=N1]

Prepared following analogous procedures to those described for the preparation of Examples 10 and 24. LC-MS: Rt=0.91 min; MS m/z [M+H]+ 503.1/505.1; UPLC-MS 1.

Example 84: (S)-8-(difluoromethoxy)-5'-fluoro-6'-methoxy-6-(trifluoromethyl)-3',4'-dihydro-2'H,3H-spiro[imidazo[1,2-a]pyridine-2,1'-naphthalene]

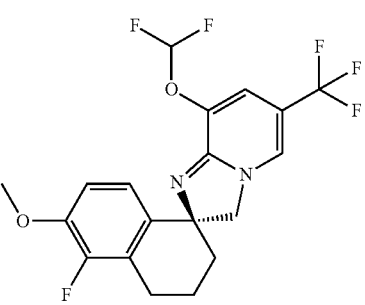 [SMILES: COc1ccc2c(c1F)CCC[C@@]21CN2C=C(C(F)(F)F)C=C(OC(F)F)C2=N1]

Prepared following analogous procedures to those described for the preparation of Intermediates K, P, Example 28 and general procedures Scheme 5. LC-MS: Rt=0.80 min; MS m/z [M+H]+ 419.2; UPLC-MS 1.

Example 85: (S)-8-(difluoromethoxy)-5',6'-difluoro-6-(trifluoromethyl)-3',4'-dihydro-2'H,3H-spiro[imidazo[1,2-a]pyridine-2,1'-naphthalene]

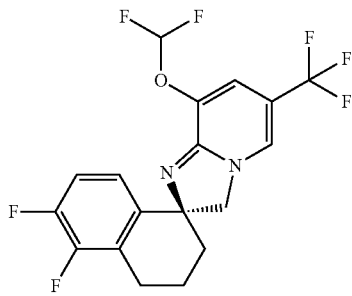

Prepared following analogous procedures to those described for the preparation of Intermediates A, J steps 1 and 2, K, P and Example 28. LC-MS: Rt=0.79 min; MS m/z [M+H]+ 407.1; UPLC-MS 1.

Example 86: (S)-8-(difluoromethoxy)-6,6'-bis(trifluoromethyl)-3',4'-dihydro-2'H,3H-spiro[imidazo[1,2-a]pyridine-2,1'-naphthalene]

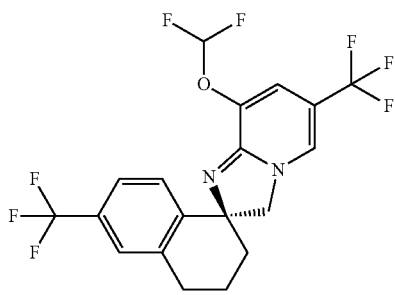 [SMILES: FC(F)OC1=CC(C(F)(F)F)=CN2C[C@@]3(CCCc4cc(C(F)(F)F)ccc43)N=C12]

Prepared following analogous procedures to those described for the preparation of Intermediates A, J steps 1 and 2, K, O, Q and Examples 28 and 3. LC-MS: Rt=0.90 min; MS m/z [M+H]+ 439.2; UPLC-MS 1.

Example 87: rac-8-(difluoromethoxy)-5',6-bis(trifluoromethyl)-3',4'-dihydro-2'H,3H-spiro[imidazo[1,2-a]pyridine-2,1'-naphthalene]

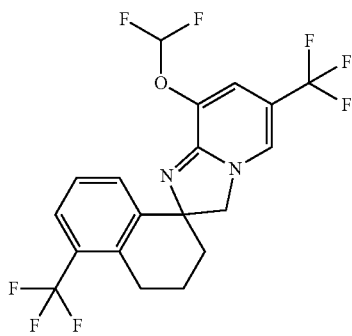 [SMILES: FC(F)OC1=CC(C(F)(F)F)=CN2CC3(CCCc4c(C(F)(F)F)cccc43)N=C12]

Prepared following analogous procedures to those described for the preparation of Intermediates J steps 1 and 2, K, O, Q and Examples 28 and 3. LC-MS: Rt=0.88 min; MS m/z [M+H]+ 439.2; UPLC-MS 1.

Example 88: (S)-5'-chloro-8-(difluoromethoxy)-6-(trifluoromethyl)-3',4'-dihydro-2'H,3H-spiro[imidazo[1,2-a]pyridine-2,1'-naphthalene]

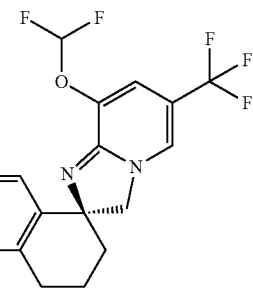

Prepared following analogous procedures to those described for the preparation of Intermediates J steps 1 and 2, K, O, Q and Examples 3 and 28. LC-MS: Rt=0.84 min; MS m/z [M+H]+ 405.2/407.2; UPLC-MS 1.

Example 89: (S)-6'-bromo-6-chloro-8-(difluoromethoxy)-5'-fluoro-3',4'-dihydro-2'H,3H-spiro[imidazo[1,2-a]pyridine-2,1'-naphthalene]

Prepared following analogues procedures to those described for the preparation of Intermediates K, O, Q and Example 3 and 28. LC-MS: Rt=0.85 min; MS m/z [M+H]+ 433.1/435.1/437.1; UPLC-MS 1.

Example 90: (S)-6'-bromo-8-(difluoromethoxy)-6-(trifluoromethyl)-2',3'-dihydro-3H,4'H-spiro[imidazo[1,2-a]pyridine-2,1'-naphthalen]-4'-one

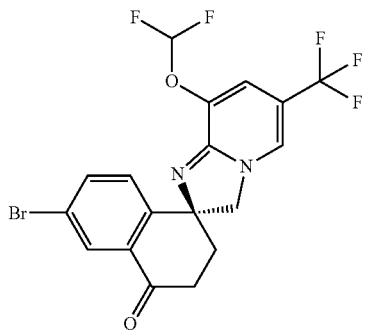 [SMILES: O=C1CC[C@@]2(CN3C=C(C(F)(F)F)C=C(OC(F)F)C3=N2)c2ccc(Br)cc21]

Prepared following analogous procedures to those described for the preparation of Intermediates A, AQ steps 1-4, K, Z steps 1-3 and Example 23. LC-MS: Rt=3.32 min; MS m/z [M+H]+ 463.2/465.2; UPLC-MS 4.

Example 91: (S)-8-(difluoromethoxy)-5',6'-difluoro-3',4'-dihydro-2'H,3H-spiro[imidazo[1,2-a]pyridine-2,1'-naphthalene]-6-carbonitrile

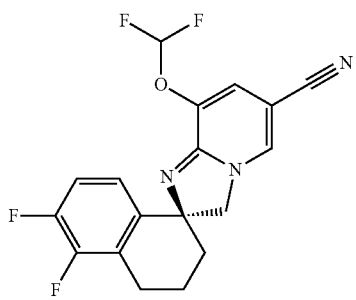

Prepared following analogous procedures to those described for the preparation of Intermediates B, J steps 1 and 2, K and Example 2. LC-MS: Rt=0.72 min; MS m/z [M+H]+ 364.2; UPLC-MS 1.

Example 92: (S)-6'-bromo-8-(difluoromethoxy)-4',4',5'-trifluoro-3',4'-dihydro-2'H,3H-spiro[imidazo[1,2-a]pyridine-2,1'-naphthalene]-6-carbonitrile

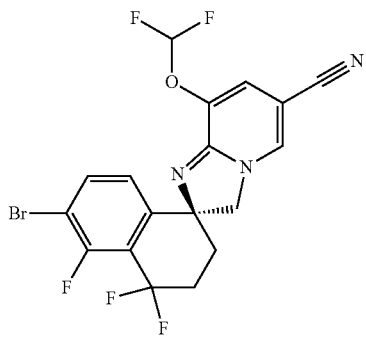 [SMILES: N#CC1=CN2C[C@@]3(CCC(F)(F)c4c3ccc(Br)c4F)N=C2C(OC(F)F)=C1]

Prepared following analogous procedures to those described for the preparation of Intermediates B, J steps 1 and 2, K, Z steps 1-3, G, Examples 4 and 23. LC-MS: Rt=4.17 min; MS m/z [M+H]+ 460.2/462.2; UPLC-MS 4.

Example 93: rac-8-(difluoromethoxy)-6-(trifluoromethyl)-7',8'-dihydro-3H,6'H-spiro[imidazo[1,2-a]pyridine-2,5'-isoquinoline]

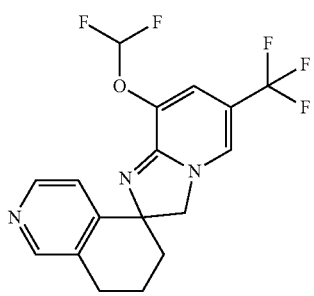 [SMILES: FC(F)OC1=CC(C(F)(F)F)=CN2CC3(CCCc4cnccc43)N=C12]

Prepared following analogous procedures to those described for the preparation of Intermediates A, K and Example 4. LC-MS: Rt=0.52 min; MS m/z [M+H]+ 372.3; UPLC-MS 1.

Example 94: (S)-1'-chloro-8-(difluoromethoxy)-7',8'-dihydro-3H,6'H-spiro[imidazo[1,2-a]pyridine-2,5'-isoquinoline]-6-carbonitrile

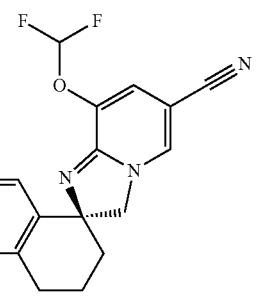

Prepared following analogous procedures to those described for the preparation of Intermediates B, J steps 1 and 2, K and Example 2. LC-MS: Rt=0.59 min; MS m/z [M+H]+ 363.2; UPLC-MS 1.

Example 95: (S)-8-chloro-8'-(fluoromethoxy)-6'-(trifluoromethyl)-3'H-spiro[chromane-4,2'-imidazo[1,2-a]pyridine]

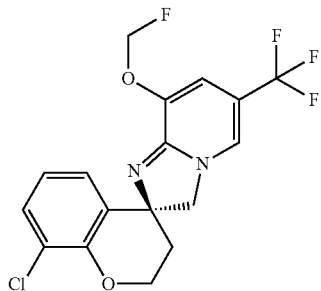 [SMILES: FCOC1=CC(C(F)(F)F)=CN2C[C@@]3(CCOc4c(Cl)cccc43)N=C12]

Prepared following analogous procedures to those described for the preparation of Intermediates E, J steps 1 and 2, K and Example 4. LC-MS: Rt=0.70 min; MS m/z [M+H]$^+$ 389.1/391.2; UPLC-MS 1.

Example 96: (S)-8-chloro-8'-(difluoromethoxy)-6'-(trifluoromethyl)-3'H-spiro[chromane-4,2'-imidazo[1,2-a]pyridine]-7-carbonitrile

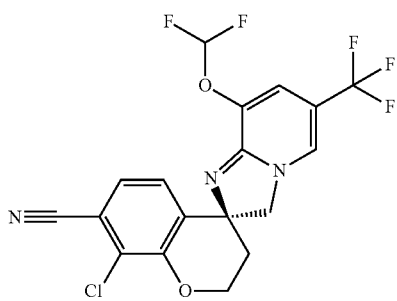 [SMILES: N#Cc1ccc2c(c1Cl)OCC[C@@]21CN2C=C(C(F)(F)F)C=C(OC(F)F)C2=N1]

Prepared following analogous procedures to those described for the preparation of Intermediates A, AQ steps 1-4, G, H, I and Example 28. LC-MS: Rt=0.82 min; MS m/z [M+H]$^+$ 432.1/434.1; UPLC-MS 1.

Example 97: (3R,4S)-7-chloro-8'-(difluoromethoxy)-3,8-difluoro-6'-(trifluoromethyl)-3'H-spiro[chromane-4,2'-imidazo[1,2-a]pyridine]

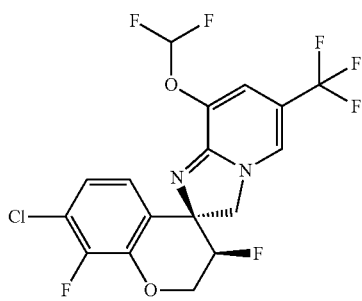 [SMILES: Fc1c(Cl)ccc2c1OC[C@H](F)[C@@]21CN2C=C(C(F)(F)F)C=C(OC(F)F)C2=N1]

Prepared following analogous procedures to those described for the preparation of Intermediates A, AB, AQ steps 1-4, K, G, H, I and Examples 9 and 28 and general procedure Scheme 5. LC-MS: Rt=0.84 min; MS m/z [M+H]$^+$ 443.1/445.0; UPLC-MS 1.

Example 98: (3R,4S)-8'-(difluoromethoxy)-3,7,8-trifluoro-6'-(trifluoromethyl)-3'H-spiro[chromane-4,2'-imidazo[1,2-a]pyridine]

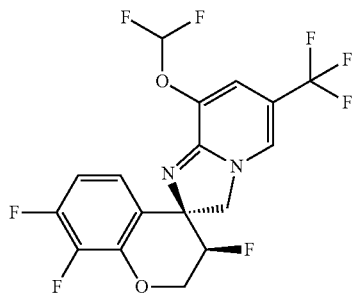

Prepared following analogous procedures to those described for the preparation of Intermediates A, AB, AQ steps 1-4, K and Examples 4 and 9. LC-MS: Rt=0.78 min; MS m/z [M+H]$^+$ 427.1; UPLC-MS 1.

Example 99: (S)-8'-(difluoromethoxy)-8-fluoro-7-(methylthio)-6'-(trifluoromethyl)-3'H-spiro[chromane-4,2'-imidazo[1,2-a]pyridine]

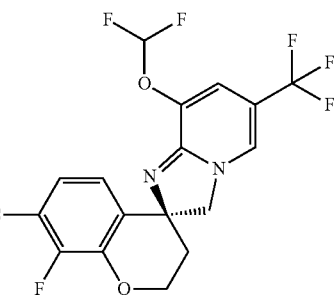

Prepared following analogous procedures to those described for the preparation of Intermediates A, J steps 1 and 2, K, AW, BH and Example 4. LC-MS: Rt=0.80 min; MS m/z [M+H]$^+$ 437.0; UPLC-MS 1.

Example 100: (S)-7-bromo-8-chloro-8'-(difluoromethoxy)-6'-(trifluoromethyl)-3'H-spiro[chromane-4,2'-imidazo[1,2-a]pyridine]

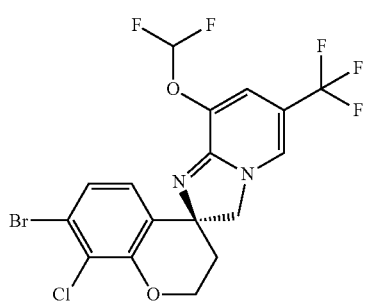

Prepared following analogous procedures to those described for the preparation of Intermediates A, AQ steps 1-4, K, G, H, I and Example 28. LC-MS: Rt=0.88 min; MS m/z [M+H]⁺ 485.1/487.0/489.0; UPLC-MS 1.

Example 101: rac-8'-(difluoromethoxy)-3,8-difluoro-6'-(trifluoromethyl)-3'H-spiro[chromane-4,2'-imidazo[1,2-a]pyridine]

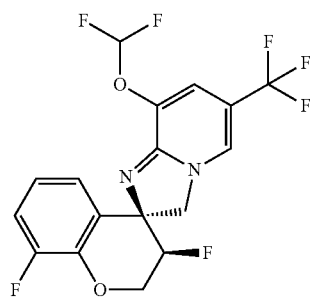 [SMILES: Fc1cccc2c1OC[C@H](F)[C@@]21CN2C=C(C(F)(F)F)C=C(OC(F)F)C2=N1]

Prepared following analogous procedures to those described for the preparation of Intermediates A, AB, AQ steps 1-4, K, G, H, I and Examples 9 and 28. LC-MS: Rt=0.71 min; MS m/z [M+H]⁺ 409.2; UPLC-MS 1.

Example 102: (S)-7,8-dibromo-8'-(difluoromethoxy)-6'-(trifluoromethyl)-3'H-spiro[chromane-4,2'-imidazo[1,2-a]pyridine]

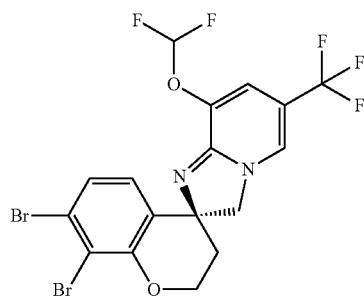

Prepared following analogous procedures to those described for the preparation of Intermediates A, AQ steps 1-4, K, G, H, I and Example 28. LC-MS: Rt=0.89 min; MS m/z [M+H]⁺ 529.0/531.0/533.0; UPLC-MS 1.

Example 103: (S)-8'-(difluoromethoxy)-8-fluoro-7-methoxy-6'-(trifluoromethyl)-3'H-spiro[chromane-4,2'-imidazo[1,2-a]pyridine]

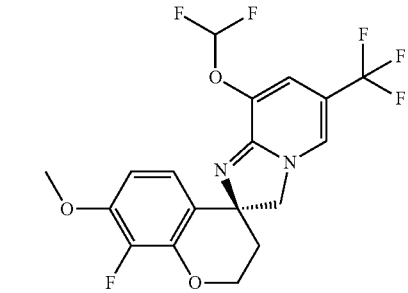

Prepared following analogous procedures to those described for the preparation of Intermediates A, J steps 1 and 2, K, Example 4 and general procedures Scheme 5. LC-MS: Rt=0.71 min; MS m/z [M+H]⁺ 421.2; UPLC-MS 1.

Example 104: (S)-8'-(difluoromethoxy)-6',8-bis(trifluoromethyl)-3'H-spiro[chromane-4,2'-imidazo[1,2-a]pyridine]

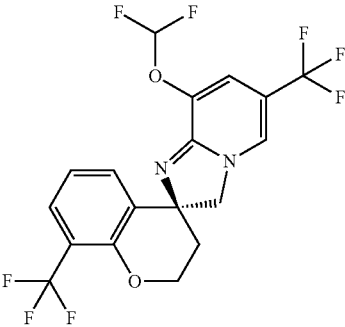 [SMILES: FC(F)OC1=CC(C(F)(F)F)=CN2C[C@@]3(CCOc4c(C(F)(F)F)cccc43)N=C12]

Prepared following analogous procedures to those described for the preparation of Intermediates A, J steps 1 and 2, K and Example 28. LC-MS: Rt=3.79 min; MS m/z [M+H]⁺ 441.2; UPLC-MS 4.

Example 105: (S)-8'-(difluoromethoxy)-8-fluoro-7-(trifluoromethoxy)-6'-(trifluoromethyl)-3'H-spiro[chromane-4,2'-imidazo[1,2-a]pyridine]

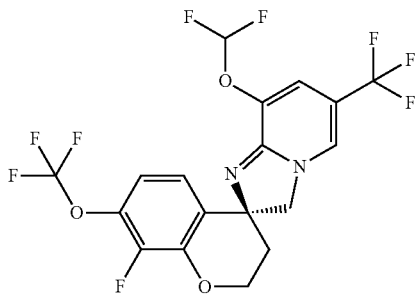 [SMILES: Fc1c(OC(F)(F)F)ccc2c1OCC[C@@]21CN2C=C(C(F)(F)F)C=C(OC(F)F)C2=N1]

Prepared following analogous procedures to those described for the preparation of Intermediates A, AQ steps 1-4, K, G, H, I and Example 28. LC-MS: Rt=0.92 min; MS m/z [M+H]+ 475.2; UPLC-MS 1.

Example 106: (S)-8'-(difluoromethoxy)-7-((difluoromethyl)thio)-8-fluoro-6'-(trifluoromethyl)-3'H-spiro[chromane-4,2'-imidazo[1,2-a]pyridine]

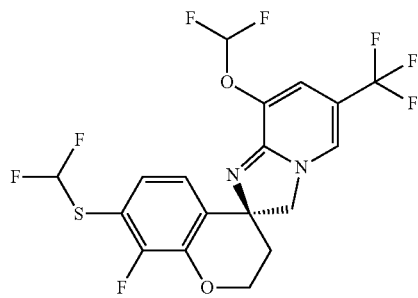 [SMILES: Fc1c(SC(F)F)ccc2c1OCC[C@@]21CN2C=C(C(F)(F)F)C=C(OC(F)F)C2=N1]

Prepared following analogous procedures to those described for the preparation of Intermediates A, AQ steps 1-4, K, AW, L steps 1 and 2 and Example 28. LC-MS: Rt=0.89 min; MS m/z [M+H]⁺ 473.1; UPLC-MS 1.

Example 107: (S)-8-bromo-8'-(difluoromethoxy)-6'-(trifluoromethyl)-3'H-spiro[chromane-4,2'-imidazo[1,2-a]pyridine]

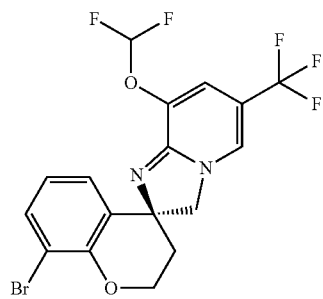

Prepared following analogous procedures to those described for the preparation of Intermediates A, J steps 1 and 2, K, G, H, I and Example 28. LC-MS: Rt=0.77 min; MS m/z [M+H]⁺ 451.0/453.0; UPLC-MS 1.

Example 108: rac-8-(difluoromethoxy)-8'-fluoro-6,7'-bis(trifluoromethyl)-3H-spiro[imidazo[1,2-a]pyridine-2,4'-isochroman]

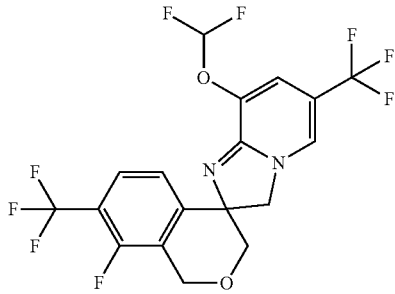 [SMILES: Fc1c(C(F)(F)F)ccc2c1COCC21CN2C=C(C(F)(F)F)C=C(OC(F)F)C2=N1]

Prepared following analogous procedures to those described for the preparation of Intermediates A, BZ steps 1-6, 0 and Example 28. LC-MS: Rt=0.97 min; MS m/z [M+H]⁺ 459.1; UPLC-MS 1.

Example 109: (2S)-8-(difluoromethoxy)-8'-fluoro-3H-spiro[imidazo[1,2-a]pyridine-2,4'-thiochromane]-6-carbonitrile-2',2',3'-d₃

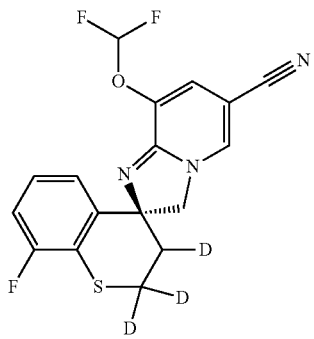 [SMILES: [2H]C1C([2H])([2H])Sc2c(F)cccc2[C@]12CN1C=C(C#N)C=C(OC(F)F)C1=N2]

Prepared following analogous procedures to those described for the preparation of Intermediates B, AQ steps 1-4, K, G, H, I, CF step 2, CB step 3 and Example 28. LC-MS: Rt=2.71 min; MS m/z [M+H]⁺ 367.3/368.3; UPLC-MS 4.

Example 110: (S)-7'-bromo-8-(difluoromethoxy)-8'-fluoro-3H-spiro[imidazo[1,2-a]pyridine-2,4'-thiochromane]-6-carbonitrile

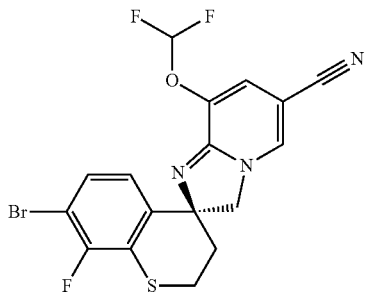

Prepared following analogous procedures to those described for the preparation of Intermediates B, CB step 1-4, AO, J steps 1 and 2, K and Example 2. LC-MS: Rt=3.94 min; MS m/z [M+H]+ 442.1/444.1; UPLC-MS 4.

Example 111: (S)-8-(difluoromethoxy)-8'-fluoro-6-(trifluoromethyl)-3H-spiro[imidazo[1,2-a]pyridine-2,4'-thiochromane]-7'-carbonitrile

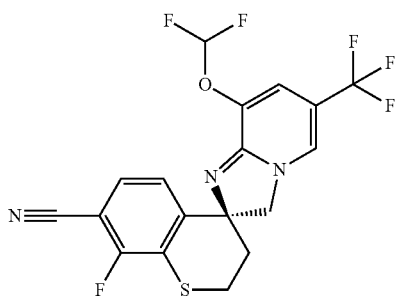

Prepared following analogous procedures to those described for the preparation of Intermediates A, CB steps 1-4, AO, Example 2 and Example 15. LC-MS: Rt=3.43 min; MS m/z [M+H]+ 432.2/433.2; UPLC-MS 4.

Example 112: (S)-8-(difluoromethoxy)-7',8'-difluoro-3H-spiro[imidazo[1,2-a]pyridine-2,4'-thiochromane]-6-carbonitrile

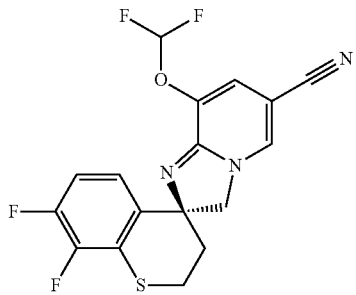 [SMILES: N#CC1=CN2C[C@@]3(CCSc4c3ccc(F)c4F)N=C2C(OC(F)F)=C1]

Prepared following analogous procedures to those described for the preparation of Intermediates B, CB steps 1-4, AO, G, H, I and Example 28. LC-MS: Rt=0.79 min; MS m/z [M+H]+ 382.2; UPLC-MS 1.

Example 113: (S)-8-(difluoromethoxy)-7',8'-difluoro-6-(trifluoromethyl)-3H-spiro[imidazo[1,2-a]pyridine-2,4'-thiochromane]

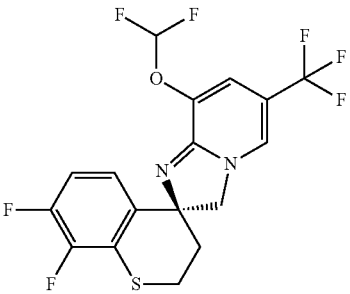

Prepared following analogous procedures to those described for the preparation of Intermediates A, CB steps 1-4, AO, G, H, I and Example 28. LC-MS: Rt=0.81 min; MS m/z [M+H]+ 425.2; UPLC-MS 1.

Example 114: (S)-8'-fluoro-8-(fluoromethoxy)-6,7'-bis(trifluoromethyl)-2',3'-dihydro-3H-spiro[imidazo[1,2-a]pyridine-2,4'-thiopyrano[3,2-c]pyridine]

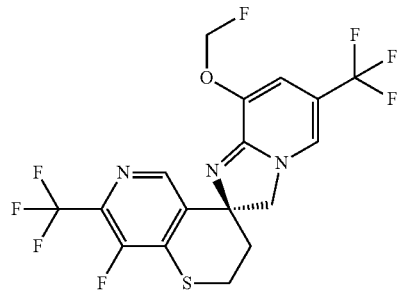 [SMILES: FCOC1=CC(C(F)(F)F)=CN2C[C@@]3(CCSc4c3cnc(C(F)(F)F)c4F)N=C12]

Prepared following analogous procedures to those described for the preparation of Intermediates E, CF steps 1-9 and Example 4. LC-MS: Rt=0.82 min; MS m/z [M+H]+ 458.1; UPLC-MS 1.

Example 115: (S)-8-(difluoromethoxy)-8'-fluoro-6-(trifluoromethyl)-3H-spiro[imidazo[1,2-a]pyridine-2,4'-isothiochromane]

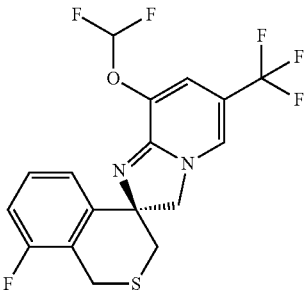

Prepared following analogous procedures to those described for the preparation of Intermediates A, CG, J steps 1 and 2, K and Example 2. LC-MS: Rt=3.43 min; MS m/z [M+H]+ 407.1; UPLC-MS 4.

Example 116: (S)-8-(difluoromethoxy)-7'-fluoro-6-(trifluoromethyl)-3H-spiro[imidazo[1,2-a]pyridine-2,4'-isothiochromane]

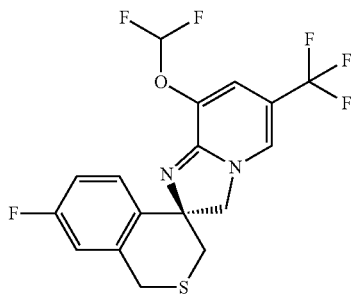

Prepared following analogues procedures to those described for the preparation of Intermediates A, CB steps 1 and 2, J steps 1 and 2, K and Example 2. LC-MS: Rt=3.33 min; MS m/z [M+H]+ 407.1; UPLC-MS 4.

Example 117: (S)-8'-(difluoromethoxy)-8,9-difluoro-6'-(trifluoromethyl)-3,4-dihydro-2H,3'H-spiro[benzo[b]oxepine-5,2'-imidazo[1,2-a]pyridine]

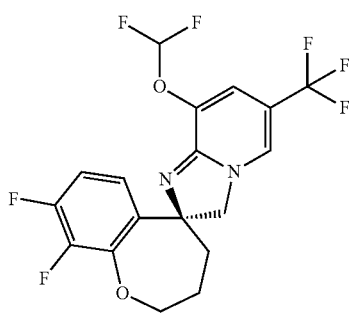 [SMILES: Fc1ccc2c(c1F)OCCC[C@@]21CN2C=C(C(F)(F)F)C=C(OC(F)F)C2=N1]

Prepared following analogous procedures to those described for the preparation of Intermediates A, CH steps 1-9, G and Example 28. LC-MS: Rt=0.78 min; MS m/z [M+H]+ 423.2; UPLC-MS 1.

Example 118: rac-9-chloro-8'-(difluoromethoxy)-6'-(trifluoromethyl)-3,4-dihydro-2H,3'H-spiro[benzo[b]oxepine-5,2'-imidazo[1,2-a]pyridine]

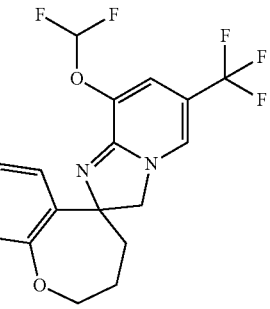

Prepared following analogous procedures to those described for the preparation of Intermediates A, CH steps 1 and 2, J steps 1 and 2 and Example 2. LC-MS: Rt=0.76 min; MS m/z [M+H]+ 421.1/423.1; UPLC-MS 1.

Example 119: (S)-8-chloro-8'-(difluoromethoxy)-9-fluoro-6'-(trifluoromethyl)-3,4-dihydro-1H,3'H-spiro[benzo[c]oxepine-5,2'-imidazo[1,2-a]pyridine]

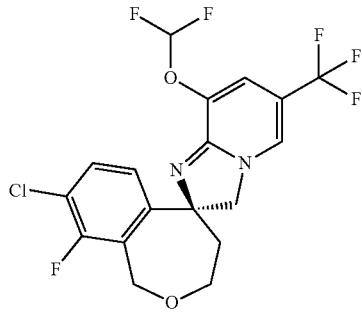 [SMILES: Fc1c(Cl)ccc2c1COCC[C@@]21CN2C=C(C(F)(F)F)C=C(OC(F)F)C2=N1]

Prepared following analogous procedures to those described for the preparation of Intermediates A, CJ steps 1-10, G and Example 28. LC-MS: Rt=0.78 min; MS m/z [M+H]+ 439.2/441.2; UPLC-MS 1.

Preparation of Intermediates

Intermediate A: 2-chloro-3-(difluoromethoxy)-5-(trifluoromethyl)pyridine

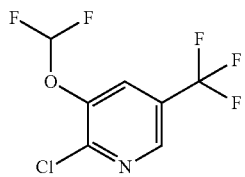 [SMILES: FC(F)Oc1cc(C(F)(F)F)cnc1Cl]

Using a Vapourtec (R2C/R4/Vapourtec Flow Commander R Series Platform Report Version: 1.9.9.5) a solution of 2-chloro-5-(trifluoromethyl)pyridin-3-ol in acetonitrile (0.5 mol/L, flow rate 3.08 mL/min) was mixed with a solution of KOH in water (6 mol/L, flow rate 3.85 mL/min) followed by the addition of a solution of diethyl (bromodifluoromethyl)phosphonate in acetonitrile (1 mol/L, flow rate 3.08 mL/min) via a second T-piece, and then reacted in a 10 mL PFA coil with a residence time of 1 min. The resulting biphasic mixture was stirred over night at RT, the layers were separated and the aq layer was extracted with TBME. The combined organic layers were washed 2× with aq 2N NaOH, then 2× with brine, dried over $Na_2SO_4$, filtered and concentrated using a Rotavap (lowest pressure 10 mbar/bath temperature 40° C.). The crude product was distilled and the product containing fractions were combined to give the title compound as a colorless liquid.

$^1$H NMR (600 MHz, DMSO-$d_6$) δ 8.77 (dd, 1H), 8.30 (d, 1H), 7.50 (t, 1H).

Intermediate A can also be synthesized via the following alternative route:

Diethyl (bromodifluoromethyl)phosphonate (17.4 mL, 101 mmol) was added dropwise to a solution of 2-chloro-5-(trifluoromethyl)pyridin-3-ol (10 g, 50.6 mmol) and KOH (56.8 g, 1012 mmol) in acetonitrile (100 mL) and water (100 mL) cooled with an ice bath: CAUTION: EXOTHERMIC REACTION! After stirring for 10 min at 0° C. the reaction mixture was stirred for a further 1 hr at RT and then partitioned between water and DCM. The organic layer was washed with brine, dried over $Na_2SO_4$ and concentrated under vacuum to give the title compound as a yellow oil.

Intermediate B:
6-chloro-5-(difluoromethoxy)nicotinonitrile

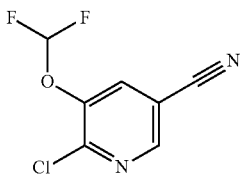 [SMILES: N#Cc1cnc(Cl)c(OC(F)F)c1]

Tetrakis(triphenylphospinepalladium(0) (0.61 g, 0.52 mmol) was added to a mixture of 2-chloro-3-(difluoromethoxy)-5-iodopyridine (Intermediate C, 2.0 g, 5.24 mmol) and zinc cyanide (0.62 g, 5.24 mmol) in DMF (15 mL) under an argon atmosphere and the RM heated in an oil bath at 90° C. for 16 hr. The cooled RM was then partitioned between TBME and $H_2O$, the suspension was then filtered through Hyflo and the layers separated. The aq layer was washed with TBME, the combined organic layers were then washed with brine, dried over $Na_2SO_4$, filtered and evaporated. The residue was adsorbed onto Isolute and purified by normal phase chromatography (24 g silica gel cartridge, eluent hexane:DCM from 95:5 to 50:50). Product containing fractions were combined and evaporated to give the title compound as a white solid.

$^1$H NMR (400 MHz, DMSO-$d_6$) δ 8.80 (d, 1H), 8.47 (d, 1H), 7.39 (t, 1H).

Intermediate C:
2-chloro-3-(difluoromethoxy)-5-iodopyridine

A mixture of 5-bromo-2-chloro-3-(difluoromethoxy)pyridine (Intermediate D, 20.8 g, 72.4 mmol), sodium iodide (21.7 g, 145 mmol), copper(I) iodide (0.69 g, 3.62 mmol) and trans-N,N-dimethyl-1,2-cyclohexanediamine (1.14 mL, 7.24 mmol) in 1,4-dioxane (150 mL) was heated with stirring for 16 hr at 110° C. under N2. The cooled RM was filtered through Hyflo evaporated and the residue partitioned between TBME and brine. The aqueous layer was extracted a further 2× with TBME, the combined organic layers washed with saturated aq $NH_4Cl$, followed by brine, dried over $Na_2SO_4$, and evaporated to give the title compound as a brown solid.

$^1$H NMR (400 MHz, DMSO-$d_6$) δ 8.54 (s, 1H), 8.22 (s, 1H), 7.38 (t, 1H).

LC-MS: Rt=1.04 min; MS m/z [M+H]$^+$; 305.8/307.8; UPLC-MS 1.

Intermediate D:
5-bromo-2-chloro-3-(difluoromethoxy)pyridine

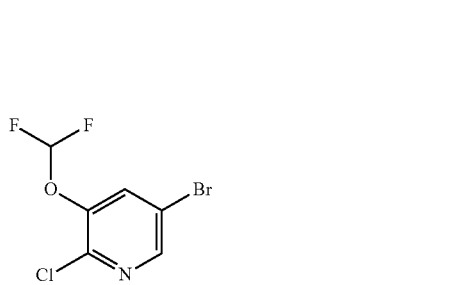

The title compound was prepared by a method similar to that of Intermediate A by replacing 2-chloro-5-(trifluoromethyl)pyridin-3-ol with 5-bromo-2-chloro-3-hydroxypyridine. After the reaction, the two phase system is collected and stirred at RT. The phases were separated and the aq layer was extracted with TBME. The combined organic layers were washed 2× with aq 2N NaOH, then 3× with brine, dried over $Na_2SO_4$, filtered and concentrated on rotary evaporator (175 mbar/40° C.). The residue was dissolved in DCM and extracted 2× with aq 2N HCl, washed with brine and the phases were separated using a phase separator. The organic layer was concentrated on a rotary evaporator (lowest pressure 100 mbar/bath temperature 40° C.) to give the title compound as a yellow liquid.

$^1$H NMR (600 MHz, DMSO-$d_6$) δ 8.50 (d, 1H), 8.22 (d, 1H), 7.42 (t, 1H).

Intermediate E: 2-chloro-3-(fluoromethoxy)-5-(trif-luoromethyl)pyridine

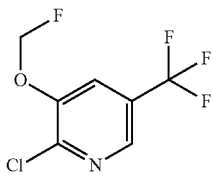 [SMILES: FCOc1cc(C(F)(F)F)cnc1Cl]

Sodium hydride (60% dispersion in mineral oil, 0.81 g, 20.2 mmol) was added portion wise to a solution of 2-chloro-5-(trifluoromethyl)pyridin-3-ol (3.50 g, 17.5 mmol) in DMF (40 mL) at RT. After stirring for 30 min at RT, bromofluoromethane in acetonitrile (17.5 mL, 35.1 mmol) was added dropwise over 2 min and the RM was stirred 18 hr at RT. The RM was then partitioned between EtOAc and $H_2O$, the aq layers further extracted with EtOAc, the combined organic layers were then washed with brine, dried over $Na_2SO_4$, and evaporated. The crude product was adsorbed onto Isolute and purified by normal phase chromatography (80 g silica gel cartridge, hexane:TBME 100:0 to 50:50). Product containing fractions were combined and evaporated to give the title compound as a white crystalline solid.

$^1$H NMR (400 MHz, DMSO-$d_6$) δ 8.71-8.52 (m, 1H), 8.13 (s, 1H), 6.12 (d, 2H).

Intermediate F: 2-bromo-5-chloro-3-(difluoromethoxy)pyridine

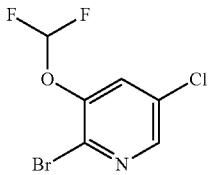 [SMILES: FC(F)Oc1cc(Cl)cnc1Br]

Sodium 2-chloro-2,2-difluoroacetate (731 mg, 4.80 mmol) was added to a mixture of 2-bromo-5-chloropyridin-3-ol (500 mg, 2.40 mmol) and potassium carbonate (398 mg, 2.88 mmol) in DMF (6 mL) and water (0.75 mL) at RT, and the RM then heated at 100° C. for 17 hr. The cooled RM was poured into water and was extracted 3× with EtOAc, the combined organic layers were washed 2× with water, and separated with a phase separator. The organic layers were concentrated in vacuo to give the title compound as a yellow liquid oil.

$^1$H NMR (600 MHz, DMSO-$d_6$) δ 8.44 (d, 1H), 8.07 (d, 1H), 7.43 (t, 1H).

Intermediate G: (S)-(5-bromo-1-((3-(difluoromethoxy)-5-(trifluoromethyl)pyridin-2-yl)amino)-4-fluoro-2,3-dihydro-1H-inden-1-yl)methanol

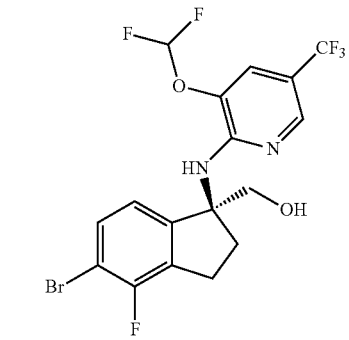 [SMILES: OC[C@]1(Nc2ncc(C(F)(F)F)cc2OC(F)F)CCc2c1ccc(Br)c2F]

To a suspension of (S)-5-bromo-3'-(3-(difluoromethoxy)-5-(trifluoromethyl)pyridin-2-yl)-4-fluoro-2,3-dihydrospiro[indene-1,4'-oxazolidin]-2'-one (Intermediate H, 820 mg, 1.24 mmol) in EtOH (4 mL) was added THF (10 mL), followed by aq 30% NaOH (2.47 mL, 9.90 mmol). The RM was stirred for 4 hr at 70° C., cooled and partitioned between saturated aq $Na_2CO_3$ and EtOAc. The aqueous layer was extracted with EtOAc, the combined organic layers were washed with brine, dried over $Na_2SO_4$ and evaporated. The crude product was adsorbed onto Isolute and purified by normal phase chromatography (40 g $SiO_2$-column, eluent hexane:[DCM-MeOH 95:5] 90:10 to 40:60). The product containing fractions were combined and evaporated to give the title compound as a brown resin.

$^1$H NMR (400 MHz, DMSO-$d_6$) δ 8.02 (s, 1H), 7.57 (s, 1H), 7.55-7.16 (m, 2H), 6.88 (d, 1H), 6.61 (s, 1H), 5.54 (t, 1H), 3.59 (m, 2H), 3.12 (dd, 1H), 2.94 (m, 1H), 2.65 (q, 1H), 2.34-2.18 (m, 1H). LC-MS: Rt=1.30 min; MS m/z [M+H]$^+$ 471.0/472.9; UPLC-MS 1.

Intermediate H: (5)-5-bromo-3'-(3-(difluoromethoxy)-5-(trifluoromethyl)pyridin-2-yl)-4-fluoro-2,3-dihydrospiro[indene-1,4'-oxazolidin]-2'-one

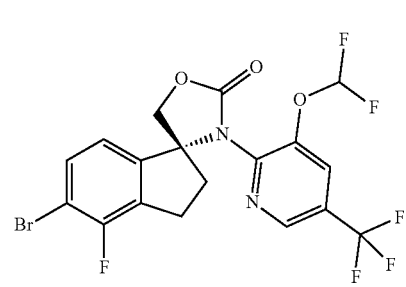 [SMILES: O=C1OC[C@]2(CCc3c2ccc(Br)c3F)N1c1ncc(C(F)(F)F)cc1OC(F)F]

To a solution of (S)-5-bromo-4-fluoro-2,3-dihydrospiro[indene-1,4'-oxazolidin]-2'-one (Intermediate I, 1.0 g, 3.29 mmol) in DMF (12 mL) was added 2-chloro-3-(difluoromethoxy)-5-(trifluoromethyl)pyridine (Intermediate A, 1.06 g, 4.27 mmol), $Cs_2CO_3$ (2.14 g, 6.57 mmol) and copper(I) bromide (0.24 g, 1.64 mmol) under an Ar-atmosphere. The RM was stirred for 1 hr at 120° C. in a heating block, and then for 1 hr at 140° C. in a microwave. Additional 2-chloro-3-(difluoromethoxy)-5-(trifluoromethyl)pyridine (Intermediate A, 400 mg, 1.62 mmol) was added, and the RM was stirred for a further 1.5 hr at 120° C. in a heating block. The cooled RM was then filtered through a pad of Hyflo filter aid and the filtrate partitioned between saturated aq NaHCO₃ and EtOAc. The aq layers were extracted with EtOAc, the combined organic layers washed with H₂O and brine, dried over Na₂SO₄ and evaporated. The crude product was adsorbed onto Isolute and purified by normal phase chromatography (40 g SiO₂-column, eluent hexane:TBME 100:0 to 40:60). Product containing fractions were combined and evaporated to give the title compound as a red-brown solid.

¹H NMR (400 MHz, DMSO-d₆) δ 8.63 (s, 1H), 8.09 (s, 1H), 7.64-7.16 (m, 2H), 7.13 (d, 1H), 4.67 (dd, 2H), 2.97 (q, 3H), 2.57 (dt, 1H).

LC-MS: Rt=1.26 min; MS m/z [M+H]⁺ 496.8/498.8; UPLC-MS 1.

Intermediate I: (S)-5-bromo-4-fluoro-2,3-dihydrospiro[indene-1,4'-oxazolidin]-2'-one

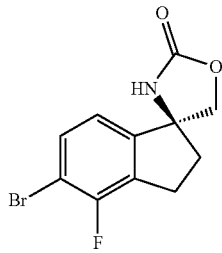 [SMILES: O=C1N[C@]2(CCc3c2ccc(Br)c3F)CO1]

To a solution of (S)-(1-amino-5-bromo-4-fluoro-2,3-dihydro-1H-inden-1-yl)methanol (Intermediate J, 10 g, 38.1 mmol) and Et₃N (11.1 mL, 80 mmol) in DCM (150 mL) was added dropwise triphosgene (4.52 g, 15.2 mmol) in DCM (50 mL) over 1 hr whilst maintaining the temperature below 25° C. The RM was stirred for 1 hr at RT, quenched with saturated aq NH₄Cl (100 mL) and then stirred for 15 min at RT. The mixture was diluted with saturated aq NH₄Cl and DCM. The aqueous layer extracted 2× with DCM, the combined organic layers dried over Na₂SO₄ and evaporated to give the title compound as a beige solid.

LC-MS: Rt=0.85 min; MS m/z [M+H]⁺ 286.0/287.9; UPLC-MS 1.

Intermediate J: (S)-(1-amino-5-bromo-4-fluoro-2,3-dihydro-1H-inden-1-yl)methanol Step 1: rac-5'-bromo-4'-fluoro-2',3'-dihydrospiro[imidazolidine-4,1'-indene]-2,5-dione

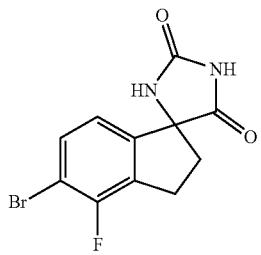 [SMILES: O=C1NC(=O)C2(CCc3c2ccc(Br)c3F)N1]

To a mixture of 5-bromo-4-fluoroindanone (100 g, 436 mmol) and ammonium carbonate (502 g, 5.23 mol) in methanol (1.2 L) and water (1.2 L) was added KCN (35.5 g, 545 mmol) and the reaction mixture was stirred at 60° C. for 24 hr. MeOH was then removed from the cooled RM under reduced pressure and the precipitated product was collected by filtration. The solid was washed 3× with water (500 mL), and dried under high vacuum for 8 hr at 50° C. to give the title compound as a black solid.

¹H NMR: (400 MHz, DMSO-d₆) δ 10.93 (br, s, 1H), 8.49 (s, 1H), 7.60-7.55 (m, 1H), 6.99 (d, 1H), 3.12-2.98 (m, 2H), 2.65-2.54 (m, 1H), 2.26-15 (m, 1H).

Step 2: rac-1-amino-5-bromo-4-fluoro-2,3-dihydro-1H-indene-1-carboxylic acid

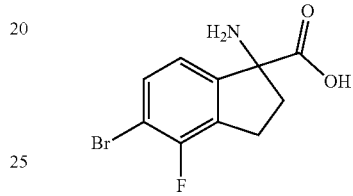

To 5'-bromo-4'-fluoro-2',3'-dihydrospiro[imidazolidine-4,1'-indene]-2,5-dione (Step 1, 120 g, 401 mmol) in H₂O (1.2 L) was added KOH (225 g, 4.01 mol) and the RM heated to reflux for 16 hr. The RM was cooled to RT, neutralized to pH=6-7 with aq 6N HCl, and the precipitate collected by filtration, washing with water (500 mL) and TBME (500 mL). The solid was dried under vacuum at 50° C. for 6 hr to give the title compound as a black solid.

¹H NMR: (400 MHz, DMSO-d₆) δ 7.58-7.51 (m, 1H), 7.19-7.12 (m, 1H), 3.13-2.99 (m, 2H), 2.75-2.60 (m, 1H), 2.16-2.02 (m, 1H).

Step 3: rac-ethyl 1-amino-5-bromo-4-fluoro-2,3-dihydro-1H-indene-1-carboxylate

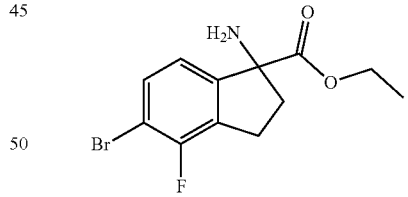

SOCl₂ (156 mL) was added to EtOH (2.0 L) cooled at −10° C. and the solution stirred at −10° C. for 30 min. DMF (7 mL) and 1-amino-5-bromo-4-fluoro-2,3-dihydro-1H-indene-1-carboxylic acid (Step 2, 130 g, 474 mmoL) were then added to the solution, and the mixture heated at 80° C. for 4.5 hr. The RM was evaporated and the residue was dissolved in H₂O (500 mL) and DCM (1.0 L). Saturated aq K₂CO₃ (400 mL) was added, the aqueous phase extracted 2× with EtOAc, the combined organic layers washed with brine, dried and concentrated to give the title compound as a black oil.

¹H NMR (400 MHz, DMSO-d₆) δ 7.64-7.49 (m, 1H), 7.17 (d, 1H), 4.13-4.01 (m, 2H), 3.19-2.91 (m, 2H), 2.77-2.58 (m, 1H), 2.24-2.04 (m, 1H), 1.13 (t, 3H).

Step 4: (S)-(1-amino-5-bromo-4-fluoro-2,3-dihydro-1H-inden-1-yl)methanol

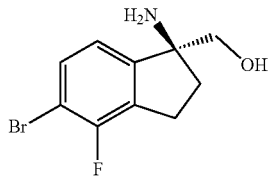 [SMILES: N[C@@]1(CO)CCc2c1ccc(Br)c2F]

Ethyl 1-amino-5-bromo-4-fluoro-2,3-dihydro-1H-indene-1-carboxylate (Step 3, 135 g, 447 mmol) was dissolved in THF (1.5 L) and the solution cooled with an ice bath. LiAlH$_4$ (22 g, 581 mmol) was then added portion wise at 0° C. to the stirred RM, and stirring continued for a further 3 hr at RT. The RM was then recooled to 0° C., and water (20 mL) carefully added drop-wise followed by aq 15% NaOH (60 mL) and water (20 mL). MgSO$_4$ was added and the suspension stirred for 30 min, and the mixture filtered. The filtrate was concentrated, and the crude product purified by normal phase chromatography (silica gel, eluent petroleum ether:EtOAc 50:50 to 0:100) to give the racemic product as a grey solid. The racemate was then separated by SFC (instrument: Thar 200 preparative SFC; column: Cellulose-2, 300×50 mm I.D., 10 μm, 38° C.; eluent: CO$_2$: [isopropanol+0.1% NH$_4$OH] 80:20; flow rate: 200 mL/min; detection: 220 nm; BPR: 100 bar; injections: 600×5 mL) to give the title compound as the first eluting peak.

$^1$H NMR (400 MHz, DMSO-d$_6$) δ 7.51-7.40 (m, 1H), 7.08 (d, 1H), 3.34 (d, 2H), 3.00-2.84 (m, 1H), 2.84-2.65 (m, 1H), 2.33-2.19 (m, 1H), 1.88-1.71 (m, 1H).

LC-MS: Rt=0.55 min; MS m/z [M+H]$^+$ 260.1/262.0; UPLC-MS 2.

Chiral-HPLC: Rt=6.19 min; with (R)-(1-amino-5-bromo-4-fluoro-2,3-dihydro-1H-inden-1-yl)methanol eluting as the second peak Rt=7.31 min; C-HPLC 3.

Intermediate J can also be synthesized via the following alternative route:

Step 1A: rac-5-bromo-1-((tert-butoxycarbonyl)amino)-4-fluoro-2,3-dihydro-1H-indene-1-carboxylic Acid

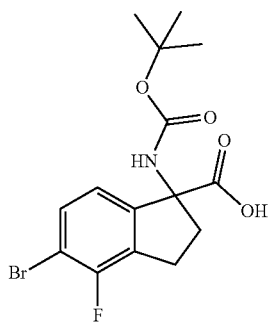 [SMILES: CC(C)(C)OC(=O)NC1(C(=O)O)CCc2c1ccc(Br)c2F]

Boc-anhydride (11.14 ml, 48.0 mmol) and Na$_2$CO$_3$ (8.48 g, 80 mmol) were added to a mixture of rac-1-amino-5-bromo-4-fluoro-2,3-dihydro-1H-indene-1-carboxylic acid (Step 2, 10.96 g, 40 mmol) in water (20 mL) and AcCN (100 mL) and stirred for 2 hr at RT. The RM was then cooled with an ice bath and acidified with 20% aq KHSO$_4$ solution and the mixture extracted with EtOAc, the combined organic layers washed with brine, dried over MgSO$_4$, filtered and concentrated. The residue was triturated with Et$_2$O-hexane 2:1, filtered and dried to give the title compound as a beige solid.

LC-MS: Rt=1.07 min; MS m/z [M−H]$^-$ 372.0/374.0; UPLC-MS 1.

Step 2A: (S)-5-bromo-1-((tert-butoxycarbonyl)amino)-4-fluoro-2,3-dihydro-1H-indene-1-carboxylic acid To a suspension of rac-5-bromo-1-((tert-butoxycarbonyl)amino)-4-fluoro-2,3-dihydro-1H-indene-1-carboxylic acid (Step 1A, 12.72 g, 34 mmol) in EtOH (50 mL) was added cinchonidine (6.01 g, 20.40 mmol) and NEt$_3$ (1.90 mL, 13.60 mmol) and the mixture was heated to give a clear solution. The clear solution was concentrated (removal of ca. 90-95% of the EtOH) and the remaining oil dissolved in TBME (80 mL) at 55° C., then seeded with crystals of (R)-5-bromo-1-((tert-butoxycarbonyl)amino)-4-fluoro-2,3-dihydro-1H-indene-1-carboxylic acid cinchonidine salt, and the RM slowly allowed to cool to RT. Hexane (25 mL) was added to the suspension and stirring continued for 18 hr. Additional hexane was added (10 mL) and the RM cooled with an ice bath and the beige solid collected by filtration. The solid was dissolved in iPrOH (40 mL) at 75° C. and TBME (30 mL) and heptane (40 mL) added and the solution seeded with crystals of (R)-5-bromo-1-((tert-butoxycarbonyl)amino)-4-fluoro-2,3-dihydro-1H-indene-1-carboxylic acid cinchonidine salt. The mixture was allowed to stand for 18 hr and the crystals were collected by filtration and dried to give the (R)-5-bromo-1-((tert-butoxycarbonyl)amino)-4-fluoro-2,3-dihydro-1H-indene-1-carboxylic acid cinchonidine salt (99% ee). Crystallisation of the mother liquor from the second crystallisation 2× from iPrOH-TBME-hexane gave the cinchonidine salt of the title compound as a light beige solid (99.6% ee).

Step 3A: (S)-5-bromo-1-((tert-butoxycarbonyl)amino)-4-fluoro-2,3-dihydro-1H-indene-1-carboxylic acid

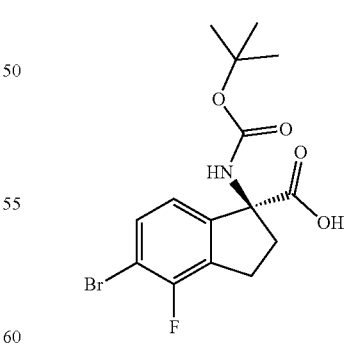

A suspension of (S)-5-bromo-1-((tert-butoxycarbonyl)amino)-4-fluoro-2,3-dihydro-1H-indene-1-carboxylic acid cinchonidine salt (Step 2A, 1.34 g, 2.0 mmol) was suspended in EtOH and cooled with an ice bath. Aq HCl (4N) was added to pH 3-4 and the RM stirred for 10 min and extracted 3× with EtOAc. The combined organic layers were washed with cold aq HCl (0.2N) the 2× with brine, dried over MgSO$_4$, filtered and concentrated to give the title compound as a foam.

Alternatively, rac-5-bromo-1-((tert-butoxycarbonyl)amino)-4-fluoro-2,3-dihydro-1H-indene-1-carboxylic acid can be separated by chiral SFC (instrument: Thar 200 preparative SFC; column: Chiralpak AD 300×50 mm I.D. 10 μm, 38° C.; eluent: CO$_2$: [MeOH+0.1% NH$_4$OH] 70:30; flow rate: 200 mL/min; detection: 220 nm; BPR: 100 bar) to give the title compound as the first eluting peak.

LC-MS: Rt=1.03 min; MS m/z [M–H]⁻ 372.1/374.1; UPLC-MS 2.

Chiral-HPLC: Rt=2.74 min; with (R)-5-bromo-1-((tert-butoxycarbonyl)amino)-4-fluoro-2,3-dihydro-1H-indene-1-carboxylic acid eluting as the second peak Rt=3.82 min; C-SFC 19.

Step 4A: (S)-1-amino-5-bromo-4-fluoro-2,3-dihydro-1H-indene-1-carboxylic acid hydrochloride

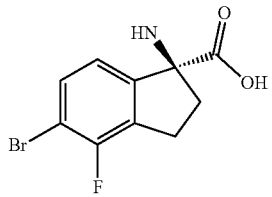 [SMILES: N[C@@]1(C(=O)O)CCc2c1ccc(Br)c2F]

A solution of HCl in 1,4-dioxane (4N, 10 mL, 40 mmol) was added to a solution of (S)-5-bromo-1-((tert-butoxycarbonyl)amino)-4-fluoro-2,3-dihydro-1H-indene-1-carboxylic acid (Step 3A, 2.13 g, 5.7 mmol) in DCM (3 mL) and the RM stirred for 1 hr at RT. The RM was concentrated and the residue was triturated with Et$_2$O. The title compound was obtained as a white crystalline solid after filtration and drying.

¹H NMR (400 MHz, DMSO-d$_6$) δ 7.72-7.63 (m, 1H), 7.35 (d, 1H), 3.33-3.25 (m, 1H), 3.23-3.15 (m, 1H), 2.86-2.82 (m, 1H), 2.51-2.42 (m, 1H).

Step 5A: (S)-(1-amino-5-bromo-4-fluoro-2,3-dihydro-1H-inden-1-yl)methanol hydrochloride

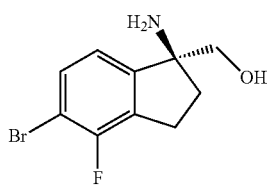 [SMILES: N[C@@]1(CO)CCc2c1ccc(Br)c2F]

To a suspension of (S)-1-amino-5-bromo-4-fluoro-2,3-dihydro-1H-indene-1-carboxylic acid hydrochloride (Step 4A, 1.77 g, 5.7 mmol) in THF (30 mL) was added a solution of BH$_3$ in THF (1M, 17.10 mL, 17.10 mmol) at RT under a positive pressure of argon. The RM was stirred at RT for 18 hr and then quenched by the dropwise addition of a MeOH/THF mixture. The RM was evaporated 3× with MeOH, a solution of HCl in Et$_2$O (2M, 3.1 mL, 6.2 mmol) added, and the mixture diluted with further Et$_2$O and stirred for 1 hr with ice bath cooling. The white solid was collected by filtration and dried to give the title compound.

¹H NMR (400 MHz, DMSO-d$_6$) δ 8.62 (s, 2H), 7.63 (t, 1H), 7.47 (d, 1H), 3.81-3.69 (m, 2H), 3.25-2.90 (m, 2H), 2.52-2.43 (m, 1H), 2.35-2.22 (m, 1H).

Intermediate K: (S)-(1-amino-4,5-difluoro-2,3-dihydro-1H-inden-1-yl)methanol

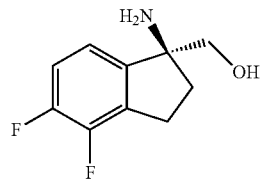 [SMILES: N[C@@]1(CO)CCc2c1ccc(F)c2F]

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with rac-1-amino-4,5-difluoro-2,3-dihydro-1H-indene-1-carboxylic acid. The enantiomers were separated by chiral HPLC: (instrument: VWR LaPrep HPLC prep; column: Chiralcel OZ-I 20 μm, 5×42 cm; eluent: Heptane: EtOH: MeOH 95:2.5:2.5+0.1% Et$_2$NH; flow rate: 100 mL/min; detection: 260 nm) to give the title compound as the first eluting peak.

LC-MS: Rt=0.41 min; MS m/z [M+H]⁺ 200.1; UPLC-MS 1.

Chiral-HPLC: Rt=5.60 min; with (R)-(1-amino-4,5-difluoro-2,3-dihydro-1H-inden-1-yl)methanol as the second eluting peak, Rt=8.8 min; C-HPLC 1.

Intermediate L: (S)-8-(difluoromethoxy)-4'-fluoro-6-(trifluoromethyl)-2',3'-dihydro-3H-spiro[imidazo[1,2-a]pyridine-2,1'-indene]-5'-thiol Step 1: 2-ethylhexyl 3-(((S)-8-(difluoromethoxy)-4'-fluoro-6-(trifluoromethyl)-2',3'-dihydro-3H-spiro[imidazo[1,2-a]pyridine-2,1'-inden]-5'-yl)thio)propanoate

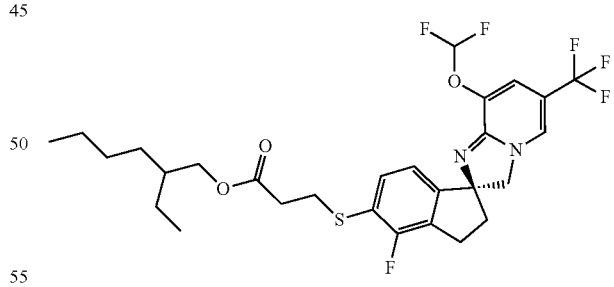

A mixture of (S)-5'-bromo-8-(difluoromethoxy)-4'-fluoro-6-(trifluoromethyl)-2',3'-dihydro-3H-spiro[imidazo[1,2-a]pyridine-2,1'-indene] (Example 1, 30.0 mg, 0.07 mmol), 2-ethylhexyl 3-mercaptopropanoate (0.023 mL, 0.10 mmol), xantphos (3.83 mg, 6.62 μmol), DIPEA (0.017 mL, 0.10 mmol), Pd$_2$(dba)$_3$ (6.06 mg, 6.62 μmol) and 1,4-dioxane (0.5 mL) was stirred for 24 hr at 100° C. The cooled RM was partitioned between EtOAc and water, the aq phase extracted 2× with EtOAc, and the dried organic layers evaporated. The isolated material was purified by normal phase chromatography (10 g SNAP cartridge, eluent hexane:

EtOAc 100:0 to 0:100) and the product containing fractions evaporated to give the title compound.

LC-MS: Rt=1.22 min; MS m/z [M+H]⁺ 591.3; UPLC-MS 1.

Step 2: (S)-8-(difluoromethoxy)-4'-fluoro-6-(trifluoromethyl)-2',3'-dihydro-3H-spiro[imidazo[1,2-a]pyridine-2,1'-indene]-5'-thiol

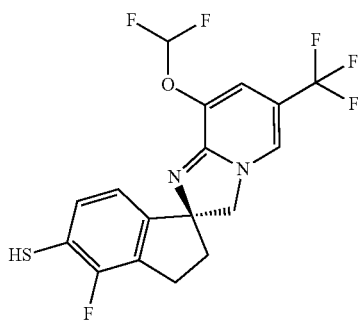 [SMILES: Fc1c(S)ccc2c1CC[C@@]21CN2C=C(C(F)(F)F)C=C(OC(F)F)C2=N1]

NaOEt in EtOH (28 μl, 0.075 mmol) was added to a solution of 2-ethylhexyl 3-(((S)-8-(difluoromethoxy)-4'-fluoro-6-(trifluoromethyl)-2',3'-dihydro-3H-spiro[imidazo[1,2-a]pyridine-2,1'-inden]-5'-yl)thio)propanoate (Step 1, 22.49 mg, 0.038 mmol) in EtOH (0.5 mL). After stirring for 1 hr at RT the RM was partitioned between saturated aq NH₄Cl and EtOAc, and the dried organic layer evaporated. The isolated material was purified by normal phase chromatography (10 g SNAP cartridge, eluent hexane:EtOAc 100:0 to 50:50) and the product containing fractions evaporated to give the title compound as a yellow solid.

LC-MS: Rt=0.76 min; MS m/z [M+H]⁺ 407.2; UPLC-MS 1.

Intermediate M: (S)-3,6'-bis(trifluoromethyl)-5,6-dihydro-3'H-spiro[cyclopenta[c]pyridine-7,2'-imidazo[1,2-a]pyridin]-8'-ol Step 1: 5-bromo-2-(trifluoromethyl)isonicotinaldehyde

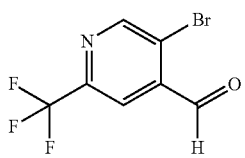

A solution of lithium diisopropylamide (2 M, 11.68 mL, 23.36 mmol) in THF (25 mL) was cooled to −78° C. using an acetone/dry ice bath and a solution of 5-bromo-2-(trifluoromethyl)pyridine (4.4 g, 19.47 mmol) in THF (5 mL) was added dropwise. The RM was stirred at this temperature for 1 hr, then DMF (1.81 mL, 23.36 mmol) was added and the RM stirred for additional 1 hr. The RM was quenched with saturated aq NaHCO₃, slowly warmed up to RT and extracted with EtOAc. The organic layer was successively washed with brine, dried with a phase separator and concentrated in vacuo. The residue was purified by normal phase chromatography (eluent cyclohexane:EtOAc 100:0 to 80:20) to give the title compound.

¹H NMR (400 MHz, DMSO-d₆): δ 10.18 (s, 1H), 9.19 (s, 1H), 8.10 (s, 1H).

Step 2: (E)-3-(5-bromo-2-(trifluoromethyl)pyridin-4-yl)-N-methoxy-N-methylacrylamide

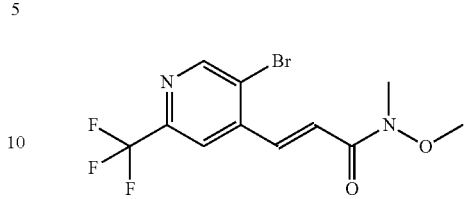

To a solution of 5-bromo-2-(trifluoromethyl)isonicotinaldehyde (Step 1, 2.0 g, 7.64 mmol) in DCM (50 mL) was added N-methoxy-N-methyl-2-(triphenylphosphoranylidene)-acetamide (4.16 g, 11.46 mmol). The RM was stirred at RT for 30 min, then quenched with brine and extracted with DCM. The organic layers were combined, dried with a phase separator and concentrated in vacuo. The crude residue was purified by normal phase chromatography (eluent cyclohexane:EtOAc 100:0 to 80:20) to afford the title compound.

LC-MS: Rt=1.00 min; MS m/z [M+H]⁺ 339.0; UPLC-MS 1.

Step 3: 3-(5-bromo-2-(trifluoromethyl)pyridin-4-yl)-N-methoxy-N-methylpropanamide

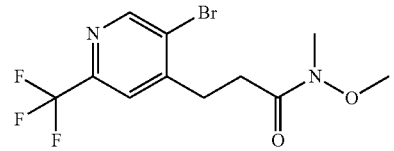 [SMILES: CON(C)C(=O)CCc1cc(C(F)(F)F)ncc1Br]

Into a glass autoclave (Hastelloy) were charged (E)-3-(5-bromo-2-(trifluoromethyl)pyridin-4-yl)-N-methoxy-N-methylacrylamide (Step 2, 2.69 g, 7.93 mmol), Rh alumina powder 5% (Engelhard 8011, 675 m g) and EtOAc (100 mL). The autoclave was sealed and a 2.1 bar H₂ pressure applied. The reaction was stirred under these conditions at RT for 5 hr. Additional catalyst were then added (0.2 g) and the reaction was stirred for 2 hr under a H₂ atmosphere (2.1 bar). The RM was filtered through a pad of Celite. The Celite was washed twice with EtOAc and the combined filtrates concentrated in vacuo. The crude product was used in the next step without further purification.

LC-MS: Rt=0.98 min; MS m/z [M+H]⁺ 341.1; UPLC-MS 1.

Step 4: 3-(trifluoromethyl)-5,6-dihydro-7H-cyclopenta[c]pyridin-7-one

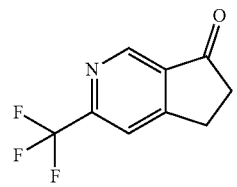 [SMILES: O=C1CCc2cc(C(F)(F)F)ncc21]

A solution of 3-(5-bromo-2-(trifluoromethyl)pyridin-4-yl)-N-methoxy-N-methylpropanamide (Step 3, 2.64 g, 7.20 mmol) in THF (60 mL) was cooled to −78° C., using an acetone/dry ice bath, and a solution of n-BuLi in hexanes (1.6 M, 6.75 mL, 10.80 mmol) added dropwise. The reaction was stirred at −78° C. for 1 hr. The reaction mixture was then quenched with a saturated aq NH$_4$OH, warmed up to RT and extracted with EtOAc. The organic layers were successively washed with a 1 N aq HCl, dried over a phase separator and concentrated. The residue was purified by normal phase chromatography (eluent cyclohexane:EtOAc 100:0 to 70:30) to give the title compound.

LC-MS: Rt=0.77 min; MS m/z [M+H]$^+$ 202.1; UPLC-MS 1.

Step 5: 3-(trifluoromethyl)-5,6-dihydrospiro[cyclopenta[c]pyridine-7,4'-imidazolidine]-2',5'-dione

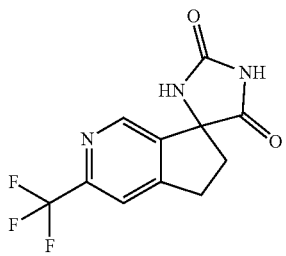 [SMILES: O=C1NC(=O)C2(CCc3cc(C(F)(F)F)ncc32)N1]

A mixture of 3-(trifluoromethyl)-5,6-dihydro-7H-cyclopenta[c]pyridin-7-one (Step 4, 1.25 g, 5.66 mmol), ammonium carbonate (6.52 g, 67.9 mmol), EtOH (25 mL), water (25 mL) and KCN (921 mg, 14.1 mmol) was heated at 50° C. for 15 hr. To the cooled RM was added water and the RM extracted with EtOAc. The combined organic layers were successively washed with a 1 N aq HCl, dried over a phase separator and concentrated in vacuo to give the title compound which was used without further purification.

LC-MS: Rt=0.62 min; MS m/z [M+H]$^+$ 272.1; UPLC-MS 1.

Step 6: 7-amino-3-(trifluoromethyl)-6,7-dihydro-5H-cyclopenta[c]pyridine-7-carboxylic acid

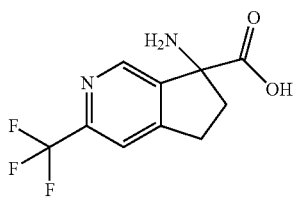 [SMILES: NC1(C(=O)O)CCc2cc(C(F)(F)F)ncc21]

A mixture of 3-(trifluoromethyl)-5,6-dihydrospiro[cyclopenta[c]pyridine-7,4'-imidazolidine]-2',5'-dione (Step 5, 1.31 g, 4.83 mmol), KOH (1.491 g, 26.6 mmol) and water (20 mL) was heated at 100° C. for 2 days with stirring. The cooled RM was acidified to pH 3-4 using a 1 N aq HCl and washed with EtOAc. The aq layer was lyophilized to afford the title compound, which contains NaCl, and was used in the following step without further purification.

LC-MS: Rt=0.34 min; MS m/z [M+H]$^+$ 247.2; UPLC-MS 1.

Step 7: (S)-(7-amino-3-(trifluoromethyl)-6,7-dihydro-5H-cyclopenta[c]pyridin-7-yl)methanol

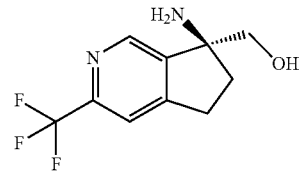 [SMILES: N[C@@]1(CO)CCc2cc(C(F)(F)F)ncc21]

To a solution of 7-amino-3-(trifluoromethyl)-6,7-dihydro-5H-cyclopenta[c]pyridine-7-carboxylic acid (Step 6, 2.40 g, 4.84 mmol) in THF (30 mL) at RT was added borane tetrahydrofuran complex (1M, 15.0 mL, 15.0 mmol). The RM was stirred for 4 hr at RT, then carefully quenched with methanol and concentrated. The residue was redissolved in methanol and concentrated to dryness two additional times. HCl in ethanol (1.25 N, 50 mL) was then added, the resulting mixture stirred for 15 min at RT and concentrated to dryness using a rotavap. The residue was basified with saturated aq NaHCO$_3$ and extracted with ethyl acetate. The combined organic layers were successively washed with brine, dried over a phase separator and concentrated in vacuo to afford the racemic product. The racemate was then separated by chiral HPLC (instrument: Gilson Prep HPLC system; column: LuxCel-2, 5 μM, 21.2×250 mm, 25° C.; eluent: heptane:MeOH:EtOH 90:5:5+0.1% Et$_2$NH; flow rate: 10 mL/min; detection: 254 nm; injection volume: 2 mL) to give the title compound as the first eluting peak.

LC-MS: Rt=0.41 min; MS m/z [M+H]$^+$ 233.2; UPLC-MS 1.

Chiral-HPLC: Rt=11.82 min; with (R)-(7-amino-3-(trifluoromethyl)-6,7-dihydro-5H-cyclopenta[c]pyridin-7-yl)methanol eluting as the second peak, Rt=16.08 min; C-HPLC 17.

Step 8: (S)-(7-(((3-fluoro-5-(trifluoromethyl)pyridin-2-yl)amino)-3-(trifluoromethyl)-6,7-dihydro-5H-cyclopenta[c]pyridin-7-yl)methanol

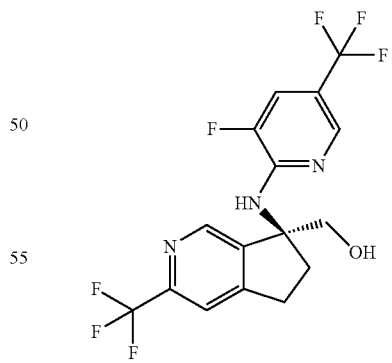

A microwave vial was charged with (S)-(7-amino-3-(trifluoromethyl)-6,7-dihydro-5H-cyclopenta[c]pyridin-7-yl)methanol (Step 7, 148 mg, 637 μmol), 2,3-difluoro-5-(trifluoromethyl)pyridine (95 μL, 765 μmol), iPrOH (3 mL) and diisopropylethylamine (334 μL, 1.91 mmol). The vial was sealed and heated to 160° C. in a microwave for 6 hours. The RM was quenched with a saturated aq NaHCO$_3$ and extracted with EtOAc. The organic layers were dried over a phase separator and concentrated. The crude residue was purified by normal phase chromatography (eluent cyclohexane:EtOAc 100:0 to 50:50) to afford the title compound.

LC-MS: Rt=1.16 min; MS m/z [M+H]⁺ 396.2; UPLC-MS 1.

Step 9: (S)-8'-fluoro-3,6'-bis(trifluoromethyl)-5,6-dihydro-3'H-spiro[cyclopenta[c]pyridine-7,2'-imidazo[1,2-a]pyridine]

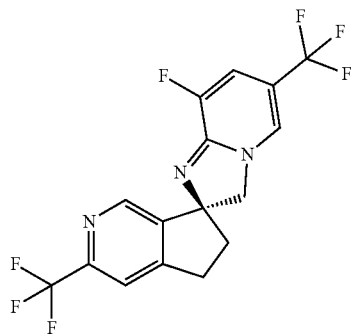 [SMILES: FC1=CC(C(F)(F)F)=CN2C[C@@]3(CCc4cc(C(F)(F)F)ncc43)N=C12]

To a solution of (S)-(7-((3-fluoro-5-(trifluoromethyl)pyridin-2-yl)amino)-3-(trifluoromethyl)-6,7-dihydro-5H-cyclopenta[c]pyridin-7-yl)methanol (Step 8, 140 mg, 350 µmol) in toluene (5 mL) was added thionyl chloride (260 µL, 3.54 mmol). The RM was heated to 80° C. for 1 hr then quenched with MeOH and concentrated to dryness. The residue was basified using saturated aq NaHCO₃ and extracted with EtOAc. The organic layers were dried over a phase separator and concentrated in vacuo. The crude residue was purified by normal phase chromatography (eluent cyclohexane:EtOAc 100:0 to 0:100) to afford the title compound.

LC-MS: Rt=0.66 min; MS m/z [M+H]⁺ 378.2; UPLC-MS 1.

Step 10: (S)-3,6'-bis(trifluoromethyl)-5,6-dihydro-3'H-spiro[cyclopenta[c]pyridine-7,2'-imidazo[1,2-a]pyridin]-8'-ol

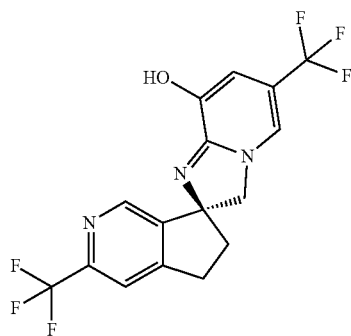 [SMILES: OC1=CC(C(F)(F)F)=CN2C[C@@]3(CCc4cc(C(F)(F)F)ncc43)N=C12]

A solution of 2-(methylsulfonyl)ethanol (92 mg, 0.73 mmol) in DMF (3 mL) was cooled to 0° C. using an ice bath and NaH (60% in mineral oil, 35.0 mg, 0.88 mmol) was added. After 30 min, a solution of (S)-8'-fluoro-3,6'-bis(trifluoromethyl)-5,6-dihydro-3'H-spiro[cyclopenta[c]pyridine-7,2'-imidazo[1,2-a]pyridine] (Step 9, 110 mg, 290 µmol) in DMF (1 mL) was added dropwise. The RM was allowed to warm up to RT and stirred for 4 hr. The RM was quenched with water and extracted with EtOAc. The combined organic layers were washed with brine, dried (phase separator) and concentrated. The crude residue was purified by normal phase chromatography (eluent DCM:MeOH 100:0 to 80:20) to afford the title compound.

LC-MS: Rt=0.67 min; MS m/z [M+H]⁺ 376.2; UPLC-MS 1.

Intermediate N: (S)-5-bromo-4-fluoro-3'-(3-(fluoromethoxy)-5-(trifluoromethyl)pyridin-2-yl)-2,3-dihydrospiro[indene-1,4'-oxazolidin]-2'-one

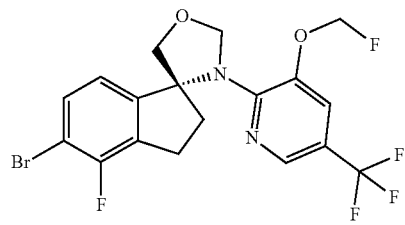 [SMILES: FCOc1cc(C(F)(F)F)cnc1N1COC[C@]12CCc1c2ccc(Br)c1F]

A mixture of (S)-5-bromo-4-fluoro-2,3-dihydrospiro[indene-1,4'-oxazolidin]-2'-one (Intermediate I, 40 mg, 0.120 mmol), 2-chloro-3-(fluoromethoxy)-5-(trifluoromethyl)pyridine (Intermediate E, 41.4 mg, 0.180 mmol), CuI (11.45 mg, 0.060 mmol) and Cs₂CO₃ (78 mg, 0.240 mmol) in DMF (2 mL) was stirred for 4 hr at 120° C. in an ace pressure tube. The cooled RM was diluted with EtOAc, the organic phase washed 2× with saturated aq NaHCO₃, dried and concentrated. The residue was purified by reversed phase chromatography (silica gel, eluent c-hexane/EtOAc 100/0 to 50/50) and the product containing fractions were combined and evaporated to give the title compound as a yellow solid.

LC-MS: Rt=1.24 min; MS m/z [M+H]⁺ 479.1/481.1; UPLC-MS 1.

Intermediate O: (S)-(5-bromo-4-fluoro-1-((3-fluoro-5-(trifluoromethyl)pyridin-2-yl)amino)-2,3-dihydro-1H-inden-1-yl)methanol

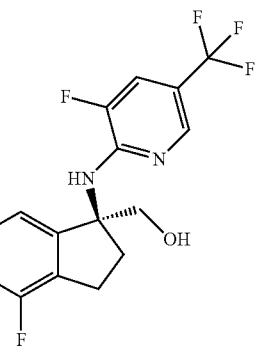

A mixture of (S)-(1-amino-5-bromo-4-fluoro-2,3-dihydro-1H-inden-1-yl)methanol (Intermediate J, 900 mg, 3.39 mmol), 2,3-difluoro-5-(trifluoromethyl)pyridine (517 µL, 4.07 mmol) and DIPEA (2.4 mL, 13.56 mmol) in iPrOH (2.6 mL) was heated in a microwave for 2 hr at 160° C. The cooled RM was evaporated, the residue taken up into DCM and evaporated onto Isolute for purification by normal phase chromatography (12 g column, eluent from 0% to 60% EtOAc in c-hexane). Product containing fractions were combined and evaporated to give the title compound.

LC-MS: Rt=6.59 min; MS m/z [M+H]⁺ 423.2/425.1; UPLC-MS 4.

The following intermediates O1, O2 and O3 were prepared using the methods used to prepare Intermediate O.

| Intermediate | Structure | Characterising data |
| --- | --- | --- |
| O1 | 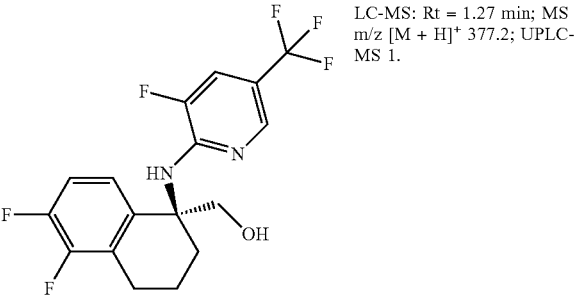<br>(S)-(5,6-difluoro-1-((3-fluoro-5-(trifluoro-methyl)pyridin-2-yl)amino)-1,2,3,4-tetra-hydronaphthalen-1-yl)methanol | LC-MS: Rt = 1.27 min; MS m/z [M + H]$^+$ 377.2; UPLC-MS 1. |
| O2 | 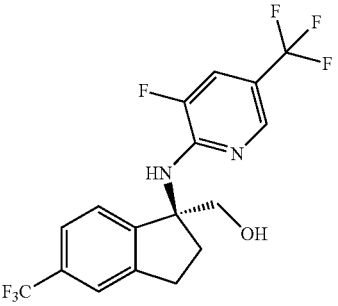<br>(S)-(1-((3-fluoro-5-(trifluoromethyl)-pyridin-2-yl)amino)-5-(trifluoromethyl)-2,3-dihydro-1H-inden-1-yl)methanol | LC-MS: Rt = 1.28 min; MS m/z [M + H]$^+$ 395.1; UPLC-MS 1. |
| O3 | 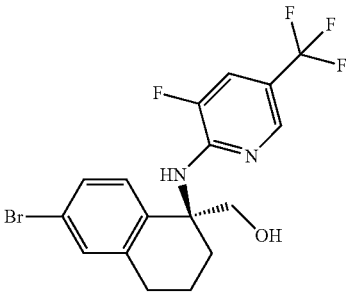<br>(S)-(6-bromo-1-((3-fluoro-5-(trifluoro-methyl)pyridin-2-yl)amino)-1,2,3,4-tetrahydronaphthalen-1-yl)methanol | LC-MS: Rt = 1.36 min; MS m/z [M + H]$^+$ 419.1/421.1; UPLC-MS 1. |

Intermediate P: (S)-(5-bromo-1-((3-chloro-5-(trifluoromethyl)pyridin-2-yl)amino)-2,3-dihydro-1H-inden-1-yl)methanol

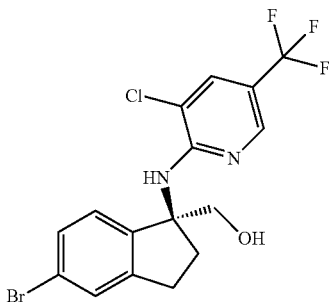 [SMILES: OC[C@]1(Nc2ncc(C(F)(F)F)cc2Cl)CCc2cc(Br)ccc21]

To a solution of (S)-(1-amino-5-bromo-2,3-dihydro-1H-inden-1-yl)methanol (Intermediate CL, 5.15 g, 21.27 mmol) in iPrOH (22 mL) was added 3-chloro-2-fluoro-5-(trifluoromethyl)pyridine (4.80 g, 24.04 mmol) and DIPEA (7.43 mL, 42.5 mmol) at RT. The RM was sonicated and stirred for 10 min at RT then heated in a microwave for 80 min at 170° C. The RM was poured into saturated aq NaHCO$_3$ and extracted 2× with EtOAc. The organic layer was washed with saturated aq NaHCO$_3$ and brine and evaporated The residue was purified by normal phase chromatography (120 g silica RediSep column, eluent Heptane:EtOAc) to give the title compound.

LC-MS: Rt=1.36 min; MS m/z [M+H]$^+$ 421.1/423.1; UPLC-MS 1.

The following intermediates P1 and P2 were prepared using the methods used to prepare Intermediate P.

| Intermediate | Structure | Characterising data |
| --- | --- | --- |
| P1 | (S)-(6-bromo-1-((3-chloro-5-(trifluoromethyl)pyridin-2-yl)amino)-5-fluoro-1,2,3,4-tetrahydronaphthalen-1-yl)methanol | LC-MS: Rt = 1.43 min; MS m/z [M + H]$^+$ 453.1/455.1; UPLC-MS 1. |
| P2 | rac-(4-((3-chloro-5-(trifluoromethyl)pyridin-2-yl)amino)-7-(trifluoromethyl)chroman-4-yl)methanol | LC-MS: Rt = 1.96 min; MS m/z [M + H]$^+$ 427.2/429.2; UPLC-MS 5 |

Intermediate Q: (S)-5',6-bis(trifluoromethyl)-2',3'-dihydro-3H-spiro[imidazo[1,2-a]pyridine-2,1'-inden]-8-ol Step 1: (S)-8-fluoro-5',6-bis(trifluoromethyl)-2',3'-dihydro-3H-spiro[imidazo[1,2-a]pyridine-2,1'-indene]

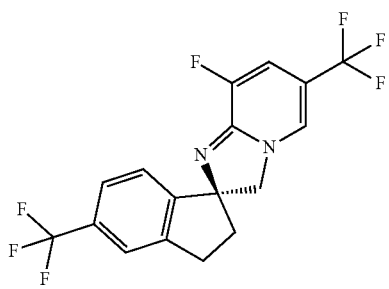 [SMILES: FC1=CC(C(F)(F)F)=CN2C[C@@]3(CCc4cc(C(F)(F)F)ccc43)N=C12]

SOCl$_2$ (0.54 mL, 7.41 mmol) was added to a solution of (S)-(1-((3-fluoro-5-(trifluoromethyl)pyridin-2-yl)amino)-5-(trifluoromethyl)-2,3-dihydro-1H-inden-1-yl)methanol (Intermediate 02, 292 mg, 0.741 mmol) in toluene (2 mL) at RT in a sealed vial. The RM was stirred and heated at 80° C. for 30 min, cooled, and then diluted with DCM. The organic phase was washed with saturated aq NaHCO$_3$ followed by brine, separating with a phase separator cartridge. Concentration of the organic layer gave a yellow oil which was triturated with MeOH, filtered and dried to give the title compound as a yellow powder.

$^1$H NMR (400 MHz, MeOH-d$_4$) δ 7.80 (s, 1H), 7.49-7.64 (m, 2H), 7.45 (d, 1H), 7.11 (d, 1H), 4.23-4.51 (m, 2H), 3.08-3.22 (m, 1H), 2.91-3.08 (m, 1H), 2.26-2.52 (m, 2H).

LC-MS: Rt=3.30 min; MS m/z [M+H]$^+$ 377.1; UPLC-MS 4.

Step 2: (S)-5',6-bis(trifluoromethyl)-2',3'-dihydro-3H-spiro[imidazo[1,2-a]pyridine-2,1'-inden]-8-ol

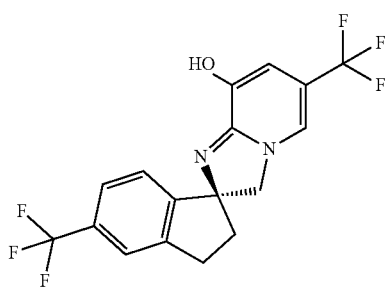 [SMILES: OC1=CC(C(F)(F)F)=CN2C[C@@]3(CCc4cc(C(F)(F)F)ccc43)N=C12]

Sodium hydride (57 mg, 1.35 mmol) was added to a stirred solution of 2-(methylsulfonyl)ethanol (57 mg, 459 µmol) in DMF (1.5 mL) cooled with an ice bath. The RM was stirred for 10 min at 0° C. before the addition of (S)-8-fluoro-5',6-bis(trifluoromethyl)-2',3'-dihydro-3H-spiro[imidazo[1,2-a]pyridine-2,1'-indene] (Step 1 169 mg, 450 µmol). After stirring for 90 min the RM was recooled to 0° C. and an additional 0.3 equiv of the sodium alkoxide solution in DMF was prepared and added. After a further 30 min at RT the RM was then poured into saturated aq NH$_4$Cl, extracted 2× with EtOAc, the combined organic phases washed with brine, and concentrated. The residue was purified by normal phase chromatography (10 g SiO$_2$ SNAP cartridge, Eluent DCM:MeOH 100:0 to 90:10) to give the title compound as a grey powder.

LC-MS: Rt=0.78 min; MS m/z [M+H]$^+$ 375.1; UPLC-MS 1.

Intermediate R: (S)-(1-amino-6-bromo-5-fluoro-1,2,3,4-tetrahydronaphthalen-1-yl)methanol hydrochloride

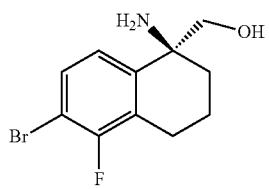 [SMILES: N[C@@]1(CO)CCCc2c1ccc(Br)c2F]

(S)-1-Amino-6-bromo-5-fluoro-1,2,3,4-tetrahydronaphthalene-1-carboxylic acid (5 g, 15.3 mmol) was suspended in THF (10 mL) under Ar and cooled to 0° C. To the RM borane THF complex in THF (1M, 100 ml, 100 mmol) was added dropwise over 30 min. The RM was stirred at RT for 18 hours, then quenched carefully with MeOH and evaporated, co-evaporating a further 3× with MeOH. The residue was diluted with MeOH and 2M HCl solution in Et$_2$O (10 ml, 20 mmol) was added. Additional Et$_2$O was added until a precipitate formed, and the RM was stirred at RT for 30 min. The solid was collected by filtration and dried to give the title compound as a white solid.

$^1$H NMR (400 MHz, DMSO-d$_6$) δ 8.52 (s, 3H), 7.65 (t, 1H), 7.51 (d, 1H), 5.79 (t, 1H), 3.65 (d, 2H), 2.85-2.73 (m, 1H), 2.73-2.60 (m, 1H), 2.22 (dd, 1H), 1.95-1.82 (m, 1H), 1.82-1.69 (m, 2H).

LC-MS: Rt=0.57 min; MS m/z [M+H]$^+$ 274.1/276.1; UPLC-MS 1.

Intermediate S: (S)-6'-bromo-8-(difluoromethoxy)-5'-fluoro-6-(trifluoromethyl)-2',3'-dihydro-3H-dispiro[imidazo[1,2-a]pyridine-2,1'-naphthalene-4',2"-[1,3]dithiolane]

Step 1: (S)-6'-bromo-3-(3-(difluoromethoxy)-5-(trifluoromethyl)pyridin-2-yl)-5'-fluoro-2',3'-dihydro-dispiro[oxazolidine-4,1'-naphthalene-4',2"-[1,3]dithiolan]-2-one

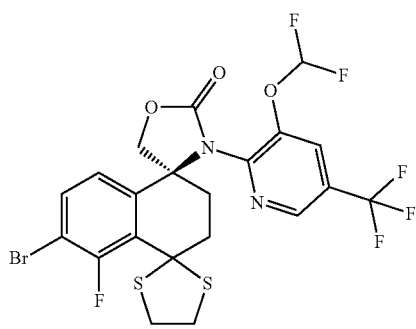 [SMILES: O=C1OC[C@@]2(CCC3(SCCS3)c3c2ccc(Br)c3F)N1c1ncc(C(F)(F)F)cc1OC(F)F]

A mixture of (S)-6'-bromo-5'-fluoro-2',3'-dihydrodispiro[oxazolidine-4,1'-naphthalene-4',2''-[1,3]dithiolan]-2-one (Intermediate T, 795 mg, 1.96 mmol), 2-chloro-3-(difluoromethoxy)-5-(trifluoromethyl)pyridine (Intermediate A, 963 mg, 3.85 mmol), copper(I) iodide (235 mg, 1.23 mmol) and cesium carbonate (1.28 g, 3.91 mmol) in DMF (13 mL) was heated in a microwave at 120° C. for 2.5 hr under Ar. Additional 2-chloro-3-(difluoromethoxy)-5-(trifluoromethyl)pyridine (Intermediate A, 198 mg, 0.8 mmol) and copper(I) iodide (50 mg, 260 μmol) were added, and heating continued at 120° C. for a further 2 hr. This procedure was repeated with 2-chloro-3-(difluoromethoxy)-5-(trifluoromethyl)pyridine (Intermediate A, 198 mg, 0.8 mmol) and copper(I) iodide (50 mg, 260 μmol). The cooled RM was diluted with saturated aq NaHCO₃ and extracted with EtOAc. The combined organic layers were washed with brine, dried over Na₂SO₄, filtered and evaporated. The residue was absorbed onto Isolute and purified by normal phase chromatography (120 g SiO₂-column; eluent heptane:EtOAc 100:0 to 85:15). Product containing fractions were combined and evaporated to give the title compound as an off white foam.

LC-MS: Rt=1.36 min; MS m/z [M+H]⁺ 600.8/603.0; UPLC-MS 1.

Step 2: (S)-(7'-bromo-4'43-(difluoromethoxy)-5-(trifluoromethyl)pyridin-2-yl)amino)-8'-fluoro-3',4'-dihydro-2'H-spiro[[1,3]dithiolane-2,1'-naphthalen]-4'-yl)methanol

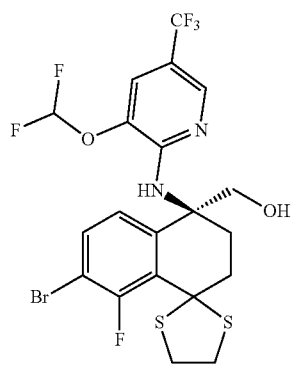 [SMILES: OC[C@]1(Nc2ncc(C(F)(F)F)cc2OC(F)F)CCC2(SCCS2)c2c1ccc(Br)c2F]

Aq NaOH (2M, 11 mL, 22 mmol) was added to (S)-6'-bromo-3-(3-(difluoromethoxy)-5-(trifluoromethyl)pyridin-2-yl)-5'-fluoro-2',3'-dihydrodispiro[oxazolidine-4,1'-naphthalene-4',2''-[1,3]dithiolan]-2-one (Step 1, 1.8 g, 2.84 mmol) suspended in EtOH (15 mL) and the RM stirred at 80° C. for 135 min. The RM was diluted with water and extracted 2× with EtOAc. The combined organic layers were washed with brine, dried over Na₂SO₄, filtered and evaporated to give the title compound as an off white foam which was used directly for the following step.

LC-MS: Rt=1.37 min; MS m/z [M+H]⁺ 575.0/577.0; UPLC-MS 1.

Step 3: (S)-6'-bromo-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane]

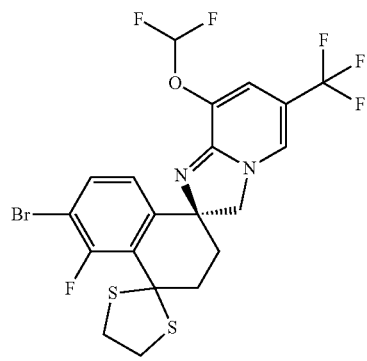 [SMILES: Fc1c(Br)ccc2c1C1(CC[C@@]23CN2C=C(C(F)(F)F)C=C(OC(F)F)C2=N3)SCCS1]

SOCl₂ (0.35 ml, 4.8 mmol) was added dropwise to a solution of (S)-(7'-bromo-4'43-(difluoromethoxy)-5-(trifluoromethyl)pyridin-2-yl)amino)-8'-fluoro-3',4'-dihydro-2'H-spiro[[1,3]dithiolane-2,1'-naphthalen]-4'-yl)methanol (Step 2, 1.6 g, 2.59 mmol) in toluene (15 mL) and the RM heated at 80° C. for 1 hr under Ar. The RM was quenched with saturated aq NaHCO₃ and extracted with EtOAc. The combined organic layers were washed with brine, dried over Na₂SO₄, filtered and evaporated. The residue was absorbed onto Isolute and purified by normal phase chromatography (120 g SiO₂-column; eluent heptane:EtOAc 100:0 to 75:25). Product containing fractions were combined and evaporated to give the title compound as a yellow solid.

LC-MS: Rt=0.96 min; MS m/z [M+H]⁺ 557.0/559.1; UPLC-MS 1.

Intermediate T: (S)-6'-bromo-5'-fluoro-2',3'-dihydrodispiro[oxazolidine-4,1'-naphthalene-4',2''-[1,3]dithiolan]-2-one Step 1: (S)-6-bromo-5-fluoro-3,4-dihydro-2H-spiro[naphthalene-1,4'-oxazolidin]-2'-one

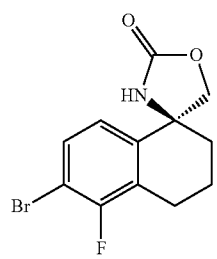 [SMILES: O=C1N[C@]2(CCCc3c2ccc(Br)c3F)CO1]

A solution of triphosgene (1.06 g, 3.57 mmol) in DCM (50 mL) was added dropwise to a solution of (S)-(1-amino-6-bromo-5-fluoro-1,2,3,4-tetrahydronaphthalen-1-yl)methanol (Intermediate R, 2.5 g, 8.94 mmol) and Et₃N (2.62 mL, 18.77 mmol) in DCM (50 mL) at 0° C. and stirred for 45 min at RT. The RM was quenched with saturated aq NH₄Cl and DCM. The RM was stirred for 20 min at RT, extracted with DCM, the combined organic layers washed with brine, dried (Phase Separator) and concentrated to give the title compound which was used directly for the following step.

LC-MS: Rt=0.96 min; MS m/z [M+H]⁺ 300.1/302.1; UPLC-MS 1.

Step 2: (S)-6-bromo-5-fluoro-2H-spiro[naphthalene-1,4'-oxazolidine]-2',4(3H)-dione

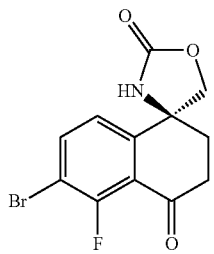 [SMILES: O=C1N[C@]2(CCC(=O)c3c2ccc(Br)c3F)CO1]

Iron(III) nitrate nonahydrate (662 mg, 1.61 mmol) was added to a solution of (S)-6-bromo-5-fluoro-3,4-dihydro-2H-spiro[naphthalene-1,4'-oxazolidin]-2'-one (Step 1, 2.51 g, 8.03 mmol) and N-hydroxyphthalimide (0.327 g, 2.01 mmol) in AcCN (50 mL) and the RM stirred at 35° C. for 18 hr under an O₂ atmosphere. The RM was extracted with DCM, the organic layers washed with brine, dried (Phase Separator) and concentrated. The residue was triturated with DCM and the title compound was obtained as a white solid after filtration. Additional material could be obtained by purification of the mother liquor by normal phase chromatography (silica gel: c-hexane:EtOAc 100:0 to 50:50) to give the title compound after trituration with DCM.

LC-MS: Rt=0.69 min; no significant molecular ion signal; UPLC-MS 1.

Step 3: (S)-6'-bromo-5'-fluoro-2',3'-dihydrodispiro[oxazolidine-4,1'-naphthalene-4',2''-[1,3]dithiolan]-2-one

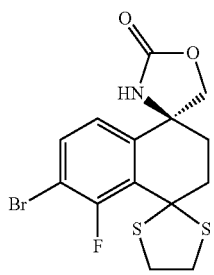 [SMILES: O=C1N[C@]2(CCC3(SCCS3)c3c2ccc(Br)c3F)CO1]

Boron trifluoride etherate (303 µL, 2.39 mmol) was added dropwise to a solution of (S)-6-bromo-5-fluoro-2H-spiro[naphthalene-1,4'-oxazolidine]-2',4(3H)-dione (Step 2, 1.5 g, 4.78 mmol) and ethane-1,2-dithiol (803 µL, 9.55 mmol) in DCM (30 mL) at 0° C. and the RM stirred at RT for 18 hr. The RM mixture was poured into aq NaOH (1N, 100 mL), extracted with DCM, dried (Phase Separator) and concentrated. The residue was purified by normal phase chromatography (silica gel, eluent c-hexane:EtOAc 100:0 to 50:50) to give the title compound.

LC-MS: Rt=0.98 min; no significant molecular ion signal; UPLC-MS 1.

Intermediate U: (S)-6'-bromo-4'-((tert-butyldimethylsilyl)oxy)-8-(difluoromethoxy)-5'-fluoro-6-(trifluoromethyl)-2'H,3H-spiro[imidazo[1,2-a]pyridine-2,1'-naphthalene]

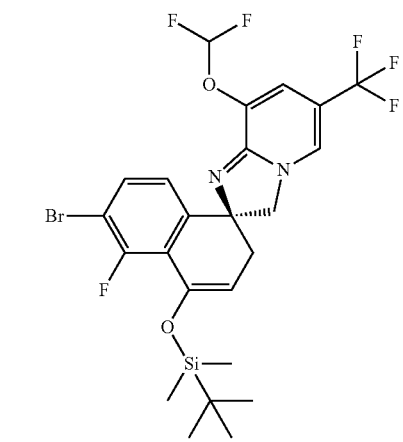 [SMILES: CC(C)(C)[Si](C)(C)OC1=CC[C@@]2(CN3C=C(C(F)(F)F)C=C(OC(F)F)C3=N2)c2ccc(Br)c(F)c21]

tert-Butyldimethylsilyl trifluoromethanesulfonate (90 µL, 381 µmol) was added dropwise to (S)-6'-bromo-8-(difluoromethoxy)-5'-fluoro-6-(trifluoromethyl)-2'H,3H-spiro[imidazo[1,2-a]pyridine-2,1'-naphthalen]-4'(3M-one (Example 8, 121 mg, 249 µmol) and triethylamine (173 µL, 1.25 mmol) in DCM (2 mL) at 0° C. under Ar. The RM was stirred at 0° C. for 10 min then at RT for 20 min, diluted with water and extracted with EtOAc. The combined organic layers were washed with brine, dried over Na₂SO₄ and evaporated. The residue was absorbed onto Isolute and purified by normal phase chromatography (40 g SiO₂-column, eluent heptane:EtOAc 100:0 to 75:25). Product containing fractions were combined, evaporated and dried to give the title compound as a yellow solid.

LC-MS: Rt=1.38 min; MS m/z [M+H]⁺ 595.1/597.1; UPLC-MS 1.

Intermediate V: (S)-(1-amino-6-bromo-1,2,3,4-tetrahydronaphthalen-1-yl)methanol

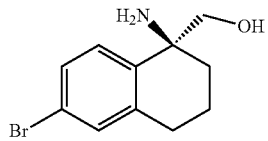

The title compound was prepared by a method similar to that of Intermediate M, Step 7 by replacing 7-amino-3-(trifluoromethyl)-6,7-dihydro-5H-cyclopenta[c]pyridine-7-carboxylic acid (Intermediate M, step 6) with rac-1-amino-6-bromo-1,2,3,4-tetrahydronaphthalene-1-carboxylic acid (Intermediate AU8). The enantiomers were separated by chiral HPLC: (instrument: Gilson Trilution HPLC prep system; column: Chiralpak ID 5 µm, 3×25 cm, 25° C.; eluent: Heptane: TBME: EtOH 80:10:10+0.05% Et₂NH; flow rate: 10 mL/min; detection: 230 nm) to give the title compound as the first eluting peak, Rt=8.82 min; C-HPLC 7.

LC-MS: Rt=0.56 min; MS m/z [M+H]⁺ 256.1/258.1; UPLC-MS 1.

Chiral-HPLC: Rt=8.82 min; with (R)-(1-amino-6-bromo-1,2,3,4-tetrahydronaphthalen-1-yl)methanol as the second eluting peak, Rt=11.87 min; C-HPLC 7.

Intermediate W: (S)-6'-bromo-6-(trifluoromethyl)-3', 4'-dihydro-2'H,3H-spiro[imidazo[1,2-a]pyridine-2, 1'-naphthalen]-8-ol Step 1: (S)-6'-bromo-8-fluoro-6-(trifluoromethyl)-3', 4'-dihydro-2'H,3H-spiro[imidazo[1,2-a]pyridine-2, 1'-naphthalene]

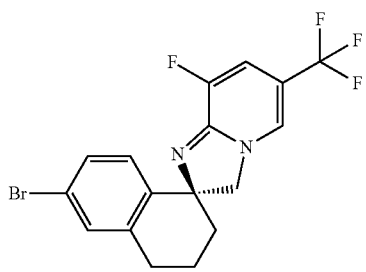 [SMILES: FC1=CC(C(F)(F)F)=CN2C[C@@]3(CCCc4cc(Br)ccc43)N=C12]

SOCl₂ (74 µl, 1.01 mmol) was added (6-bromo-1-((3-fluoro-5-(trifluoromethyl)pyridin-2-yl)amino)-1,2,3,4-tetrahydronaphthalen-1-yl)methanol (Intermediate 03, 330 mg, 779 µmol) in toluene (2.5 mL) under argon. The RM was heated to 80° C. for 75 min. The RM was quenched with saturated aq NaHCO₃ and extracted with EtOAc. The combined organic layers were washed with brine, dried over Na₂SO₄ and evaporated. The residue was absorbed onto Isolute and purified by normal phase chromatography (40 g SiO₂-column, eluent heptane:EtOAc 100:0 to 70:30). Product containing fractions were combined, evaporated and dried to give the title compound.

LC-MS: Rt=0.79 min; MS m/z [M+H]⁺ 401.2/403.2; UPLC-MS 1.

Step 2: (S)-6'-bromo-6-(trifluoromethyl)-3',4'-dihydro-2'H,3H-spiro[imidazo[1,2-a]pyridine-2,1'-naphthalen]-8-ol

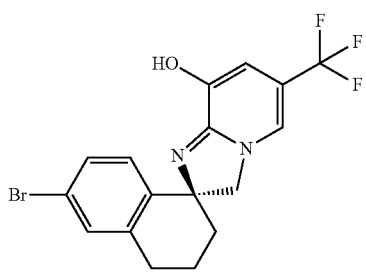 [SMILES: OC1=CC(C(F)(F)F)=CN2C[C@@]3(CCCc4cc(Br)ccc43)N=C12]

NaH (55% dispersion in mineral oil, 98 mg, 2.24 mmol) was added to 2-(methylsulfonyl)ethanol (122 mg, 972 µmol) in DMF (1.5 mL) at RT under Ar. The RM was cooled to 0° C., stirred at 0° C. for 15 min and a solution of (S)-6'-bromo-8-fluoro-6-(trifluoromethyl)-3',4'-dihydro-2'H,3H-spiro [imidazo[1,2-a]pyridine-2,1'-naphthalene] (Step 1, 300 mg, 748 µmol) in DMF (4.5 mL) added. The RM was stirred at RT for 30 min, then quenched with saturated aq NH₄Cl and extracted with EtOAc. The combined organic layers were washed with brine, dried over Na₂SO₄ and evaporated to give the title compound as an orange solid.

LC-MS: Rt=0.83 min; MS m/z [M+H]⁺ 399.1/401.1; UPLC-MS 1.

Intermediate X: (S)-6'-bromo-4'-((tert-butyldimethyl silyl)oxy)-8-(difluoromethoxy)-3',5'-difluoro-6-(trifluoromethyl)-2'H,3H-spiro[imidazo[1,2-a]pyridine-2, 1'-naphthalene]

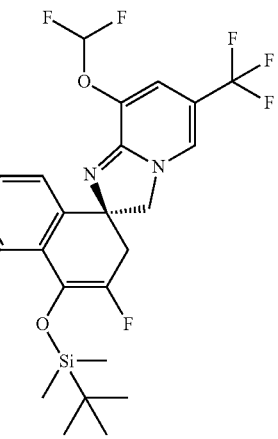

The title compound was prepared in analogy to the method described for Intermediate U by replacing (S)-6'-bromo-8-(difluoromethoxy)-5'-fluoro-6-(trifluoromethyl)-2'H,3H-spiro[imidazo[1,2-a]pyridine-2,1'-naphthalen]-4' (3M-one (Example 8) with (1'S)-6'-bromo-8-(difluoromethoxy)-3',5'-difluoro-6-(trifluoromethyl)-2'H, 3H-spiro[imidazo[1,2-a]pyridine-2,1'-naphthalen]-4'(3H')-one (Examples 9 as a diastereomeric mixture). The crude product was purified by normal phase chromatography (40 g SiO₂-column; eluent heptane:EtOAc 100:0 to 80:20) to give the title compound as a yellow solid.

LC-MS: Rt=1.49 min; MS m/z [M+H]⁺ 613.0/614.9; UPLC-MS 1.

Intermediate Y: (S)-8-(difluoromethoxy)-5'-fluoro-6-(trifluoromethyl)-2',3'-dihydro-3H-dispiro[imidazo [1,2-a]pyridine-2,1'-naphthalene-4',2''-[1,3]dithiolane]

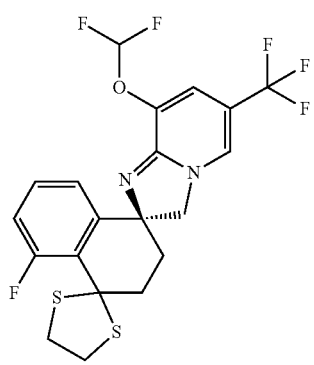 [SMILES: Fc1cccc2c1C1(CC[C@@]23CN2C=C(C(F)(F)F)C=C(OC(F)F)C2=N3)SCCS1]

The title compound was prepared by a method similar to that of Intermediate S by replacing (S)-6'-bromo-5'-fluoro- 2',3'-dihydrodispiro[oxazolidine-4, 1'-naphthalene-4',2"-[1,3]dithiolan]-2-one (Intermediate T) with (S)-5'-fluoro-2',3'-dihydrodispiro[oxazolidine-4,1'-naphthalene-4',2"-[1,3]dithiolan]-2-one (Intermediate Z). The crude product was used without purification in the following step.

$^1$H NMR (600 MHz, DMSO-d$_6$) δ 7.91 (s, 1H), 7.51-7.23 (m, 2H), 7.07 (q, 2H), 7.01 (s, 1H), 4.31 (d, 1H), 4.12 (d, 1H), 3.65-3.50 (m, 3H), 3.43-3.36 (m, 1H), 2.47 (dd, 1H), 2.32 (dd, 1H), 2.09-2.00 (m, 2H).

LC-MS: Rt=0.84 min; MS m/z [M+H]$^+$ 479.0; UPLC-MS 1.

Intermediate Z: (5)-5'-fluoro-2',3'-dihydrodispiro[oxazolidine-4,1'-naphthalene-4',2"-[1,3]dithiolan]-2-one Step 1: (S)-5-fluoro-3,4-dihydro-2H-spiro[naphthalene-1,4'-oxazolidin]-2'-one

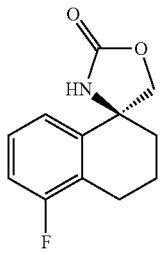 [SMILES: O=C1N[C@]2(CCCc3c(F)cccc32)CO1]

To a solution of (S)-(1-amino-5-fluoro-1,2,3,4-tetrahydronaphthalen-1-yl)methanol (Intermediate AA, 1.08 g, 5.53 mmol) and Et$_3$N (1.62 mL, 11.6 mmol) in DCM (30 mL) at 0-5° C. was added dropwise a solution of triphosgene (0.66 g, 2.21 mmol) in DCM (30 mL). The yellow solution was stirred at RT for 30 min. The RM was poured into saturated aq NaHCO$_3$ and extracted 2× with DCM. The combined organic extracts were dried (phase separator) and evaporated to give the title compound as a beige solid.

$^1$H NMR (400 MHz, DMSO-d$_6$) δ 8.22 (s, 1H), 7.33-7.29 (m, 2H), 7.11 (m, 1H), 4.35 (d, 1H), 4.18 (d, 1H), 2.70-2.57 (m, 2H), 2.02-1.72 (m, 4H).

LC-MS: Rt=0.81 min; MS m/z [M+NH$_4$]$^+$ 239.2; UPLC-MS 1.

Step 2: (S)-5-fluoro-2H-spiro[naphthalene-1,4'-oxazolidine]-2',4(3H)-dione

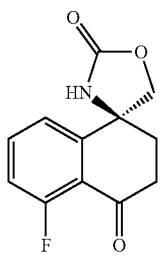 [SMILES: O=C1N[C@]2(CCC(=O)c3c(F)cccc32)CO1]

(S)-5-fluoro-3,4-dihydro-2H-spiro[naphthalene-1,4'-oxazolidin]-2'-one (500 mg, 2.26 mmol), N-hydroxyphtalimide (92 mg, 0.56 mmol) and iron(III) nitrate nonahydrate (186 mg, 0.45 mmol) were placed in a microwave vial. CH$_3$CN (14 mL) was added and the mixture was flushed with O2. The vial was capped and a balloon filled with O$_2$ connected to the vial via a needle. The RM was stirred under O$_2$ atmosphere at 35° C. for 16 hr. The RM was then filtered through a pad of Celite, washed with EtOAc and MeOH and the filtrate evaporated. The crude mixture was suspended in CH$_2$Cl$_2$ and filtered to give the title compound as a brownish solid.

$^1$H NMR (400 MHz, DMSO-d$_6$) δ 8.45 (s, 1H), 7.76 (m, 1H), 7.43 (d, 1H), 7.30 (dd, 1H), 4.59 (d, 1H), 4.26 (d, 1H), 2.87-2.79 (m, 1H), 2.66-2.60 (m, 1H), 2.31-2.27 (m, 2H).

LC-MS: Rt=0.53 min; MS m/z [M−H]$^-$ 234.2; UPLC-MS 1.

Step 3: (S)-5'-fluoro-2',3'-dihydrodispiro[oxazolidine-4,1'-naphthalene-4',2"-[1,3]dithiolan]-2-one

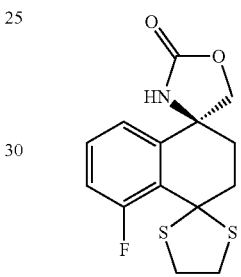

The title compound was prepared by a method similar to that of Intermediate T by replacing (S)-(1-amino-6-bromo-5-fluoro-1,2,3,4-tetrahydronaphthalen-1-yl)methanol (Intermediate R) with (S)-(1-amino-5-fluoro-1,2,3,4-tetrahydronaphthalen-1-yl)methanol (Intermediate AA). The crude product was purified by normal phase chromatography (80 g SiO$_2$-column; eluent heptane:EtOAc 100:0 to 40:60) to give the title compound as a brown solid.

$^1$H NMR (600 MHz, DMSO-d$_6$) δ 8.26 (s, 1H), 7.42 (td, 1H), 7.28 (d, 1H), 7.14 (dd, 1H), 4.45 (d, 1H), 4.21 (d, 1H), 3.66-3.58 (m, 1H), 3.53 (dd, 2H), 3.38-3.35 (m, 1H), 2.44-2.30 (m, 2H), 2.11 (t, 2H).

LC-MS: Rt=0.87 min; MS m/z [M+H]$^+$ 312.0; UPLC-MS 1.

Intermediate AA: (S)-(1-amino-5-fluoro-1,2,3,4-tetrahydronaphthalen-1-yl)methanol

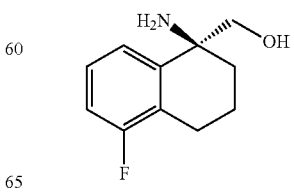

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with rac-1-amino-5-fluoro-1,2,3,4-tetrahydronaphthalene-1-carboxylic acid (Intermediate AU9). The enantiomers were separated by chiral SFC: (instrument: Sepiatec SFC 100; column: Lux i-Cel 5; 5 μm, 250×30 mm, 40° C.; eluent: $CO_2$/MeOH 80:20+1% $iPrNH_2$; flow rate: 80 mL/min; detection: 260 nm; injection volume: 4 mL ethanol (300 mg/injection)) to give the title compound as the first eluting peak, as a beige solid.

$^1$H NMR (400 MHz, DMSO-$d_6$) δ 7.40 (d, 1H), 7.16 (m, 1H), 6.95 (m, 1H), 4.79 (br s, 1H), 3.45 (d, 1H), 3.29 (d, 1H), 2.65-2.61 (m, 2H), 2.13-1.98 (m, 3H), 1.84-1.76 (m, 1H), 1.75-1.66 (m, 1H), 1.48 (m, 1H).

LC-MS: Rt=0.45 min; MS m/z [M+H]$^+$ 196.1; UPLC-MS 1.

Chiral-HPLC: Rt=7.45 min; with (R)-(1-amino-5-fluoro-1,2,3,4-tetrahydronaphthalen-1-yl)methanol eluting as the second peak, Rt=8.79 min; C-HPLC 47.

Intermediate AB: (S)-4'-((tert-butyldimethylsilyl)oxy)-8-(difluoromethoxy)-5'-fluoro-6-(trifluoromethyl)-2'H,3H-spiro[imidazo[1,2-a]pyridine-2,1'-naphthalene]

Step 1: (S)-8-(difluoromethoxy)-5'-fluoro-6-(trifluoromethyl)-2'H,3H-spiro[imidazo[1,2-a]pyridine-2,1'-naphthalen]-4'(3'H)-one

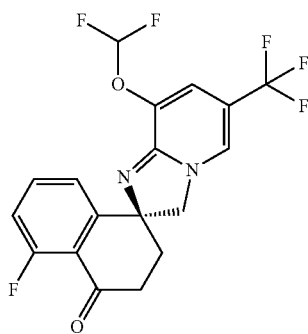 [SMILES: O=C1CC[C@@]2(CN3C=C(C(F)(F)F)C=C(OC(F)F)C3=N2)c2cccc(F)c21]

(S)-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane] (Intermediate Y, 4.27 g, 8.03 mmol) in acetone (120 mL) and water (12 mL) was cooled to 0° C. and NBS (11.4 g, 64.3 mmol) added. After stirring at 0° C. for 5 min saturated aq sodium thiosulfate was added to the RM. The RM was basified with saturated aq $NaHCO_3$ and extracted with EtOAc. The combined organic layers were washed with brine, dried over $Na_2SO_4$, filtered and evaporated. The residue was absorbed onto Isolute and purified by normal phase chromatography (120 g $SiO_2$-column; eluent DCM:MeOH 100:0 to 94:6). Product containing fractions were combined and evaporated to give the title compound.

LC-MS: Rt=0.59 min; MS m/z [M+H]$^+$ 403.0; UPLC-MS 1.

Step 2: (S)-4'-((tert-butyldimethylsilyl)oxy)-8-(difluoromethoxy)-5'-fluoro-6-(trifluoromethyl)-2'H,3H-spiro[imidazo[1,2-a]pyridine-2,1'-naphthalene]

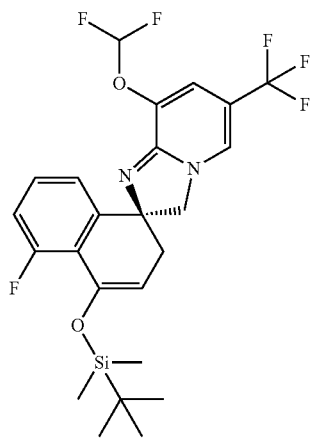 [SMILES: CC(C)(C)[Si](C)(C)OC1=CC[C@@]2(CN3C=C(C(F)(F)F)C=C(OC(F)F)C3=N2)c2cccc(F)c21]

The title compound was prepared by a method similar to that of Intermediate U by replacing (S)-6'-bromo-8-(difluoromethoxy)-5'-fluoro-6-(trifluoromethyl)-2'H,3H-spiro[imidazo[1,2-a]pyridine-2,1'-naphthalen]-4'(3'H)-one (Example 8) with (S)-8-(difluoromethoxy)-5'-fluoro-6-(trifluoromethyl)-2'H,3H-spiro[imidazo[1,2-a]pyridine-2,1'-naphthalen]-4'(3'H)-one (Step 1). The crude product was purified by normal phase chromatography (120 g $SiO_2$-column, eluent heptane:EtOAc 100:0 to 75:25) to give the title compound as a yellow solid.

LC-MS: Rt=1.21 min; MS m/z [M+H]$^+$ 517.1; UPLC-MS 1.

Intermediates AC and AD: (2S,4'S)-6'-bromo-8-(difluoromethoxy)-5'-fluoro-4'-hydroxy-3',4'-dihydro-2'H,3H-spiro[imidazo[1,2-a]pyridine-2,1'-naphthalene]-6-carbonitrile and (2S,4'R)-6'-bromo-8-(difluoromethoxy)-5'-fluoro-4'-hydroxy-3',4'-dihydro-2'H,3H-spiro[imidazo[1,2-a]pyridine-2,1'-naphthalene]-6-carbonitrile Step 1: (S)-6-(6'-bromo-5'-fluoro-2-oxo-2',3'-dihydrodispiro[oxazolidine-4,1'-naphthalene-4',2''-[1,3]dithiolan]-3-yl)-5-(difluoromethoxy)nicotinonitrile

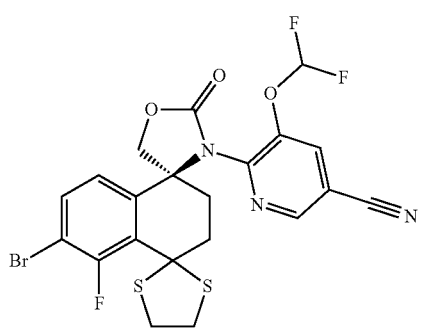 [SMILES: N#Cc1cnc(N2C(=O)OC[C@@]23CCC2(SCCS2)c2c3ccc(Br)c2F)c(OC(F)F)c1]

The title compound was prepared by a method similar to that of Intermediate S, Step 1 by replacing 2-chloro-3-(difluoromethoxy)-5-(trifluoromethyl)pyridine (Intermediate A) with 6-chloro-5-(difluoromethoxy)nicotinonitrile. The crude product was purified by normal phase chromatography (80 g SiO$_2$-column; eluent heptane:EtOAc 100:0 to 70:30) to give the title compound as a white foam.

LC-MS: Rt=1.24 min; MS m/z [M+H]$^+$ 558.1/559.9; UPLC-MS 1.

Step 2: (S)-6-((7'-bromo-8'-fluoro-4'-(hydroxymethyl)-3',4'-dihydro-2'H-spiro[[1,3]dithiolane-2,1'-naphthalen]-4'-yl)amino)-5-(difluoromethoxy)nicotinonitrile

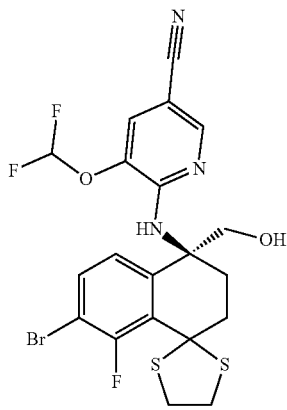 [SMILES: N#Cc1cnc(N[C@@]2(CO)CCC3(SCCS3)c3c2ccc(Br)c3F)c(OC(F)F)c1]

(S)-6-(6'-bromo-5'-fluoro-2-oxo-2',3'-dihydrodispiro[oxazolidine-4,1'-naphthalene-4',2''-[1,3]dithiolan]-3-yl)-5-(difluoromethoxy)nicotinonitrile (Step 1, 1.57 g, 2.53 mmol) and cesium carbonate (495 mg, 1.52 mmol) were suspended in MeOH (16 mL) under Ar. The RM was stirred at 80° C. for 35 min, then diluted with water and extracted with EtOAc. The combined organic layers were washed with brine, dried over Na$_2$SO$_4$, filtered evaporated and dried to give the title compound as a white foam.

LC-MS: Rt=1.22 min; MS m/z [M+H]$^+$ 532.0/534.0; UPLC-MS 1.

Step 3: (S)-6'-bromo-8-(difluoromethoxy)-5'-fluoro-2',3'-dihydro-3H-dispiro[imidazo[1,2-a]pyridine-2,1'-naphthalene-4',2''-[1,3]dithiolane]-6-carbonitrile

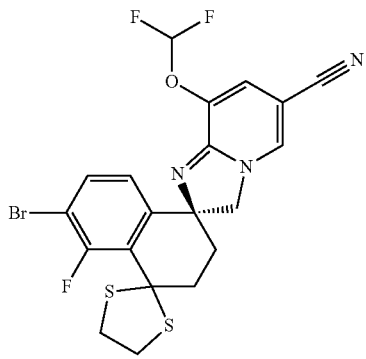 [SMILES: N#CC1=CN2C[C@@]3(CCC4(SCCS4)c4c3ccc(Br)c4F)N=C2C(OC(F)F)=C1]

The title compound was prepared by a method similar to that of Intermediate S, Step 3 by replacing (S)-(7-bromo-4'-((3-(difluoromethoxy)-5-(trifluoromethyl)pyridin-2-yl)amino)-8'-fluoro-3',4'-dihydro-2'H-spiro[[1,3]dithiolane-2,1'-naphthalen]-4'-yl)methanol (Intermediate S, Step 2) with (S)-6-((7'-bromo-8'-fluoro-4'-(hydroxymethyl)-3',4'-dihydro-2'H-spiro[[1,3]dithiolane-2,1'-naphthalen]-4'-yl)amino)-5-(difluoromethoxy)nicotinonitrile (Intermediates AC and AD, Step 2). The crude product was purified by normal phase chromatography (40 g SiO$_2$-column; eluent heptane:EtOAc 100:0 to 70:30) to give the title compound as a yellow solid.

$^1$H NMR (400 MHz, DMSO-d$_6$) δ 8.13 (d, 1H), 7.61 (dt, 1H), 7.46-6.99 (m, 3H), 4.31 (dd, 1H), 4.12 (dd, 1H), 3.69-3.59 (m, 1H), 3.57 (d, 2H), 3.40 (s, 1H), 2.35 (d, 2H), 2.03 (d, 2H).

LC-MS: Rt=0.93 min; MS m/z [M+H]$^+$ 514.0/516.0; UPLC-MS 1.

Step 4: (S)-6'-bromo-8-(difluoromethoxy)-5'-fluoro-4'-oxo-3',4'-dihydro-2'H,3H-spiro[imidazo[1,2-a]pyridine-2,1'-naphthalene]-6-carbonitrile

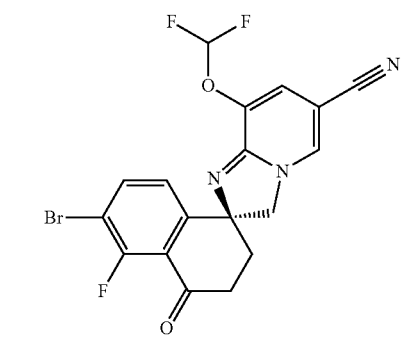 [SMILES: N#CC1=CN2C[C@@]3(CCC(=O)c4c3ccc(Br)c4F)N=C2C(OC(F)F)=C1]

Water (2.5 mL) was added to (S)-6'-bromo-8-(difluoromethoxy)-5'-fluoro-2',3'-dihydro-3H-dispiro[imidazo[1,2-a]pyridine-2,1'-naphthalene-4',2''-[1,3]dithiolane]-6-carbonitrile (step 3, 867 mg, 1.65 mmol) in acetone (25 mL) cooled with an ice bath. NBS (2.94 g, 16.5 mmol) was added and the RM stirred at 0° C. for 5 min. The reaction was quenched with saturated aq sodium thiosulfate, basified with saturated aq NaHCO$_3$ and extracted twice with EtOAc. The combined organic layers were washed with brine, dried over Na$_2$SO$_4$, filtered and evaporated. The residue was purified by SFC (SFC 1) and the product containing fractions were combined and evaporated to give the title compound.

LC-MS: Rt=0.72 min, broad peak; MS m/z [M+H]+ 438.0/440.0; UPLC-MS 1.

Step 5: (2S,4'S)-6'-bromo-8-(difluoromethoxy)-5'-fluoro-4'-hydroxy-3',4'-dihydro-2'H,3H-spiro[imidazo[1,2-a]pyridine-2,1'-naphthalene]-6'-carbonitrile and (2S,4'R)-6'-bromo-8-(difluoromethoxy)-5'-fluoro-4'-hydroxy-3',4'-dihydro-2'H,3H-spiro[imidazo[1,2-a]pyridine-2,1'-naphthalene]-6'-carbonitrile

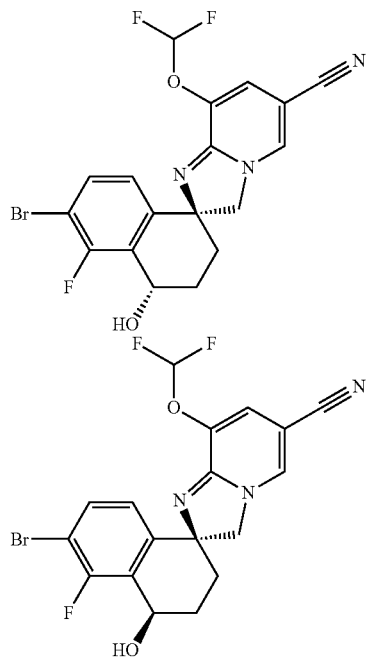

Sodium tetrahydroborate (20.3 mg, 514 μmol) was added to (S)-6'-bromo-8-(difluoromethoxy)-5'-fluoro-4'-oxo-3',4'-dihydro-2'H,3H-spiro[imidazo[1,2-a]pyridine-2,1'-naphthalene]-6'-carbonitrile (Step 4, 256 mg, 467 μmol) suspended in EtOH (5 mL) cooled to 0° C. under Ar. The RM was stirred at 0° C. for 30 minutes, then quenched with saturated aq NaHCO₃ and extracted with EtOAc. The combined organic layers were washed with brine, dried over Na₂SO₄ and evaporated. The residue was absorbed onto Isolute and purified by normal phase chromatography (40 g SiO₂-column; eluent DCM:MeOH 100:0 to 95:5) followed by SFC (SFC 1) to give the title compounds as a diastereomeric mixture. The diastereomers were separated by chiral SFC (Waters SFC100 prep system, column: Chiralpak IG, 5 μm, 250×30 mm; eluent: CO₂: MeOH+0.1% NH₃ 65:35; temperature: 23° C.; flow rate: 80 mL/min) to give (1'S)-6'-bromo-8-(difluoromethoxy)-5'-fluoro-4'-hydroxy-3',4'-dihydro-2'H,3H-spiro[imidazo[1,2-a]pyridine-2,1'-naphthalene]-6'-carbonitrile (alcohol stereochemistry unassigned) as the first eluting peak, Rt 1.03 min.

LC-MS: Rt=0.59 min; MS m/z [M+H]+ 440.0/442.0; UPLC-MS 1.

(1'S)-6'-bromo-8-(difluoromethoxy)-5'-fluoro-4'-hydroxy-3',4'-dihydro-2'H,3H-spiro[imidazo[1,2-a]pyridine-2,1'-naphthalene]-6'-carbonitrile (alcohol stereochemistry unassigned) was obtained as the second eluting peak, Rt 2.01 min.

LC-MS: Rt=0.59 min; MS m/z [M+H]+ 440.1/442.1; UPLC-MS 1.

Intermediates AE and AF: (1'S,4'S)-8-(difluoromethoxy)-5'-fluoro-4'-hydroxy-6-(trifluoromethyl)-3',4'-dihydro-2'H,3H-spiro[imidazo[1,2-a]pyridine-2,1'-naphthalene]-6'-carbonitrile and (1'S,4'R)-8-(difluoromethoxy)-5'-fluoro-4'-hydroxy-6-(trifluoromethyl)-3',4'-dihydro-2'H,3H-spiro[imidazo[1,2-a]pyridine-2,1'-naphthalene]-6'-carbonitrile Step 1: (S)-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane]-6'-carbonitrile

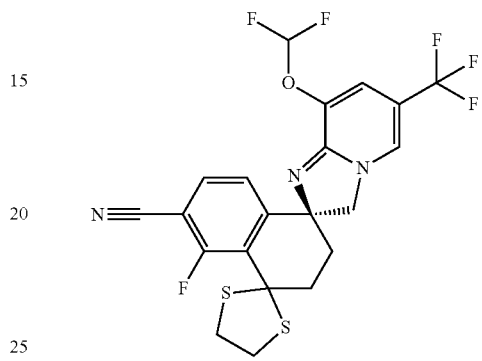

A mixture of (S)-6'-bromo-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane] (Intermediate S, 150 mg, 223 μmol), XPhos Pd G3 (18.91 mg, 22 μmol), XPhos (21.73 mg, 45 μmol), potassium ferricyanide trihydrate (47.2 mg, 112 μmol) and KOAc (3.29 mg, 34 μmol) in 1,4-dioxane (2 mL) and water (2 mL) was stirred for 1.5 hr in a microwave at 100° C. The RM was diluted with EtOAc, washed with saturated aq NaHCO₃, dried and concentrated. The residue was taken up into DCM (5 mL) and SiliaMetS®Thiol (66 μmol, 48 mg) was added, the mixture stirred for 0.5 hr, then filtered, washing with DCM, and the filtrate concentrated. The residue was purified by normal phase column chromatography (silica gel: eluent c-hexane:EtOAc 100:0 to 70:30) to give the title compound.

LC-MS: Rt=0.90 min; MS m/z [M+H]+ 504.3; UPLC-MS 1.

Step 2: (S)-8-(difluoromethoxy)-5'-fluoro-4'-oxo-6-(trifluoromethyl)-3',4'-dihydro-2'H,3H-spiro[imidazo[1,2-a]pyridine-2,1'-naphthalene]-6'-carbonitrile

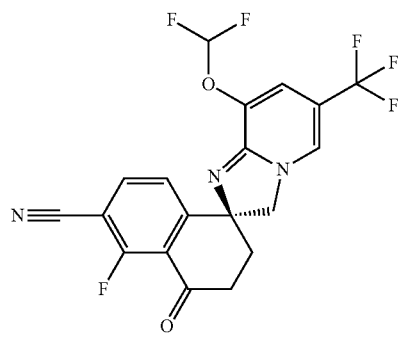 [SMILES: N#Cc1ccc2c(c1F)C(=O)CC[C@@]21CN2C=C(C(F)(F)F)C=C(OC(F)F)C2=N1]

To a solution of N-iodosuccinimide (168 mg, 0.747 mmol) in DCM (1.5 mL), cooled with a dry ice/acetone bath, was added dropwise hydrogen fluoride pyridine (70%, 93

μL, 0.747 mmol), followed by the dropwise addition of a solution of (S)-8-(difluoromethoxy)-5'-fluoro-6-(trifluoromethyl)-2',3'-dihydro-3H-dispiro[imidazo[1,2-a]pyridine-2,1'-naphthalene-4',2''-[1,3]dithiolane]-6'-carbonitrile (step 1, 100 mg, 0.187 mmol) in DCM (1 mL). The RM was stirred for 1 hr at −70° C., and then poured into a solution of saturated aq NaHCO$_3$ (50 mL) cooled with an ice bath. An aq solution of Na$_2$S$_2$O$_3$ (10%, 50 mL) was added and the mixture extracted with DCM, the organic layers dried by passing through a phase separator cartridge, and concentrated. The residue was purified by reversed phase chromatography (RP-HPLC 3) to give (S)-8-(difluoromethoxy)-4',4',5'-trifluoro-6-(trifluoromethyl)-3',4'-dihydro-2'H,3H-spiro[imidazo[1,2-a]pyridine-2,1'-naphthalene]-6'-carbonitrile (Example 15) followed by the title compound as a yellow solid.

LC-MS: Rt=2.67 min; MS m/z [M+H]$^+$ 428.3; UPLC-MS 4.

Step 3: (1'S,4'S)-8-(difluoromethoxy)-5'-fluoro-4'-hydroxy-6-(trifluoromethyl)-3',4'-dihydro-2'H,3H-spiro[imidazo[1,2-a]pyridine-2,1'-naphthalene]-6'-carbonitrile and (1'S,4'R)-8-(difluoromethoxy)-5'-fluoro-4'-hydroxy-6-(trifluoromethyl)-3',4'-dihydro-2'H,3H-spiro[imidazo[1,2-a]pyridine-2,1'-naphthalene]-6'-carbonitrile

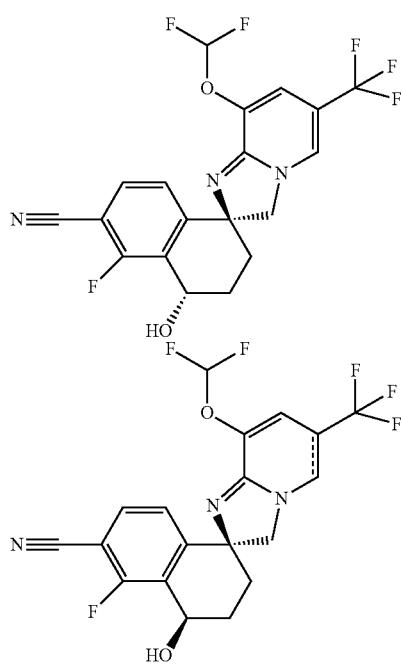

The title compounds were prepared by a method similar to that of Intermediates AC and AD by replacing (S)-6'-bromo-8-(difluoromethoxy)-5'-fluoro-4'-oxo-3',4'-dihydro-2'H,3H-spiro[imidazo[1,2-a]pyridine-2,1'-naphthalene]-6-carbonitrile (Intermediate AC and AD, Step 1) with (S)-8-(difluoromethoxy)-5'-fluoro-4'-oxo-6-(trifluoromethyl)-3',4'-dihydro-2'H,3H-spiro[imidazo[1,2-a]pyridine-2,1'-naphthalene]-6'-carbonitrile (Intermediates AE and AF, step 2). The diastereomers were separated by SFC (SFC 1) to give the first eluting diastereomer, Rt 6.65 min.

$^1$H NMR (400 MHz, DMSO-d$_6$) δ 8.00 (s, 1H), 7.79 (t, 1H), 7.50-7.09 (m, 2H), 7.00 (s, 1H), 5.41 (d, 1H), 4.93 (s, 1H), 4.45 (d, 1H), 4.22 (d, 1H), 2.16 (d, 2H), 1.80 (d, 2H).

LC-MS: Rt=0.62 min; MS m/z [M+H]$^+$ 430.2; UPLC-MS 1. followed by the second eluting diastereomer, Rt 8.51 min.

$^1$H NMR (600 MHz, DMSO-d$_6$) δ 7.91 (t, 1H), 7.80 (dd, 1H), 7.41 (t, 1H), 7.33 (d, 1H), 7.06 (d, 1H), 5.46 (d, 1H), 4.90 (s, br, 1H), 4.30 (d, 1H), 3.84 (d, 1H), 2.25-2.19 (m, 1H), 1.96-1.80 (m, 2H), 1.76-1.72 (m, 1H).

LC-MS: Rt=0.63 min; MS m/z [M+H]$^+$ 430.2; UPLC-MS 1.

Intermediate AG: (S)-(1-amino-5-fluoro-1,2,3,4-tetrahydronaphthalen-1-yl-4,4-d$_2$)methanol Step 1: (1S,4S)-5-fluoro-4-hydroxy-3,4-dihydro-2H-spiro[naphthalene-1,4'-oxazolidin]-2'-one-4-d and (1S,4R)-5-fluoro-4-hydroxy-3,4-dihydro-2H-spiro[naphthalene-1,4'-oxazolidin]-2'-one-4-d

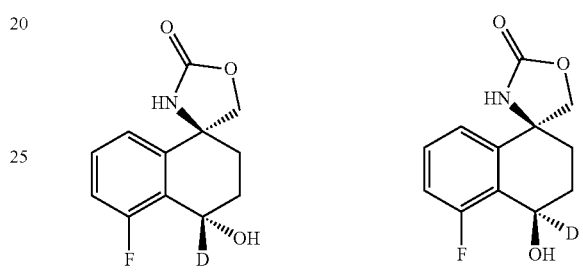

A mixture of (S)-5-fluoro-2H-spiro[naphthalene-1,4'-oxazolidine]-2',4(3H)-dione (Intermediate Z step 2, 32 mg, 0.16 mmol) and NaBD$_4$ (Cambridge Isotope Laboratories, 99 atom % D; 11.5 mg, 0.27 mmol) in MeOD (1.4 mL) was stirred at RT under a nitrogen atmosphere for 1.5 hr. The reaction mixture was poured into water and extracted 3× with DCM. The combined organic extracts were dried (phase separator) and evaporated to give the title compound as a white solid as a mixture diastereomers (ratio 6:4).

$^1$H NMR (600 MHz, DMSO-d$_6$) δ 8.42 (s, 0.6H), 8.22 (s, 0.4H), 7.42 (m, 1H), 7.29 (m, 1H), 7.15 (m, 1H), 5.24 (s, 0.4H), 5.17 (s, 0.6H), 4.51 (d, 0.6H), 4.37 (d, 0.4H), 4.34 (d, 0.6H), 3.94 (d, 0.4H), 2.24 (m, 1H), 2.02 (m, 0.6H), 1.85-1.74 (m, 2.4H).

LC-MS: Rt=0.44 and 0.54 min; MS m/z [M+NH$_4$]$^+$ 256.3; UPLC-MS 1.

Step 2: (S)-5-fluoro-3,4-dihydro-2H-spiro[naphthalene-1,4'-oxazolidin]-2'-one-4,4-d$_2$

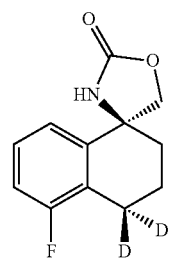

To a mixture of (1S,4S)-5-fluoro-4-hydroxy-3,4-dihydro-2H-spiro[naphthalene-1,4'-oxazolidin]-2'-one-4-d and (1S,4R)-5-fluoro-4-hydroxy-3,4-dihydro-2H-spiro[naphthalene-1,4'-oxazolidin]-2'-one-4-d (Step 1, 25 mg, 0.10 mmol)

suspended in DCM (0.65 mL) cooled at −65° C. were added Et₃SiD (50 μL, 0.31 mmol) and BF₃.Et₂O (27 μL, 0.21 mmol) under a nitrogen atmosphere. The RM was allowed to warm RT and stirred for 2 hr. The RM was poured into saturated aq NaHCO₃ and extracted 3× with DCM. The combined organic extracts were dried (phase separator) and evaporated to give the title compound as a white solid.

¹H NMR (600 MHz, DMSO-d₆) δ 8.25 (s, 1H), 7.35-7.30 (m, 2H), 7.11 (t, 1H), 4.36 (d, 1H), 4.18 (d, 1H), 1.99 (m, 1H), 1.90 (m, 1H), 1.84 (m, 1H), 1.74 (m, 1H).

LC-MS: Rt=0.79 min; MS m/z [M+NH₄]⁺ 241.3; UPLC-MS 1.

Step 3: (S)-(1-amino-5-fluoro-1,2,3,4-tetrahydronaphthalen-1-yl-4,4-d₂)methanol

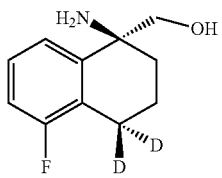

A solution of (S)-5-fluoro-3,4-dihydro-2H-spiro[naphthalene-1,4'-oxazolidin]-2'-one-4,4-d₂ (Step 2, 23 mg, 0.10 mmol) and NaOH (4N, 0.25 mL, 1.01 mmol) in ethanol (0.4 mL) was stirred at 80° C. for 15 hr. The RM was poured into water and extracted 3× with EtOAc. The combined organic extracts were dried (phase separator) and evaporated to give the title compound as a white solid which was used without purification in the next step.

¹H NMR (600 MHz, DMSO-d₆) δ 7.40 (d, 1H), 7.17 (m, 1H), 6.95 (t, 1H), 4.79 (t, 1H), 3.45 (dd, 1H), 3.29 (dd, 1H), 2.03-1.98 (m, 1H), 1.97-1.76 (m, 3H), 1.71 (m, 1H), 1.47 (m, 1H).

LC-MS: Rt=0.45 min; MS m/z [M+H]⁺ 198.3; UPLC-MS 1.

Intermediate AH: (S)-1'-chloro-8,8',8'-trifluoro-6-(trifluoromethyl)-7',8'-dihydro-3H,6'H-spiro[imidazo[1,2-a]pyridine-2,5'-isoquinoline]

Step 1: (S)-1'-chloro-3-(3-fluoro-5-(trifluoromethyl)pyridin-2-yl)-6',7'-dihydrodispiro[oxazolidine-4,5'-isoquinoline-8',2''-[1,3]dioxolan]-2-one

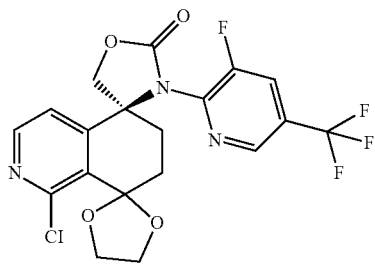

A mixture of (S)-1'-chloro-6',7'-dihydrodispiro[oxazolidine-4,5'-isoquinoline-8',2''-[1,3]dioxolan]-2-one (Intermediate AI, 500 mg, 1.57 mmol), 2-chloro-3-fluoro-5-(trifluoromethyl)pyridine (494 mg, 2.35 mmol), CuBr (112 mg, 0.784 mmol), Cs₂CO₃ (1.02 g, 3.13 mmol) and DMF (15 mL) was heated for 1.5 hr at 130° C. under an argon atmosphere in a sealed reaction vessel. Saturated aq NH₄Cl was added to the cooled RM which was extracted 2× with EtOAc, the combined organic layers were dried and concentrated. The residue was purified by normal phase chromatography (silica gel, eluent heptane:EtOAc 100:0 to 20:80) to give the title compound as a yellow powder.

LC-MS: Rt=1.03 min; MS m/z [M+H]⁺ 460.1/462.1; UPLC-MS 1.

Step 2: (S)-1-chloro-3'-(3-fluoro-5-(trifluoromethyl)pyridin-2-yl)-6,7-dihydro-8H-spiro[isoquinoline-5,4'-oxazolidine]-2',8-dione

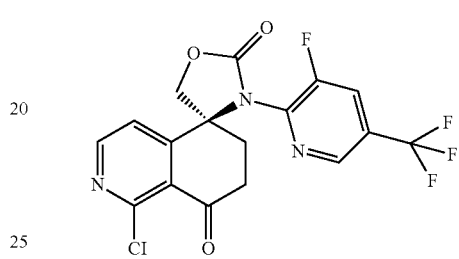

A solution of (S)-1'-chloro-3-(3-fluoro-5-(trifluoromethyl)pyridin-2-yl)-6',7'-dihydrodispiro[oxazolidine-4,5'-isoquinoline-8',2''-[1,3]dioxolan]-2-one (Step 1, 761 mg, 1.39 mmol) in THF (7.8 mL) and 1N aq HCl (6.95 ml, 6.95 mmol) was heated for 18 hr at 80° C. in a sealed reaction vessel. The cooled RM was poured into saturated aq NaHCO₃, extracted 3× with DCM, the combined organic layers were dried by passing through a phase separator and concentrated. The residue was purified by normal phase chromatography (silica gel, eluent heptane:EtOAc 100:0 to 20:80) to give the title compound as a white powder.

LC-MS: Rt=1.00 min; MS m/z [M+H]⁺ 416.1/418.1; UPLC-MS 1.

Step 3: (S)-1-chloro-8,8-difluoro-3'-(3-fluoro-5-(trifluoromethyl)pyridin-2-yl)-7,8-dihydro-6H-spiro[isoquinoline-5,4'-oxazolidin]-2'-one

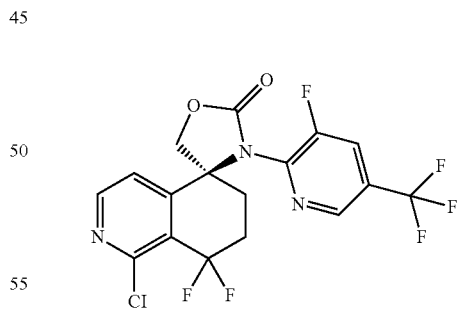

DAST (1.49 ml, 11.24 mmol) was added to a solution of (S)-1-chloro-3'-(3-fluoro-5-(trifluoromethyl)pyridin-2-yl)-6,7-dihydro-8H-spiro[isoquinoline-5,4'-oxazolidine]-2',8-dione (Step 2, 492 mg, 1.12 mmol) in DCM (6 mL) at RT under argon, and the RM heated for 2 days at 40° C. in a sealed reaction vessel. The cooled RM was slowly added to saturated aq NaHCO₃, cooled with an ice bath, CAUTION: EXOTHERMIC! The mixture was extracted 3× with DCM, the combined organic layers dried by passing through a phase separator and concentrated. The residue was purified by flash column chromatography (silica gel: eluent heptane: EtOAc 100:0 to 30:70) to give the title compound as a white powder.

LC-MS: Rt=1.13 min; MS m/z [M+H]+ 438.1/440.1; UPLC-MS 1.

Step 4: (S)-(1-chloro-8,8-difluoro-5-((3-fluoro-5-(trifluoromethyl)pyridin-2-yl)amino)-5,6,7,8-tetrahydroisoquinolin-5-yl)methanol

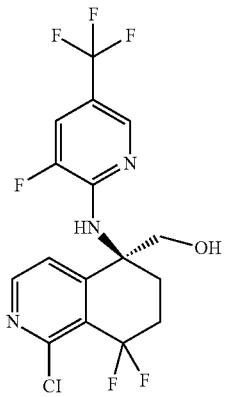

(S)-1-chloro-8,8-difluoro-3'-(3-fluoro-5-(trifluoromethyl)pyridin-2-yl)-7,8-dihydro-6H-spiro[isoquinoline-5,4'-oxazolidin]-2'-one (Step 3, 487.4 mg, 1.10 mmol) was suspended in EtOH (9 mL) and aq NaOH (4M, 2.76 ml, 11.02 mmol) was added at RT. The RM was stirred for 30 min at RT, then partitioned between saturated aq NaHCO₃ and DCM, extracted 3× with DCM, the combined organic layers were dried by passing through a phase separator and evaporated to give the title compound which was used directly without further purification.

LC-MS: Rt=1.14 min; MS m/z [M+H]+ 412.1/414.1; UPLC-MS 1.

Step 5: (S)-1'-chloro-8,8',8'-trifluoro-6-(trifluoromethyl)-7',8'-dihydro-3H,6'H-spiro[imidazo[1,2-a]pyridine-2,5'-isoquinoline]

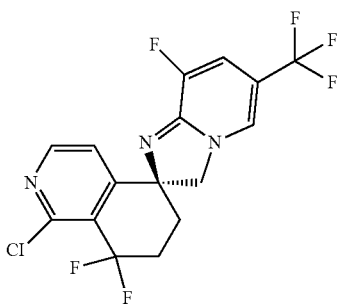

SOCl₂ (0.140 mL, 1.91 mmol) was added to a solution of (S)-(1-chloro-8,8-difluoro-5-((3-fluoro-5-(trifluoromethyl) pyridin-2-yl)amino)-5,6,7,8-tetrahydroisoquinolin-5-yl) methanol (step 4, 458 mg, 957 µmol) in toluene (7 mL) at RT. The RM was heated for 20 min at 80° C., cooled, MeOH added and evaporated. The residue was dissolved in DCM containing 1-2% MeOH and partitioned with saturated aq NaHCO₃ solution, the aqueous phase extracted 2× with DCM, the combined organic layers were dried by passing through a phase separator and concentrated. The residue was purified by normal phase column chromatography (silica gel, eluent heptane:EtOAc 100:0 to 40:60) to give the title compound as a yellow powder.

¹H NMR (400 MHz, DMSO-d₆) δ 8.49 (d, 1H), 7.97 (s, 1H), 7.51 (d, 1H), 7.33 (d, 1H), 4.35 (q, 2H), 2.71-2.28 (m, 2H), 2.21-1.98 (m, 2H).

LC-MS: Rt=3.03 min; MS m/z [M+H]+ 394.3/396.3; UPLC-MS 4.

Intermediate AI: (S)-1'-chloro-6',7'-dihydrodispiro[oxazolidine-4,5'-isoquinoline-8',2"-[1,3]dioxolan]-2-one Step 1: rac-1-(2-chloro-4-iodopyridin-3-yl)pent-4-en-1-ol

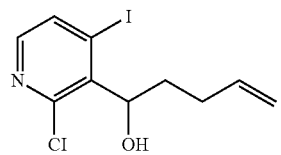

A solution of 2-chloro-4-iodopyridine (38 g, 157 mmol) in THF (140 mL) was added dropwise to a solution of LDA in THF [prepared by the addition of n-butyllithium (2.5M, 79 mL, 196 mmol) to a solution of diisopropylamine (28.0 mL, 196 mmol) in THF (90 mL) whilst maintaining the internal temperature below 0° C.], under a positive pressure of argon, and cooled with a dry-ice acetone bath so as to maintain the internal temperature below −75° C. After stirring the RM for 30 min below −75° C., a solution of pent-4-enal (23.47 mL, 238 mmol) in THF (40 mL) was added over 30 min, the RM was then warmed to 0° C. with an ice-bath, and stirred at 0° C. for 15 min. Saturated aq NaHCO₃ (250 mL) and water (11 mL) were added and the mixture extracted with EtOAc (1×300 mL, 1×200 mL), the combined organic layers were washed with brine, dried over sodium sulfate, and concentrated. The residue was absorbed onto silica gel and purified by normal phase column chromatography (2×220 g silica gel columns, eluent heptane: EtOAc 100:0 to 70:30) to give the title compound as a clear brown oil.

LC-MS: Rt=0.97 min; MS m/z [M+H]+ 324.1/326.1; UPLC-MS 1.

Intermediate AI, step 1 can also be synthesized via the following alternative route:

A solution of but-3-en-1-ylmagnesium bromide in THF (0.5 M, 1 L) was added to a mixture of LiCl (21.7 g, 508 mmol) and ZnCl₂ (71.4 g, 508 mmol), in THF (80 mL) cooled with an ice bath, under a positive N2 pressure, at such as rate that the internal temperature remained below 15° C. The RM was stirred at ambient temperature for 1 hr. A solution of 2-chloro-4-iodonicotinaldehyde (27.0 g, 100 mmol) in THF (80 mL) was then added, and the RM allowed to stir at ambient temperature for 2 hr. The RM was cooled to 0° C. and saturated aq potassium sodium tartrate tetrahydrate (240 mL) was added slowly and the mixture stirred for 1 hr, then filtered and the filter cake washed with EtOAc (300 mL). The biphasic filtrate was separated, and the aq phase extracted with EtOAc (3×300 mL). The combined organic layers were washed with brine (500 mL), dried over anhydrous Na$_2$SO$_4$ and evaporated to give the title compound.

Step 2: 1-(2-chloro-4-iodopyridin-3-yl)pent-4-en-1-one

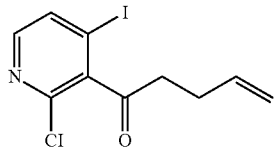

To a stirred solution of rac-1-(2-chloro-4-iodopyridin-3-yl)pent-4-en-1-ol (Step 1, 32.0 g, 94 mmol) in DCM (400 mL) was added portion wise Dess-Martin periodinane reagent (47.8 g, 113 mmol) over 30 min, slightly exothermic, and the RM warms up to 35° C. The RM was stirred at RT for 1.5 hr before saturated aq Na$_2$S$_2$O$_3$ was added and the stirring continued for 0.5 hr at RT. The mixture was extracted 3× with DCM, the combined organic layers were washed with saturated aq NaHCO$_3$, dried by passing through a phase separator cartridge and evaporated. The residue was adsorbed onto Isolute and purified by normal phase chromatography (2×120 g SiO$_2$-column, eluent hexane:EtOAc from 0-15%) to give the title compound as a yellow oil.

LC-MS: Rt=1.12 min; MS m/z [M+H]$^+$ 321.9/323.9; UPLC-MS 1.

Intermediate AI, step 2 can also be synthesized via the following alternative route:

PhI(OAc)$_2$ (4.45 g, 13.8 mmol, 1.95 equiv) was added to a mixture of 1-(2-chloro-4-iodopyridin-3-yl)pent-4-en-1-ol (Step 1, 2.7 g, 7.1 mmol) and TEMPO (0.28 g, 1.8 mmol) in DCM (25 mL) cooled with an ice bath. The mixture was stirred at RT for 1 hr, and water (50 mL), followed by Na$_2$SO$_3$ (1.5 g) were added. The phases were separated and the aq phase extracted with DCM (2×25 mL). The combined organic layers were dried over anhydrous Na$_2$SO$_4$, and concentrated to give the title compound as a brown oil.

Step 3: 1-chloro-5-methylene-6,7-dihydroisoquinolin-8(5H)-one

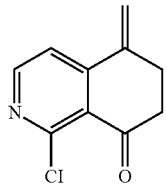

A mixture of 1-(2-chloro-4-iodopyridin-3-yl)pent-4-en-1-one (Step 2, 34.7 g, 106 mmol), Ag$_2$CO$_3$ (21.98 g, 79 mmol), P(2-furyl)$_3$ (3.76 g, 15.86 mmol), Pd(OAc)$_2$ (1.80 g, 7.93 mmol) and AcCN (563 mL) was heated at 55-60° C. for 3.5 hr under an atmosphere of argon. The RM was filtered through Hyflo filter aid, washing with acetonitrile, and evaporated. The residue was purified by normal phase chromatography (2×220 g silica gel columns, eluent heptane:EtOAc 10:90 to 45:55), product containing fractions were combined, evaporated and triturated with heptane:EtOAc 60:40 to give the title compound as a yellow powder.

LC-MS: Rt=0.78 min; MS m/z [M+H]$^+$ 194.0/196.0; UPLC-MS 1.

Step 4: 1-chloro-5-methylene-6,7-dihydro-5H-spiro[isoquinoline-8,2'-[1,3]dioxolane]

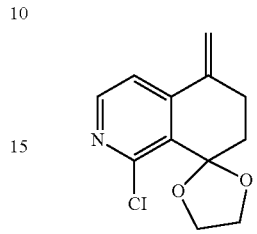

A mixture of 1-chloro-5-methylene-6,7-dihydroisoquinolin-8(5H)-one (Step 3, 16 g, 79 mmol), HC(OEt)$_3$ (39.2 ml, 236 mmol), para-toluenesulfonic acid (2.70 g, 15.70 mmol) and ethylene glycol (88 ml, 1570 mmol) were heated at 60° C. for 1.5 hr under an atmosphere of argon. The RM was partitioned between DCM and saturated aq NaHCO$_3$, the aqueous layer extracted 2× with DCM, the combined organic layers were dried by passing through a phase separator and concentrated. Purification of the residue by normal phase column chromatography (2×220 g silica gel columns, eluent heptane:EtOAc 0:100 to 40:60) gave the title compound as a clear pale yellow oil.

LC-MS: Rt=3.71 min; MS m/z [M+H]$^+$ 238.2/240.2; UPLC-MS 4.

Step 5: (R)-(1-chloro-6,7-dihydro-5H-spiro[isoquinoline-8,2'-[1,3]dioxolan]-5-yl)methanol

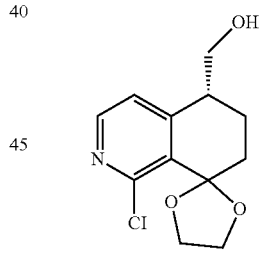

A solution of 9-BBN in THF (0.5M, 616 mL, 308 mmol) was added dropwise to a solution of 1-chloro-5-methylene-6,7-dihydro-5H-spiro[isoquinoline-8,2'-[1,3]dioxolane] (Step 4, 37 g, 154 mmol) in THF (118 mL) cooled with an ice bath under an atmosphere of argon. The RM was stirred for 1 hr at 0° C., 30 min at RT, 2 hr at 50° C., and then for 18 hr at RT. The RM was then cooled with an ice bath and aq NaOH (4N, 193 ml, 771 mmol) was added followed by the dropwise addition of aq hydrogen peroxide (30%, 79 ml, 771 mmol), CAUTION EXOTHERMIC! The RM was stirred for 30 min at RT, diluted with brine, extracted 2× with EtOAc, the combined organic layers washed 2× with 10% aq Na$_2$S$_2$O$_3$ (negative peroxide test for the organic layer), dried over sodium sulfate and concentrated. The residue was purified by normal phase chromatography (silica gel, 330 g column, eluent DCM:EtOH 98:2 to 90:10), product containing fractions were evaporated and triturated with diethyl ether containing 2% DCM to give the racemic product as a white powder. Further racemic product was obtained by normal phase chromatography purification of the filtrate (silica gel, 330 g column, eluent DCM:EtOH 98:2 to 90:10). The enantiomers were separated by chiral SFC: (instrument: Thar 350 preparative SFC; column: Chiralpak AD 10 300× 50 mm 38° C.; eluent: $CO_2$: MeOH with 0.1% $NH_4OH$, 80:20; flow rate: 200 mL/min; Detection: 254 nm) to give the title compound as the predominant second-eluting peak.

LC-MS: Rt=2.02 min; MS m/z $[M+H]^+$ 256.3/258.3; UPLC-MS 4.

Chiral-SFC: Rt=3.45 min; with (S)-(1-chloro-6,7-dihydro-5H-spiro[isoquinoline-8,2'-[1,3]dioxolan]-5-yl)methanol as the first-eluting peak, Rt=3.78 min; C-SFC 8.

Step 6: (R)-(1-chloro-6,7-dihydro-5H-spiro[isoquinoline-8,2'-[1,3]dioxolan]-5-yl)methyl Carbamate

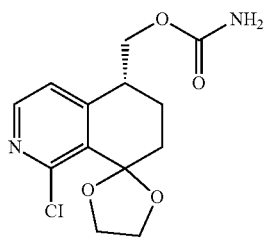

Trichloroacetyl isocyanate (9.28 mL, 78 mmol) was slowly added to a solution of (R)-(1-chloro-6,7-dihydro-5H-spiro[isoquinoline-8,2'-[1,3]dioxolan]-5-yl)methanol (Step 5, 16.76 g, 64.9 mmol) in DCE (300 mL) cooled with an ice bath, under an argon atmosphere. After stirring 30 min at 0° C. $K_2CO_3$ (897 mg, 6.49 mmol) was added followed by MeOH (300 mL) and the RM stirred overnight at RT. The RM was poured into saturated aq $NaHCO_3$, the mixture extracted 2× with DCM. On standing a precipitate formed in the organic extracts which was collected by filtration and dried to give the title compound as a white powder. Additional product was obtained after drying the filtrate over sodium sulfate, evaporating and triturating with diethyl ether.

LC-MS: Rt=2.26 min; MS m/z $[M+H]^+$ 299.3/301.3; UPLC-MS 4.

Step 7: (S)-1'-chloro-6',7'-dihydrodispiro[oxazolidine-4,5'-isoquinoline-8',2"-[1,3]dioxolan]-2-one

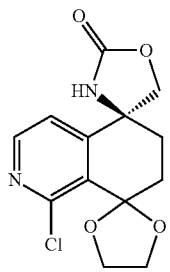

A mixture of (R)-(1-chloro-6,7-dihydro-5H-spiro[isoquinoline-8,2'-[1,3]dioxolan]-5-yl)methyl carbamate (Step 6, 4.0 g, 13.26 mmol), diacetoxyiodobenzene (6.10 g, 18.56 mmol), MgO (1.29 g, 30.5 mmol) and $Rh_2(esp)_2$ (262 mg, 331 µmol) in DCM (133 mL) was heated at 45° C. for 21 hr in an Ace Pressure Tube, under an atmosphere of argon. Additional diacetoxyiodobenzene (1.28 g, 3.98 mmol), MgO (267 mg, 6.63 mmol) and $Rh_2(esp)_2$ (50 mg, 66 µmol) were added to the RM, the vessel flushed with argon and heated for a further 21 hr at 45° C. The cooled RM was poured into saturated aq $NaHCO_3$, the mixture extracted 3× with DCM, the combined organic layers were dried over $Na_2SO_4$, filtered and concentrated. Purification of the residue by normal phase column chromatography (silica gel, eluent heptane:EtOAc 100:0 to 0:100) gave the title compound as a beige powder.

LC-MS: Rt=0.57 min; MS m/z $[M+H]^+$ 297.3/299.3; UPLC-MS 1.

Intermediate AI can also be synthesized via the following alternative route:

Step 1A: (S)-1-chloro-5-methylene-5,6,7,8-tetrahydroisoquinolin-8-ol

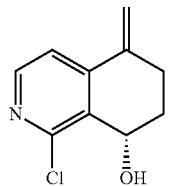

A solution of RuCl(p-cymene)[(S,S)-Ts-DPEN] (371 mg, 583 µmol) in DCM (20 mL) was added dropwise to a solution of 1-chloro-5-methylene-6,7-dihydroisoquinolin-8(5H)-one (Step 3, 8.0 g, 38.8 mmol) in DCM (100 mL) under a positive pressure of argon. The RM was cooled with an ice bath and formic acid (4.47 mL, 117 mmol) was added dropwise. After stirring for 2 hr at 5° C. and 18 hr at RT the RM was partitioned between DCM (200 mL) and saturated aq $NaHCO_3$ (100 mL), extracted 2× with DCM (50 mL), the combined organic layers were dried by passing through a phase separator cartridge and evaporated. The residue was purified by normal phase chromatography (120 g $SiO_2$ column, eluent hexane:EtOAc 100:0 to 70:30) to give the title compound as a beige solid.

LC-MS: Rt=0.70 min; MS m/z $[M+H]^+$ 196.1/198.1; UPLC-MS 1.

Step 2A: (S)-8-((tert-butyldimethylsilyl)oxy)-1-chloro-5-methylene-5,6,7,8-tetrahydroisoquinoline

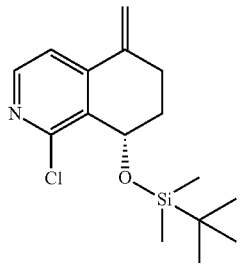 [SMILES: C=C1CC[C@H](O[Si](C)(C)C(C)(C)C)c2c1ccnc2Cl]

tert-Butyldimethylsilyl chloride (9.31 g, 61.8 mmol) was added to a solution of (S)-1-chloro-5-methylene-5,6,7,8-tetrahydroisoquinolin-8-ol (Step 1A, 8.95 g, 41.2 mmol) and imidazole (4.48 g, 65.9 mmol) in DCM (150 mL) at RT under a positive pressure of argon. The RM was stirred for 20 hr at RT, 8 hr at 40° C. and stood for 66 hr at RT, diluted with water (150 mL), extracted 2× with DCM (30 mL), the combined organic layers washed with saturated aq NaHCO$_3$, dried and evaporated. The residue was suspended in diethyl ether (30 mL) and hexane (120 mL), stirred for 30 min at RT and filtered. The filtrate was evaporated and purified by normal phase chromatography (40 g SiO$_2$ column, eluent hexane:EtOAc 100:0 to 70:30) to give the title compound as a white solid.

LC-MS: Rt=1.59 min; MS m/z [M+H]$^+$ 310.2/312.1; UPLC-MS 1.

Step 3A: ((5R,8S)-8-((tert-butyldimethylsilyl)oxy)-1-chloro-5,6,7,8-tetrahydroisoquinolin-5-yl)methanol

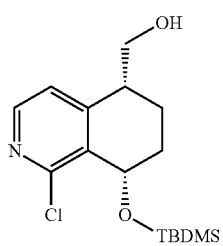

A solution of 9-borabicyclo[3.3.1]nonane in THF (0.5M, 167 mL, 84 mmol) was added dropwise to a solution of (S)-8-((tert-butyldimethyl silyl)oxy)-1-chloro-5-methyl ene-5,6,7,8-tetrahydroisoquinoline (Step 2A, 10.9 g, 33.4 mmol) in 1,2-DCE (100 mL) at RT under a positive pressure of argon. The RM was stirred for 4 hr at 60° C., cooled to 5° C., and aq NaOH (4M, 37.6 mL, 150 mmol) and aq H$_2$O$_2$ (30%, 17.1 mL, 167 mmol) added, and stirring continued for 30 min at RT. The RM was partitioned between DCM and saturated aq NaHCO$_3$, extracted 2× with DCM, the combined organic layers washed with aq Na$_2$S$_2$O$_3$, dried by passing through a phase separator cartridge and evaporated. The residue was purified by normal phase chromatography (220 g SiO$_2$ column, eluent hexane:EtOAc 95:5 to 60:40) to give the title compound as a white solid.

LC-MS: Rt=1.31 min; MS m/z [M+H]$^+$ 328.1/320.1; UPLC-MS 1.

Step 4A: ((5R,8S)-8-((tert-butyldimethylsilyl)oxy)-1-chloro-5,6,7,8-tetrahydroisoquinolin-5-yl)methyl Carbamate

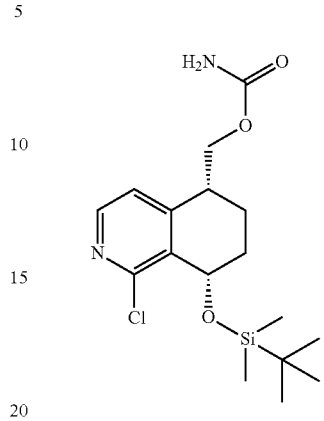

Trichloroacetyl isocyanate (4.69 mL, 39.6 mmol) was added dropwise to a solution of ((5R,8S)-8-((tert-butyldimethylsilyl)oxy)-1-chloro-5,6,7,8-tetrahydroisoquinolin-5-yl) methanol (Step 3A, 11.5 g, 33.0 mmol) in 1,2-DCE (150 mL) cooled with an ice bath. The RM was stirred for 2.5 hr at 0° C. and K$_2$CO$_3$ (0.46 g, 3.30 mmol) and MeOH (150 mL) were added and stirring continued at RT for 16 hr. The RM was diluted with saturated aq NaHCO$_3$ (200 mL) and DCM (150 mL), the aq layer extracted 2× with DCM (100 mL), the combined organic layers dried by passing through a phase separator and evaporated to give the title compound as a white crystalline solid which was used directly without further purification.

LC-MS: Rt=1.27 min; MS m/z [M+H]$^+$ 371.2/373.2; UPLC-MS 1.

Step 5A: (5S,8S)-8-((tert-butyldimethyl silyl)oxy)-1-chloro-7,8-dihydro-6H-spiro[isoquinoline-5,4'-oxazolidin]-2'-one

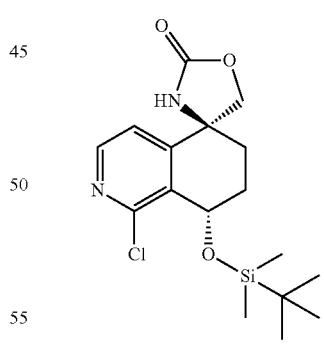

A mixture of ((5R,8S)-8-((tert-butyldimethylsilyl)oxy)-1-chloro-5,6,7,8-tetrahydroisoquinolin-5-yl)methyl carbamate (Step 4A, 14.0 g, 32.1 mmol), diacetoxyiodobenzene (14.76 g, 44.9 mmol), MgO (2.97 g, 73.8 mmol) and Rh$_2$(esp)$_2$ (487 mg, 642 µmol) in DCM (170 mL) was stirred at 45° C. for 48 hr under a positive pressure of N2. Additional Rh$_2$(esp)$_2$ (122 mg, 160 µmol) was added and the RM was stirred for a further 24 hr at 45° C. The RM was partitioned between saturated aq NaHCO$_3$ (150 mL) and DCM (100 mL), the aq layer extracted 2× with DCM (60 mL), the combined organic layers dried by passing through a phase separator cartridge, and evaporated. The residue was purified by normal phase chromatography (120 g SiO$_2$ column, eluent hexane:EtOAc 90:10 to 50:50) to give the title compound.

LC-MS: Rt=1.21 min; MS m/z [M+H]$^+$ 369.2/371.1; UPLC-MS 1.

Step 6A: (5S,8S)-1-chloro-8-hydroxy-7,8-dihydro-6H-spiro[isoquinoline-5,4'-oxazolidin]-2'-one

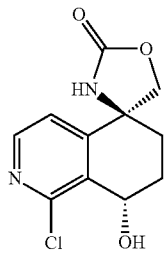 [SMILES: O=C1N[C@]2(CC[C@H](O)c3c2ccnc3Cl)CO1]

A solution of tetra-n-butylammonium fluoride in THF (1M, 30.0 mL, 30.0 mmol) was added to a solution of (5S,8S)-8-((tert-butyldimethyl silyl)oxy)-1-chloro-7,8-dihydro-6H-spiro[isoquinoline-5,4'-oxazolidin]-2'-one (Step 5A, 9.72 g, 25.03 mmol) in THF (100 mL) cooled with an ice bath. The RM was stirred for 1 hr at 0° C. and 16 hr at RT then diluted with saturated aq NaHCO$_3$ (250 mL) and DCM (150 mL), the aq layer extracted 3× with DCM (150 mL) and 2× with EtOAc (100 mL), the combined organic layers dried by passing through a phase separator cartridge, and evaporated. The residue was triturated 2× with EtOAc and the off-white solid collected by filtration to give the title compound which was used directly without further purification.

LC-MS: Rt=0.36 min; MS m/z [M+H]$^+$ 255.1/257.1; UPLC-MS 1.

Step 7A: (S)-1-chloro-6,7-dihydro-8H-spiro[isoquinoline-5,4'-oxazolidine]-2',8-dione

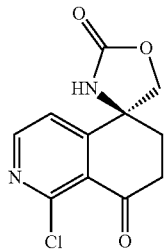 [SMILES: O=C1N[C@]2(CCC(=O)c3c2ccnc3Cl)CO1]

Dess-Martin periodinane (4.41 g, 10.41 mmol) was added to a suspension of (5S,8S)-1-chloro-8-hydroxy-7,8-dihydro-6H-spiro[isoquinoline-5,4'-oxazolidin]-2'-one (Step 6A, 5.3 g, 5.20 mmol) in DCM (80 mL) at RT and stirred for 1.5 hr at RT. The RM was then diluted with aq Na$_2$S$_2$O$_3$ (40 mL) and stirred for 30 min at RT, extracted 4× with a mixture of DCM:MeOH 3:1, the combined organic layers dried by passing through a phase separator and evaporated. The residue was purified by normal phase chromatography (silica gel, eluent heptane:EtOAc 80:20 to 0:100). Product containing fractions were combined, evaporated, and stirred with a mixture of DCM/heptane for 20 min at RT. The insoluble material was removed by filtration and the filtrate evaporated to give the title compound as an off-white solid.

LC-MS: Rt=0.48 min; MS m/z [M−H]$^-$ 251.0/253.0; UPLC-MS 1.

Step 8A: (5)-1'-chloro-6',7'-dihydrodispiro[oxazolidine-4,5'-isoquinoline-8',2''-[1,3]dioxolan]-2-one

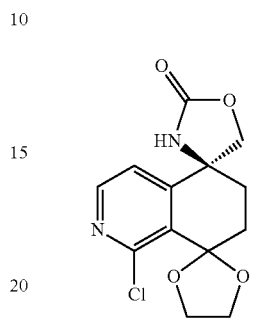

A mixture of (S)-1-chloro-6,7-dihydro-8H-spiro[isoquinoline-5,4'-oxazolidine]-2',8-dione (Step 7A, 600 mg, 950 μmol), ethylene glycol (159 μL, 2.85 mmol), triethyl orthoformate (506 μL, 3.04 μmol) and p-toluenesulfonic acid (32.7 mg, 190 μmol) in toluene (10 mL) was stirred for 2 hr at 70° C. and for 18 hr at RT. Additional ethylene glycol (2 mL) was added and the RM stirred for 4 hr at 70° C. The RM was diluted with saturated aq NaHCO$_3$ (40 mL), extracted 3× with DCM, the combined organic layers dried by passing through a phase separator cartridge and evaporated. The residue was purified by normal phase chromatography (40 g SiO$_2$ column, eluent heptane:EtOAc 90:10 to 0:100) to give the title compound as an off-white solid.

Intermediate AJ: (S)-(1-chloro-5-((3-(difluoromethoxy)-5-(trifluoromethyl)pyridin-2-yl)amino)-8,8-difluoro-5,6,7,8-tetrahydroisoquinolin-5-yl)methanol Step 1: (S)-1-chloro-3'-(3-(difluoromethoxy)-5-(trifluoromethyl)pyridin-2-yl)-8,8-difluoro-7,8-dihydro-6H-spiro[isoquinoline-5,4'-oxazolidin]-2'-one

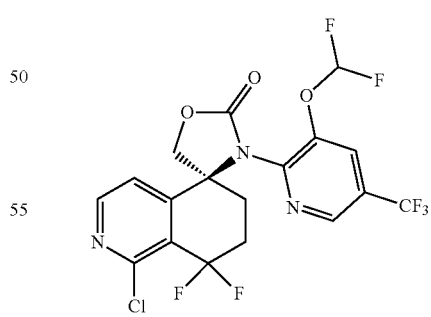

DAST (2.76 mL, 20.9 mmol) was added to a solution of (S)-1-chloro-3'-(3-(difluoromethoxy)-5-(trifluoromethyl)pyridin-2-yl)-6,7-dihydro-8H-spiro[isoquinoline-5,4'-oxazolidine]-2',8-dione (Intermediate AK, 1.0 g, 2.16 mmol) in DCM (10 mL), under an atmosphere of argon, and the RM heated at 40° C. for 72 hr in a sealed vial. The cooled reaction mixture was added dropwise to saturated aq NaHCO₃, CAUTION: EXOTHERMIC!, extracted 3× with DCM, the combined organic layers were dried over sodium sulfate, filtered and concentrated. The residue was purified by normal phase chromatography (330 g silica gel column, eluent heptane:EtOAc 100:0 to 20:80) to give the title compound as a yellow powder.

LC-MS: Rt=5.74 min; MS m/z [M+H]⁺ 486.4/488.4; UPLC-MS 4.

Step 2: (S)-(1-chloro-5-((3-(difluoromethoxy)-5-(trifluoromethyl)pyridin-2-yl)amino)-8,8-difluoro-5,6,7,8-tetrahydroisoquinolin-5-yl)methanol

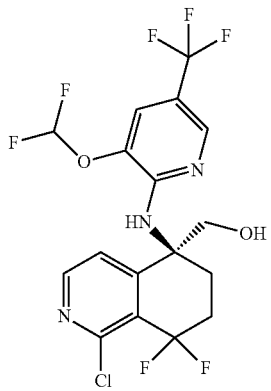 [SMILES: OC[C@]1(Nc2ncc(C(F)(F)F)cc2OC(F)F)CCC(F)(F)c2c1ccnc2Cl]

Aq NaOH (4M, 66.7 ml, 267 mmol) was carefully added to (S)-1-chloro-3'-(3-(difluoromethoxy)-5-(trifluoromethyl)pyridin-2-yl)-8,8-difluoro-7,8-dihydro-6H-spiro[isoquinoline-5,4'-oxazolidin]-2'-one (Step 1, 13.22 g, 26.7 mmol) in EtOH (200 mL) cooled with an ice bath. The RM was then stirred at RT for 1 hr, diluted into saturated aq NaHCO₃, extracted 3× with DCM, the combined organic layers dried over sodium sulfate, filtered and concentrated. The residue was purified by normal phase chromatography (330 g silica gel column, eluent heptane:EtOAc 100:0 to 0:100 in 40 min) the title compound was obtained as a yellow powder.

Intermediate AJ step 2 can also be synthesized via the following alternative procedure: Aqueous NaOH solution (2 wt %, 181.2 g, 90.58 mmol) was carefully added to (S)-1-chloro-3'-(3-(difluoromethoxy)-5-(trifluoromethyl)pyridin-2-yl)-8,8-difluoro-7,8-dihydro-6H-spiro[isoquinoline-5,4'-oxazolidin]-2'-one (Step 1, 20.0 g, 41.17 mmol) in EtOH (200 mL) cooled with an ice bath. The reaction mixture was then stirred at 40° C. for 16 hr. The reaction mixture was extracted with DCM (200 mL). The aqueous phase was separated and again extracted with DCM (200 mL). The organic phases were combined and washed with H₂O (200 mL), The crude oil was purified by filtration through 50 g of silica gel, eluted by MTBE. The elute containing product was concentrated under reduced pressure to give the title compound as a brown oil.

LC-MS: Rt=5.84 min; MS m/z [M+H]⁺ 460.4/462.4; UPLC-MS 4.

Intermediate AK: (S)-1-chloro-3'-(3-(difluoromethoxy)-5-(trifluoromethyl)pyridin-2-yl)-6,7-dihydro-8H-spiro[isoquinoline-5,4'-oxazolidine]-2',8-dione

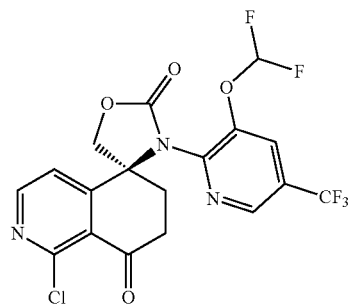 [SMILES: O=C1CC[C@@]2(COC(=O)N2c2ncc(C(F)(F)F)cc2OC(F)F)c2ccnc(Cl)c21]

HCl (1N, 174 ml, 174 mmol) was added dropwise to a solution of (S)-1'-chloro-3-(3-(difluoromethoxy)-5-(trifluoromethyl)pyridin-2-yl)-6',7'-dihydrodispiro[oxazolidine-4,5'-isoquinoline-8',2''-[1,3]dioxolan]-2-one (Intermediate AL, 18.23 g, 34.8 mmol) in THF (200 mL) at RT, and the RM heated at 80° C. for 18 hr. The RM was poured into saturated aq NaHCO₃, extracted 3× with DCM, the combined organic layers dried over sodium sulfate, filtered and concentrated. The residue was purified by normal phase chromatography (2×330 g silica gel columns, eluent heptane:EtOAc 95:5 to 0:100 in 30 min) to give the title compound as a beige powder.

LC-MS: Rt=5.00 min; MS m/z [M+H]⁺ 464.1/466.0; UPLC-MS 4.

Intermediate AK can also be synthesized via the following alternative route:

Step 1: (4'R,5'R)-1-chloro-4',5'-dimethyl-5-methylene-6,7-dihydro-5H-spiro[isoquinoline-8,2'-[1,3]dioxolane]

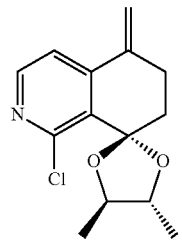

A mixture of 1-chloro-5-methylene-6,7-dihydroisoquinolin-8(5H)-one (Intermediate AI, step 3, 3.5 g, 17.2 mmol), (2R,3R)-butane-2,3-diol (3.14 mL, 34.3 mmol), HC(OEt)₃ (8.58 mL, 51.5 mmol) and p-toluenesulfonic acid (591 mg, 3.43 mmol) in toluene (50 mL) was heated at 60° C. for 5 hr under a N2 atmosphere. The cooled RM was partitioned between DCM and saturated aq NaHCO₃, the aq layer was extracted a further 2× with DCM, the combined organic layers dried by passing through a phase separator cartridge and evaporated. The residue was adsorbed onto Isolute and purified by normal phase chromatography (40 g SiO₂ column, eluent heptane:EtOAc 100:0 to 20:80) to give the title compound as a yellow solid.

LC-MS: Rt=1.10 min; MS m/z [M+H]⁺ 266.4/268.4; UPLC-MS 1.

Step 2: ((4'R,5R,5'R)-1-chloro-4',5'-dimethyl-6,7-dihydro-5H-spiro[isoquinoline-8,2'-[1,3]dioxolan]-5-yl)methanol and ((4'R,5S,5'R)-1-chloro-4',5'-dimethyl-6,7-dihydro-5H-spiro[isoquinoline-8,2'-[1,3]dioxolan]-5-yl)methanol

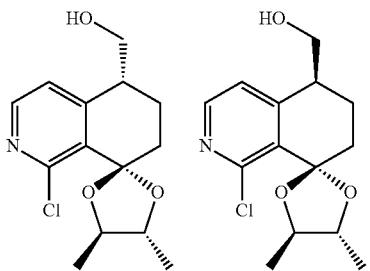

A solution of 9-borabicyclo[3.3.1]nonane in THF (0.5M, 36.9 mL, 18.44 mmol) was added dropwise to a solution of (4'R,5'R)-1-chloro-4',5'-dimethyl-5-methylene-6,7-dihydro-5H-spiro[isoquinoline-8,2'-[1,3]dioxolane] (Step 1, 2.0 g, 7.38 mmol) in 1,2-DCE (35 mL) at RT under a positive pressure of argon. The RM was stirred for 2 hr at 60° C. then cooled to 5° C., and aq NaOH (4M, 8.30 mL, 33.2 mmol) and aq $H_2O_2$ (30%, 3.77 mL, 36.9 mmol) were added slowly CAUTION: EXOTHERMIC REACTION! The RM was stirred for 2 hr at RT, partitioned between DCM and saturated aq $NaHCO_3$, the aq layer extracted 2× with DCM, the combined organic layers were washed with aq $Na_2S_2O_3$, dried by passing through a phase separator cartridge and evaporated. The residue was purified by normal phase chromatography (40 g $SiO_2$ column, eluent heptane:EtOAc 80:20 to 0:100) to give the title compound as an off-white foam as a 3:1 mixture of diastereoisomers.

LC-MS: Rt=3.06 and 3.08 min; MS m/z $[M+H]^+$ 284.3/286.3; UPLC-MS 4.

Step 3: ((4'R,5R,5'R)-1-chloro-4',5'-dimethyl-6,7-dihydro-5H-spiro[isoquinoline-8,2'-[1,3]dioxolan]-5-yl)methyl carbamate and ((4'R,5S,5'R)-1-chloro-4',5'-dimethyl-6,7-dihydro-5H-spiro[isoquinoline-8,2'-[1,3]dioxolan]-5-yl)methyl Carbamate

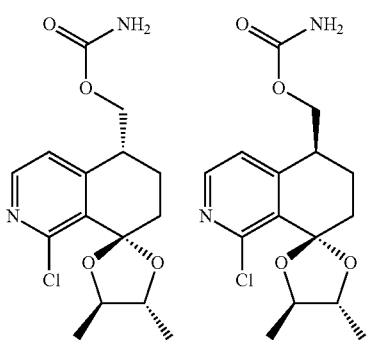

Trichloroacetyl isocyanate (1.25 mL, 10.57 mmol) was added dropwise to a solution of ((4'R,5R,5'R)-1-chloro-4',5'-dimethyl-6,7-dihydro-5H-spiro[isoquinoline-8,2'-[1,3]dioxolan]-5-yl)methanol and ((4'R,5S,5'R)-1-chloro-4',5'-dimethyl-6,7-dihydro-5H-spiro[isoquinoline-8,2'-[1,3]dioxolan]-5-yl)methanol (Step 2, 2.0 g, 7.05 mmol) in 1,2-DCE (15 mL) cooled with an ice bath. The RM was stirred for 30 min at 0° C. and for 30 min at RT, then $K_2CO_3$ (97 mg, 705 μmol) followed by MeOH (15 mL) were added and stirring continued for 48 hr at RT. The RM was partitioned between saturated aq $NaHCO_3$ (50 mL) and DCM (50 mL), the aq layer extracted 2× with DCM, the combined organic layers dried by passing through a phase separator cartridge and evaporated. The residue was adsorbed on Isolute and purified by normal phase chromatography (40 g $SiO_2$ column, eluent heptane:EtOAc 95:5 to 20:80) to give the title compounds as a white foam.

LC-MS: Rt=0.77 min; MS m/z $[M+H]^+$ 327.3/329.3; UPLC-MS 1.

Step 4: (4S,4"R,5"R)-1'-chloro-4",5"-dimethyl-6',7'-dihydrodispiro[oxazolidine-4,5'-isoquinoline-8',2"-[1,3]dioxolan]-2-one and (4R,4"R,5"R)-1'-chloro-4",5"-dimethyl-6',7'-dihydrodispiro[oxazolidine-4,5'-isoquinoline-8',2"-[1,3]dioxolan]-2-one

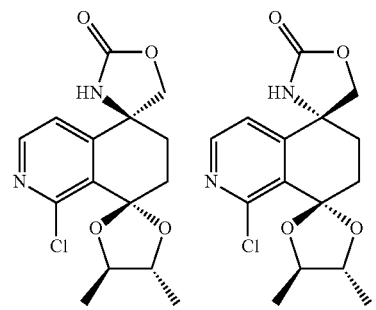

A mixture of ((4'R,5R,5'R)-1-chloro-4',5'-dimethyl-6,7-dihydro-5H-spiro[isoquinoline-8,2'-[1,3]dioxolan]-5-yl) methyl carbamate and ((4'R,5S,5'R)-1-chloro-4',5'-dimethyl-6,7-dihydro-5H-spiro[isoquinoline-8,2'-[1,3]dioxolan]-5-yl)methyl carbamate (Step 3, 2.2 g, 6.46 mmol), diacetoxyiodobenzene (2.97 g, 9.05 mmol), MgO (599 mg, 14.87 mmol) and $Rh_2(esp)_2$ (98 mg, 129 μmol) in toluene (15 mL) was stirred for 3 hr at 60° C. under a positive pressure of N2. Additional $Rh_2(esp)_2$ (25 mg, 32 μmol) was added and the RM stirred for a further 2 hr at 60° C. The cooled RM was diluted with saturated aq $NaHCO_3$ (50 mL) and DCM (50 mL), the aq layer extracted 2× with DCM (30 mL), the combined organic layers dried by passing through a phase separator cartridge and evaporated. The residue was purified by normal phase chromatography (40 g $SiO_2$ column, eluent heptane:EtOAc 90:10 to 0:100) to give the title compounds as a beige foam.

LC-MS: Rt=0.74 min; MS m/z $[M+H]^+$ 325.3/327.3; UPLC-MS 1.

Step 5: (4S,4"R,5"R)-1'-chloro-3-(3-(difluoromethoxy)-5-(trifluoromethyl)pyridin-2-yl)-4",5"-dimethyl-6',7'-dihydrodispiro[oxazolidine-4,5'-isoquinoline-8',2"-[1,3]dioxolan]-2-one

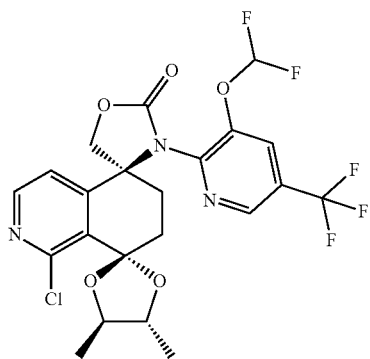

A mixture of (4S,4"R, 5"R)-1'-chloro-4",5"-dimethyl-6',7'-dihydrodispiro[oxazolidine-4,5'-isoquinoline-8',2"-[1,3]dioxolan]-2-one and (4R,4"R,5"R)-1'-chloro-4",5"-dimethyl-6',7'-dihydrodispiro[oxazolidine-4,5'-isoquinoline-8',2"-[1,3]dioxolan]-2-one (Step 4, 1.45 g, 4.29 mmol), 2-chloro-3-(difluoromethoxy)-5-(trifluoromethyl)pyridine (Intermediate A, 1.68 g, 6.43 mmol), CuBr (307 mg, 2.14 mmol) and Cs₂CO₃ (2.79 g, 8.57 mmol) in DMF (20 mL) was heated at 130° C. for 2 hr in a sealed vessel under an argon atmosphere. The cooled RM was diluted with EtOAc, filtered and partitioned with saturated aq NH₄Cl. The aq layer was further extracted with EtOAc, the combined organic layers washed with brine, dried and evaporated. The residue was purified by normal phase chromatography (silica gel, eluent heptane:TBME 60:40) to give a 2:1 diastereomeric mixture of products. The diastereomers were separated by chiral SFC: (instrument: Spiatec Prep SFC100; column: Chiralpak IG 5 250×30 mm 40° C.; eluent: CO₂: iPrOH with 0.1% NH₄OH, 85:15; flow rate: 80 mL/min; detection: 276 nm) to give the title compound as the predominant first-eluting peak.

LC-MS: Rt=1.19 min; MS m/z [M+H]⁺ 536.2/538.2; UPLC-MS 1.

Chiral-SFC: Rt=1.04 min; with (4R,4"R,5"R)-1'-chloro-3-(3-(difluoromethoxy)-5-(trifluoromethyl)pyridin-2-yl)-4", 5"-dimethyl-6',7'-dihydrodispiro[oxazolidine-4,5'-isoquinoline-8',2"-[1,3]dioxolan]-2-one as the second-eluting peak, Rt=2.21 min; C-SFC 20.

Step 6: (S)-1-chloro-3'-(3-(difluoromethoxy)-5-(trifluoromethyl)pyridin-2-yl)-6,7-dihydro-8H-spiro[isoquinoline-5,4'-oxazolidine]-2',8-dione

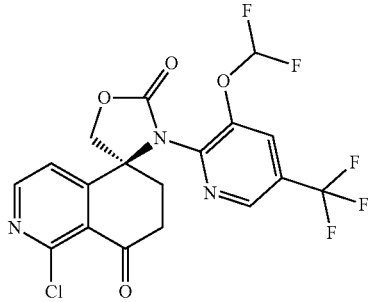 [SMILES: O=C1CC[C@@]2(COC(=O)N2c2ncc(C(F)(F)F)cc2OC(F)F)c2ccnc(Cl)c21]

A mixture of (S)-1-chloro-3'-(3-(difluoromethoxy)-5-(trifluoromethyl)pyridin-2-yl)-6,7-dihydro-8H-spiro[isoquinoline-5,4'-oxazolidine]-2',8-dione (Step 5, 722 mg, 1.35 mmol), aq HCl (5M, 1.35 mL, 6.75 mmol) and THF (5 mL) was stirred for 24 hr at 80° C. The cooled RM was partitioned between EtOAc and saturated aq Na₂CO₃, the aq layer extracted 2× with EtOAc, the combined aq layers washed with brine, dried over Na₂SO₄ and evaporated. The residue was purified by normal phase chromatography (silica gel, eluent heptane:EtOAc 100:0 to 50:50) to give the title compound. Intermediate AK can also be synthesized via a route analogous to the one shown above in which (2R, 3R)-butane-2,3-diol is replaced by (S,S)-1,2-diphenyl-1,2-ethanediol. Using this route the diastereomeric hydroboration products are obtained as a 3:1 mixture.

Intermediate AL: (5)-1'-chloro-3-(3-(difluoromethoxy)-5-(trifluoromethyl)pyridin-2-yl)-6',7'-dihydrodispiro[oxazolidine-4,5'-isoquinoline-8',2"-[1,3]dioxolan]-2-one

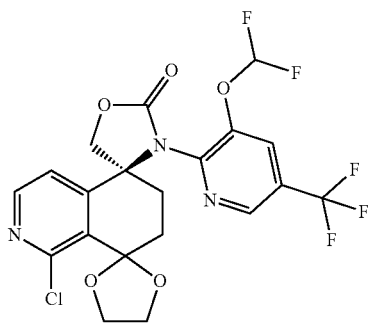 [SMILES: O=C1OC[C@@]2(CCC3(OCCO3)c3c2ccnc3Cl)N1c1ncc(C(F)(F)F)cc1OC(F)F]

A mixture of (S)-1'-chloro-6',7'-dihydrodispiro[oxazolidine-4,5'-isoquinoline-8',2"-[1,3]dioxolan]-2-one (Intermediate AI, 15.0 g, 48.0 mmol), 2-chloro-3-(difluoromethoxy)-5-(trifluoromethyl)pyridine (Intermediate A, 18.01 g, 72.0 mmol), and Cs₂CO₃ (31.3 g, 96 mmol) and CuBr (3.44 g, 24.01 mmol) in DMF (150 mL) was heated to 130° C. for 3.5 hr under an argon atmosphere in a sealed Ace Pressure Tube. The cooled RM was diluted with saturated aq NaHCO₃, extracted 3× with EtOAc, the combined organic layers dried over Na₂SO₄, filtered and concentrated. To the residue was added 2-chloro-3-(difluoromethoxy)-5-(trifluoromethyl) pyridine (18.01 g, 72.0 mmol), and Cs₂CO₃ (31.3 g, 96 mmol) and CuBr (3.44 g, 24.01 mmol) in DMF (150 mL) and the RM heated for 8 hr at 130° C. The cooled RM was diluted into saturated aq NH$_4$Cl and stirred for 30 min at RT, extracted 3× with EtOAc, the combined organic layers were washed with brine, dried and concentrated. The residue was purified by normal phase chromatography (2×220 g silica gel columns, eluent heptane:EtOAc 100:0 to 0:100), product containing fractions were combined, evaporated, and triturated with a mixture of EtOAc:Et$_2$O 1:3 to give the title compound as a brown powder.

Intermediate AL can also be synthesized via the following alternative procedure:

At ambient temperature, under N$_2$ condition, a reactor was charged with (5)-1'-chloro-6',7'-dihydrodispiro[oxazolidine-4,5'-isoquinoline-8',2"-[1,3]dioxolan]-2-one (Intermediate AI, 1.15 g, 86.9% assay, 3.37 mmol), CuTC (0.032 g, 0.168 mmol), Cs$_2$CO$_3$ (2.20 g, 6.76 mmol) and dry DMSO (10 mL). To the resulting mixture was added with solution of 2-chloro-3-(difluoromethoxy)-5-(trifluoromethyl)pyridine (1.30 g, 98.2% assay, 4.36 mmol) in dry DMSO (10 mL). The reaction mixture was allowed to stir at 80° C. for 3 h. The reaction mixture was cooled to ambient temperature. H$_2$O (60 mL) and IPAC (60 mL) were added and the layers separated. The aqueous phase was extracted 2× with IPAC. The combined organic phase was washed 3× with H$_2$O, dried over anhydrous Na$_2$SO$_4$, filtered, concentrated under reduced pressure. The residue was dissolved in EtOAc, passed through a pad of silica gel, and concentrated under reduced pressure to give the title compound as a pale-gray solid.

LC-MS: Rt=5.07 min; MS m/z [M+H]$^+$ 508.4/510.4; UPLC-MS 4.

Intermediate AM: (R)-(1-chloro-5,6,7,8-tetrahydroisoquinolin-5-yl)methanol

Step 1: 1-chloro-5-methylene-5,6,7,8-tetrahydroisoquinoline

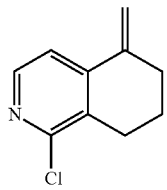

To a solution of (trimethylsilyl)methyl magnesium chloride (1M in Et$_2$O, 165 mL, 165 mmol) cooled to 0-5° C. was slowly added under, a nitrogen atmosphere, a solution of 1-chloro-7,8-dihydroisoquinolin-5(6H)-one (10 g, 55.1 mmol) in Et$_2$O/CH$_2$Cl$_2$ (120 mL/10 mL). The resulting solution was allowed to reach RT over 45 min. The RM was carefully poured into cold saturated aq NH$_4$Cl, the layers were separated and the aq layer was extracted 2× with CH$_2$Cl$_2$. The combined organic extracts were dried (phase separator) and evaporated to give a beige solid which was dissolved in CH$_2$Cl$_2$ (260 mL). To this solution, under a nitrogen atmosphere, BF$_3$.Et$_2$O (2.72 mL, 22.0 mmol) was slowly added and the RM was stirred at RT for 30 min. The RM was poured into saturated aq NaHCO$_3$ and was extracted 2× with DCM. The combined organic extracts were dried (phase separator) and evaporated to give the title compound as a yellow solid. The compound was used without purification in the next step.

$^1$H NMR (400 MHz, DMSO-d$_6$) δ 8.18 (d, 1H), 7.68 (d, 1H), 5.86 (s, 1H), 5.30 (s, 1H), 2.78 (t, 2H), 2.49 (m, 2H, overlapping with DMSO peak), 1.85 (m, 2H).

LC-MS: Rt=1.09 min; MS m/z [M+H]$^+$ 180.1/182.1; UPLC-MS 1.

Step 2: (R)-(1-chloro-5,6,7,8-tetrahydroisoquinolin-5-yl)methanol

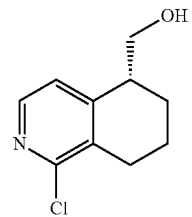 [SMILES: OC[C@@H]1CCCc2c1ccnc2Cl]

To a solution of 1-chloro-5-methylene-5,6,7,8-tetrahydroisoquinoline (Step 1, 10.1 g, 54.8 mmol) in THF (365 mL), cooled to 0-5° C. under a nitrogen atmosphere was added BH$_3$.THF (137 mL, 137 mmol). The RM was stirred at 0-5° C. for 40 min and BH$_3$.THF (71 mL, 71 mmol) was again added. The RM was further stirred for 40 min until consumption of the starting material. To the RM were then successively added dropwise at 0-5° C. NaOH (4M in water, 61.7 mL, 247 mmol) and H$_2$O$_2$ (35%, 24 mL, 274 mmol) (EXOTHERMIC) and the mixture stirred at RT for 50 min. The RM was diluted with brine and extracted 2× with EtOAc. The combined organic extracts were washed 3× with a 10% aq Na$_2$S$_2$O$_3$ and the organic layer was dried (phase separator) and evaporated. The crude material was purified by normal phase flash column chromatography (120 g SiO$_2$ column, eluent c-hexane:EtOAc 100:0 to 30:70) to give the title compound as a white solid. The enantiomers were separated by chiral SFC: (instrument: MG preparative SFC (SFC-1); column: Chiralpak IC, 250×30 mm I.D., 5 µm, 38° C.; eluent: CO$_2$/iPrOH 60:40; flow rate: 60 mL/min; detection: 220 nm) to give the title compound as the second eluting peak (light yellow oil).

$^1$H NMR (400 MHz, DMSO-d$_6$) δ 8.12 (d, 1H), 7.34 (d, 1H), 4.86 (t, 1H), 3.58 (m, 2H), 2.86 (m, 1H), 2.73-2.59 (m, 2H), 1.88-1.79 (m, 2H), 1.76-1.66 (m, 2H).

LC-MS: Rt=0.73 min; MS m/z [M+H]$^+$ 198.1/200.1; UPLC-MS 1.

Chiral-SFC: Rt=4.40 min; with (5)-(1-chloro-5,6,7,8-tetrahydroisoquinolin-5-yl)methanol eluting as the first peak, Rt=4.10 min; C-SFC 42.

Intermediate AN: (S)-1-chloro-7,8-dihydro-6H-spiro[isoquinoline-5,4'-oxazolidin]-2'-one Step 1: (R)-(1-chloro-5,6,7,8-tetrahydroisoquinolin-5-yl)methyl Carbamate

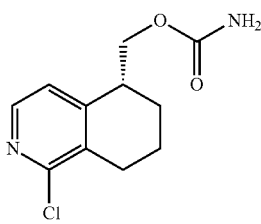 [SMILES: NC(=O)OC[C@@H]1CCCc2c1ccnc2Cl]

To a solution of (R)-(1-chloro-5,6,7,8-tetrahydroisoquinolin-5-yl)methanol (Intermediate AM, 1.6 g, 8.09 mmol) in 1,2-dichloroethane (40 mL) was slowly added at 0-5° C., under a nitrogen atmosphere, trichloroacetyl isocyanate (1.16 mL, 9.71 mmol). The RM was stirred at 0-5° C. for 30 min. UPLC indicated that the formation of the intermediate (trichloroacetyl carbamate LC-MS: Rt=1.09 min; MS m/z $[M+H]^+$ 385.1/387.1; UPLC-MS 2) was not complete. Trichloroacetyl isocyanate (1.16 mL, 9.71 mmol) was again added and the RM was further stirred for 10 min. Trichloroacetyl isocyanate (1.16 mL, 9.71 mmol) was again added to drive the reaction to completion. $K_2CO_3$ (112 mg, 0.81 mmol) was added and stirring continued for 10 min, followed by the addition of MeOH (40 mL) and further stirring at RT for 14 hr. $K_2CO_3$ (224 mg, 1.62 mmol) was again added, and the mixture stirred at RT for 3 hr, until completion of the reaction. The RM was poured into water and extracted 2× with $CH_2Cl_2$. The combined organic extracts were dried (phase separator) and evaporated. The crude residue was taken up in $Et_2O$ and filtered-off to give the title compound as a white solid.

$^1$H NMR (400 MHz, DMSO-$d_6$) δ 8.15 (d, 1H), 7.35 (d, 1H), 6.56 (m, 2H), 4.16-4.08 (m, 2H), 3.09 (m, 1H), 2.72-2.59 (m, 2H), 1.89-1.72 (m, 4H).

LC-MS: Rt=0.76 min; MS m/z $[M+H]^+$ 241.1/243.1; UPLC-MS 1.

Step 2: (S)-1-chloro-7,8-dihydro-6H-spiro[isoquinoline-5,4'-oxazolidin]-2'-one

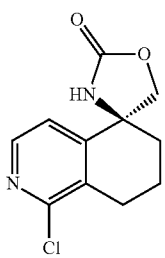 [SMILES: O=C1N[C@]2(CCCc3c2ccnc3Cl)CO1]

In an Ace pressure tube, a suspension of (R)-(1-chloro-5,6,7,8-tetrahydroisoquinolin-5-yl)methyl carbamate (Step 1, 1.46 g, 6.07 mmol), $Rh_2$(triphenylacetate)$_4$ in complex with $CH_2Cl_2$ (218 mg, 0.15 mmol), $PhI(OAc)_2$ (2.74 g, 8.49 mmol), and MgO (562 mg, 13.9 mmol) in $CH_2Cl_2$ (38 mL) was purged with nitrogen. The vial was sealed and the mixture was stirred at 45° C. for 15 hr. $Rh_2$(tpa)$_4$ in complex with $CH_2Cl_2$ (218 mg, 0.15 mmol), $PhI(OAc)_2$ (2.74 g, 8.49 mmol), and MgO (562 mg, 13.9 mmol) were again added, and the RM was stirred at 45° C. for 22 hr. The RM was poured into saturated aq $NaHCO_3$ and was extracted 3× with DCM. The combined organic extracts were dried (phase separator) and evaporated. The crude residue was purified by normal phase flash chromatography (80 g $SiO_2$ column; eluent c-hexane:EtOAc 100:0 to 0:100) to give the title compound as a white solid.

$^1$H NMR (400 MHz, DMSO-$d_6$) δ 8.32 (s, 1H), 8.30 (d, 1H), 7.48 (d, 1H), 4.36 (d, 1H), 4.22 (d, 1H), 2.76-2.61 (m, 2H), 2.03-1.90 (m, 2H), 1.86-1.74 (m, 2H).

LC-MS: Rt=0.64 min; MS m/z $[M+H]^+$ 239.1/241.2; UPLC-MS 1.

Intermediate AO: (S)-(1-amino-6-fluoro-1,2,3,4-tetrahydronaphthalen-1-yl)methanol Step 1: (S)—N-(6-fluoro-3,4-dihydronaphthalen-1(2H)-ylidene)-2-methylpropane-2-sulfinamide

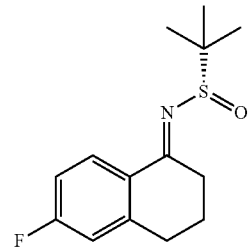 [SMILES: CC(C)(C)[S@](=O)/N=C1\CCCc2cc(F)ccc21]

(S)-2-methylpropane-2-sulfinamide (4.35 g, 35.2 mmol) was added portion wise to a mixture of 6-fluoro-1-tetralone (4.58 mL, 33.5 mmol) and $Ti(OiPr)_4$ (22.58 mL, 77 mmol) under a positive pressure of $N_2$ and heated at 50° C. for 3 days. Additional $Ti(OiPr)_4$ (3.93 ml, 13.40 mmol) was added and the RM stirred for 1 day at 50° C. THF (100 mL) and brine (60 mL) were then added and the mixture stirred for 15 min at RT, filtered through Hyflo, washing 3× with THF (30 mL). The filtrate was evaporated to leave a predominantly aq phase which was diluted with water (100 mL), and extracted 2× with TBME (200 and 100 mL), the combined organic layers were washed with brine (60 mL), dried over $Na_2SO_4$, and evaporated. The residue was purified by normal phase chromatography (120 g silica column, eluent heptane:TBME 100:0 to 70:30) to give the title compound.

LC-MS: Rt=1.06 min; MS m/z $[M+H]^+$ 268.2; UPLC-MS 1.

Step 2: N—((S)-1-cyano-6-fluoro-1,2,3,4-tetrahydronaphthalen-1-yl)-2-methylpropane-2-sulfinamide

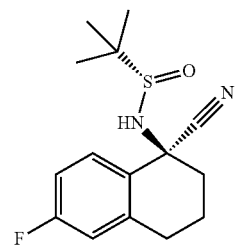 [SMILES: CC(C)(C)[S@](=O)N[C@@]1(C#N)CCCc2cc(F)ccc21]

To a stirred solution of (S)—N-(6-fluoro-3,4-dihydronaphthalen-1(2H)-ylidene)-2-methylpropane-2-sulfinamide (Step 1, 1.23 g, 4.37 mmol) in DCM (10 mL) was added CsF (1.33 g, 8.74 mmol) and tert.BuOH (836 μL, 8.74 mmol), followed by the dropwise addition of trimethylsilylcyanide (1.17 mL, 8.74 mmol) over 4 hr: CAUTION POTENTIAL FOR HCN TO BE LIBERATED! The RM was stirred for 18 hr at RT then additional trimethylsilylcyanide (2.34 mL, 17.48 mmol) was added in one portion and the RM was stirred for 4 days at RT. The RM was partitioned between EtOAc (30 mL) and aq $Na_2CO_3$ (40 mL), extracted 1× with EtOAc (30 mL), the combined organic layers washed with brine (30 mL), dried over $Na_2SO_4$, and evaporated. The residue was purified by normal phase chromatography (24 g $SiO_2$ column, eluent hexane:TBME 70:30 to 10:90), product containing fractions were combined, evaporated and the residue triturated with hexane:(iPr)$_2$O, filtered and dried to give the title compound as an 8:1 mixture of diastereomers.

LC-MS: Rt=0.94 min; MS m/z [M+H]$^+$ 295.2; UPLC-MS 1.

Step 3: (S)-1-amino-6-fluoro-1,2,3,4-tetrahydronaphthalene-1-carboxylic Acid

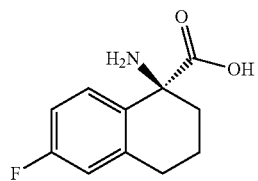 [SMILES: N[C@@]1(C(=O)O)CCCc2cc(F)ccc21]

A mixture of N—((S)-1-cyano-6-fluoro-1,2,3,4-tetrahydronaphthalen-1-yl)-2-methylpropane-2-sulfinamide (Step 2, 5.75 g, 18.95 mmol) and conc. hydrochloric acid (57.6 mL, 1.90 mol) was stirred for 10 min at 100° C., 18 hr at RT, 1 hr at 100° C., and 18 hr at RT. The RM was diluted with $H_2O$ (30 mL) and washed with DCM (50 mL), the organic layer extracted with $H_2O$ (40 mL), and the combined aq layers washed with DCM (20 mL). The combined aq layers were evaporated, and toluene was added to the residue which was evaporated to give the title compound as a brown resin which was used directly without further purification.

Step 4: (S)-(1-amino-6-fluoro-1,2,3,4-tetrahydronaphthalen-1-yl)methanol

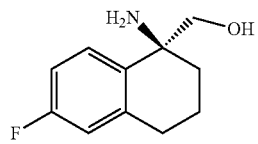

$BH_3$.THF complex (1M, 50 mL, 50.0 mmol) was added dropwise to (S)-1-amino-6-fluoro-1,2,3,4-tetrahydronaphthalene-1-carboxylic acid (Step 3, 6.75 g, 13.74 mmol) in THF (80 mL) at RT, and the RM stirred for 3 days at RT. Additional $BH_3$.THF complex (55.0 mL, 55.0 mmol) was added dropwise and the RM stirred for 24 hr at RT, followed by further $BH_3$.THF complex (20 mL, 20.00 mmol) and stirring for 24 hr at RT. The RM was quenched by the addition of $H_2O$ (50 mL)/aq HCl (4N, 2 mL) to the RM: CAUTION GAS EVOLUTION! After stirring at 40° C. for 30 min the THF was removed by evaporation, and the remaining predominantly-aqueous phase was diluted with water (100 mL) and washed 2× with TBME (100 mL). The aq layer was treated with $Na_2CO_3$ until pH 9, transferred to a separating funnel and extracted 5× with DCM (80 mL), the combined organic layers were washed with brine (70 mL), dried over $Na_2SO_4$, and evaporated. The residue was purified by reversed phase chromatography (RP-HPLC 1) to give the trifluoroacetate salt of the title compound as a white solid. The free base was obtained by taking the salt up into DCM and aq NaOH, extracting a further 2× with DCM, the combined organic layers were dried over $Na_2SO_4$, and evaporated.

$^1$H NMR (400 MHz, DMSO-d$_6$) δ 7.60-7.56 (m, 1H), 6.96-6.90 (m, 1H), 6.87-6.82 (m, 1H), 4.77 (t, 1H), 3.43-3.39 (m, 1H), 3.27-3.23 (m, 1H), 2.75-2.67 (m, 2H), 2.05-1.98 (m, 1H), 1.79-1.69 (m, 4H), 1.50-1.43 (m, 1H).

Intermediate AP: (5)-(1-chloro-5-((3-(difluoromethoxy)-5-(trifluoromethyl)pyridin-2-yl)amino)-5,6,7,8-tetrahydroisoquinolin-5-yl)methanol Step 1: (S)-1-chloro-3'-(3-(difluoromethoxy)-5-(trifluoromethyl)pyridin-2-yl)-7,8-dihydro-6H-spiro[isoquinoline-5,4'-oxazolidin]-2'-one

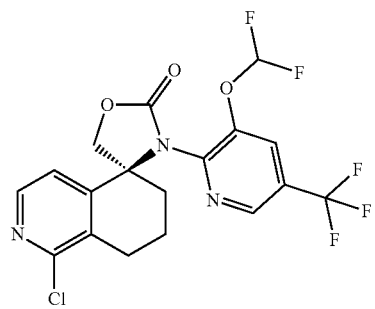 [SMILES: O=C1OC[C@@]2(CCCc3c2ccnc3Cl)N1c1ncc(C(F)(F)F)cc1OC(F)F]

In an Ace pressure tube, a solution of (S)-1-chloro-7,8-dihydro-6H-spiro[isoquinoline-5,4'-oxazolidin]-2'-one (Intermediate AN, 270 mg, 1.13 mmol), 2-chloro-3-(difluoromethoxy)-5-(trifluoromethyl)pyridine (Intermediate A, 420 mg, 1.69 mmol), CuBr (81 mg, 0.57 mmol) and $Cs_2CO_3$ (737 mg, 2.26 mmol) in DMF (11 mL) was stirred at 120° C. for 3.5 hr. The RM was poured into saturated aq $NaHCO_3$ and was extracted 3× with EtOAc. The combined organic extracts were washed 2× with water, dried (phase separator) and evaporated. The crude material was dissolved in THF (5 mL), SiliaMetS®Thiol (Particle Size: 40-63 μm, loading 1.40 mmol/g, 1.70 mmol, 1.21 g) was added and the mixture was swirled at 40° C. for 1 hr. The crude product was purified by normal phase flash chromatography (40 g $SiO_2$ column, eluent c-hexane:EtOAc 100:0 to 75:25) to give the title compound as a beige solid.

$^1$H NMR (600 MHz, DMSO-d$_6$) δ 8.61 (m, 1H), 8.25 (d, 1H), 8.16 (m, 1H), 7.46 (t, 1H), 7.34 (d, 1H), 4.72 (d, 1H), 4.52 (d, 1H), 2.82 (dd, 1H), 2.64-2.58 (m, 1H), 2.46 (m, 1H), 2.16 (m, 1H), 2.01 (m, 1H), 1.82 (m, 1H).

LC-MS: Rt=1.17 min; MS m/z [M+H]$^+$ 450.2/452.2; UPLC-MS 1.

Step 2: (S)-(1-chloro-5-((3-(difluoromethoxy)-5-(trifluoromethyl)pyridin-2-yl)amino)-5,6,7,8-tetrahydroisoquinolin-5-yl)methanol

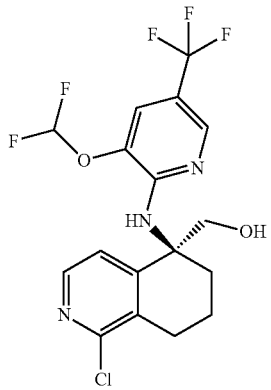 [SMILES: OC[C@]1(Nc2ncc(C(F)(F)F)cc2OC(F)F)CCCc2c1ccnc2Cl]

NaOH (1.97 mL, 7.89 mmol) was added to a mixture of (S)-1-chloro-3'-(3-(difluoromethoxy)-5-(trifluoromethyl)pyridin-2-yl)-7,8-dihydro-6H-spiro[isoquinoline-5,4'-oxazolidin]-2'-one (355 mg, 0.79 mmol) in EtOH (6.8 mL) and the RM was stirred at 90° C. for 15 min. The reaction mixture was poured into saturated aq NaHCO₃, extracted 3× with DCM, the combined organic extracts were dried (phase separator) and evaporated. The crude residue was used without purification in the next step.

¹H NMR (400 MHz, DMSO-d₆) δ 8.01 (d, 1H), 7.96 (s, 1H), 7.58 (s, 1H), 7.37 (t, 1H), 7.21 (d, 1H), 6.71 (s, 1H), 5.74 (t, 1H), 3.71 (dd, 1H), 3.45 (dd, 1H), 2.87 (m, 1H), 2.65 (m, 1H), 2.37 (m, 1H overlapping with DMSO), 1.98-1.82 (m, 3H).

LC-MS: Rt=1.19 min; MS m/z [M+H]⁺ 424.2/426.2; UPLC-MS 1.

Intermediate AQ: (S)-(3-chloro-84-(3-(difluoromethoxy)-5-(trifluoromethyl)pyridin-2-yl)amino)-5,6,7,8-tetrahydroisoquinolin-8-yl)methanol Step 1: (S)—N-(3-chloro-6,7-dihydroisoquinolin-8 (5 dene)-2-methylpropane-2-sulfinamide

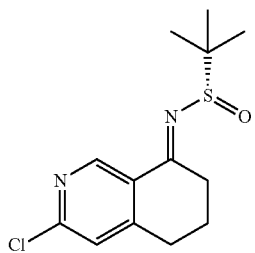 [SMILES: CC(C)(C)[S@](=O)/N=C1\CCCc2cc(Cl)ncc21]

(S)-2-Methylpropane-2-sulfinamide (712 mg, 5.75 mmol) was added to 3-chloro-6,7-dihydroisoquinolin-8(5H)-one (1 g, 5.23 mmol) and Ti(OiPr)₄ (4 ml, 12.8 mmol) at RT under a flow of N2 and the RM stirred at 50° C. for 22.5 hr with a flow of N2. The cooled RM was diluted with THF and brine, and stirred at RT for 15 min. The RM was filtered, washing with THF. The filtrate were evaporated and partitioned between water and EtOAc. The combined organic layers were washed with brine, dried over Na₂SO₄ and evaporated. The residue was absorbed onto Isolute and purified by normal phase chromatography (80 g SiO₂-column; eluent heptane:EtOAc 100:0 to 40:60). Product containing fractions were combined and evaporated to give the title compound as a yellow solid.

LC-MS: Rt=0.98 min; MS m/z [M+H]⁺ 285.1/287.2; UPLC-MS 1.

Step 2: (S)—N-(3-chloro-8-cyano-5,6,7,8-tetrahydroisoquinolin-8-yl)-2-methylpropane-2-sulfinamide

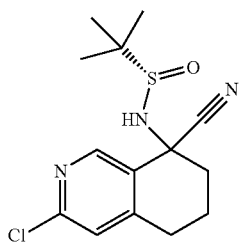 [SMILES: CC(C)(C)[S@](=O)NC1(C#N)CCCc2cc(Cl)ncc21]

Trimethylsilanecarbonitrile (6.5 ml, 48.5 mmol) followed by t-BuOH (0.764 ml, 7.98 mmol) were added to (S,E)-N-(3-chloro-6,7-dihydroisoquinolin-8 (51-1)-ylidene)-2-methylpropane-2-sulfinamide (Step 1, 1.16 g, 3.99 mmol) and cesium fluoride (1.21 g, 7.98 mmol) in DCM (12 mL) at RT under Ar. The RM was stirred at RT for 135 min and additional trimethylsilanecarbonitrile (2 mL, 14.9 mmol) added followed by 18 hr stirring at RT, then further trimethylsilanecarbonitrile (1.5 mL, 11.2 mmol) was added. After stirring at RT for a further 2.5 hours, the RM was diluted with EtOAc, the organic layer washed with brine and saturated aq NaHCO₃, dried over Na₂SO₄ and evaporated. The residue was absorbed onto Isolute and purified by normal phase chromatography (80 g SiO₂-column; eluent heptane:EtOAc 100:0 to 30:70). Product containing fractions were combined and evaporated to give the title compound as an off-white foam.

LC-MS: Rt=0.87 min; MS m/z [M+H]⁺ 312.1/314.2; UPLC-MS 1.

Step 3: 3-chloro-8-((S)-1,1-dimethylethylsulfinamido)-5,6,7,8-tetrahydroisoquinoline-8-carboxamide

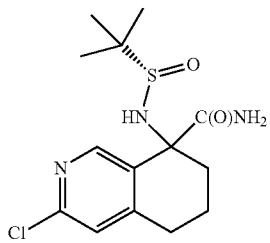

(S)—N-(3-chloro-8-cyano-5,6,7,8-tetrahydroisoquinolin-8-yl)-2-methylpropane-2-sulfinamide (Step 2, 1.05 g, 3.3 mmol) and (hydrido(dimethylphosphinous acid-kP)[hydrogen bis(dimethylphosphinito-kP)]platinum (II), (Parkin's catalyst, 142 mg, 330 µmol) were suspended in a mixture of EtOH (10 mL) and water (2.5 mL). The RM was stirred at 60° C. for 70 min, then filtered, washing with MeOH and the filtrate evaporated. The filtrate was diluted with saturated aq NaHCO₃ and extracted with EtOAc. The combined organic layers were washed with brine, dried over Na₂SO₄ and evaporated. The residue was absorbed onto Isolute and purified by normal phase chromatography (80 g SiO₂-column; eluent heptane:EtOAc 100:0 to 70:30). Product containing fractions were combined and evaporated to give the title compound as a mixture of diastereomers.

LC-MS: Rt=0.69/0.72 min; MS m/z [M+H]⁺ 330.1/332.1; UPLC-MS 1.

Step 4: 8-amino-3-chloro-5,6,7,8-tetrahydroisoquinoline-8-carboxylic Acid

A solution of 3-chloro-8-((S)-1,1-dimethylethylsulfinamido)-5,6,7,8-tetrahydroisoquinoline-8-carboxamide (Step 3, 952 mg, 2.83 mmol) in aq HCl (6M, 5 mL, 30 mmol) was stirred at 100° C. for 18 hr. The cooled RM was neutralized to pH 7 with aq NaOH (2M, 16 mL, 32 mmol) and evaporated to give the title compound as a white solid which was used in the following step without further purification.

LC-MS: Rt=0.53 min; MS m/z [M+H]⁺ 227.1/229.1; UPLC-MS 3.

Step 5: (S)-(8-amino-3-chloro-5,6,7,8-tetrahydroisoquinolin-8-yl)methanol

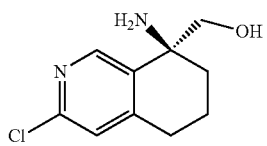 [SMILES: N[C@@]1(CO)CCCc2cc(Cl)ncc21]

A solution of borane-THF complex solution in THF (1M, 10 ml, 10 mmol) was added dropwise, over 15 min, to 8-amino-3-chloro-5,6,7,8-tetrahydroisoquinoline-8-carboxylic acid (Step 4, 635 mg, 2.8 mmol) in THF (10 mL) at 0° C. under Ar. The RM was stirred at RT for 16 hours, then carefully quenched with MeOH and evaporated, co-evaporating 3× with MeOH. The residue was diluted with MeOH and HCl in Et₂O (2M, 1.5 ml, 3 mmol) was added. Additional Et₂O was added until a precipitate formed and the RM was stirred at RT for 30 min. The RM was filtered and saturated aq NaHCO₃ added to the solid, and the aq phase extracted with EtOAc. The combined organic layers were washed with brine, dried over Na₂SO₄ and evaporated to give the title compound as a mixture of enantiomers. The enantiomers were separated by chiral HPLC: (instrument: Gilson Trilution I HPLC prep system; column: Lux i-Cel-5, 5 250×30 mm 25° C.; eluent: heptane EtOH:MeOH 80:10: 10+0.05% Et₂NH; flow rate: 15 mL/min; Detection: 220 nm) to give the title compound as the first eluting peak. Chiral-HPLC: Rt=7.60 min.

LC-MS: Rt=0.38 min; MS m/z [M+H]⁺ 213.1/215.1; UPLC-MS 1.

(R)-(8-amino-3-chloro-5,6,7,8-tetrahydroisoquinolin-8-yl)methanol as the second eluting peak, Rt=9.13 min; C-HPLC 49.

Step 6: (S)-3-chloro-6,7-dihydro-5H-spiro[isoquinoline-8,4'-oxazolidin]-2'-one

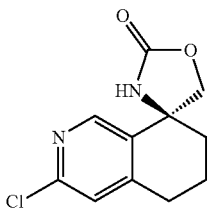 [SMILES: O=C1N[C@]2(CCCc3cc(Cl)ncc32)CO1]

A solution of bis(trichloromethyl) carbonate (86 mg, 288 µmol) in DCM (3 mL) was added dropwise to (S)-(8-amino-3-chloro-5,6,7,8-tetrahydroisoquinolin-8-yl)methanol (Step 5, 125 mg, 576 µmol) and triethylamine (169 µL, 1.21 mmol) in DCM (5 mL) at 0° C. under Ar. The RM was stirred for 1 hr at RT, then quenched with saturated aq NH₄Cl and extracted 3× with DCM. The combined organic layers were washed with brine, dried over Na₂SO₄ and evaporated to give the title compound as an off-white solid.

LC-MS: Rt=0.64 min; MS m/z [M+H]⁺ 239.1/241.1; UPLC-MS 1.

Step 7: (S)-3-chloro-3'-(3-(difluoromethoxy)-5-(trifluoromethyl)pyridin-2-yl)-6,7-dihydro-5H-spiro[isoquinoline-8,4'-oxazolidin]-2'-one

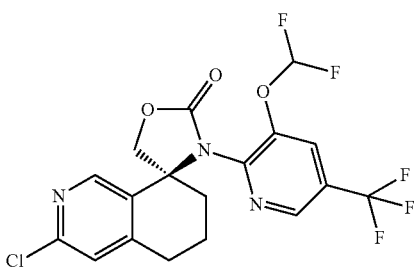 [SMILES: O=C1OC[C@@]2(CCCc3cc(Cl)ncc32)N1c1ncc(C(F)(F)F)cc1OC(F)F]

A mixture of (S)-3-chloro-6,7-dihydro-5H-spiro[isoquinoline-8,4'-oxazolidin]-2'-one (Step 6, 140 mg, 557 µmol), copper(I) iodide (53.3 mg, 280 µmol), cesium carbonate (363 mg, 1.12 mmol) and 2-chloro-3-(difluoromethoxy)-5-(trifluoromethyl)pyridine (Intermediate A, 248 mg, 1.0 mmol) in DMF (5 mL) was heated at 120° C. for 2 hr under Ar. Additional 2-chloro-3-(difluoromethoxy)-5-(trifluoromethyl)pyridine (Intermediate A, 74 mg, 0.3 mmol) and copper(I) iodide (15.2 mg, 80 µmol) were added and the RM heated at 120° C. for a further 1.5 hr. The RM was diluted with saturated aq NaHCO₃ and extracted with EtOAc. The combined organic layers were washed with brine, dried over Na₂SO₄ and evaporated. The residue was diluted with THF (15 mL) and SiliaMetS®Thiol (0.141 mmol, 141 mg, Particle Size: 40-63 µm, loading 1.41 mmol/g, Silicycle) added, and the RM stirred at 40° C. for 1 hr. The RM was filtered, washing with THF, and the filtrate evaporated. The residue was absorbed onto Isolute and purified by normal phase chromatography (40 g SiO$_2$-column, eluent heptane:EtOAc 100:0 to 80:20). Product containing fractions were combined and evaporated. The residue was triturated with hexane and filtered to give the title compound as a white foam.

$^1$H NMR (400 MHz, DMSO-d$_6$) δ 8.61 (d, 1H), 8.39 (s, 1H), 8.14 (d, 1H), 7.47 (t, 1H), 7.34 (s, 1H), 4.72 (d, 1H), 4.52 (dd, 1H), 2.79-2.65 (m, 2H), 2.57 (d, 1H), 2.22 (d, 1H), 1.96-1.87 (m, 1H), 1.85-1.75 (m, 1H).

LC-MS: Rt=1.15 min; MS m/z [M+H]$^+$ 450.1/452.1; UPLC-MS 1.

Step 8: (S)-(3-chloro-8-((3-(difluoromethoxy)-5-(trifluoromethyl)pyridin-2-yl)amino)-5,6,7,8-tetrahydroisoquinolin-8-yl)methanol

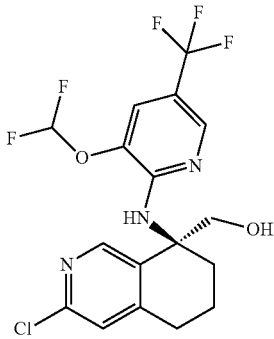 [SMILES: OC[C@]1(Nc2ncc(C(F)(F)F)cc2OC(F)F)CCCc2cc(Cl)ncc21]

(S)-3-chloro-3'-(3-(difluoromethoxy)-5-(trifluoromethyl)pyridin-2-yl)-6,7-dihydro-5H-spiro[isoquinoline-8,4'-oxazolidin]-2'-one (Step 7, 160 mg, 334 µmol) was suspended in EtOH (3 mL) and aq NaOH (2M, 1 mL, 2 mmol) was added. The RM was stirred at 80° C. for 1.5 hr, the cooled RM diluted with water and extracted with EtOAc. The combined organic layers were washed with brine, dried over Na$_2$SO$_4$ and evaporated to give the title compound.

LC-MS: Rt=1.19 min; MS m/z [M+H]$^+$ 424.1/426.2; UPLC-MS 1.

Intermediate AR: (S)-(7-bromo-4-((3-(difluoromethoxy)-5-(trifluoromethyl)pyridin-2-yl)amino)-8-fluorochroman-4-yl)methanol Step 1: (S)-7-bromo-3'-(3-(difluoromethoxy)-5-(trifluoromethyl)pyridin-2-yl)-8-fluorospiro[chroman-4,4'-oxazolidin]-2'-one

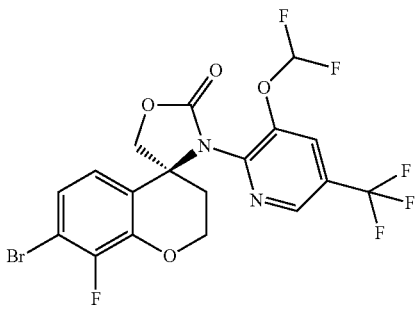 [SMILES: O=C1OC[C@@]2(CCOc3c2ccc(Br)c3F)N1c1ncc(C(F)(F)F)cc1OC(F)F]

In an Ace Pressure Tube, a solution of (S)-7-bromo-8-fluorospiro[chroman-4,4'-oxazolidin]-2'-one (Intermediate AS, 5.4 g, 17.9 mmol), 2-chloro-3-(difluoromethoxy)-5-(trifluoromethyl)pyridine (Intermediate A, 5.75 g, 23.2 mmol), CuI (1.70 g, 8.94 mmol) and cesium carbonate (11.6 g, 35.8 mmol) in DMF (140 mL) was stirred at 130° C. for 2.5 hr. 2-chloro-3-(difluoromethoxy)-5-(trifluoromethyl)pyridine (Intermediate A, 1.99 g, 8.04 mmol) was added to the RM which was further heated at 130° C. for 2 hr. The RM was poured into saturated aq NH$_4$Cl (200 mL), stirred at RT for 1 hr and then extracted 3× with EtOAc. The combined organic extracts were washed 2× with saturated aq NH$_4$Cl, dried over Na$_2$SO$_4$, filtered and evaporated. The crude residue was purified by normal phase flash chromatography (220 g RediSep Gold column, eluent, c-hexane:EtOAc 100:0 to 65:35) to give the title compound as a yellow solid.

$^1$H NMR (400 MHz, DMSO-d$_6$) δ 8.64 (s, 1H), 8.13 (s, 1H), 7.46 (t, 1H), 7.15 (dd, 1H), 7.04 (dd, 1H), 4.80 (d, 1H), 4.56-4.52 (m, 2H), 4.32 (m, 1H), 3.12 (m, 1H), 2.48-2.39 (m, 1H overlapping with DMSO peak).

LC-MS: Rt=1.24 min; MS m/z [M+HCOO]$^-$ 557.0/559.0; UPLC-MS 1.

Step 2: (S)-(7-bromo-44-(3-(difluoromethoxy)-5-(trifluoromethyl)pyridin-2-yl)amino)-8-fluorochroman-4-yl)methanol

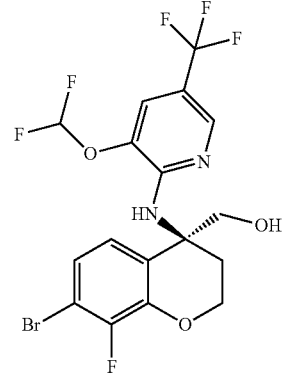 [SMILES: OC[C@]1(Nc2ncc(C(F)(F)F)cc2OC(F)F)CCOc2c1ccc(Br)c2F]

A mixture of (S)-7-bromo-3'-(3-(difluoromethoxy)-5-(trifluoromethyl)pyridin-2-yl)-8-fluorospiro[chroman-4,4'-oxazolidin]-2'-one (Step 1, 5.65 g, 11.0 mmol) and NaOH (4M, 27.5 mL, 110 mmol) in EtOH (55 mL) was stirred at 90° C. for 50 min. The RM was poured into water and extracted 2× with DCM. The combined organic extracts were dried over Na$_2$SO$_4$, filtered and evaporated to give the title compound as a light yellow foam which was used without further purification in the next step.

$^1$H NMR (400 MHz, DMSO-d$_6$) δ 8.04 (s, 1H), 7.60 (s, 1H), 7.38 (t, 1H), 7.00 (dd, 1H), 6.94 (br s, 1H), 5.73 (br t, 1H), 4.46 (m, 1H), 4.33 (m, 1H), 3.87 (dd, 1H), 3.61 (dd, 1H), 2.90 (dt, 1H), 2.05 (dt, 1H).

LC-MS: Rt=1.25 min; MS m/z [M+H]$^+$ 487.0/489.0; UPLC-MS 1.

Intermediate AS: (S)-7-bromo-8-fluorospiro[chromane-4,4'-oxazolidin]-2'-one

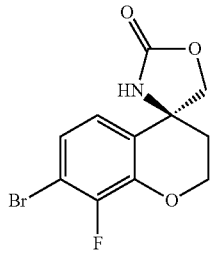 [SMILES: O=C1N[C@]2(CCOc3c2ccc(Br)c3F)CO1]

To a solution of (S)-(4-amino-7-bromo-8-fluorochroman-4-yl)methanol (Intermediate AT, 5 g, 18.1 mmol) and triethylamine (5.30 mL, 38.0 mmol) in DCM (100 mL) at 0-5° C. was added dropwise a solution of triphosgene (2.15 g, 7.24 mmol) in DCM (100 mL). The yellow solution was stirred at RT for 50 min. The RM was poured into saturated aq NaHCO$_3$ and was extracted 3× with DCM. The combined organic extracts were dried (phase separator) and evaporated to give the title compound as a beige foam.

LC-MS: Rt=0.82 min; MS m/z [M+NH$_4$]$^+$ 319.1/321.0; UPLC-MS 1.

Intermediate AT: (S)-(4-amino-7-bromo-8-fluorochroman-4-yl)methanol

Step 1: rac-methyl 4-amino-7-bromo-8-fluorochromane-4-carboxylate

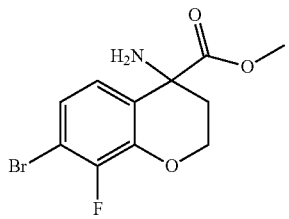 [SMILES: COC(=O)C1(N)CCOc2c1ccc(Br)c2F]

A suspension of 4-amino-7-bromo-8-fluorochromane-4-carboxylic acid (Intermediate AU, 250 g, 765 mmol, HCl salt) and SOCl$_2$ (910 g, 7.66 mol) in MeOH (2 L) was stirred at 65° C. for 16 hr. The RM was concentrated under reduced pressure, and the residue partitioned between saturated aq Na$_2$CO$_3$ (1 L) and DCM (1 L). The aq phase was extracted a further 2× with DCM (500 mL), the combined organic layers were washed with brine (600 mL), dried over Na$_2$SO$_4$, filtered and concentrated to give the title compound as a pale-yellow solid.

$^1$H NMR (400 MHz, DMSO-d$_6$) δ 8.83 (br, s, 3H), 7.51 (dd, 1H), 7.29 (dd, 1H), 5.87 (br s, 1H), 4.49-4.40 (m, 1H), 4.38-4.26 (m, 1H), 3.78 (s, 2H), 3.36 (br s, 2H), 2.44-2.34 (m, 1H), 2.18-2.07 (m, 1H).

Step 2: (S)-(4-amino-7-bromo-8-fluorochroman-4-yl)methanol

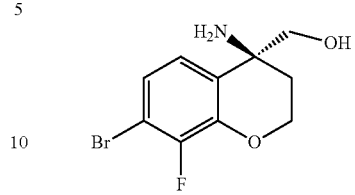

To a solution of rac-methyl 4-amino-7-bromo-8-fluorochromane-4-carboxylate (Step 1, 240 g, 723 mmol) in MeOH (2 L) was added NaBH$_4$ (137 g, 3.62 mol) at 28° C. and the RM stirred at 28° C. for 16 hr. The solvent was removed under reduced pressure and the residue taken up into DCM (1 L) and washed with brine (600 mL). The aq phase was extracted 2× with DCM (200 mL) and the combined organic layers were washed with brine (300 mL), dried over Na$_2$SO$_4$, filtered and concentrated. The residue was re-dissolved in MeOH (1.5 L) and HCl/MeOH (4 M, 1 L) added, the mixture stirred at 25° C. for 1 hr and then concentrated. The residue was triturated with MTBE (200 mL) to give the racemic title compound as an off-white solid. The enantiomers were separated by chiral SFC: (instrument: Thar 350 preparative SFC; column: Chiralpak AD, 10 μm, 50×300 cm; temperature 38° C.; eluent: CO$_2$: MeOH+0.1% NH$_4$OH, 100:0 to 65:35; flow rate: 200 mL/min; back pressure 100 bar; detection: 220 nm) to give the title compound as the second eluting peak.

LC-MS: Rt=1.75 min; MS m/z [M+H]$^+$ 276.2/278.2; UPLC-MS 4.

Chiral-HPLC: Rt=4.78 min; with (R)-(4-amino-7-bromo-8-fluorochroman-4-yl)methanol as the first eluting peak, Rt=4.16 min; C-HPLC 10.

Intermediate AU: 4-amino-7-bromo-8-fluorochromane-4-carboxylic acid

Step 1: 3-(3-bromo-2-fluorophenoxy)propanoic acid

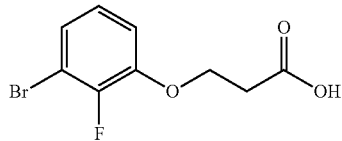 [SMILES: O=C(O)CCOc1cccc(Br)c1F]

To a dispersion of NaH in mineral oil (60%, 201 g, 5.03 mol, 60% purity) in DMF (2 L), was added 3-bromo-2-fluorophenol (800 g, 4.19 mol) at 0° C. and the mixture stirred at 28° C. for 3 hr. To the RM was added β-propiolactone (362 g, 5.03 mol) and the mixture stirred at 28° C. for 32 hr. The RM was poured into ice-water (8 L), to give an off-white precipitate. The solid was collected by filtration and slurried with acetonitrile (800 mL) to give the title compound as a white solid.

$^1$H NMR (400 MHz, DMSO-d$_6$) δ 12.46 (s, 1H), 7.29-7.18 (m, 2H), 7.14-7.06 (m, 1H), 4.26 (t, 2H), 2.72 (t, 2H).

Step 2: 7-bromo-8-fluorochroman-4-one

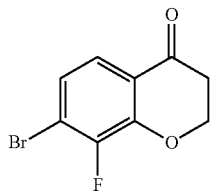 [SMILES: O=C1CCOc2c1ccc(Br)c2F]

To a suspension of P₂O₅ (421 g, 2.97 mol) in methanesulfonic acid (2 L), was added 3-(3-bromo-2-fluorophenoxy)propanoic acid (Step 1, 400 g 1.48 mol) at 80° C. After stirring at 80° C. for 15 min the RM was poured into ice-water (4 L), and then extracted 3× with ethyl acetate (800 mL). The combined organic layers were washed 2× with brine (300 mL), dried over Na₂SO₄, filtered and concentrated. The residue was slurried with AcCN (500 mL) to give the title compound as a yellow solid.
¹H NMR (400 MHz, DMSO-d₆) δ 7.50 (dd, 1H), 7.35 (dd, 1H), 4.69 (t, 2H), 2.87 (t, 2H).

Step 3: rac-7-bromo-8-fluorospiro[chromane-4,4'-imidazolidine]-2',5'-dione

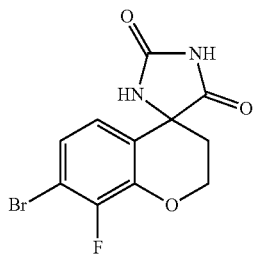 [SMILES: O=C1NC(=O)C2(CCOc3c2ccc(Br)c3F)N1]

A solution of 7-bromo-8-fluorochroman-4-one (Step 2, 452 g, 1.84 mol), KCN (179 g, 2.75 mol) and (NH₄)₂CO₃ (1.94 kg, 20.2 mol) in a mixture of EtOH (4 L) and H₂O (4 L) was stirred at 100° C. for 16 hr in a sealed tube. The reaction mixture was concentrated under reduced pressure and filtered to give the crude product. The crude product was slurried with AcCN (500 mL) to give the title compound as a light-yellow solid.
¹H NMR (400 MHz, DMSO-d₆) δ 11.08 (br, s, 1H), 8.62 (br, s, 1H), 7.34-7.15 (m, 1H), 6.91 (br, d, 1H), 4.62 (br, t, 1H), 4.33 (td, 1H), 2.70-2.64 (m, 1H), 2.38-2.29 (m, 1H), 2.23-2.12 (m, 1H).

Step 4:
rac-4-amino-7-bromo-8-fluorochromane-4-carboxylic Acid

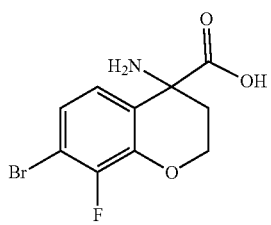

A suspension of rac-7-bromo-8-fluorospiro[chromane-4,4'-imidazolidine]-2',5'-dione (Step 3, 400 g 1.27 mol) and KOH (712 g 12.7 mol) in water (2 L) was stirred at 105° C. for 54 hr. The RM was adjusted to pH 7 resulting in the formation of a pale-yellow precipitate, which was collected by filtration. The solid was washed with water (300 mL) and dried to give the title compound as a light-yellow solid.
¹H NMR (400 MHz, DMSO-d₆) δ 8.02 (br, s, 2H), 7.20-7.16 (m, 2H), 4.62 (br, t, 1H), 4.33 (dt, 1H), 2.46-2.40 (m, 1H), 2.07-1.99 (m, 1H).

Intermediate AU can also be synthesized via the following alternative route, as a non-racemic mixture, enriched in the (S)-enantiomer:

Step 1A: (S)—N-(7-bromo-8-fluorochroman-4-ylidene)-2-methylpropane-2-sulfinamide

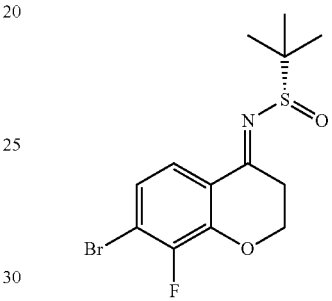

To a mixture of 7-bromo-8-fluorochroman-4-one (step 2, 4.36 g, 17.8 mmol) and Ti(OiPr)₄ (12.0 mL, 40.9 mmol) was added (S)-(−)-tert-butanesulfinamide (2.26 g, 18.7 mmol) under a nitrogen flow at RT. The RM was heated at 50° C. under continuous N2-flow for 18 hr. Water (110 mL) was added followed by EtOAc (110 mL) and the resulting suspension was stirred for 15 min. The mixture was filtered through Celite and the solid was rinsed successively with water and EtOAc. To the filtrate was added brine (100 mL) and the mixture was extracted with EtOAc. The organic layer was dried (phase separator) and evaporated. The crude residue was purified by normal phase flash chromatography (SiO₂ column, eluent, c-hexane:EtOAc 100:0 to 80:20) to give the title compound as a yellow oil.
LC-MS: Rt=1.16 min; MS m/z [M+H]⁺ 348.2/350.0; UPLC-MS 1.

Step 2A: (S)—N-(7-bromo-4-cyano-8-fluorochroman-4-yl)-2-methylpropane-2-sulfinamide

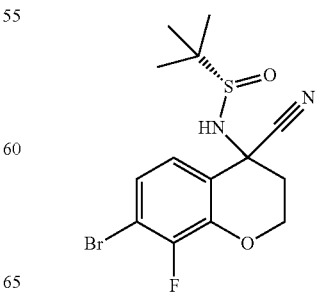

An Ace pressure tube was charged with (S)—N-(7-bromo-8-fluorochroman-4-ylidene)-2-methylpropane-2-sulfinamide (Step 1A, 3.87 g, 11.1 mmol) and cesium fluoride (3.38 g, 22.2 mmol). DCM (55 mL) was added followed by tert-butanol (2.24 mL, 22.2 mmol) and trimethylsilyl cyanide (6.95 mL, 55.6 mmol). The tube was sealed and the RM stirred at RT for 16 hr. Trimethylsilyl cyanide (6.95 mL, 27.8 mmol) was again added and the RM was further stirred for 5 hr. The RM was poured into saturated aq $NaHCO_3$ and was extracted 2× with $CH_2Cl_2$. The combined organic extracts were dried (phase separator) and evaporated. The crude material was purified by normal phase flash chromatography (100 g $SiO_2$ column, eluent c-hexane:EtOAc 100:0 to 50:50) to give the title compound as a mixture of diastereomers (dr=75:25) as a white foam.

LC-MS: Rt=4.79 and 4.84 min; MS m/z $[M+NH_4]^+$ 392.1./394.1; UPLC-MS 6.

Step 3A: 7-bromo-4-((S)-1,1-dimethyl ethyl sulfinamido)-8-fluorochroman-4-carboxamide

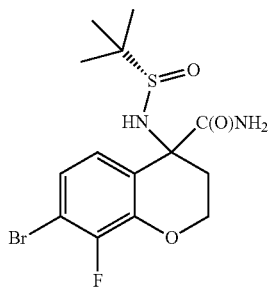

(S)—N-(7-bromo-4-cyano-8-fluorochroman-4-yl)-2-methylpropane-2-sulfinamide (Step 2A, 3:1 diastereomeric mixture, 2.97 g, 7.91 mmol) was dissolved in a mixture of THF/water 3:1 (31.6 mL). Acetamide (1.96 g, 33.2 mmol) and $PdCl_2$ (140 mg, 0.79 mmol) were added and the mixture was stirred at RT under a nitrogen atmosphere for 19 hr. The RM was poured into brine and extracted 2× with $CH_2Cl_2$. The combined organic layers were dried (phase separator) and evaporated to give the title compound as a brown foam (3:1 mixture of diastereomers), which was used in the next step without further purification.

LC-MS: Rt=0.85 and 0.87 min; MS m/z $[M+NH_4]^+$ 393.1/395.1; UPLC-MS 1.

Step 4A:
4-amino-7-bromo-8-fluorochroman-4-carboxylic Acid Hydrochloride Salt

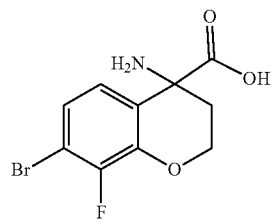 [SMILES: NC1(C(=O)O)CCOc2c1ccc(Br)c2F]

7-Bromo-4-((S)-1,1-dimethylethylsulfinamido)-8-fluorochroman-4-carboxamide (Step 3A, 3:1 diastereomeric mixture, 3.10 g, 7.17 mmol) was diluted in HCl (5M, 32.7 mL) and the mixture was refluxed for 14 hr. The RM was allowed to cool to RT and $CH_2Cl_2$ was added. The layers were separated and the aqueous layer was concentrated to give the title compound as a brown solid (3:1 mixture of diastereomers), which was used without further purification in the next step.

LC-MS: Rt=0.43 min; MS m/z $[M+H]^+$ 290.0/292.1; UPLC-MS 1.

The following intermediates AU1 to AU9 were prepared using the methods used to prepare Intermediate AU.

| Intermediate | Structure | Characterising data |
|---|---|---|
| AU1 | 4-amino-7-chlorochromane-4-carboxylic acid | LC-MS: Rt = 0.38 min; MS m/z [M + H]+ 228.1/230.1; UPLC-MS 1 |
| AU2 | 4-amino-7-(trifluoromethyl)chromane-4-carboxylic acid | LC-MS: Rt = 0.48 min; MS m/z [M + H]+ 262.3; UPLC-MS 1 |

-continued

| Intermediate | Structure | Characterising data |
|---|---|---|
| AU3 | 4-amino-7,8-difluorochromane-4-carboxylic acid | $^1$H NMR (400 MHz, DMSO-$d_6$) δ 8.85 (br s, 1H), 7.27 (m, 1H), 7.05 (dd, 1H), 4.57 (m, 1H), 4.43 (m, 1H), 2.52 (m, 1H, overlaping with DMSO peak), 2.29 (m, 1H). |
| AU4 | 4-amino-8-chlorochromane-4-carboxylic acid | LC-MS: Rt = 0.34 min; MS m/z [M + H]$^+$ 227.8/230.0; UPLC-MS 1 |
| AU5 | 4-amino-7-bromochromane-4-carboxylic acid | LC-MS: Rt = 0.41 min; MS m/z [M − H]$^-$ 270.0/272.0; UPLC-MS 1 |
| AU6 | 4-amino-8-bromochromane-4-carboxylic acid | LC-MS: Rt = 0.36 min; MS m/z [M − H]$^-$ 270.0/271.9; UPLC-MS 1 |
| AU7 | 4-amino-8-fluorothiochromane-4-carboxylic acid | LC-MS: Rt = 0.34 min; MS m/z [M − H]$^-$ 226.1; UPLC-MS 2 |
| AU 8 | rac-1-amino-6-bromo-1,2,3,4-tetrahydronaphthalene-1-carboxylic acid | LC-MS: Rt = 0.43 min; MS m/z [M + H]$^+$ 270.1/272.1; UPLC-MS 2. |
| AU 9 | rac-1-amino-5-fluoro-1,2,3,4-tetrahydronaphthalene-1-carboxylic acid | LC-MS: Rt = 0.30 min; MS m/z [M + H]$^+$ 210.1; UPLC-MS 1 |

Intermediate AV: 2-(methyl-d₃)-1,3,2-dioxaborinane

Step 1:
1,3-bis((1,3,2-dioxaborinan-2-yl)oxy)propane

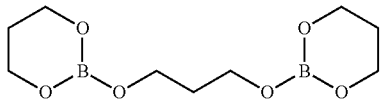 [SMILES: C1COB(OCCCOB2OCCCO2)OC1]

A mixture of propane-1,3-diol (52.1 mL, 721 mmol) and boric acid (30 g, 480 mmol) in toluene (400 mL) was heated at reflux for 13 hr in a Dean-Stark apparatus with removal of water. The cooled RM was then evaporated and the residue purified by bulb-to-bulb distillation under a vacuum of 0.5 mbar. The title compound was obtained as the fraction distilling between 200-220° C., as a viscous clear colorless oil.

¹H NMR (400 MHz, DMSO-d₆) δ 3.93 (t, 8H), 3.69 (t, 4H), 1.83 (pentuplet, 4H), 1.62 (pentuplet, 2H).

Step 2: 2-(methyl-d₃)-1,3,2-dioxaborinane

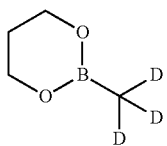

A mixture of 1,3-bis((1,3,2-dioxaborinan-2-yl)oxy)propane (Step 1, 10.0 g, 36.9 mmol) and trimethyl borate (3.84 g, 36.9 mmol) was stirred at RT for 0.5 hr. The RM was then diluted with Et₂O (110 mL), cooled with a dry ice/acetone bath, and a solution of (methyl-d₃)magnesium iodide in Et₂O (1 M, 111 mL, prepared from d3-methyl iodide and Mg, and initiated with 12) added dropwise over 1 hr. The RM was stirred at 75° C. for a further 2 hr, then allowed to warm RT, and a solution of HCl in Et₂O (2M, 55.4 mL, 111 mmol) added dropwise. After stirring at RT for 1 hr the RM was filtered, and the volume of the filtrate reduced on a rotary evaporator under a pressure of 700 mbar with a bath temperature of 35° C. The residue was transferred to a distillation apparatus and fractionally distilled with a vacuum of 100 mbar. The title compound was collected as a clear pale-yellow oil distilling between 40-45° C.

¹H NMR (400 MHz, chloroform-d) δ 4.00 (t, 4H), 1.96 (pentuplet, 2H).

Intermediate AW: (S)-8'-(difluoromethoxy)-8-fluoro-7-iodo-6'-(trifluoromethyl)-3'H-spiro[chroman-4,2'-imidazo[1,2-a]pyridine]

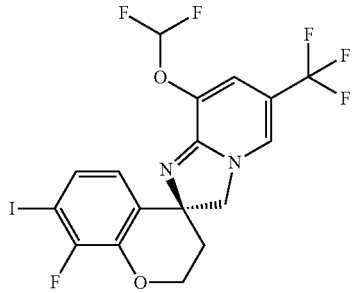 [SMILES: Fc1c(I)ccc2c1OCC[C@@]21CN2C=C(C(F)(F)F)C=C(OC(F)F)C2=N1]

A mixture of (S)-7-bromo-8'-(difluoromethoxy)-8-fluoro-6'-(trifluoromethyl)-3'H-spiro[chroman-4,2'-imidazo[1,2-a]pyridine] (Example 39, 150 mg, 320 µmol), CuI (30 mg, 160 mmol), NaI (96 mg, 639 µmol) and trans-N,N-dimethyl-1,2-cyclohexanediamine (5 µL, 32 µmol) in 1,4-dioxane (3 mL) was heated in a sealed tube at 110° C. under an atmosphere of nitrogen for 18 hr. To the cooled RM was added additional CuI (30 mg, 160 mmol), NaI (96 mg, 639 µmol) and trans-N,N-dimethyl-1,2-cyclohexanediamine (5 µL, 32 µmol) and heating continued at 110° C. for a further 18 hr. The cooled RM was partitioned between DCM and 30% aq NH₃, the aq phase extracted 3× with DCM, the combined organic phases were dried by passing through a separator phase cartridge and concentrated. The residue was purified by normal phase chromatography (50 g SiO₂ SNAP cartridge, eluent hexane:EtOAc 100:0 to 50:50) to give the title compound as a yellow solid.

LC-MS: Rt=3.70 min; MS m/z [M+H]⁺ 517.0; UPLC-MS 4.

Intermediate AX: (S)-(7-chloro-4-((3-(difluoromethoxy)-5-(trifluoromethyl)pyridin-2-yl)amino)chroman-4-yl)methanol Step 1:
(S)-(4-amino-7-chlorochroman-4-yl)methanol

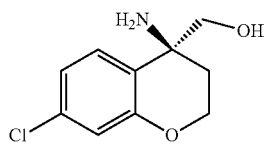 [SMILES: N[C@@]1(CO)CCOc2cc(Cl)ccc21]

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with 4-amino-7-chlorochromane-4-carboxylic acid (Intermediate AU1). The enantiomers were separated by chiral SFC: (instrument: MG preparative SFC; column: Chiralpak IC, 250×30 mm I.D., 5 µm, 38° C.; eluent: CO₂/MeOH (+0.1% NH₄OH) 75:25; flow rate: 60 mL/min; detection: 220 nm) to give the title compound as the first eluting peak, as a beige powder.

LC-MS: Rt=0.43 min; MS m/z [M+H]⁺ 214.1/216.1; UPLC-MS 1.

Chiral-HPLC: C-SFC 10: Rt=3.48 min; with (R)-(4-amino-7-chlorochroman-4-yl)methanol as the second eluting peak, Rt=3.77 min; C-SFC 10.

Step 2 and 3: (S)-(7-chloro-4-((3-(difluoromethoxy)-5-(trifluoromethyl)pyridin-2-yl)amino)chroman-4-yl)methanol

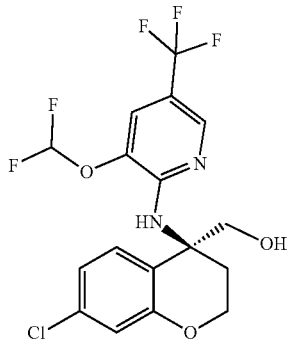 [SMILES: OC[C@]1(Nc2ncc(C(F)(F)F)cc2OC(F)F)CCOc2cc(Cl)ccc21]

The title compound was prepared by a method similar to that of Intermediates AR and AS by replacing (S)-(4-amino-7-bromo-8-fluorochroman-4-yl)methanol (Intermediate AT) with (S)-(4-amino-7-chlorochroman-4-yl)methanol (Step 1). The crude product was used without purification in the next step.

LC-MS: Rt=1.25 min; MS m/z [M+H]⁺ 425.1/427.1; UPLC-MS 1.

Intermediate AY: (S)-7-bromo-8-fluoro-3'-(3-(fluoromethoxy)-5-(trifluoromethyl)pyridin-2-yl)spiro[chroman-4,4'-oxazolidin]-2'-one

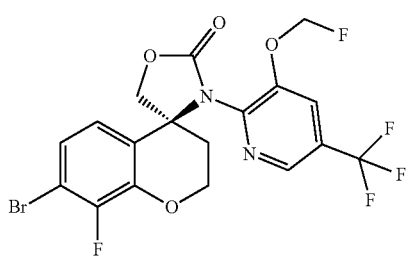 [SMILES: O=C1OC[C@@]2(CCOc3c2ccc(Br)c3F)N1c1ncc(C(F)(F)F)cc1OCF]

The title compound was prepared by a method similar to that of Intermediate N by replacing (S)-5-bromo-4-fluoro-2,3-dihydrospiro[indene-1,4'-oxazolidin]-2'-one (Intermediate I) with (S)-7-bromo-8-fluorospiro[chromane-4,4'-oxazolidin]-2'-one (Intermediate AS). The crude product was purified by normal phase chromatography (silica gel, eluent c-hexane:EtOAc 100:0 to 70:30).

LC-MS: Rt=1.24 min; MS m/z [M+HCO₂⁻]⁻ 539.3/541.2; UPLC-MS 1.

Intermediate AZ: (S)-8'-(difluoromethoxy)-8-fluoro-7-(4,4,5,5-tetramethyl-1,3,2-dioxaborolan-2-yl)-6'-(trifluoromethyl)-3'H-spiro[chroman-4,2'-imidazo[1,2-a]pyridine]

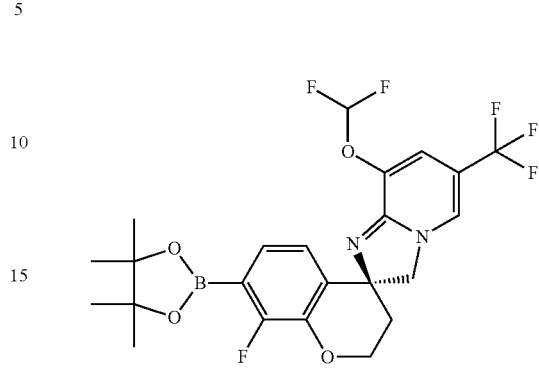

In a microwave vial, (S)-7-bromo-8'-(difluoromethoxy)-8-fluoro-6'-(trifluoromethyl)-3'H-spiro[chroman-4,2'-imidazo[1,2-a]pyridine] (Example 39, 500 mg, 1.07 mmol), bis(pinacolato)diboron (541 mg, 2.13 mmol), PdCl₂(dppf).CH₂Cl₂ adduct (43.5 mg, 0.05 mmol) and KOAc (314 mg, 3.20 mmol) were charged. The vial was placed under argon and 1,4-dioxane (8 mL) was added and the vial closed. The RM was stirred at 100° C. for 5 hr. The RM was poured in saturated aq NaHCO₃ and extracted 2× with EtOAc. The combined organic extracts were dried (phase separator) and evaporated to give the title compound as a brown oil. The compound was used without purification in the next step.

LC-MS: Rt=0.96 min; MS m/z [M+H]⁺ 517.2; UPLC-MS 1.

Intermediate BA: (S)-(4-((3-(difluoromethoxy)-5-(trifluoromethyl)pyridin-2-yl)amino)-7-(trifluoromethyl)chroman-4-yl)methanol

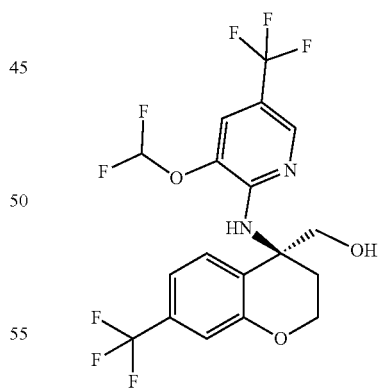

The title compound was prepared by a method similar to that of Intermediates AR and AS by replacing (S)-(4-amino-7-bromo-8-fluorochroman-4-yl)methanol (Intermediate AT) with (S)-(4-amino-7-(trifluoromethyl)chroman-4-yl)methanol (Intermediate BB). The crude product was used without purification in the next step.

LC-MS: Rt=1.27 min; MS m/z [M+H]⁺ 459.1; UPLC-MS 1.

Intermediate BB: (S)-(4-amino-7-(trifluoromethyl)chroman-4-yl)methanol

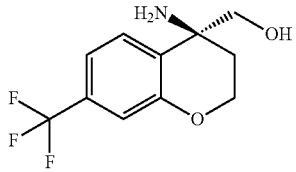

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with 4-amino-7-(trifluoromethyl)chromane-4-carboxylic acid (Intermediate AU2). The enantiomers were separated by chiral HPLC (instrument: THAR 200 preparative SFC; column: Chiralpak 1C, 10 300×50 mm I.D., 38° C.; eluent: CO$_2$/MeOH (+0.1% NH$_4$OH) 85:15; flow rate: 200 mL/min; detection: 220 nm) to give the title compound as the first eluting peak.

LC-MS: Rt=0.54 min; MS m/z [M+H]$^+$ 248.2; UPLC-MS 1.

Chiral-SFC: Rt=2.11 min; with (R)-(4-amino-7-(trifluoromethyl)chroman-4-yl)methanol as the second eluting peak, Rt=2.34 min; C-SFC 43.

Intermediate BC: (S)-(4-((3-(difluoromethoxy)-5-(trifluoromethyl)pyridin-2-yl)amino)-7,8-difluoro-chroman-4-yl)methanol

Step 1: (S)-7,8-difluorospiro[chromane-4,4'-oxazolidin]-2'-one

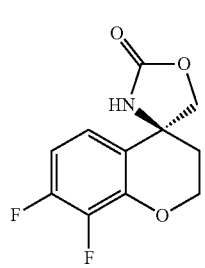

The title compound was prepared by a method similar to that of Intermediates AS by replacing (5)-(4-amino-7-bromo-8-fluorochroman-4-yl)methanol (Intermediate AT) with (S)-(4-amino-7,8-difluorochroman-4-yl)methanol (Intermediate BD). The crude product was used without purification in the next step.

LC-MS: Rt=0.72 min; MS m/z [M−H]$^−$ 240.1; UPLC-MS 1.

Steps 2 and 3: (S)-(4-((3-(difluoromethoxy)-5-(trifluoromethyl)pyridin-2-yl)amino)-7,8-difluorochroman-4-yl)methanol

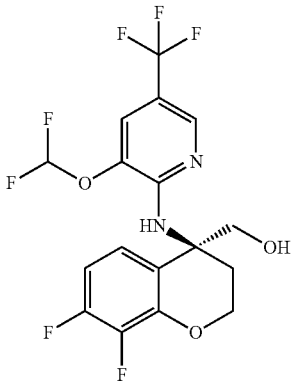 [SMILES: OC[C@]1(Nc2ncc(C(F)(F)F)cc2OC(F)F)CCOc2c1ccc(F)c2F]

The title compound was prepared by a method similar to that of Intermediates AR by replacing (5)-7-bromo-8-fluorospiro[chroman-4,4'-oxazolidin]-2'-one (Intermediate AS) with (S)-7,8-difluorospiro[chromane-4,4'-oxazolidin]-2'-one (Step 1). The crude product was used without purification in the next step.

LC-MS: Rt=1.19 min; MS m/z [M+H]$^+$ 427.2; UPLC-MS 1.

Intermediate BC, Step 1 (S)-7,8-difluorospiro[chromane-4,4'-oxazolidin]-2'-one can also be synthesized via the following alternative route:

Step 1: 1,2-difluoro-3-(prop-2-yn-1-yloxy)benzene

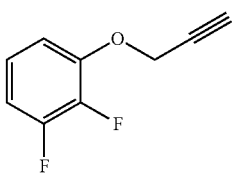

A mixture of 2,3-difluorophenol (20 g, 151 mmol), 3-bromoprop-1-yne 80% in toluene (21.1 mL, 196 mmol) and K$_2$CO$_3$ (41.6 g, 301 mmol) in DMF (350 mL) was heated at 50° C. for 2.5 hr. The cooled RM was diluted with EtOAc, and the organic phase was washed with water and brine. The combined aq layers were extracted again with EtOAc, the combined organic phases dried over Na$_2$SO$_4$, filtered and concentrated. The residue was absorbed onto silica gel from DCM and purified by normal phase chromatography (silica, eluent heptane:EtOAc 100:0 to 60:40) to give the title compound as a yellow oil.

$^1$H NMR (400 MHz, DMSO-d$_6$) δ 7.24-7.00 (m, 3H), 4.94 (s, 2H), 3.65 (s, 1H).

Step 2: 4-(2,3-difluorophenoxy)but-2-yn-1-ol

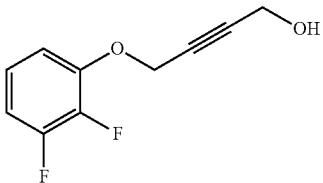

A solution of n-BuLi in hexane (1.6M, 52.5 mL, 84 mmol) was added dropwise to a solution of 1,2-difluoro-3-(prop-2-yn-1-yloxy)benzene (Step 1, 11.88 g, 69.9 mmol) in THF (253 mL), cooled with a dry-ice ethanol bath, at such a rate so as to maintain the internal temperature below −60° C. The RM was stirred for 45 min at −70° C. before paraformaldehyde (3.15 g, 105 mmol) was added. The RM was then warmed to RT and stirred at RT for 18 hr. The RM was partitioned between saturated aq NaHCO$_3$ solution and EtOAc, the organic phase washed with water and brine, the combined aq layers extracted with EtOAc, the combined organic phases dried over Na$_2$SO$_4$, filtered and concentrated. The residue was purified by normal phase chromatography (silica gel, heptane:EtOAc 100:0 to 20:80) to give the title compound as a yellow oil which solidified on standing at 4° C.

$^1$H NMR (400 MHz, DMSO-d$_6$) δ 7.23-6.98 (m, 3H), 5.24 (t, 1H), 4.97 (s, 2H), 4.12 (d, 2H).

Step 3: (7,8-difluoro-2H-chromen-4-yl)methanol

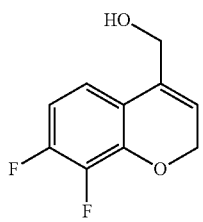 [SMILES: OCC1=CCOc2c1ccc(F)c2F]

A mixture of 4-(2,3-difluorophenoxy)but-2-yn-1-ol (Step 2, 22.2 g, 104 mmol) and indium(III) iodide (6.09 g, 31.3 mmol) in 1,2-DCE (651 mL) was heated at 60° C. for 2 days. Silica gel was added directly to the cooled RM which was then evaporated. The residue was purified by normal phase chromatography (silica gel, eluent heptane:EtOAc 100:0 to 10:90) to give the title compound as a beige solid.

$^1$H NMR (400 MHz, DMSO-d$_6$) δ 7.06-7.00 (m, 1H), 6.95-6.86 (m, 1H), 5.91-5.87 (m, 1H), 5.27 (t, 1H), 4.89 (dt, 2H), 4.26 (d, 2H).

Step 4: (R)-(7,8-difluorochroman-4-yl)methanol

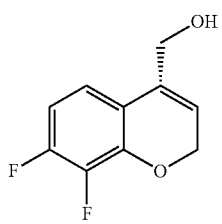

A mixture of Rh(NBD)$_2$BF$_4$ (215 mg, 575 μmol) and (S,R,R)-Chenphos (429 mg, 575 μmol) in DCM (150 mL) was stirred under a N2 atmosphere at RT for 30 min in a Hastelloy autoclave. A solution of (7,8-difluoro-2H-chromen-4-yl)methanol (Step 3, 6.0 g, 28.8 mmol) in DCM (25 mL) was added and a H$_2$ atmosphere introduced up to a pressure of 25 bar. The RM was stirred under a H2 pressure of 25 bar at RT for 16 hr. The reaction vessel was flushed with N2 and the RM was partitioned between saturated aq NaHCO$_3$ and DCM, the aq layer extracted with DCM, the combined organic layers were dried by passing through a phase separator and evaporated. The residue was purified by normal phase chromatography (silica gel, eluent heptane:EtOAc 100:0 to 0:100) to give the title compound as a yellow oil.

$^1$H NMR (400 MHz, DMSO-d$_6$) δ 7.10-7.03 (m, 1H), 6.89-6.80 (m, 1H), 4.87 (t, 1H), 4.31-4.14 (m, 2H), 3.68-3.61 (m, 1H), 3.56-3.38 (m, 1H), 2.90-2.82 (m, 1H), 2.04-1.90 (m, 2H).

Step 5: (R)-(7,8-difluorochroman-4-yl)methyl Carbamate

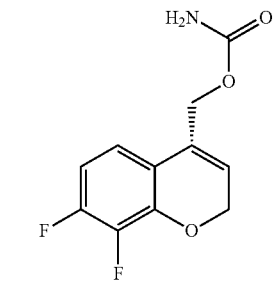

Trichloroacetyl isocyanate (8.49 ml, 71.2 mmol) was added dropwise to a solution of (R)-(7,8-difluorochroman-4-yl)methanol (Step 4, 12.51 g, 59.5 mmol) in 1,2-DCE (171 mL) cooled with an ice bath and the RM stirred for 1 hr at 0° C. K$_2$CO$_3$ (2.46 g, 17.81 mmol) was then added and the RM stirred for 10 min at 0° C., before MeOH (171 mL) and water (49 mL) were added slowly and the RM then stirred at RT for 18 hr. The RM was partitioned between saturated aq NaHCO$_3$ and DCM, the aq layer extracted with DCM, the combined organic layers dried by passing through a phase separator cartridge and evaporated. The residue was purified by normal phase chromatography (silica gel, heptane:EtOAc 100:0 to 0:100) to give the title compound as a white powder of 89% ee.

$^1$H NMR (400 MHz, DMSO-d$_6$) δ 7.13-7.08 (m, 1H), 6.95-6.85 (m, 1H), 6.54 (s, br, 2H), 4.34-4.03 (m, 4H), 3.13-3.04 (m, 1H), 2.08-1.83 (m, 2H).

The optical purity was determined by chiral HPLC (C-HPLC 21) with the title compound as the second-eluting enantiomer, Rt=1.98 min, and (S)-(7,8-difluorochroman-4-yl)methyl carbamate as the first-eluting enantiomer, Rt=1.80 min.

Step 6: (S)-7,8-difluorospiro[chromane-4,4'-oxazolidin]-2'-one

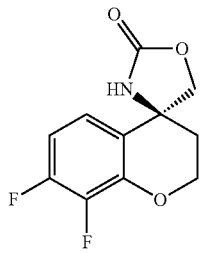 [SMILES: O=C1N[C@]2(CCOc3c2ccc(F)c3F)CO1]

A mixture of (R)-(7,8-difluorochroman-4-yl)methyl carbamate (Step 5, 4.3 g, 17.15 mmol), diacetoxyiodobenzene (7.73 g, 24.0 mmol), MgO (1.59 g, 39.4 mmol) and rhodium (II)triphenylacetate dimer DCM adduct (617 mg, 429 μmol) in DCM (90 mL) was heated with stirring at 45° C. under an argon atmosphere for 18 hr. Additional diacetoxyiodobenzene (2.32 g, 7.2 mmol), MgO (0.80 g, 19.7 mmol) and rhodium(II)triphenylacetate dimer DCM adduct (123 mg, 86 μmol) was added and heating continued at 45° C. for a further 24 hr. The cooled RM was filtered through Hyflo, and the filtrate partitioned between saturated aq NaHCO$_3$ and DCM. The aq layer was further extracted with DCM, the combined organic layers dried by passing through a phase separator cartridge and evaporated. The residue was purified by normal phase chromatography (silica gel, eluent DCM: MeOH 100:0 to 85:15 followed by a second column eluting with DCM:EtOAc 100:0 to 50:50) to give the tile compound as a beige powder.

LC-MS: Rt=0.72 min; MS m/z [M−H]⁻ 240.1; UPLC-MS 1.

Intermediate BD: (S)-(4-amino-7,8-difluorochroman-4-yl)methanol

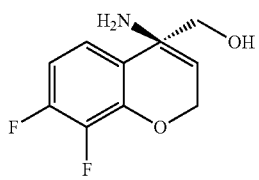

4-Amino-7,8-difluorochromane-4-carboxylic acid (Intermediate AU3, 24.6 mmol) was suspended in THF (123 mL) and cooled to 0-5° C. (ice bath), BH$_3$.THF (1M in THF, 61.6 ml, 61.6 mmol) was added slowly via a dropping funnel under a nitrogen atmosphere and the yellow suspension was allowed to warm to RT and stirred for 16 hr. MeOH (220 mL) was slowly added, the mixture was stirred at RT for 2 hr and was evaporated. The residue was dissolved in MeOH (220 mL) and Biotage MP-503H resin (loading 4.56 mmol/g, 28.6 g) was added. The mixture was shaken at RT for 3 hr, filtered and washed with MeOH. The resin (batch-1) was kept aside. The filtrate was evaporated, dissolved in MeOH (220 mL) and treated again with Biotage MP-503H resin (loading 4.56 mmol/g, 28.6 g), shaken for 2 days and filtered to give the resin batch-2. Resin batch 1 and 2 were combined and a solution of NH$_3$ (2N in MeOH, 100 mL) was added, the mixture was shaken for 15 min at RT and filtered. The filtrate was evaporated to give (rac)-(4-amino-7,8-difluorochroman-4-yl)methanol as a beige solid. The enantiomers were separated by chiral HPLC: (instrument: VWR LaPrep HPLC prep; column: Chiralpak AD 20 μm, 7.65×39.3 cm; eluent: heptane:EtOH:MeOH 85:7.5:7.5+0.05% Et$_2$NH; flow rate: 120 mL/min; detection: 220 nm) to give the title compound as the second eluting peak, as a yellow solid.

LC-MS: Rt=0.42 min; MS m/z [M+H]⁺ 216.1; UPLC-MS 1.

Chiral-HPLC: Rt=13.8 min; with (R)-(4-amino-7,8-difluorochroman-4-yl)methanol as the first eluting peak, Rt=7.8 min; C-HPLC 44.

Intermediate BE: (S)-(4-amino-8-chlorochroman-4-yl)methanol

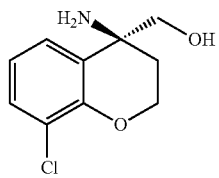 [SMILES: N[C@@]1(CO)CCOc2c(Cl)cccc21]

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with 4-amino-8-chlorochromane-4-carboxylic acid (Intermediate AU4). The enantiomers were separated by chiral HPLC: (instrument: Gilson Trilution; column: Chiralpak AD-H 5 μm, 30×250 mm; eluent: Heptane:EtOH: MeOH 80:10:10+0.1% Et$_2$NH; flow rate: 20 mL/min; detection: 220 nm) to give the title compound as the second eluting peak.

LC-MS: Rt=0.40 min; MS m/z [M−NH$_2$]⁺ 197.1/199.2; UPLC-MS 1.

Preparative chiral HPLC: Rt=12.2 min; with (R)-(4-amino-8-chlorochroman-4-yl)methanol as the first eluting peak, Rt=8.27 min.

Intermediate BF: (S)-(7-bromo-4-((3-(difluoromethoxy)-5-(trifluoromethyl)pyridin-2-yl)amino)chroman-4-yl) methanol

Step 1: (S)-7-bromospiro[chroman-4,4'-oxazolidin]-2'-one

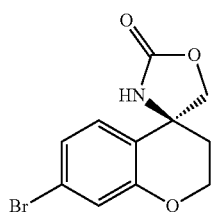 [SMILES: O=C1N[C@]2(CCOc3cc(Br)ccc32)CO1]

(S)-7-bromospiro[chroman-4,4'-oxazolidin]-2'-one was prepared in analogy to the method described for Intermediate I by replacing (S)-(1-amino-5-bromo-4-fluoro-2,3-dihydro-1H-inden-1-yl)methanol (Intermediate J) with (S)-(4-amino-7-bromochroman-4-yl)methanol (Intermediate BG). The crude product was used without purification in the next step.

$^1$H NMR (400 MHz, Chloroform-d$_6$) δ 7.33 (d, 1H), 7.12 (dd, 1H), 7.01 (d, 1H), 5.49 (s, 1H), 4.35-4.26 (m, 1H), 4.21-4.07 (m, 1H), 3.09 (dq, 2H), 2.22 (dd, 2H).

Step 2: (S)-(7-bromo-4-((3-(difluoromethoxy)-5-(trifluoromethyl)pyridin-2-yl)amino)chroman-4-yl)methanol

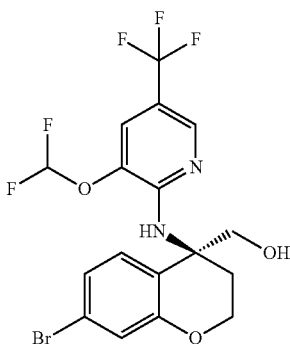 [SMILES: OC[C@]1(Nc2ncc(C(F)(F)F)cc2OC(F)F)CCOc2cc(Br)ccc21]

The title compound was prepared by a method similar to that of Intermediates AR and AS by replacing (S)-(4-amino-7-bromo-8-fluorochroman-4-yl)methanol (Intermediate AT) with (S)-(4-amino-7-bromochroman-4-yl)methanol (Step 1). The isolated material was used in the following reaction without further purification.

LC-MS: Rt=1.29 min; MS m/z [M+H]$^+$ 469.2/471.2; UPLC-MS 1.

Intermediate BG:
(S)-(4-amino-7-bromochroman-4-yl)methanol

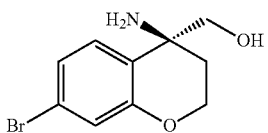 [SMILES: N[C@@]1(CO)CCOc2cc(Br)ccc21]

The title compound was prepared by analogy to the method described for Intermediate M, step 7 by replacing 7-amino-3-(trifluoromethyl)-6,7-dihydro-5H-cyclopenta[c]pyridine-7-carboxylic acid (Intermediate M, step 6) with 4-amino-7-bromochromane-4-carboxylic acid (Intermediate AU5). The enantiomers were separated by chiral HPLC: (instrument: Gilson Trilution HPLC system; column: Chiralpak ID, 5 250×20 mm 25° C.; eluent: heptane:EtOH 80:20+0.1% Et$_2$NH; flow rate: 10 mL/min; Detection: 220 nm) to give the title compound as the first eluting peak.

LC-MS: Rt=0.50 min; MS m/z [M+H]$^+$ 258.0/260.0; UPLC-MS 1.

Chiral-SFC: Rt=6.9 min; with (R)-(4-amino-7-bromochroman-4-yl)methanol eluting as the second peak, Rt=13.0 min; C-SFC 50.

Intermediate BH: (S)-8'-(difluoromethoxy)-8-fluoro-7-(methylthio)-6'-(trifluoromethyl)-3'H-spiro[chromane-4,2'-imidazo[1,2-a]pyridine]

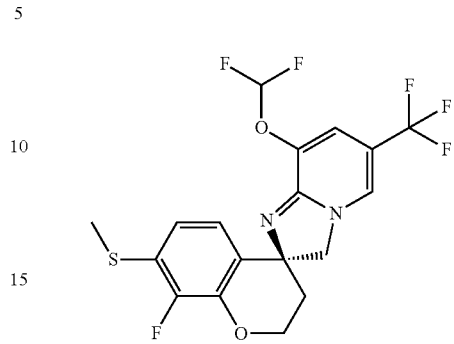

A mixture of (S)-8'-(difluoromethoxy)-8-fluoro-7-iodo-6'-(trifluoromethyl)-3'H-spiro[chroman-4,2'-imidazo[1,2-a]pyridine] (Intermediate AW, 134 mg, 259 μmol), CuI (53 mg, 272 μmol) and DABCO (58 mg, 517 μmol) in DMSO (2 mL) was heated at 140° C. for 24 hr in a sealed vessel under a N2 atmosphere. The cooled RM was diluted with DCM, the organic phase washed with H$_2$O then brine, dried by passing through a phase separator cartridge, and concentrated to give the title compound which was used directly without further purification.

LC-MS: Rt=0.80 min; MS m/z [M+H]$^+$ 436.9; UPLC-MS 1.

Intermediate BI: (S)-8'-(difluoromethoxy)-8-fluoro-6'-(trifluoromethyl)-3'H-spiro[chroman-4,2'-imidazo[1,2-a]pyridin]-7-ol

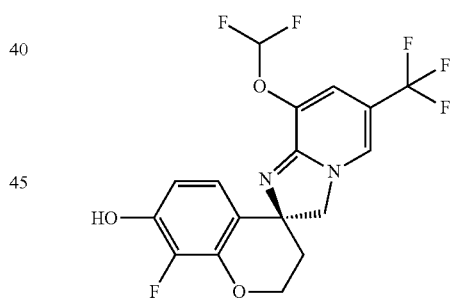

A microwave vial was charged with (S)-7-bromo-8'-(difluoromethoxy)-8-fluoro-6'-(trifluoromethyl)-3'H-spiro[chroman-4,2'-imidazo[1,2-a]pyridine] (Example 39, 50 mg, 0.11 mmol), morpholine (11 μL, 0.13 mmol), RuPhos-Pd-G3 (8.9 mg, 10.7 μmol), RuPhos (5 mg, 10.7 μmol) and sodium tert-butoxide (15.4 mg, 0.16 mmol) in THF (1 mL). The vial was flushed with nitrogen, sealed and the RM was stirred at 100° C. under microwave irradiation for 1.5 hr. Morpholine (11 μL, 0.13 mmol), RuPhos-Pd-G3 (8.9 mg, 10.7 μmol), RuPhos (5 mg, 10.7 μmol) and sodium tert-butoxide (60 mg, 0.63 mmol) were again added and the RM was further stirred at 100° C. under microwave heating for 2 hr. The RM was poured into water and extracted 2× with CH$_2$Cl$_2$. The combined organic extracts were dried (phase separator) and concentrated in vacuo and the crude residue purified by normal phase flash chromatography (12 g SiO$_2$ column, eluent c-hexane:EtOAc 100:0 to 0:100 then DCM:MeOH 100:0 to 90:10) to give the title compound as a yellow foam.

$^1$H NMR (400 MHz, DMSO-$d_6$) δ 7.23 (s, 1H), 7.06 (d, 1H), 6.65 (t, 1H), 6.20 (s, 1H), 4.76 (d, 1H), 4.68 (d, 1H), 4.50 (m, 1H), 4.27 (m, 1H), 3.74 (m, 4H), 3.20 (m, 4H), 2.30 (m, 2H).

LC-MS: Rt=0.70 min; MS m/z [M+H]$^+$ 426.2; UPLC-MS 1.

Intermediate BJ: (S)-8'-(difluoromethoxy)-6'-(trifluoromethyl)-3'H-spiro[chromane-4,2'-imidazo[1,2-a]pyridine]-8-carbaldehyde Step 1: (S)-(4-amino-8-bromochroman-4-yl)methanol

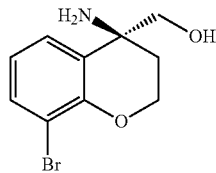 [SMILES: N[C@@]1(CO)CCOc2c(Br)cccc21]

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with rac-4-amino-8-bromochromane-4-carboxylic acid (Intermediate AU6). The enantiomers were separated by chiral HPLC: (instrument: Gilson Trilution; column: Chiralpak AD-H 5 μm, 25×250 mm; eluent: heptane:EtOH:MeOH 80:10:10+0.1% Et$_2$NH; flow rate: 15 mL/min; detection: 220 nm) to give the title compound as the second eluting peak.

LC-MS: Rt=1.32 min; MS m/z [M+H]$^+$ 241.0/242.9; UPLC-MS 4.

Chiral-HPLC: Rt=11.40 min; with (R)-(4-amino-8-bromochroman-4-yl)methanol as the second eluting peak, Rt=7.92 min; C-HPLC 12.

Step 2: (S)-8'-(difluoromethoxy)-8-iodo-6'-(trifluoromethyl)-3'H-spiro[chromane-4,2'-imidazo[1,2-a]pyridine]

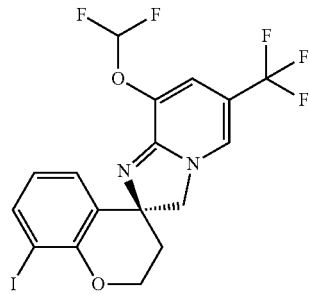 [SMILES: FC(F)OC1=CC(C(F)(F)F)=CN2C[C@@]3(CCOc4c(I)cccc43)N=C12]

The title compound was prepared by a methods similar to that of Intermediates AS, AR, Y and AW by replacing (S)-(4-amino-7-bromo-8-fluorochroman-4-yl)methanol (Intermediate AT) with (S)-(4-amino-8-bromochroman-4-yl)methanol (Step 1). The title compound was obtained as a beige foam after normal phase chromatography (silica column, eluent hexane:TBME 90:10 to 30:70).

LC-MS: Rt=0.83 min; MS m/z [M+H]$^+$ 499.0; UPLC-MS 1.

Step 3: (S)-8'-(difluoromethoxy)-6'-(trifluoromethyl)-3'H-spiro[chromane-4,2'-imidazo[1,2-a]pyridine]-8-carbaldehyde

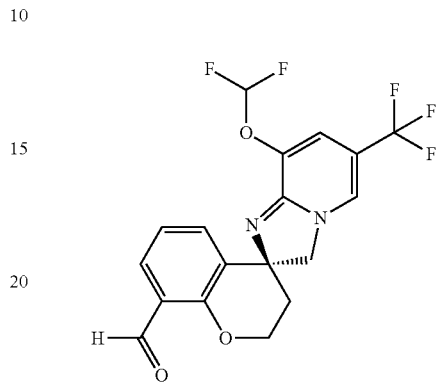

A solution n-BuLi in hexanes (1M, 298 μL, 298 μmol) was added dropwise to a solution of (S)-8'-(difluoromethoxy)-8-iodo-6'-(trifluoromethyl)-3'H-spiro[chromane-4,2'-imidazo[1,2-a]pyridine] (Step 1, 150 mg, 271 μmol) in THF (2.5 mL) cooled with a dry ice acetone bath, under a positive pressure of argon. The RM was stirred at −75° C. for 10 min and DMF (210 μL, 2.71 mmol) was added. After stirring for 1 hr at −75° C. saturated aq NaHCO$_3$ was added and the mixture extracted 3× with DCM, the combined organic layers dried by passing through a phase separator cartridge and evaporated. The residue was purified by normal phase chromatography (4 g SiO$_2$ column, eluent hexane:TBME 90:10 to 10:90) to give the title compound as a beige foam.

LC-MS: Rt=0.64 min; MS m/z [M+H]$^+$ 401.2; UPLC-MS 1.

Intermediate BK: (S)-8'-chloro-3-(3-(difluoromethoxy)-5-(trifluoromethyl)pyridin-2-yl)-2',3'-dihydrospiro[oxazolidine-4,4'-pyrano[2,3-c]pyridin]-2-one

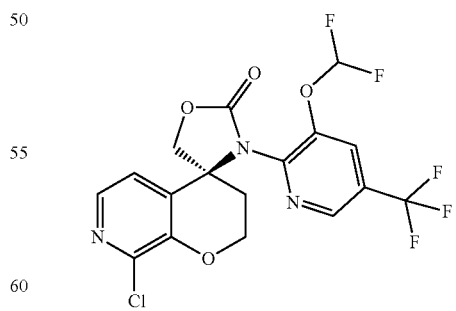

The title compound was prepared by methods similar to that of Intermediates AS and AR by replacing (S)-(4-amino-7-bromo-8-fluorochroman-4-yl)methanol (Intermediate AT) with (S)-(4-amino-8-chloro-3,4-dihydro-2H-pyrano[2,3-c]pyridin-4-yl)methanol (Intermediate BL). The title compound was obtained after normal phase chromatography (silica column, eluent c-hexane:EtOAc 100:0 to 50:50).

LC-MS: Rt=1.07 min; MS m/z [M+H]⁺ 452.1/454.0; UPLC-MS 1.

Intermediate BL: (S)-(4-amino-8-chloro-3,4-dihydro-2H-pyrano[2,3-c]pyridin-4-yl)methanol

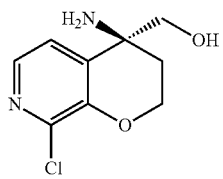 [SMILES: N[C@@]1(CO)CCOc2c1ccnc2Cl]

The title compound was prepared by methods similar to that of Intermediates AU and M, step 7 by replacing 7-bromo-8-fluorochroman-4-one with 8-chloro-2,3-dihydro-4H-pyrano[2,3-c]pyridin-4-one (Intermediate BM). Using the route with Ellman's (S)-sulfinamide auxiliary the enantiomeric ratio was 3:2 S:R. The enantiomers were separated by chiral HPLC: (instrument: Knauer HPLC System; column: Chiralpak IC 20 μm, 375×76.5 mm; eluent: heptane:iPrOH 70:30+0.1% Et₂NH for 120 min then 50:50 for 50 min; flow rate: 120 mL/min; detection: 280 nm) to give the title compound as the first eluting peak.

LC-MS: Rt=0.32 min; MS m/z [M+H]⁺ 215.1/217.1; UPLC-MS 2.

Chiral-HPLC: Rt=6.70 min; with (R)-(4-amino-8-chloro-3,4-dihydro-2H-pyrano[2,3-c]pyridin-4-yl)methanol as the second eluting peak, Rt=17.2 min; C-HPLC 15.

Intermediate BM: 8-chloro-2,3-dihydro-4H-pyrano[2,3-c]pyridin-4-one

Step 1: tert-butyl 3-((2-chloro-4-iodopyridin-3-yl)oxy)propanoate

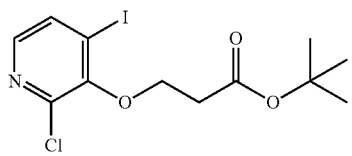 [SMILES: CC(C)(C)OC(=O)CCOc1c(I)ccnc1Cl]

To a solution of 2-chloro-4-iodopyridin-3-ol (Intermediate BN, 7.3 g, 28.6 mmol), DIAD (6.67 mL, 34.3 mmol) and PPh₃ (8.99 g, 34.3 mmol) in THF (120 mL) at 20° C. was added tert-butyl 3-hydroxypropanoate (5.06 mL, 34.3 mmol). The RM was stirred for 2 hr, then tert-butyl 3-hydroxypropanoate (0.42 mL, 2.86 mmol), PPh3 (749 mg, 2.86 mmol) and DIAD (0.56 mL, 2.86 mmol) were added additionally. The RM was stirred for additional 0.5 hr, concentrated and the residue purified by normal phase chromatography (silica gel, eluent c-hexane:EtOAc 100:0 to 80:20) to give the title compound.

LC-MS: Rt=1.24 min; MS m/z [M+H]⁺ 384.1/386.1; UPLC-MS 1.

Step 2: 3-((2-chloro-4-iodopyridin-3-yl)oxy)propanoic acid

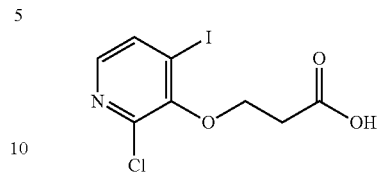

To a solution of tert-butyl 3-((2-chloro-4-iodopyridin-3-yl)oxy)propanoate (Step 1, 10.58 g, 27.3 mmol) in DCM (120 mL) at 20° C. was added CF₃CO₂H (42.1 mL, 546 mmol). The RM was stirred for 1.5 hr at 20° C. and concentrated to give the title compound which was used directly without further purification.

LC-MS: Rt=0.74 min; MS m/z [M+H]⁺ 328.0/330.0; UPLC-MS 1.

Step 3: 3-((2-chloro-4-iodopyridin-3-yl)oxy)-N-methoxy-N-methylpropanamide

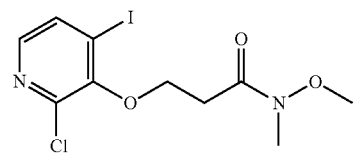 [SMILES: CON(C)C(=O)CCOc1c(I)ccnc1Cl]

To a solution of 3-((2-chloro-4-iodopyridin-3-yl)oxy)propanoic acid (Step 2, 13.67 g, 27.2 mmol) in DCM (90 mL) was added oxalyl chloride (4.77 mL, 54.5 mmol) and DMF (105 μL, 1.36 mmol). The RM was stirred for 1 hr at 20° C. and concentrated. The residue was redissolved in DCM (90 mL) and the resulting solution added to a stirred solution of NaHCO₃ (4.81 g, 57.2 mmol) and N,O-dimethylhydroxylamine hydrochloride (2.92 g, 30.0 mmol) in water (90 mL). The RM was stirred for 1 hr at 20° C., the phases separated and the aq layer extracted with DCM, the combined organic layers washed with saturated aq NaHCO₃, dried by passing through a phase separator cartridge and concentrated. The residue was purified by normal phase chromatography (silica gel, eluent c-hexane:EtOAc 100; 0 to 70:30) to give the title compound.

LC-MS: Rt=0.88 min; MS m/z [M+H]⁺ 371.1/373.1; UPLC-MS 1.

Step 4: 8-chloro-2H-pyrano[2,3-c]pyridin-4(3H)-one

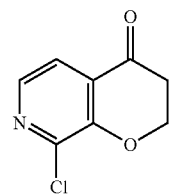 [SMILES: O=C1CCOc2c1ccnc2Cl]

To a solution of 3-((2-chloro-4-iodopyridin-3-yl)oxy)-N-methoxy-N-methylpropanamide (Step 3, 9.38 g, 24.55 mmol) in THF (120 mL) cooled with a dry ice/acetone batch was added dropwise a solution of nBuLi in hexane (1.6M, 30.7 mL, 49.1 mmol) at a rate that maintained the internal temperature below −70° C. The RM was stirred for 1 hr at −75° C., quenched by the addition of saturated aq. NH₄Cl, warmed to rt, extracted with EtOAc, the organic layer washed with brine, dried and concentrated. The title compound was obtained after normal phase chromatography (silica column, eluent c-hexane:EtOAc 100:0 to 0:100).

¹H NMR (400 MHz, DMSO-d₆) δ 8.12 (t, 1H), 7.63 (d, 1H), 4.80-4.74 (m, 2H), 3.01-2.92 (m, 2H).

Intermediate BN: 2-chloro-4-iodopyridin-3-ol

Step 1:
2-chloro-4-iodo-3-(methoxymethoxy)pyridine

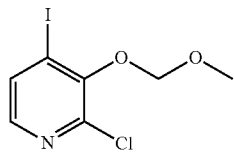

A solution of n-BuLi in hexanes (1.6M, 23.5 mL, 37.6 mmol) was added dropwise to a solution of 2-chloro-3-(methoxymethoxy)pyridine (5.93 g, 34.2 mmol) in THF (100 mL) cooled with a dry ice/acetone bath. The RM was stirred for 1 hr at −78° C. then a solution of I₂ (13.0 g, 51.2 mmol) in THF (50 mL) was added dropwise and the RM stirred at −78° C. for a further 2 hr. The RM was quenched with saturated aq NH₄Cl, warmed to RT, extracted with EtOAc, the combined organic layers washed with 10% aq Na₂S₂O₃ then brine, dried and concentrated. The residue was purified by normal phase chromatography (silica gel, eluent c-hexane/EtOAc 100/0 to 70/30) to give the title compound.

LC-MS: Rt=0.96 min; MS m/z [M+H]⁺ 300.0/302.0; UPLC-MS 1.

Step 2: 2-chloro-4-iodopyridin-3-ol

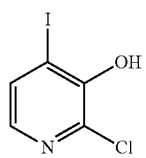

To a solution of 2-chloro-4-iodo-3-(methoxymethoxy) pyridine (Step 1, 8.6 g, 28.5 mmol) in MeOH (50 mL) was added HCl in 1,4-dioxane (4M, 71 mL, 285 mmol) at RT. The RM was stirred for 0.5 hr at RT then concentrated. The residue was taken up into saturated aq NaHCO₃ and washed with EtOAc, the aq layer was acidified with 1N HCl (pH 2-3), extracted with EtOAc, the combined organic layers dried and concentrated to give the title compound which was used directly without further purification.

LC-MS: Rt=0.69 min; MS m/z [M+H]⁺ 255.9/258.0; UPLC-MS 1.

Intermediate BO: ((3R,4S)-4-amino-7-bromo-3,8-difluorochroman-4-yl)methanol

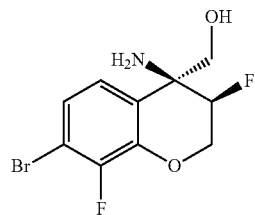 [SMILES: N[C@]1(CO)c2ccc(Br)c(F)c2OC[C@@H]1F]

The title compound was prepared by a method similar to that of Intermediate M, step 7 by replacing 7-amino-3-(trifluoromethyl)-6,7-dihydro-5H-cyclopenta[c]pyridine-7-carboxylic acid (Intermediate M, step 6) with (3R,4S)-4-amino-7-bromo-3,8-difluorochromane-4-carboxylic acid (Intermediate BP). The title compound which was used directly without further purification.

LC-MS: Rt=0.51 min; MS m/z [M+H]⁺ 338.1/340.1; UPLC-MS 1.

Intermediate BP: (3R,4S)-4-amino-7-bromo-3,8-difluorochromane-4-carboxylic Acid

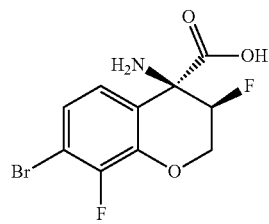 [SMILES: N[C@]1(C(=O)O)c2ccc(Br)c(F)c2OC[C@@H]1F]

The title compound was prepared by a method similar to that of Intermediate AU, Step 4 by replacing 7-bromo-4-((S)-1,1-dimethylethylsulfinamido)-8-fluorochroman-4-carboxamide (Intermediate AU, step 3) with (3R,4S)-7-bromo-4-(((S)-tert-butylsulfinyl)amino)-3,8-difluorochromane-4-carboxamide (Intermediate BQ). The hydrochloride salt of the title compound was obtained as a pale-beige solid which was used directly without further purification.

LC-MS: Rt=0.47 min; MS m/z [M+H]⁺ 308.0/310.0; UPLC-MS 1.

Intermediate BQ: (3R,4S)-7-bromo-4-(((S)-tert-butylsulfinyl)amino)-3,8-difluorochromane-4-carboxamide

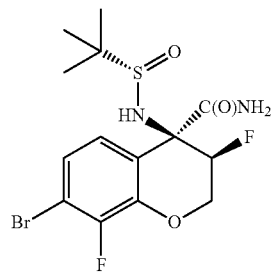

A mixture of (S)—N-((3S,4R)-7-bromo-4-cyano-3,8-difluorochroman-4-yl)-2-methylpropane-2-sulfinamide and (S)—N-((3R,4S)-7-bromo-4-cyano-3,8-difluorochroman-4-yl)-2-methylpropane-2-sulfinamide (Intermediate BR, 1.45 g, 3.17 mmol), acetamide (1.22 g, 19.0 mmol) and PdCl$_2$ (140 mg, 475 μmol) in THF (40 mL) and water (13 mL) were heated at 50° C. for 140 min under an atmosphere of N2 in a sealed vial. The cooled RM was diluted with brine, extracted with DCM, the combined organic layers dried and concentrated. The residue was purified by normal phase chromatography (silica gel, eluent DCM:(TBME:EtOH 2:1) 100:0 to 50:50) to give the title compound as the second eluting peak, as a beige foam.

LC-MS: Rt=0.85 min; MS m/z [M+H]$^+$ 411.1/413.1; UPLC-MS 1.

(3S,4R)-7-bromo-4-(((S)-tert-butylsulfinyl)amino)-3,8-difluorochromane-4-carboxamide is obtained as the first eluting peak, as a beige foam.

LC-MS: Rt=0.88 min; MS m/z [M+H]$^+$ 411.1/413.1; UPLC-MS 1.

Intermediates BR and BS: (S)—N-((3S,4R)-7-bromo-4-cyano-3,8-difluorochroman-4-yl)-2-methylpropane-2-sulfinamide and (S)—N-((3R,4S)-7-bromo-4-cyano-3,8-difluorochroman-4-yl)-2-methylpropane-2-sulfinamide and (S)—N-((3S,4S)-7-bromo-4-cyano-3,8-difluorochroman-4-yl)-2-methylpropane-2-sulfinamide and (S)—N-((3R,4R)-7-bromo-4-cyano-3,8-difluorochroman-4-yl)-2-methylpropane-2-sulfinamide

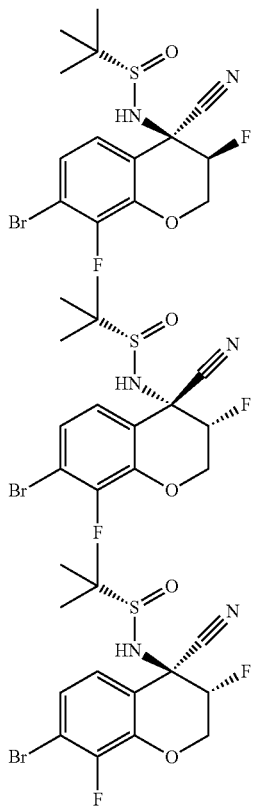

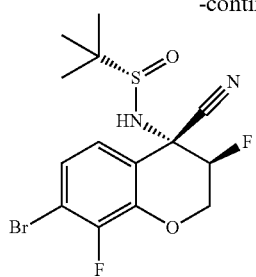

To a solution of (S)—N—((R)-7-bromo-3,8-difluorochroman-4-ylidene)-2-methylpropane-2-sulfinamide and (S)—N—((S)-7-bromo-3,8-difluorochroman-4-ylidene)-2-methylpropane-2-sulfinamide (Intermediate BT, 3.64 g, 8.24 mmol) in DCM (40 mL) were added CsF (2.5 g, 16.5 mmol), trimethylsilycyanide (5.52 mL, 41.2 mmol) and tert-BuOH (1.58 mL, 16.5 mmol) at RT under a positive pressure of N2: CAUTION POTENTIAL FOR HCN RELEASE! The RM was stirred for 4.5 hr at RT, diluted with saturated aq NaHCO$_3$ (150 mL), extracted with DCM, the combined organic layers dried over Na$_2$SO$_4$ and concentrated. The residue was purified by normal phase chromatography (50 g SiO$_2$ SNAP column, eluent hexane:TBME 100:0 to 0:100) to give recovered Intermediate BT as the first eluting peak. Intermediate BR ((S)—N-((3S,4R)-7-bromo-4-cyano-3,8-difluorochroman-4-yl)-2-methylpropane-2-sulfinamide and (S)—N-((3R,4S)-7-bromo-4-cyano-3,8-difluorochroman-4-yl)-2-methylpropane-2-sulfinamide, ratio 6:4) was obtained as the second eluting peak, as a white foam.

LC-MS: Rt=1.01 and 1.02 min; MS m/z [M+H]$^+$ 393.1/395.1; UPLC-MS 1.

Intermediate BS ((S)—N-((3S,4S)-7-bromo-4-cyano-3,8-difluorochroman-4-yl)-2-methylpropane-2-sulfinamide and (S)—N-((3R,4R)-7-bromo-4-cyano-3,8-difluorochroman-4-yl)-2-methylpropane-2-sulfinamide, ratio 6:4) was obtained as the third eluting peak, as a pink solid.

LC-MS: Rt=1.01 and 1.02 min; MS m/z [M+H]$^+$ 393.1/395.1; UPLC-MS 1.

Intermediate BT: (S)—N—((R)-7-bromo-3,8-difluorochroman-4-ylidene)-2-methylpropane-2-sulfinamide and (S)—N—((S)-7-bromo-3,8-difluorochroman-4-ylidene)-2-methylpropane-2-sulfinamide Step 1: ((7-bromo-8-fluoro-2H-chromen-4-yl)oxy)(tert-butyl)dimethylsilane

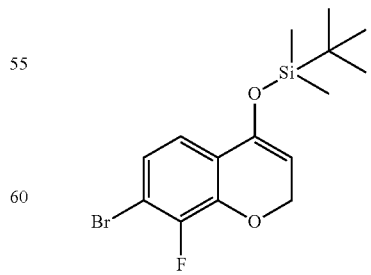

Tert-butyldimethylsilyl trifluoromethanesulfonate (7.1 mL, 30.6 mmol) was added dropwise to a solution of 7-bromo-8-fluorochroman-4-one (Intermediate AU step 2, 5.0 g, 20.40 mmol) and Et$_3$N (14.1 mL, 102 mmol) in DCM (50 mL) cooled with an ice bath. The RM was stirred for 10 min at 0° C. the cooling bath removed and stirring continued for an additional 20 min. The RM was diluted with H$_2$O, the organic phase washed with H$_2$O then brine, dried by passing through a phase separator cartridge and concentrated. The residue was purified by normal phase chromatography (50 g SiO$_2$ SNAP cartridge, eluent hexane: EtOAc 100:0 to 90:10) to give the title compound as a colorless oil.

$^1$H NMR (400 MHz, DMSO-d$_6$) δ 7.23 (dd, 1H), 7.01 (dd, 1H), 5.14 (t, 1H), 4.92 (d, 2H), 0.96 (s, 9H), 0.22 (s, 6H).

Step 2: rac-7-bromo-3,8-difluorochroman-4-one

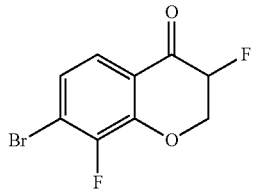 [SMILES: O=C1c2ccc(Br)c(F)c2OCC1F]

Selectfluor (7.25 g, 20.46 mmol) was added to a solution of ((7-bromo-8-fluoro-2H-chromen-4-yl)oxy)(tert-butyl)dimethylsilane (Step 1, 7.0 g, 19.48 mmol) in AcCN (50 mL) cooled with an ice bath and under a positive pressure of N2. The RM was stirred for 30 min at 0° C. and then evaporated. The residue was taken up into DCM, the organic layer washed with H$_2$O then 2× with saturated aq NaHCO$_3$ and brine. The organic phase was dried by passing through a phase separator cartridge and concentrated to give the title compound as a white solid which was used directly without further purification.

$^1$H NMR (400 MHz, DMSO-d$_6$) δ 7.56 (dd, 1H), 7.45 (dd, 1H), 5.57-5.35 (m, 1H), 5.02-4.77 (m, 2H).

Step 3: (S)—N—((R)-7-bromo-3,8-difluorochroman-4-ylidene)-2-methylpropane-2-sulfinamide and (S)—N—((S)-7-bromo-3,8-difluorochroman-4-ylidene)-2-methylpropane-2-sulfinamide

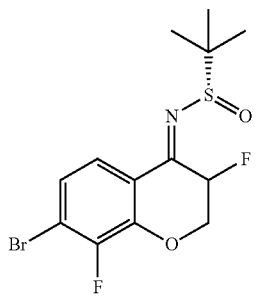

A mixture of rac-7-bromo-3,8-difluorochroman-4-one (Step 2, 4.98 g, 18.93 mmol), (S)-2-methylpropane-2-sulfinamide (2.81 g, 22.72 mmol) and tetraethoxytitanium (10.36 g, 45.4 mmol) in THF (10 mL) was heated at 72° C. (heating block temperature) for 4.5 hr with a continuous N2 flow across the top of the reaction vessel. The cooled RM was then diluted with EtOAc, poured into brine and the mixture stirred for 15 min at RT. The resulting suspension was then filtered through Hyflo, washing with EtOAc. The biphasic filtrate was separated and the organic layer washed with H$_2$O then brine, dried and concentrated. The residue was purified by normal phase chromatography (2×50 g SiO$_2$ SNAP cartridges, eluent hexane:EtOAc 100:0 to 70:30) to give the title compounds as a yellow foam in a 3:2 ratio.

LC-MS: Rt=1.18 and 1.20 min; MS m/z [M+H]$^+$ 366.0/368.0; UPLC-MS 1.

Intermediate BU: ((3S,4S)-4-amino-7-bromo-3,8-difluorochroman-4-yl)methanol

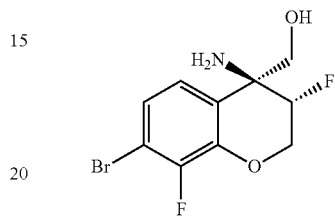

The title compound was prepared by methods similar to that of Intermediates BO, BP and BQ by replacing (S)—N-((3S,4R)-7-bromo-4-cyano-3,8-difluorochroman-4-yl)-2-methylpropane-2-sulfinamide and (S)—N-((3R,4S)-7-bromo-4-cyano-3,8-difluorochroman-4-yl)-2-methylpropane-2-sulfinamide (Intermediate BR) with (S)—N-((3S,4S)-7-bromo-4-cyano-3,8-difluorochroman-4-yl)-2-methylpropane-2-sulfinamide and (S)—N-((3R,4R)-7-bromo-4-cyano-3,8-difluorochroman-4-yl)-2-methylpropane-2-sulfinamide (Intermediate BS). The enantiomers were separated by chiral HPLC: (instrument: Gilson Trilution HPLC System; column: Chiralpak AD-H 5 µm, 250×25 mm; eluent: heptane:EtOH:MeOH 80:10:10+ 0.05% Et$_2$NH; flow rate: 15 mL/min; detection: 230 nm) to give the title compound as the second eluting peak.

LC-MS: Rt=2.25 min; MS m/z [M+H]$^+$ 294.1/296.1; UPLC-MS 4.

Chiral-HPLC: Rt=16.27 min; with ((3R,4R)-4-amino-7-bromo-3,8-difluorochroman-4-yl)methanol as the first eluting peak, Rt=9.62 min; C-HPLC 16.

LC-MS: Rt=2.25 min; MS m/z [M+H]$^+$ 294.0/296.0; UPLC-MS 4.

Intermediate BV: ((3R,4S)-4-amino-7-bromo-3-fluorochroman-4-yl)methanol

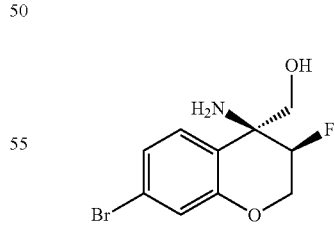

The title compound was prepared by methods similar to that of Intermediates BT, BR, BQ, BP and BO by replacing 7-bromo-8-fluorochroman-4-one (Intermediate AU step 2) with 7-bromochroman-4-one. The title compound was obtained as a white powder which was used directly without further purification.

LC-MS: Rt=0.51 min; MS m/z [M+H]$^+$ 276.1/278.1; UPLC-MS 1.

Intermediate BW: ((3R,4S)-4-amino-3,8-difluorochroman-4-yl)methanol

Step 1: (R)—N-((3R,4S)-3,8-difluoro-4-(hydroxymethyl)chroman-4-yl)-2-methylpropane-2-sulfinamide

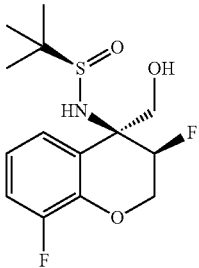 [SMILES: CC(C)(C)[S@@](=O)N[C@]1(CO)c2cccc(F)c2OC[C@@H]1F]

Oxygen was bubbled through a solution of (R)—N-((3R,4R)-3,8-difluoro-4-vinylchroman-4-yl)-2-methylpropane-2-sulfinamide (Intermediate BX, 17.64 g, 52.6 mmol) in DCM (180 mL) and MeOH (180 mL), cooled with a dry ice/acetone bath. After 5 min of bubbling $O_2$ through the solution a mixture of $O_3/O_2$ was then bubbled through at −78° C. until a grey/blue colour persisted in the solution (ca. 40 min). argon was then bubbled through the solution, to purge the $O_3/O_2$ from the system, and sodium borohydride (4.38 g, 116 mmol) added. After stirring for 40 min at −78° C. saturated aq $NH_4Cl$ was added, the mixture warmed to RT, extracted 3× with DCM, the combined organic layers washed with saturated aq $NaHCO_3$, dried and concentrated. The residue was purified by normal phase chromatography (silica gel, eluent DCM:(TBME:MeOH 2:1) 100:0 to 80:20) to give the title compound.

LC-MS: Rt=0.77 min; MS m/z [M+H]$^+$ 320.1; UPLC-MS 1.

Step 2: ((3R,4S)-4-amino-3,8-difluorochroman-4-yl)methanol

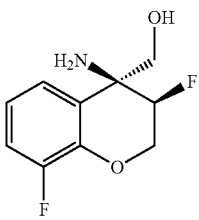 [SMILES: N[C@]1(CO)c2cccc(F)c2OC[C@@H]1F]

A mixture of (R)—N-((3R,4S)-3,8-difluoro-4-(hydroxymethyl)chroman-4-yl)-2-methylpropane-2-sulfinamide (Step 1, 27.1 g, 83 mmol) in MeOH (300 mL) and aq HCl (4N, 104 mL, 416 mmol) was stirred for 30 min at RT. The RM was concentrated, partitioned between saturated aq $NaHCO_3$ and EtOAc, extracted 2× with EtOAc, the combined organic layers dried and concentrated to give the title compound which was used directly without further purification.

LC-MS: Rt=0.32 min; MS m/z [M+H]$^+$ 216.1; UPLC-MS 2.

Intermediate BX: (R)—N-((3R,4R)-3,8-difluoro-4-vinylchroman-4-yl)-2-methylpropane-2-sulfinamide

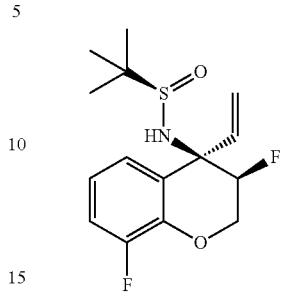

A solution dimethylzinc in toluene (2M, 126 mL, 252 mmol) was added dropwise to a solution of vinylmagnesium bromide in THF (1M, 126 mL, 126 mmol) at RT, the RM stirred for 30 min at RT, then cooled to −78° C. with a dry ice/acetone bath. A solution of (R)—N—((R)-3,8-difluorochroman-4-ylidene)-2-methylpropane-2-sulfinamide and (R)—N—((S)-3,8-difluorochroman-4-ylidene)-2-methylpropane-2-sulfinamide (Intermediate BY, 18.64 g, 62.9 mmol) in THF (200 mL) was added dropwise and the RM stirred for 0.5 hr at −78° C. and for 0.5 hr with an ice bath. The RM was then recooled to −70° C. and saturated aq $NH_4Cl$ added dropwise (200 mL): CAUTION! EXOTHERMIC REACTION. The mixture was warmed to RT, extracted 2× with $Et_2O$, the combined organic layers washed with brine, dried over $Na_2SO_4$, filtered and concentrated. The residue was purified by normal phase chromatography (silica gel, eluent DCM:(TBME/EtOH 2:1) 100:0 to 90:10) to give the title compound as the predominant component in a mixture of diastereomers and recovered (R)—N—((S)-3,8-difluorochroman-4-ylidene)-2-methylpropane-2-sulfinamide. The diastereomers were separated by chiral SFC: (instrument: Thar 350 preparative SFC (SFC-18); column: Chiralcel OJ 10 μm, 300×50 mm; temp: 38° C.; eluent: $CO_2$:MeOH+0.1% $NH_4OH$ 90:10; flow rate: 200 mL/min; detection: 220 nm) to give the title compound.

LC-MS: Rt=1.00 min; MS m/z [M+H]$^+$ 316.1; UPLC-MS 1.

Intermediate BY: (R)—N—((R)-3,8-difluorochroman-4-ylidene)-2-methylpropane-2-sulfinamide and (R)—N—((S)-3,8-difluorochroman-4-ylidene)-2-methylpropane-2-sulfinamide

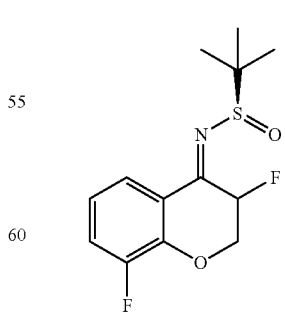

The title compound was prepared by a method similar to that of Intermediate BT by replacing 7-bromo-8-fluorochroman-4-one (Intermediate AU, step 2) with 8-fluorochroman- 4-one. The title compounds were obtained after normal phase chromatography purification (silica gel, eluent c-hexane:EtOAc 100:0 to 70:30) as a 1:1 mixture of diastereomers.

LC-MS: Rt=1.05 and 1.07 min; MS m/z [M+H]+ 288.1; UPLC-MS 1.

Intermediate BZ: rac-(4-((3-(difluoromethoxy)-5-(trifluoromethyl)pyridin-2-yl)amino)-8-fluoroisochroman-4-yl)methanol Step 1: (2-bromo-6-fluorophenyl)methanol

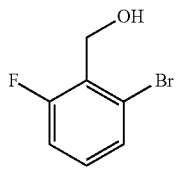

To a solution of 2-bromo-6-fluorobenzoic acid (6 g, 27.4 mmol) in THF (120 mL) under a nitrogen atmosphere was added at 0° C. BH$_3$.THF (1M in THF, 54.8 mL, 54.8 mmol) and the RM stirred at 50° C. for 16 hr. The RM was slowly poured into HCl (2N solution) and extracted 2× with EtOAc. The combined organic extracts were dried (phase separator) and concentrated to give the title compound as a yellow solid which was used without purification in the next step.

$^1$H NMR (400 MHz, DMSO-d$_6$) δ 7.45 (d, 1H), 7.31-7.20 (m, 2H), 5.20 (m, 1H), 4.57 (m, 2H).

Step 2: 2-((2-bromo-6-fluorobenzyl)oxy)-N-methoxy-N-methyl acetamide

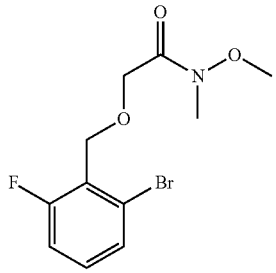 [SMILES: CON(C)C(=O)COCc1c(F)cccc1Br]

To a suspension of NaH (1.07 g, 26.8 mmol) in THF (150 mL) was slowly added (2-bromo-6-fluorophenyl)methanol (Step 1, 5.25 g, 24.33 mmol) at 0° C. under a nitrogen atmosphere. The mixture was stirred at 0° C. for 15 min, before addition of 2-bromo-N-methoxy-N-methylacetamide (3.48 mL, 26.8 mmol). The RM was stirred at 0° C. for 1 hr. The RM was poured into water and extracted 2× with EtOAc. The combined organic extracts were dried (phase separator) and evaporated. The crude residue was purified twice by normal phase flash chromatography (120 g SiO$_2$ column, eluent c-hexane:EtOAc 100:0 to 30:70) to give the title compound containing 15% of 2-bromo-N-methoxy-N-methylacetamide. The mixture was dissolved in THF (100 mL), PL-TPP Resin (Particle Size: 150-300 μm, loading 1.52 mmol/g, 14.6 mmol, 9.60 g) was added and the mixture was shaken at RT for 16 hr, filtered and concentrated to give the title compound as a pale yellow oil.

LC-MS: Rt=0.90 min; MS m/z [M+H]+ 306.2/308.2; UPLC-MS 1.

Step 3: 8-fluoroisochroman-4-one

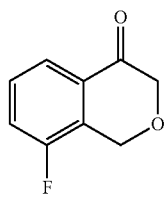

To a solution of 2-((2-bromo-6-fluorobenzyl)oxy)-N-methoxy-N-methylacetamide (Step 2, 6.4 g, 20.9 mmol) in THF (110 mL) was added dropwise at 78° C. nBuLi (1.6M in hexane, 17.0 mL, 27.2 mmol) under an argon atmosphere. The RM was stirred at 78° C. for 1 hr, then was poured in saturated aq NH$_4$Cl and extracted 2× with EtOAc. The combined organic extracts were dried (phase separator) and evaporated. The crude residue was purified by normal phase flash chromatography (80 g SiO$_2$ column, eluent c-hexane:EtOAc 100:0 to 30:70) to give the title compound as a white solid.

$^1$H NMR (400 MHz, DMSO-d$_6$) δ 7.78 (d, 1H), 7.62-7.52 (m, 2H), 4.99 (s, 2H), 4.41 (s, 2H).

Step 4: 8'-fluorospiro[imidazolidine-4,4'-isochroman]-2,5-dione

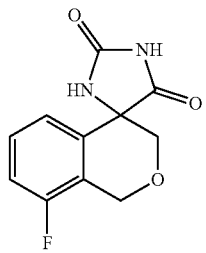 [SMILES: O=C1NC(=O)C2(COCc3c(F)cccc32)N1]

An Ace pressure tube was charged with 8-fluoroisochroman-4-one (Step 3, 2.36 g, 14.2 mmol), ammonium carbonate (15.01 g, 156 mmol), EtOH (20 mL), water (20 mL) and KCN (1.39 g, 21.3 mmol). The reaction mixture was sealed and stirred at 70° C. for 16 hr. The cooled RM was extracted 4× with EtOAc. The combined organic extracts were dried over Na$_2$SO$_4$, filtered and concentrated under reduced pressure. The crude residue was purified by normal phase flash chromatography (80 g SiO$_2$ column: eluent c-hexane:EtOAc 100:0 to 0:100) to give the title compound as a white solid.

LC-MS: Rt=0.52 min; MS m/z [M−H]− 235.2; UPLC-MS 1.

Step 5: 4-amino-8-fluoroisochroman-4-carboxylic Acid

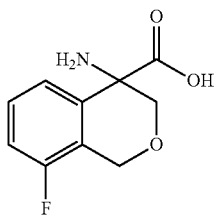 [SMILES: NC1(C(=O)O)COCc2c(F)cccc21]

A solution of KOH (4.22 g, 75 mmol) in water (25 mL) was added to 8'-fluorospiro[imidazolidine-4,4'-isochroman]-2,5-dione (Step 4, 1.87 g, 7.52 mmol) and the RM was stirred at 100° C. for 5 days. The RM was slowly poured into aq HCl (6M, 12.5 mL, 75 mmol) and the acidic mixture was concentrated under reduced pressure and dried (high vacuum, 40° C.) to give the title compound (containing KCl) which will be used without purification in the next step.

$^1$H NMR (600 MHz, DMSO-d$_6$) δ 9.03 (m, 3H), 7.48 (q, 1H), 7.35 (t, 1H), 7.20 (d, 1H), 4.94 (d, 1H), 4.85 (d, 1H), 4.30 (d, 1H), 4.16 (d, 1H).

Step 6: (4-amino-8-fluoroisochroman-4-yl)methanol

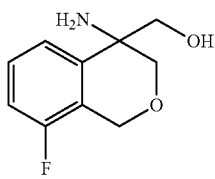 [SMILES: NC1(CO)COCc2c(F)cccc21]

To a suspension of 4-amino-8-fluoroisochroman-4-carboxylic acid (containing KCl, 7.52 mmol) in THF (45 mL) at 0-5° C. was added BH$_3$.THF (1M in THF, 18.8 mL, 18.8 mmol) under a nitrogen atmosphere. The RM was allowed to reach RT and was stirred for 24 hr. MeOH was slowly added, the solvents were evaporated and the residue was suspended in MeOH. Biotage MP-503H (5.45 g, loading 4.14 mmol/g) was added and the mixture was shaken at RT for 16 hr, and filtered. To the residual resin was added NH$_3$ (2N in MeOH, 70 mL) and the mixture was shaken for 30 min at RT, filtered and evaporated to give the title compound as a pale yellow solid.

LC-MS: Rt=0.38 min; MS m/z [M+H]$^+$ 198.3; UPLC-MS 1.

Step 7-9: rac-(4-((3-(difluoromethoxy)-5-(trifluoromethyl)pyridin-2-yl)amino)-8-fluoroisochroman-4-yl)methanol

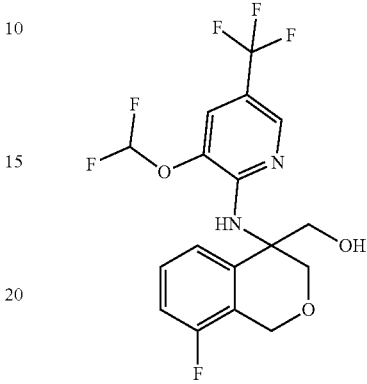

The title compound was prepared by a method similar to that of Intermediates AS and AR by replacing (4-amino-8-fluoroisochroman-4-yl)methanol (Intermediate AT) by (4-amino-8-fluoro-2-methylchroman-4-yl)methanol. The title compound was used without purification in the next step.

LC-MS: Rt=1.18 min; MS m/z [M+H]$^+$ 409.2; UPLC-MS 1.

Intermediate CA: rac-6-(7'-chloro-8'-fluoro-2-oxospiro[oxazolidine-4,4'-thiochroman]-3-yl)-5-(difluoromethoxy)nicotinonitrile

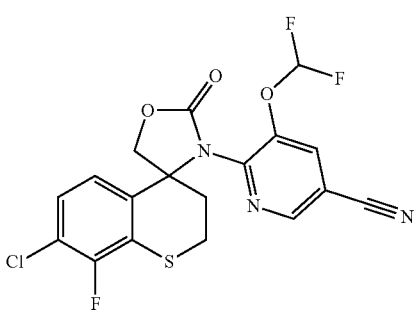 [SMILES: N#Cc1cnc(N2C(=O)OCC23CCSc2c3ccc(Cl)c2F)c(OC(F)F)c1]

The title compound was prepared by methods similar to that described for the preparation of intermediates AS and AR by replacing (S)-(4-amino-7-bromo-8-fluorochroman-4-yl)methanol (Intermediate AT) with rac-(4-amino-7-chloro-8-fluorothiochroman-4-yl)methanol (Intermediate CB).

LC-MS: Rt=1.15 min; MS m/z [M+Na]$^+$ 465.0; UPLC-MS 1.

Intermediate CB: rac-(4-amino-7-chloro-8-fluorothiochroman-4-yl)methanol

Step 1: methyl 3-((3-chloro-2-fluorophenyl)thio)propanoate

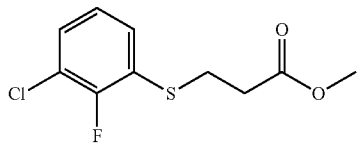

A mixture of 1-chloro-2-fluoro-3-iodobenzene (8.47 ml, 66.3 mmol), methyl 3-mercaptopropanoate (8.99 ml, 80 mmol), Pd$_2$dba$_3$ (3.04 g, 3.31 mmol), DPPF (2.57 g, 4.64 mmol), Et$_3$N (15.92 mL) and DMF (80 mL) was heated at 110° C. for 3 hr under an argon atmosphere. The cooled RM was diluted with EtOAc and washed 2× with saturated aq NaHCO$_3$. The organic phase was then washed with brine, dried (phase separator) and concentrated. The residue was purified by normal phase chromatography (silica gel, eluent heptane/EtOAc 100:0 to 70:30) to give the title compound as a yellow oil.

$^1$H NMR (400 MHz, DMSO-d$_6$) δ 7.49-7.42 (m, 2H), 7.23 (t, 1H), 2.93 (s, 3H), 3.21 (t, 2H), 2.65 (t, 2H).

Step 2: 3-((3-chloro-2-fluorophenyl)thio)propanoic acid

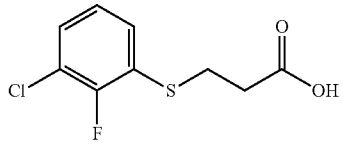 [SMILES: O=C(O)CCSc1cccc(Cl)c1F]

LiOH (2.82 g, 118 mmol) was added to methyl 3-((3-chloro-2-fluorophenyl)thio)propanoate (14.64 g, 58.9 mmol) in THF (337 mL) and water (112 mL) and stirred for 5 hr at RT. The RM was concentrated, diluted with 1N aq HCl, and extracted 2× with EtOAc. The combined organic layers were dried (phase separator) and concentrated to give the title compound as a yellow powder which was used without purification in the following step.

LC-MS: Rt=0.92 min; MS m/z [M−H]$^-$ 233.0/235.0; UPLC-MS 1.

Step 3: 7-Chloro-8-fluorothiochroman-4-one

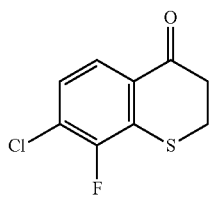 [SMILES: O=C1CCSc2c1ccc(Cl)c2F]

DMF (459 μL, 5.92 mmol) was added to a solution of 3-((3-chloro-2-fluorophenyl)thio)propanoic acid (13.9 g, 59.2 mmol) and oxalyl chloride (9.33 ml, 107 mmol) in DCM (147 mL). The RM was stirred for 30 min at RT and then concentrated to give the acid chloride. The residue was dissolved in DCM (147 mL) and AlCl$_3$ (23.69 g, 178 mmol) added portion wise under argon. The RM was stirred 30 min at RT then cooled to 0-5° C. and quenched with methanol and 6M aq HCl. The mixture was stirred for 30 min at RT, diluted with water, and extracted 2× with DCM. The combined organic layers were dried (phase separator) and evaporated to give the title compound as a brown powder which was used without purification in the following step.

LC-MS: Rt=1.06 min; no significant molecular ion signal; UPLC-MS 1.

Step 4: rac-(4-amino-7-chloro-8-fluorothiochroman-4-yl)methanol

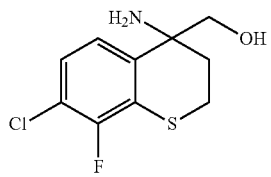 [SMILES: NC1(CO)CCSc2c1ccc(Cl)c2F]

The title compound was prepared by methods similar to that described for the preparation of intermediate AO replacing 6-fluoro-1-tetralone with 7-chloro-8-fluorothiochroman-4-one (Step 3).

LC-MS: Rt=0.43 min; MS m/z [M+H]$^+$ 214.1; UPLC-MS 1.

Intermediate CC: 2-bromo-3-(difluoromethoxy)-5-(trifluoromethyl)pyridine

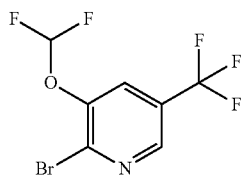 [SMILES: FC(F)Oc1cc(C(F)(F)F)cnc1Br]

Diethyl (bromodifluoromethyl)phosphonate (711 μL, 4.13 mmol) was added to a solution of 2-bromo-5-(trifluoromethyl)pyridin-3-ol (500 mg, 2.07 mmol) and KOH (2.32 g, 41.3 mmol) in AcCN (5 mL) and water (5 mL). The RM was stirred for 1 hr at RT, then extracted with DCM, the organic layer washed with brine, dried (Phase Separator) and carefully concentrated under vacuum. The residue was purified by normal phase chromatography (silica gel, eluent DCM:MeOH 100:0 to 90:10) to give the title compound.

$^1$H NMR (400 MHz, DMSO-d$_6$) δ 8.72 (s, 1H), 8.18 (s, 1H), 7.48 (t, 1H).

Intermediate CD: (S)-5-(difluoromethoxy)-6-(8'-fluoro-2-oxospiro[oxazolidine-4,4'-thiochroman]-3-yl)nicotinonitrile

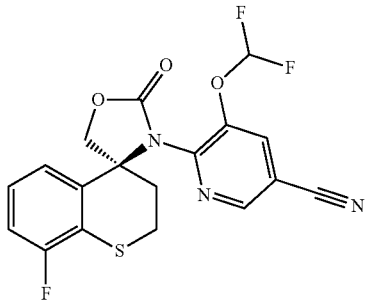 [SMILES: N#Cc1cnc(N2C(=O)OC[C@@]23CCSc2c(F)cccc23)c(OC(F)F)c1]

The title compound was prepared by methods similar to that described for the preparation of intermediates AS and AR by replacing (S)-(4-amino-7-bromo-8-fluorochroman-4-yl)methanol (Intermediate AT) with (S)-(4-amino-8-fluorothiochroman-4-yl)methanol (Intermediate CE).

LC-MS: Rt=1.11 min; MS m/z [M+H]$^+$ 408.2; UPLC-MS 1.

Intermediate CE: (S)-(4-amino-8-fluorothiochroman-4-yl)methanol

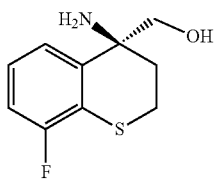

4-Amino-8-fluorothiochroman-4-carboxylic acid (Intermediate AU7, 79 g, 59.1 mmol) was dissolved in THF (80 mL) under argon and cooled to 0° C. BH$_3$.THF complex in THF (1M, 148 mL, 148 mmol) was added slowly to the RM, CAUTION GAS EVOLUTION! The RM was stirred for 1 hr at 0° C., the ice bath removed and the RM was stirred for 2 days at RT. The RM was recooled to 0° C. and quenched by the slow addition of a mixture of HCl (37%, 24.26 mL, 295 mmol) in water (100 mL) followed by the addition of MeOH (100 mL). The RM was stirred for 1 hr at RT, then concentrated in vacuo and co-evaporated 3× with MeOH. The residue was diluted with water and basified by the addition of 2N NaOH, followed by extracting 3× with DCM. The combined organic phases were washed with brine, filtered through a phase separator cartridge and concentrated in vacuo to give the racemic title compound as a brown oil. The enantiomers were separated by chiral column chromatography (column: AmyC 20 mm×250 mm, 5 µm, 40° C., flow rate 50 mL/min, BPR 100 BarG, detection: 210 nm, isocratic conditions: 20:80 EtOH:CO$_2$ (0.2% v/v NH$_3$) to give the title compound as the first eluting peak.

LC-MS: Rt=0.44 min; MS m/z [M+H]$^+$ 214.1; UPLC-MS 1.

Chiral-HPLC: Rt=9.39 min; with (R)-(4-amino-8-fluorothiochroman-4-yl)methanol eluting as the second peak, Rt=11.77 min; C-HPLC 45.

Intermediate CF: (S)-(4-((3-(difluoromethoxy)-5-(trifluoromethyl)pyridin-2-yl)amino)-8-fluoro-7-(trifluoromethyl)-3,4-dihydro-2H-thiopyrano[3,2-c]pyridin-4-yl)methanol Step 1: 5-bromo-3-fluoro-2-(trifluoromethyl)pyridine-4-thiol

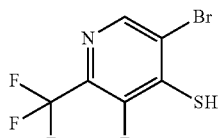

A solution of LDA in THF was prepared by the dropwise addition of a solution of nBuLi in hexane (1.6 M, 10.8 mL, 17.21 mmol) to iPr$_2$NH (2.25 mL, 15.78 mmol) cooled with an ice bath under a positive pressure of argon. After stirring for 20 min below 5° C.; the RM was diluted with THF (35 mL) and the resulting solution added dropwise to a solution of 5-bromo-3-fluoro-2-(trifluoromethyl)pyridine (3.5 g, 14.35 mmol) in THF (60 mL) cooled with a dry ice/acetone bath. Stirring was continued for 1 hr at −75° C., and the RM warmed to 0° C., and stirred at 0° C. for 30 min before the addition of sulfur (0.55 g, 17.21 mmol). The RM was stirred for 30 min at 0° C., aq NH$_4$Cl was added, and extracted 2× with TBME, the combined organic layers washed with brine, dried over Na$_2$SO$_4$ and evaporated to give the title compound as a brown solid which was used directly without further purification.

LC-MS: Rt=0.61 min; MS m/z [M−H]$^-$ 274.0/276.0; UPLC-MS 1.

Step 2: 3-((5-bromo-3-fluoro-2-(trifluoromethyl)pyridin-4-yl)thio)propanoic acid

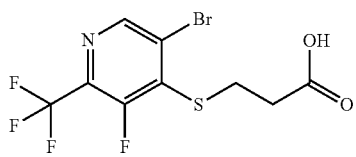 [SMILES: O=C(O)CCSc1c(Br)cnc(C(F)(F)F)c1F]

3-Bromopropanoic acid (2.0 g, 13.04 mmol) was added in four portions, over 30 min, to a suspension of K$_2$CO$_3$ (5.41 g, 39.1 mmol) and 5-bromo-3-fluoro-2-(trifluoromethyl)pyridine-4-thiol (Step 1, 4.5 g, 13.04 mmol) in DMF (40 mL) cooled with an ice bath. The RM was stirred for 30 min at 0° C., allowed to warm to RT, and stirred for 4 hr at RT. Additional 3-bromopropanoic acid (600 mg, 3.94 mmol) was added and the RM was stirred for 16 hr at RT. Subsequently additional 3-bromopropanoic acid (600 mg, 3.94 mmol) and K$_2$CO$_3$ (1.8 g, 13.0 mmol) were added and the RM was stirred for a further 2 hr at RT. The RM was partitioned between DCM (150 mL) and H$_2$O (200 mL) the aq layers extracted 2× with DCM (100 mL), the combined organic layers washed with brine (100 mL), dried by passing through a phase separator cartridge and evaporated to give the title compound, containing traces of DMF, which was used directly without further purification.

LC-MS: Rt=0.98 min; MS m/z [M+H]$^+$ 348.1/350.0; UPLC-MS 1.

Step 3: 3-((5-bromo-3-fluoro-2-(trifluoromethyl)pyridin-4-yl)thio)-N-methoxy-N-methylpropanamide

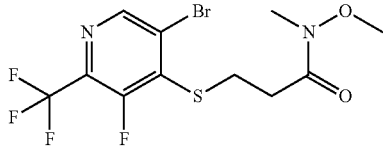 [SMILES: CON(C)C(=O)CCSc1c(Br)cnc(C(F)(F)F)c1F]

Oxalyl chloride (980 μL, 11.20 mmol) was added to a solution of 3-((5-bromo-3-fluoro-2-(trifluoromethyl)pyridin-4-yl)thio)propanoic acid (Step 2, 5.0 g, 8.62 mmol) in DCM (40 mL) at RT and the RM stirred for 2.5 hr at RT. Additional oxalyl chloride (226 μL, 2.59 mmol) was added and the RM stirred for 0.5 hr at RT and the RM evaporated. The residue was taken up into DCM (40.0 mL) and added dropwise to a stirred solution of NaHCO$_3$ (1.52 g, 18.10 mmol) and N,O-dimethylhydroxylamine hydrochloride (925 mg, 9.48 mmol) in water (40.0 mL). The biphasic RM was stirred for 18 hr at RT, diluted with DCM (100 mL) and saturated aq NaHCO$_3$ (120 mL), the aq layer further extracted 2× with DCM (50 mL), the combined organic layers washed with brine (100 mL), dried by passing through a phase separator cartridge and evaporated. The residue was adsorbed onto Isolute and purified by normal phase chromatography (80 g SiO$_2$ column; eluent hexane:TBME from 100:0 to 40:60) to give the title compound as a yellow oil LC-MS: Rt=1.09 min; MS m/z [M+H]$^+$ 391.1/393.1; UPLC-MS 1.

Step 4: 8-fluoro-7-(trifluoromethyl)-2,3-dihydro-4H-thiopyrano[3,2-c]pyridin-4-one

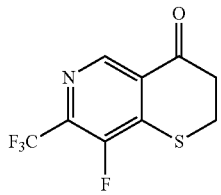 [SMILES: O=C1CCSc2c1cnc(C(F)(F)F)c2F]

A solution of tert-BuLi in pentane (7.11 mL, 12.08 mmol) was added to a solution of 3-((5-bromo-3-fluoro-2-(trifluoromethyl)pyridin-4-yl)thio)-N-methoxy-N-methylpropanamide (Step 3, 2.14 g, 5.25 mmol) in THF (30 mL) cooled with a dry ice/acetone batch under a positive pressure of argon. The RM was stirred for 45 min at −75° C., then allowed to warm to RT and saturated aq NH$_4$Cl (50 mL) and TBME (30 mL) added. The aq layer was extracted with TBME (50 mL), the combined organic layers were washed with brine, dried over Na$_2$SO$_4$, and evaporated. The residue was purified by normal phase chromatography (40 g SiO$_2$ column; eluent hexane:TBME 100:0 to 40:60) to give the title compound as a beige solid.
LC-MS: Rt=0.97 min; MS m/z [M+H]$^+$ 252.1; UPLC-MS 1.

Step 5: (S)—N-(8-fluoro-7-(trifluoromethyl)-2,3-dihydro-4H-thiopyrano[3,2-c]pyridin-4-ylidene)-2-methylpropane-2-sulfinamide

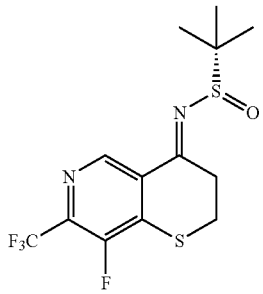

(S)-2-methylpropane-2-sulfinamide (552 mg, 4.46 mmol) was added to a mixture of 8-fluoro-7-(trifluoromethyl)-2,3-dihydro-4H-thiopyrano[3,2-c]pyridin-4-one (Step 4, 880 mg, 3.43 mmol) and Ti(OiPr)$_4$ (3.02 mL, 10.30 mmol) in THF (10 mL) at RT. The RM was stirred for 4 hr at 70° C., cooled and DCM (50 mL), H$_2$O (30 mL) and brine (20 mL) added. The aqueous layer was further extracted 2× with DCM (30 mL), the combined organic layers dried by passing through a phase separator and evaporated to give the title compound as a brown resin which was used directly without further purification.
LC-MS: Rt=1.14 min; MS m/z [M+H]$^+$ 355.1; UPLC-MS 1.

Step 6: (S)—N—((S)-4-cyano-8-fluoro-7-(trifluoromethyl)-3,4-dihydro-2H-thiopyrano[3,2-c]pyridin-4-yl)-2-methylpropane-2-sulfinamide and (S)—N—((R)-4-cyano-8-fluoro-7-(trifluoromethyl)-3,4-dihydro-2H-thiopyrano[3,2-c]pyridin-4-yl)-2-methylpropane-2-sulfinamide

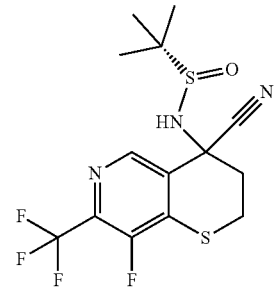

To a solution of (S)—N-(8-fluoro-7-(trifluoromethyl)-2,3-dihydro-4H-thiopyrano[3,2-c]pyridin-4-ylidene)-2-methylpropane-2-sulfinamide (Step 5, 1.03 g, 2.47 mmol) in THF (12 mL) was added sequentially CsF (751 mg, 4.94 mmol), trimethylsilylcyanide (994 μL, 7.41 mmol) and tert-BuOH (473 μL, 4.94 mmol), and the RM stirred for 2.5 hr at RT. The RM was partitioned between DCM (70 mL), saturated aq NaHCO$_3$ (20 mL) and H$_2$O (70 mL), the aq layer further extracted 2× with DCM (40 mL), the combined organic layers washed with brine, dried by passing through a phase separator cartridge and evaporated. The residue was purified by normal phase chromatography (40 g SiO$_2$ column; eluent hexane:TBME 90:10 to 0:100) to give the title compound as a beige solid (1:4 mixture of diastereomers).

LC-MS: Rt=1.01 min; MS m/z [M+H]⁺ 382.1; UPLC-MS 1.

Step 7: (S)-4-(((S)-tert-butylsulfinyl)amino)-8-fluoro-7-(trifluoromethyl)-3,4-dihydro-2H-thiopyrano[3,2-c]pyridine-4-carboxamide

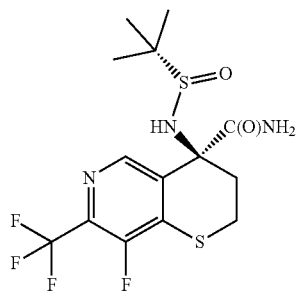

To a solution of (S)—N—((S)-4-cyano-8-fluoro-7-(trifluoromethyl)-3,4-dihydro-2H-thiopyrano[3,2-c]pyridin-4-yl)-2-methylpropane-2-sulfinamide and (S)—N—((R)-4-cyano-8-fluoro-7-(trifluoromethyl)-3,4-dihydro-2H-thiopyrano[3,2-c]pyridin-4-yl)-2-methylpropane-2-sulfinamide (Step 6, 780 mg, 1.74 mmol) in EtOH (10 mL) and water (2 mL) was added hydrido(dimethylphosphinous acid-kP)[hydrogen bis (dimethylphosphinito-kP)]platinum (II) (74.6 mg, 174 µmol) at RT under a positive pressure of argon. The RM was stirred for 1 hr at 80° C., cooled, and partitioned between DCM (50 mL) and brine (30 mL), the aq layer extracted 2× with DCM (20 mL), the combined organic layers dried by passing through a phase separator cartridge and evaporated. The residue was purified by normal phase chromatography (24 g SiO₂ Gold Column, eluent hexane:(TBME:MeOH 95:5) 80:20 to 0:100) to give two major components. The title compound was isolated as the first eluting peak as a white solid.

LC-MS: Rt=0.86 min; MS m/z [M+H]⁺ 400.1; UPLC-MS 1.

(R)-4-(((S)-tert-butyl sulfinyl)amino)-8-fluoro-7-(trifluoromethyl)-3,4-dihydro-2H-thiopyrano[3,2-c]pyridine-4-carboxamide was isolated as the second eluting peak as a white crystalline solid.

LC-MS: Rt=0.89 min; MS m/z [M+H]⁺ 400.2; UPLC-MS 1.

Step 8: (S)-4-amino-8-fluoro-7-(trifluoromethyl)-3,4-dihydro-2H-thiopyrano[3,2-c]pyridine-4-carboxylic Acid

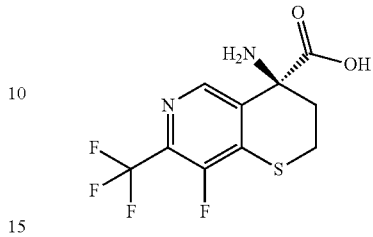

A suspension of (S)-4-(((S)-tert-butylsulfinyl)amino)-8-fluoro-7-(trifluoromethyl)-3,4-dihydro-2H-thiopyrano[3,2-c]pyridine-4-carboxamide (Step 7, 154 mg, 308 µmol) in aq HCl (4M, 3.1 mL, 12.34 mmol) was heated at 80° C. for 20 hr. Additional aq HCl (4M, 1.0 mL) was added and the RM stirred for a further 24 hr at 80° C. The cooled RM was evaporated, redissolved in toluene and evaporated to dryness twice, to give the title compound which was used directly without further purification.

LC-MS: Rt=0.50 min; MS m/z [M+H]⁺ 297.1; UPLC-MS 1.

Step 9: (S)-(4-amino-8-fluoro-7-(trifluoromethyl)-3,4-dihydro-2H-thiopyrano[3,2-c]pyridin-4-yl)methanol

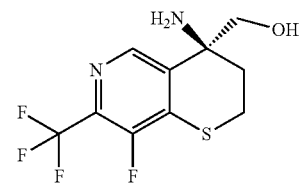

A solution of borane in THF (1M, 1.06 mL, 1.06 mmol) was added dropwise to a solution of (S)-4-amino-8-fluoro-7-(trifluoromethyl)-3,4-dihydro-2H-thiopyrano[3,2-c]pyridine-4-carb oxylic acid (Step 8, 250 mg, 211 µmol) in THF (5 mL) at RT. Additional aliquots of borane in THF (1M) were added to the stirred RM at RT after: 1 hr (1 mL); 20 hr (2 mL); 48 hr (2 mL); 72 hr (1.5 mL). The reaction mixture was stirred for a further 24 hr at RT and MeOH was added dropwise CAUTION: GAS EVOLUTION! The RM was evaporated and the residue heated at 40° C. for 30 min in 4M aq HCl, then cooled and evaporated to dryness. The residue was partitioned between DCM (20 mL) and water (20 mL), the aq layer basified by the addition of saturated aq Na₂CO₃ (10 mL), and extracted 2× with DCM (10 mL), the combined organic layers from the basic extractions dried by passing through a phase separator cartridge and evaporated to give the title compound as a yellow resin which was used directly without further purification.

LC-MS: Rt=0.54 min; MS m/z [M+H]⁺ 283.1; UPLC-MS 1.

Step 10: (S)-8'-fluoro-7'-(trifluoromethyl)-2',3'-dihydrospiro[oxazolidine-4,4'-thiopyrano[3,2-c]pyridin]-2-one

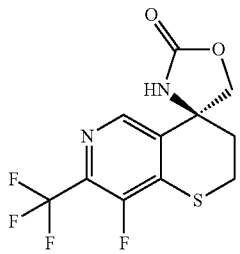 [SMILES: O=C1N[C@]2(CCSc3c2cnc(C(F)(F)F)c3F)CO1]

A solution of triphosgene (26.8 mg, 90 μmol) in DCM (1 mL) was added dropwise at RT to a solution of (S)-(4-amino-8-fluoro-7-(trifluoromethyl)-3,4-dihydro-2H-thiopyrano[3,2-c]pyridin-4-yl)methanol (Step 9, 60 mg, 181 μmol) and Et$_3$N (63 μL, 452 μmol) in DCM (2 mL). The RM was stirred for 1 hr at RT and saturated aq NH$_4$Cl (3 mL) added. After stirring for 30 min at RT the biphasic mixture was diluted with saturated aq NH$_4$Cl (10 mL) and H$_2$O (10 mL), extracted 3× with DCM (10 mL), the combined organic layers dried by passing through a phase separator cartridge, and evaporated. The residue was purified by normal phase chromatography (12 g SiO$_2$ column, eluent hexane:(TBME:MeOH 95:5) 90:10 to 10:90) to give the title compound as a colorless resin.

LC-MS: Rt=0.80 min; MS m/z [M+H]$^+$ 309.1; UPLC-MS 1.

Step 11: (S)-3-(3-(difluoromethoxy)-5-(trifluoromethyl)pyridin-2-yl)-8'-fluoro-7'-(trifluoromethyl)-2',3'-dihydrospiro[oxazolidine-4,4'-thiopyrano[3,2-c]pyridin]-2-one

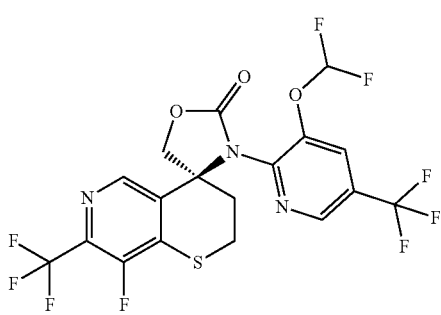 [SMILES: O=C1OC[C@@]2(CCSc3c2cnc(C(F)(F)F)c3F)N1c1ncc(C(F)(F)F)cc1OC(F)F]

A mixture of (S)-8'-fluoro-7'-(trifluoromethyl)-2',3'-dihydrospiro[oxazolidine-4,4'-thiopyrano[3,2-c]pyridin]-2-one (Step 10, 44 mg, 134 μmol), 2-chloro-3-(difluoromethoxy)-5-(trifluoromethyl)pyridine (Intermediate A, 40 μL, 242 μmol), Cs$_2$CO$_3$ (87 mg, 268 μmol) and CuBr (3.85 mg, 27 μmol) in DMF (2.0 mL) was heated at 120° C. for 1 hr in a microwave. The cooled RM was filtered through Hyflo, the filtrate diluted with EtOAc (30 mL) and H$_2$O (20 mL), the aqueous layer extracted 2× with EtOAc, the combined organic layers washed with brine, dried over Na$_2$SO$_4$, and evaporated. The residue was adsorbed onto Isolute and purified by normal phase chromatography (12 g SiO$_2$ column, eluent hexane:TBME from 100:0 to 60:40) to give the title compound as a beige resin.

LC-MS: Rt=1.22 min; MS m/z [M+H]$^+$ 520.0; UPLC-MS 1.

Step 12: (S)-(4-((3-(difluoromethoxy)-5-(trifluoromethyl)pyridin-2-yl)amino)-8-fluoro-7-(trifluoromethyl)-3,4-dihydro-2H-thiopyrano[3,2-c]byridin-4-yl)methanol

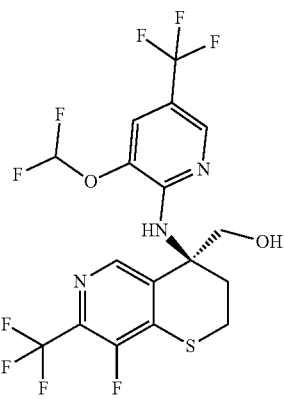 [SMILES: OC[C@]1(Nc2ncc(C(F)(F)F)cc2OC(F)F)CCSc2c1cnc(C(F)(F)F)c2F]

A mixture of (S)-3-(3-(difluoromethoxy)-5-(trifluoromethyl)pyridin-2-yl)-8'-fluoro-7'-(trifluoromethyl)-2',3'-dihydrospiro[oxazolidine-4,4'-thiopyrano[3,2-c]pyridin]-2-one (Step 11, 72 mg, 125 μmol), aq NaOH (4M, 156 μL, 624 μmol), EtOH (1 mL) and THF (2 mL) was stirred for 1 hr at 50° C. The cooled RM was diluted with saturated aq Na$_2$CO$_3$ and extracted 2× with DCM, the combined organic layers washed with brine, and evaporated to give the title compound as a beige foam which was used directly without further purification.

LC-MS: Rt=1.25 min; MS m/z [M+H]$^+$ 494.1; UPLC-MS 1.

Intermediate CG: (4-amino-8-fluoroisothiochroman-4-yl)methanol

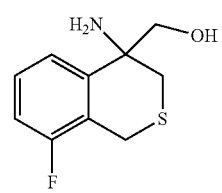 [SMILES: NC1(CO)CSCc2c(F)cccc21]

The title compound was prepared by methods similar to that described for the preparation of intermediate AU, steps 3 and 4, and intermediate CF, step 9, by replacing 7-bromo-8-fluorochroman-4-one (Intermediate AU, step 2) with 8-fluoroisothiochroman-4-one.

LC-MS: Rt=1.25 min; MS m/z 214.1 [M+H]$^+$; UPLC-MS 4.

Intermediate CH: 3'-(3-(difluoromethoxy)-5-(trifluoromethyl)pyridin-2-yl)-9-fluoro-3,4-dihydro-2H-spiro[benzo[b]oxepine-5,4'-oxazolidin]-2'-one

Step 1: 1-(2-(2-bromoethoxy)-3-fluorophenyl)ethanone

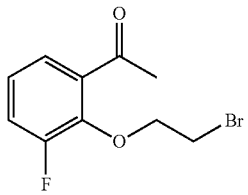

1,2-Dibromoethane (28.0 mL, 324 mmol) was added to a mixture of 1-(3-fluoro-2-hydroxyphenyl)ethanone (10 g, 64.9 mmol) and $K_2CO_3$ (18.83 g, 136 mmol) in butanone (125 mL) at RT. The yellow suspension was heated under reflux for 18 hr, cooled to RT, filtered, washing with EtOAc. The filtrate was washed 3× with water, dried (phase separator) and concentrated to give the title compound as a yellow oil which was used in the next step without further purification.

LC-MS: Rt=1.00 min; MS m/z 261.1 [M+H]$^+$; UPLC-MS 1.

Step 2: 9-fluoro-3,4-dihydrobenzo[b]oxepin-5(2H)-one

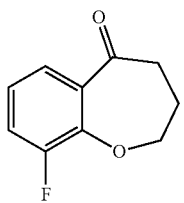 [SMILES: O=C1CCCOc2c(F)cccc21]

A solution of 1-(2-(2-bromoethoxy)-3-fluorophenyl)ethanone (Step 1, 17.51 g, 57.7 mmol) in THF (30 mL) was slowly added to a slurry of NaH (60% in mineral oil, 3.69 g, 92 mmol) in THF (45 mL) at RT under a positive pressure of argon. The RM was heated to 70° C. for 1.5 hr, cooled to RT, quenched by the addition of water and extracted with EtOAc. The organic phase was washed with brine. The combined aqueous phases were extracted again with EtOAc. All the organic phases were combined, dried (phase separator cartridge) and concentrated. The residue was purified by normal phase chromatography (silica gel, eluent heptane: EtOAc 100:0 to 70:30) to give the title compound as a yellow powder.

LC-MS: Rt=3.53 min; MS m/z 181.1 [M+H]$^+$; UPLC-MS 4.

Steps 3, 4, 5, 6, 7 and 8: rac-9-fluoro-3,4-dihydro-2H-spiro[benzo[b]oxepine-5,4'-oxazolidin]-2'-one

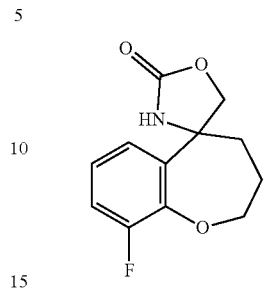

The title compound was prepared by methods similar to that described for the preparation of intermediate CF, steps 5 to 10, by replacing 8-fluoro-7-(trifluoromethyl)-2,3-dihydro-4H-thiopyrano[3,2-c]pyridin-4-one (Intermediate CF, Step 4) with 9-fluoro-3,4-dihydrobenzo[b]oxepin-5(2H)-one (Step 2).

LC-MS: Rt=2.81 min; MS m/z 238.1 [M+H]$^+$; UPLC-MS 4.

Step 9: rac-3'-(3-(difluoromethoxy)-5-(trifluoromethyl)pyridin-2-yl)-9-fluoro-3,4-dihydro-2H-spiro[benzo[b]oxepine-5,4'-oxazolidin]-2'-one

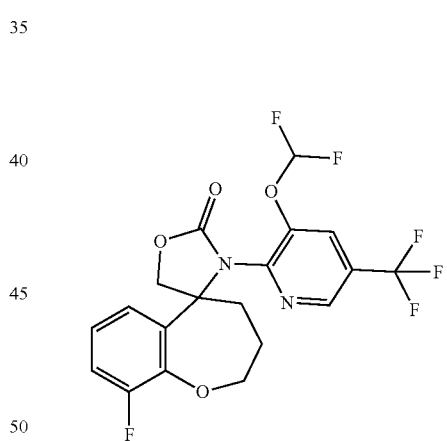

A mixture of rac-9-fluoro-3,4-dihydro-2H-spiro[benzo[b]oxepine-5,4'-oxazolidin]-2'-one (Step 8, 1.86 g, 7.76 mmol), 2-chloro-3-(difluoromethoxy)-5-(trifluoromethyl)pyridine (Intermediate A, 2.88 g, 11.64 mmol), CuI (739 mg, 3.88 mmol) and $Cs_2CO_3$ (5.06 g, 15.52 mmol) in DMF (58 mL) was heated at 120° C. for 3 hr under argon. The RM was diluted with EtOAc, washed with aq NaHCO$_3$, and the aq layer extracted 2× with EtOAc. The combined organic layers were washed with brine, dried over Na$_2$SO$_4$ and concentrated. The residue was purified by normal phase chromatography (silica gel, eluent heptane/EtOAc 100:0 to 0:100) to give the title compound as a yellow powder.

LC-MS: Rt=1.19 min; MS m/z 449.2 [M+H]$^+$; UPLC-MS 1.

Intermediate CI: (S)-8-(difluoromethoxy)-8',8'-difluoro-6-(trifluoromethyl)-7',8'-dihydro-3H,6'H-spiro[imidazo[1,2-a]pyridine-2,5'-isoquinoline]-1'-carbaldehyde

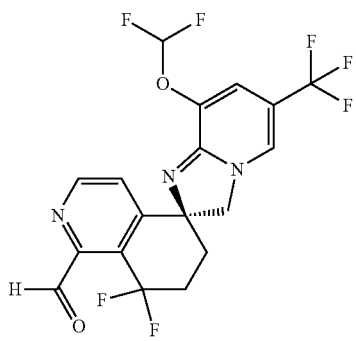 [SMILES: O=Cc1nccc2c1C(F)(F)CC[C@@]21CN2C=C(C(F)(F)F)C=C(OC(F)F)C2=N1]

SeO$_2$ (78 mg, 705 µmol) was added to (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline] (Example 32, 200 mg, 470 µmol) in 1,4-dioxane (4 mL) at RT. The RM was heated at 110° C. for 20 hr, cooled and partitioned between DCM and saturated aq NaHCO$_3$. The aq layer was extracted with DCM, the combined organic layers dried (phase separator) and evaporated. The residue was purified by normal phase chromatography (12 g SiO$_2$-column, eluent heptane:EtOAc 90:10 to 20:80) to give the title compound as a beige foam.

LC-MS: Rt=0.64/0.68 min broad double peak; MS m/z [M+H]$^+$ 436.5; UPLC-MS 1.

Intermediate CJ: 3'-(3-(difluoromethoxy)-5-(trifluoromethyl)pyridin-2-yl)-9-fluoro-3,4-dihydro-1H-spiro[benzo[c]oxepine-5,4'-oxazolidin]-2'-one

Step 1: 1-bromo-2-((but-3-en-1-yloxy)methyl)-3-fluorobenzene

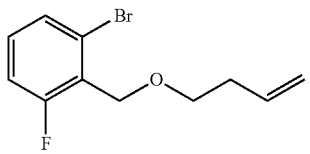

NaH as a dispersion in oil (21.27 mg, 532 µmol) was added to a stirred solution of but-3-en-1-ol (48 µL, 532 µmol) in THF (1 mL) at 0° C. The RM was stirred for 15 min at 0° C. and 1-bromo-2-(bromomethyl)-3-fluorobenzene (100 mg, 355 µmol) in THF (1 ml) was added. The yellow RM was allowed to warm up to RT and stirred at RT for 18 hr, diluted with water and extracted 2× with EtOAc. The combined organic phases were dried (phase separator) and concentrated. The residue was purified by normal phase chromatography (silica gel, eluent heptane:EtOAc 100:0 to 80:20) to give the title compound as a colorless oil of approximately 85% purity.

$^1$H NMR (400 MHz, DMSO-d$_6$) δ 7.56 (d, 1H), 7.40-7.26 (m, 2H), 5.85-5.74 (m, 1H), 5.13-4.97 (m, 2H), 4.58 (d, 2H), 3.52 (t, 2H), 2.28 (q, 2H).

Step 2: 9-fluoro-5-methylene-1,3,4,5-tetrahydrobenzo[c]oxepine

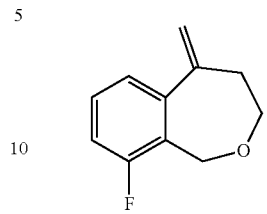

Ag$_2$CO$_3$ (77 mg, 279 µmol) then Pd[P(C$_6$H$_5$)$_3$]$_4$ (26.9 mg, 23 µmol) were added to a solution of 1-bromo-2-((but-3-en-1-yloxy)methyl)-3-fluorobenzene (Step 1, 71 mg, 233 µmol) in AcCN (3 mL) at RT under an argon atmosphere. The RM was heated at 100° C. for 18 hr, cooled to RT, concentrated, and the residue diluted with water and extracted 2× with EtOAc. The combined organic phases were dried (phase separator) and concentrated. The residue was purified by normal phase chromatography (silica gel, eluent heptane:EtOAc=100:0 to 70:30) to give the title compound as a yellow oil.

LC-MS: Rt=1.06 min; no significant molecular ion signal; UPLC-MS 1.

Step 3: 9-fluoro-3,4-dihydrobenzo[c]oxepin-5(1H)-one

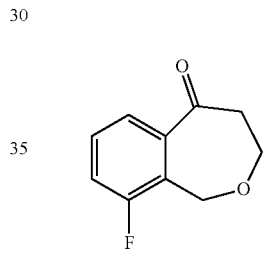

NaIO$_4$ (42.9 mg, 200 µmol) and aq OsO$_4$ (4%, 157 µL, 20 µmol) were added to a stirred solution of 9-fluoro-5-methylene-1,3,4,5-tetrahydrobenzo[c]oxepine (Step 2, 22.9 mg, 100 µmol) in THF/water (1:1, 1 mL), at 0° C. The RM was warmed to RT and stirred for 1 hr, diluted with water and extracted with EtOAc. The organic phase was washed with brine, dried (phase separator) and concentrated to give the title compound as a brown oil which was used in the next step without further purification.

LC-MS: Rt=0.78 min; no significant molecular ion signal; UPLC-MS 1.

Steps 4, 5, 6, 7, 8 and 9: 9-fluoro-3,4-dihydro-1H-spiro[benzo[c]oxepine-5,4'-oxazolidin]-2'-one

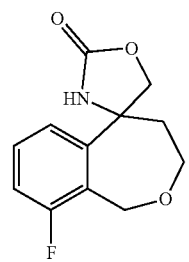 [SMILES: O=C1NC2(CCOCc3c(F)cccc32)CO1]

The title compound was prepared by methods similar to that described for the preparation of intermediate CF, steps 5 to 10, by replacing 8-fluoro-7-(trifluoromethyl)-2,3-dihydro-4H-thiopyrano[3,2-c]pyridin-4-one (Intermediate CF, Step 4) with 9-fluoro-3,4-dihydrobenzo[c]oxepin-5(1H)-one (Step 3).

LC-MS: Rt=0.67 min; MS m/z [M+H]+ 238.2; UPLC-MS 1.

Step 10: 3'-(3-(difluoromethoxy)-5-(trifluoromethyl)pyridin-2-yl)-9-fluoro-3,4-dihydro-1H-spiro[benzo[c]oxepine-5,4'-oxazolidin]-2'-one

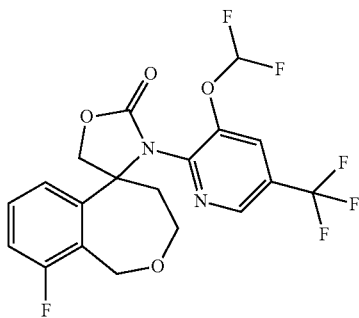 [SMILES: O=C1OCC2(CCOCc3c(F)cccc32)N1c1ncc(C(F)(F)F)cc1OC(F)F]

A mixture of 9-fluoro-3,4-dihydro-1H-spiro[benzo[c]oxepine-5,4'-oxazolidin]-2'-one (Step 9, 144 mg, 577 μmol), 2-chloro-3-(difluoromethoxy)-5-(trifluoromethyl)pyridine (Intermediate A, 214 mg, 865 μmol), CuI (54.9 mg, 288 μmol) and Cs₂CO₃ (376 mg, 1.15 mmol) in DMF (4.4 mL) was heated at 120° C. for 4 hr. The cooled RM was diluted with EtOAc, the organic layer washed 2× with saturated aq NaHCO₃, dried (phase separator) and concentrated. Purification by normal phase chromatography (silica gel, eluent heptane:EtOAc 100:0 to 50:50) gave the title compound as a yellow oil.

LC-MS: Rt=1.19 min; MS m/z [M+H]+ 449.2; UPLC-MS 1.

Intermediate CK: (S)-(1-((3-(difluoromethoxy)-5-(trifluoromethyl)pyridin-2-yl)amino)-5-fluoro-1,2,3,4-tetrahydronaphthalen-1-yl)methanol Step 1: (S)-3'-(3-(difluoromethoxy)-5-(trifluoromethyl)pyridin-2-yl)-5-fluoro-3,4-dihydro-2H-spiro[naphthalene-1,4'-oxazolidin]-2'-one

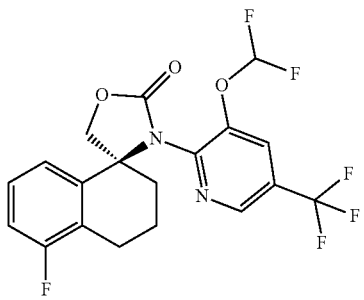 [SMILES: O=C1OC[C@@]2(CCCc3c(F)cccc32)N1c1ncc(C(F)(F)F)cc1OC(F)F]

The title compound was prepared by a method similar to that of Intermediate S, Step 1 by replacing (S)-6'-bromo-5'-fluoro-2',3'-dihydrodispiro[oxazolidine-4, 1'-naphthalene-4', 2"-[1,3]dithiolan]-2-one (Intermediate T) with (S)-5-fluoro-3,4-dihydro-2H-spiro[naphthalene-1,4'-oxazolidin]-2'-one (Intermediate Z, Step 1). The crude product was purified by normal phase chromatography (80 g SiO₂-column; eluent heptane:EtOAc 100:0 to 85:25) to give the title compound as a beige solid.

LC-MS: Rt=1.27 min; MS m/z [M+H]+ 433.3; UPLC-MS 1.

Step 2: (S)-(1-((3-(difluoromethoxy)-5-(trifluoromethyl)pyridin-2-yl)amino)-5-fluoro-1,2,3,4-tetrahydronaphthalen-1-yl)methanol

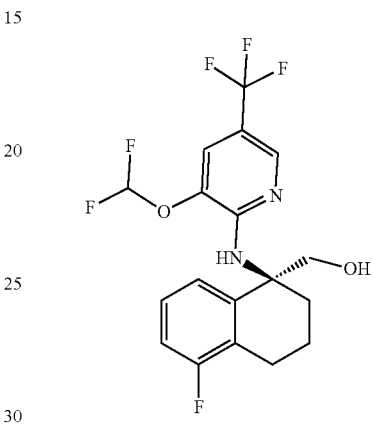

A mixture of (S)-3'-(3-(difluoromethoxy)-5-(trifluoromethyl)pyridin-2-yl)-5-fluoro-3,4-dihydro-2H-spiro[naphthalene-1,4'-oxazolidin]-2'-one (Step 1, 308 mg, 570 μmol), aq NaOH (2M, 3 mL, 6 mmol) and EtOH (6 mL) was stirred at 80° C. for 1 hr. The RM was then diluted with water and extracted with EtOAc. The combined organic layers were washed with brine, dried over Na₂SO₄ and evaporated to give the title compound as an oil.

LC-MS: Rt=1.28 min; MS m/z [M+H]+ 407.2; UPLC-MS 1.

Intermediate CL: (S)-(1-amino-5-bromo-2,3-dihydro-1H-inden-1-yl)methanol

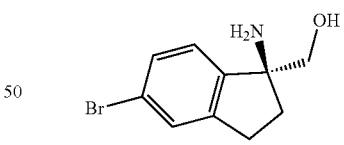

The title compound was prepared by methods similar to that described for the preparation of intermediate J steps 1 to 4 by replacing 5-bromo-4-fluoroindanone with 5-bromo-2,3-dihydro-1H-inden-1-one.

¹H NMR (400 MHz, DMSO-d₆) δ 7.34 (s, 1H), 7.31 (d, 1H), 7.21 (d, 1H), 4.75 (t, 1H), 3.30-3.23 (m, 2H), 2.88-2.68 (m, 2H), 2.20 (m, 1H), 1.88 (s, 2H), 1.73 (m, 1H).

The invention provides a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline]herein also referred to as "Form A" of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline].

(S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] can be represented by the following chemical structure according to Formula (A)

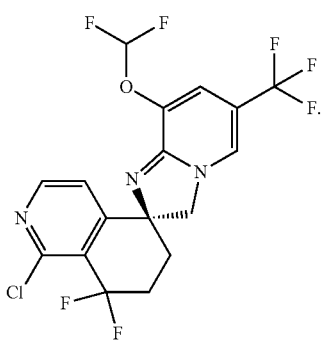

Formula (A)

The invention also provides a crystalline form of (S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] fumarate, herein also referred to as "Form A" of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate. Crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] and crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate of the present invention may be characterized by analytical methods well known in the field of the pharmaceutical industry for characterizing solids. Such methods comprise but are not limited to XRPD, SXRD, FTIR, Raman, DSC, TGA, and DVS. It may be characterized by one of the aforementioned analytical methods or by combining two or more of them. In particular, Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] or (S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] fumarate of the present invention may be characterized by any one of the following embodiments or by combining two or more of the following embodiments.

Exemplification of XRPD Embodiments

In one embodiment the invention relates to a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Form A) characterized by having a XRPD comprising reflections at 2-Theta angles of:
(9.7±0.2)°, (18.4±0.2)° and (19.4±0.2)°; or
(9.7±0.2)°, (18.4±0.2)°, (19.4±0.2)° and (13.4±0.2)°; or
(9.7±0.2)°, (18.4±0.2)°, (19.4±0.2)°, (13.4±0.2)° and (20.7±0.2)°; or
(9.7±0.2)°, (18.4±0.2)°, (19.4±0.2)°, (13.4±0.2)°, (20.7±0.2)° and (24.2±0.2)°; or
(9.7±0.2)°, (18.4±0.2)°, (19.4±0.2)°, (13.4±0.2)°, (20.7±0.2)°, (24.2±0.2)° and (22.1±0.2)°; or
(9.7±0.2)°, (18.4±0.2)°, (19.4±0.2)°, (13.4±0.2)°, (20.7±0.2)°, (24.2±0.2)°, (22.1±0.2)° and (10.3±0.2)°;

when measured at a temperature in the range of from 20 to 30° C. with Cu-Kalpha$_{1,2}$ radiation having a wavelength of 0.15406 nm.

In another embodiment, the invention relates to a crystalline form (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate (Form A) characterized by having a XRPD comprising reflections at 2-Theta angles of:
(24.9±0.2)°, (6.2±0.2)° and (20.9±0.2)°; or
(24.9±0.2)°, (6.2±0.2)°, (20.9±0.2)° and (10.9±0.2)°; or
(24.9±0.2)°, (6.2±0.2)°, (20.9±0.2)°, (10.9±0.2)° and (18.5±0.2)°; or
(24.9±0.2)°, (6.2±0.2)°, (20.9±0.2)°, (10.9±0.2)°, (18.5±0.2)° and (22.8±0.2)°; or
(24.9±0.2)°, (6.2±0.2)°, (20.9±0.2)°, (10.9±0.2)°, (18.5±0.2)°, (22.8±0.2)° and (12.9±0.2)°; or
(24.9±0.2)°, (6.2±0.2)°, (20.9±0.2)°, (10.9±0.2)°, (18.5±0.2)°, (22.8±0.2)°, (12.9±0.2)° and (16.1±0.2)°;

when measured at a temperature in the range of from 20 to 30° C. with Cu-Kalpha$_{1,2}$ radiation having a wavelength of 0.15406 nm.

In another embodiment, the present invention relates to a crystalline form of (S)-1'-chloro-8-(difluoromethoxy)-8',8'-difluoro-6-(trifluoromethyl)-7',8'-dihydro-3H,6'H-spiro [imidazo[1,2-a]pyridine-2,5'-isoquinoline] (Form A) characterized by having a XRPD essentially the same as shown in FIG. 1 of the present invention, when measured at a temperature in the range of from 20 to 30° C. with Cu-Kalpha$_{1,2}$ radiation having a wavelength of 0.15406 nm.

Figure 5:
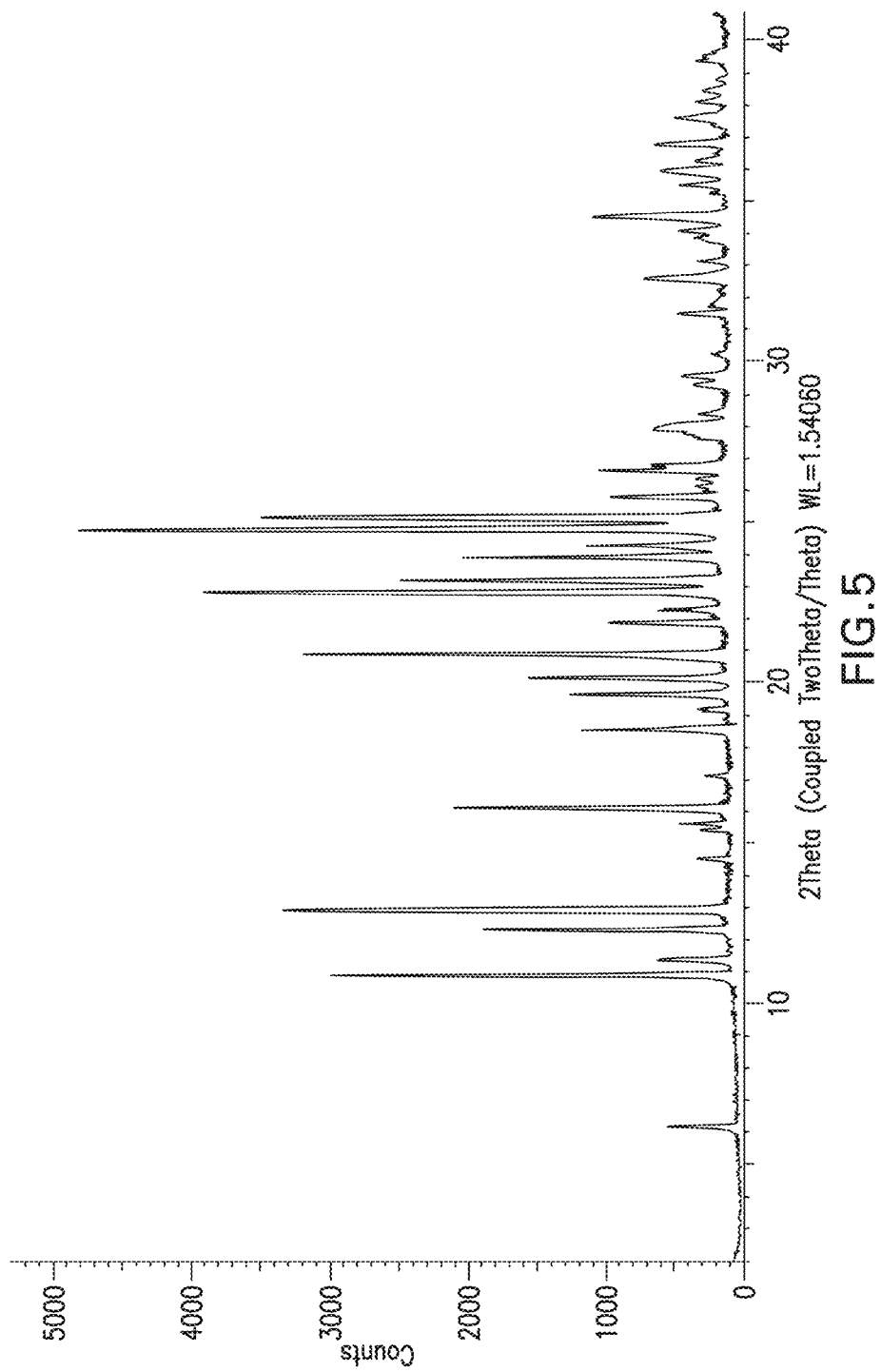
FIG. 5: illustrates a representative X-ray powder diffraction (XRPD) of Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate of the present invention. The x-axis shows the scattering angle in ° 2-Theta, the y-axis shows the intensity of the scattered X-ray beam in counts of detected photons.

In another embodiment, the present invention relates to a crystalline form of (S)-1'-chloro-8-(difluoromethoxy)-8',8'-difluoro-6-(trifluoromethyl)-7',8'-dihydro-3H,6'H-spiro [imidazo[1,2-a]pyridine-2,5'-isoquinoline] fumarate (Form A) characterized by having a XRPD essentially the same as shown in FIG. 5 of the present invention, when measured at a temperature in the range of from 20 to 30° C. with Cu-Kalpha$_{1,2}$ radiation having a wavelength of 0.15406 nm.

Exemplification of DSC Embodiments

Figure 2:
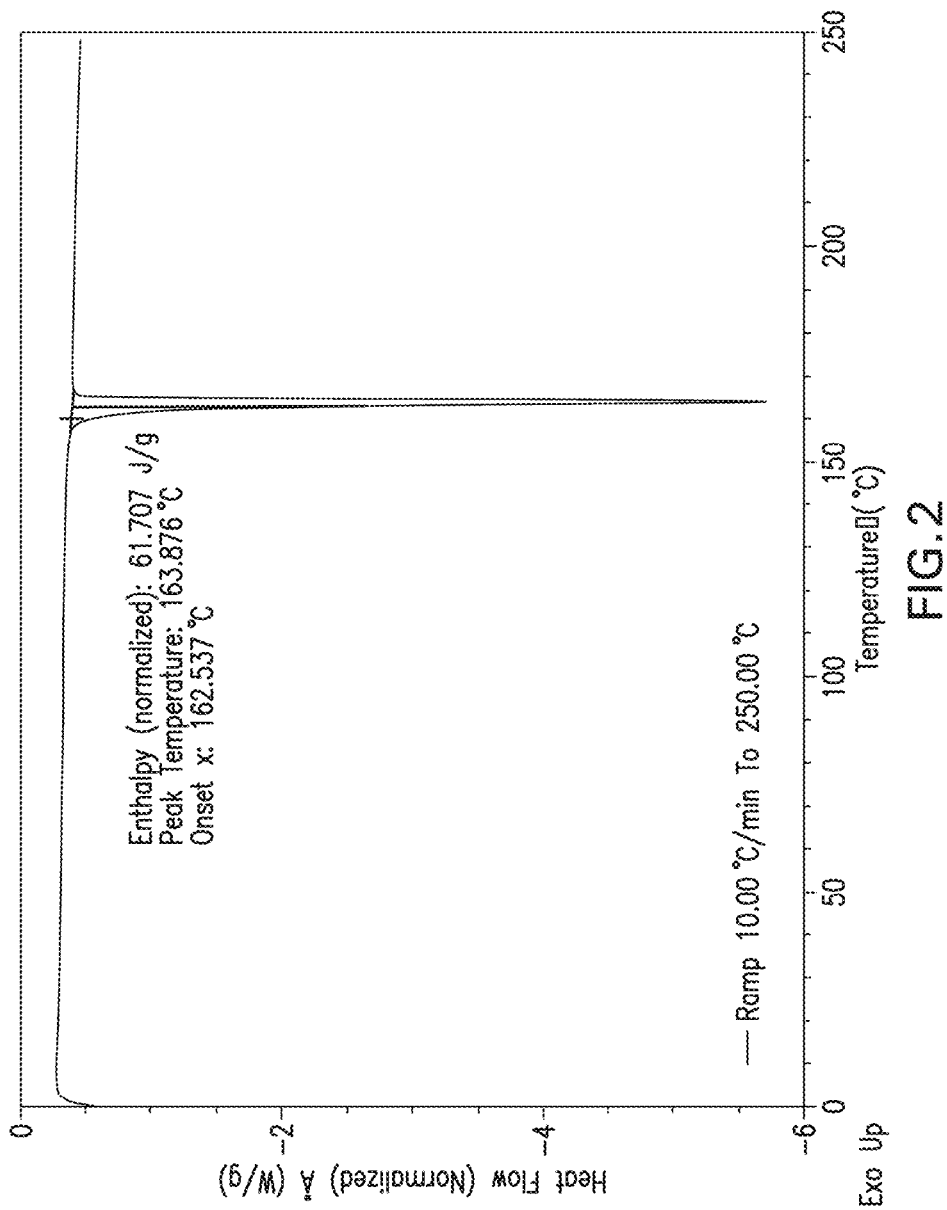
FIG. 2: illustrates a representative differential scanning calorimetry curve (DSC) of Form A of (9-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention. The x-axis shows the temperature in degree Celsius (° C.), the y-axis shows the heat flow rate in Watt per gram (W/g) with endothermic peaks going up.

In one embodiment, the present invention relates to a crystalline form of (S)-1'-chloro-8-(difluoromethoxy)-8',8'-difluoro-6-(trifluoromethyl)-7',8'-dihydro-3H,6'H-spiro [imidazo[1,2-a]pyridine-2,5'-isoquinoline] (Form A) characterized by having a DSC curve as shown in FIG. 2 comprising an endothermic peak, preferably a single endothermic peak, having an onset temperature of about 162.5° C., when measured at a heating rate of 10 K/min.

Figure 6:
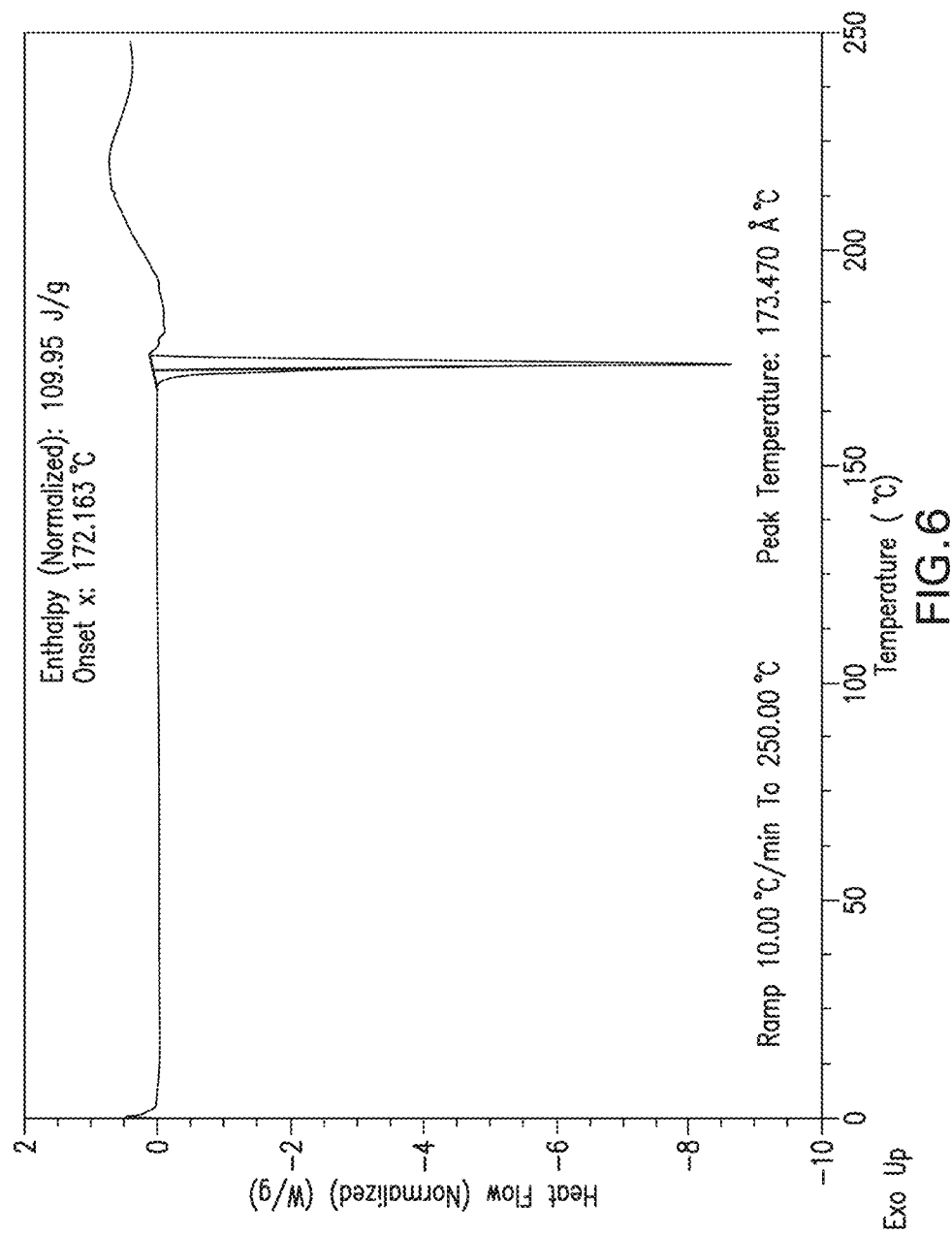
FIG. 6: illustrates a representative differential scanning calorimetry curve (DSC) of Form A of (S)-1'-chloro-8-(difluoromethoxy)-8',8'-difluoro-6-(trifluoromethyl)-7',8'-dihydro-3H, 6'H-spiro[imidazo[1,2-a]pyridine-2,5'-isoquinoline] fumarate of the present invention. The x-axis shows the temperature in degree Celsius (° C.), the y-axis shows the heat flow rate in Watt per gram (W/g) with endothermic peaks going up.

In a further embodiment, the present invention relates to a crystalline form of (S)-1'-chloro-8-(difluoromethoxy)-8',8'-difluoro-6-(trifluoromethyl)-7',8'-dihydro-3H,6'H-spiro [imidazo[1,2-a]pyridine-2,5'-isoquinoline] fumarate (Form A) characterized by having a DSC curve as shown in FIG. 6 comprising an endothermic peak, preferably a single endothermic peak, having a peak maximum temperature of about 172.2° C., when measured a heating rate of 10 K/min.

In still another embodiment, the invention relates to a crystalline form of (S)-1'-chloro-8-(difluoromethoxy)-8',8'-difluoro-6-(trifluoromethyl)-7',8'-dihydro-3H,6'H-spiro [imidazo[1,2-a]pyridine-2,5'-isoquinoline] (Form A) characterized by having a melting point onset temperature of (163.9±X)° C., when measured with DSC at a heating rate of 10 K/min.

In still another embodiment, the invention relates to a crystalline form of (S)-1'-chloro-8-(difluoromethoxy)-8',8'-difluoro-6-(trifluoromethyl)-7',8'-dihydro-3H,6'H-spiro

[imidazo[1,2-a]pyridine-2,5'-isoquinoline] fumarate (Form A) characterized by having a melting point peak maximum temperature of about 173.5° C., when measured with DSC at a heating rate of 10 K/min.

Exemplification of TGA Embodiments

Figure 3:
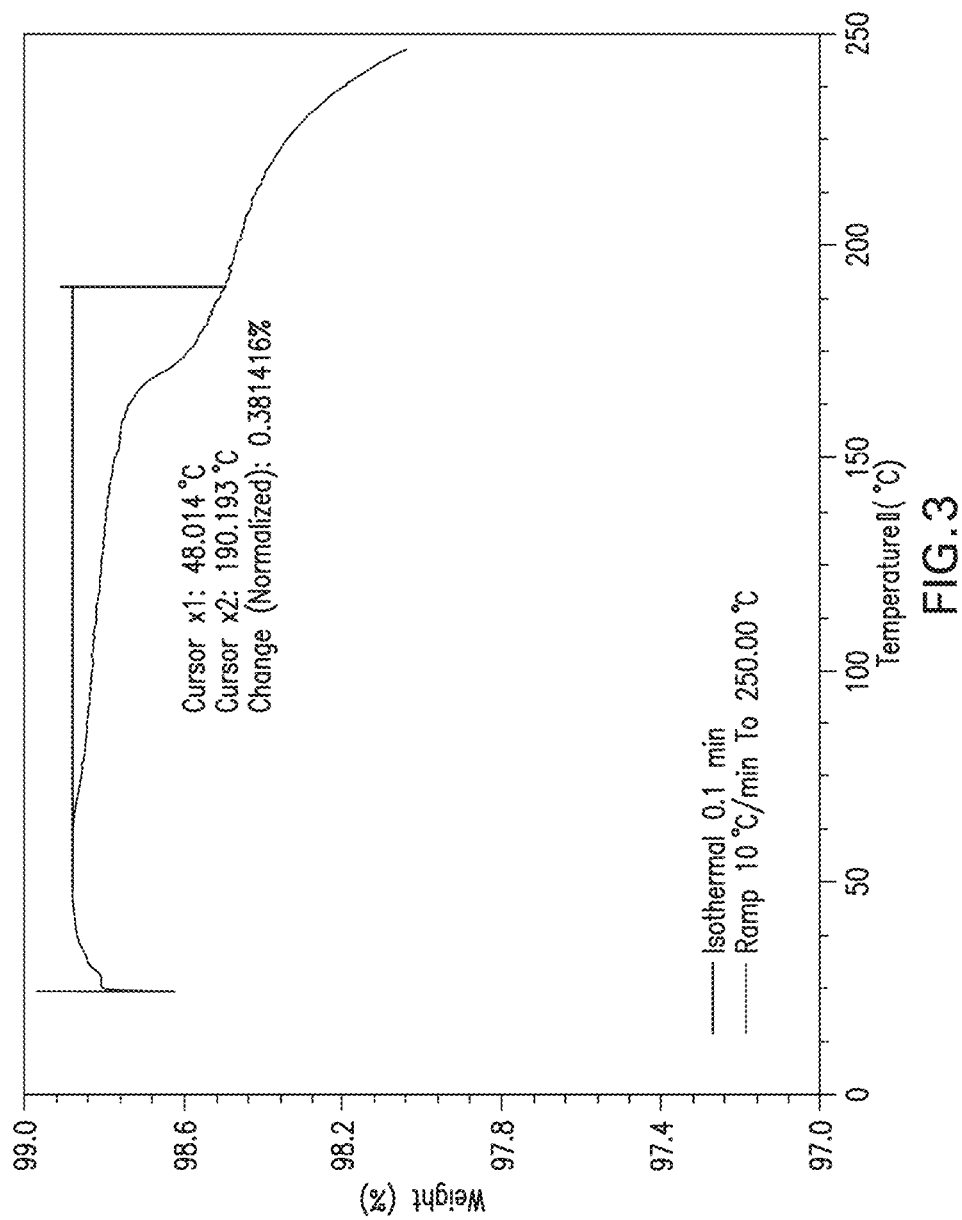
FIG. 3: illustrates a representative thermogravimetric analysis (TGA) of crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention. The x-axis shows the temperature in degree Celsius (° C.), the y-axis shows the mass (loss) of the sample in weight percent (w-%).

In one embodiment, the present invention relates to a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Form A)) characterized by having a TGA curve as shown in FIG. 3 showing a mass loss of not more than 0.4 w-% based on the weight of the crystalline form, when heated from 10 to 250° C. at a rate of 10 K/min.

Figure 7:
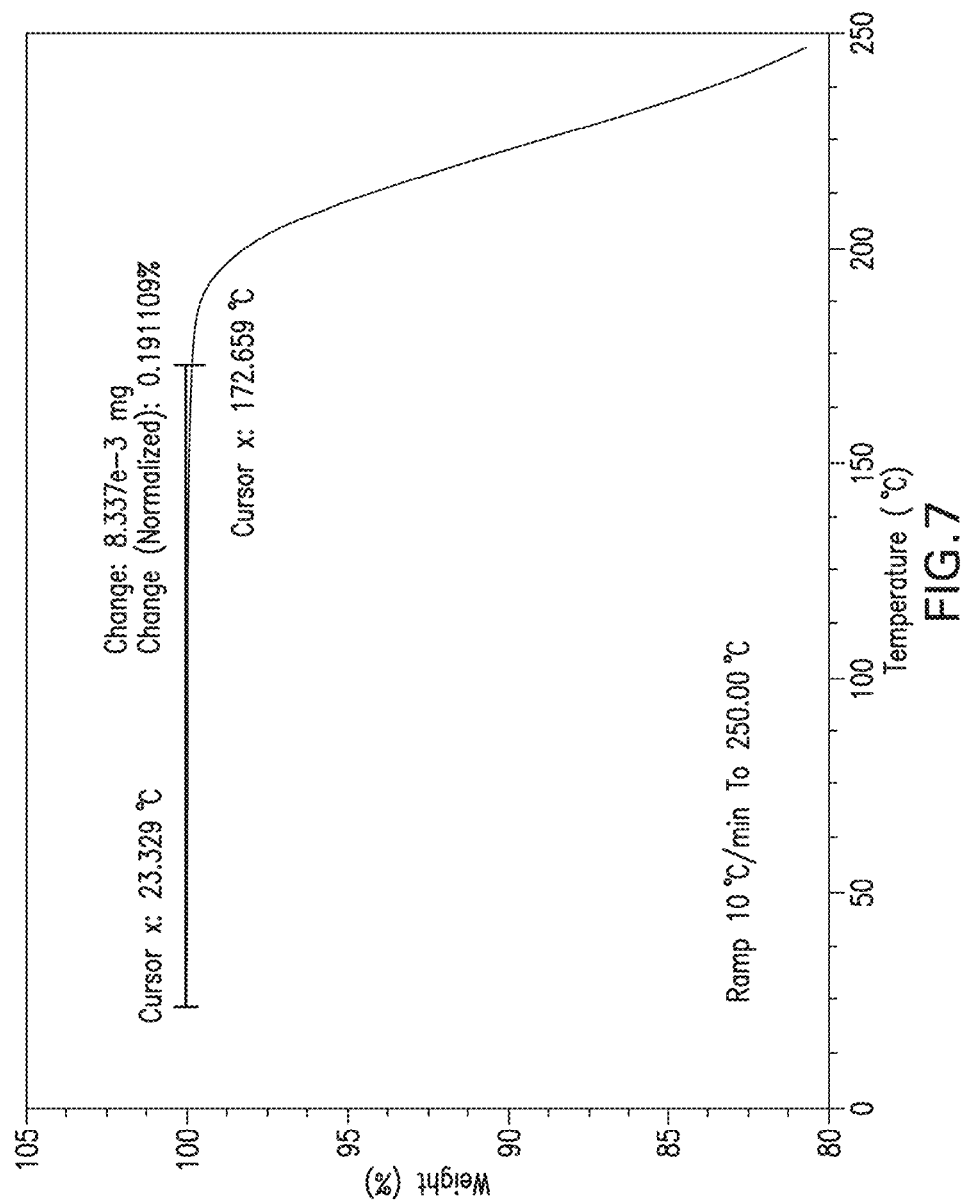
FIG. 7: illustrates a representative thermogravimetric analysis (TGA) of crystalline Form A of (5)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate of the present invention. The x-axis shows the temperature in degree Celsius (° C.), the y-axis shows the mass (loss) of the sample in weight percent (w-%).

In another embodiment, the present invention relates to a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate (Form A)) characterized by having a TGA curve as shown in FIG. 7 showing a mass loss of not more than 0.2 w-% based on the weight of the crystalline form, when heated from 10 to 250° C. at a rate of 10 K/min.

Exemplification of DVS Embodiments

Figure 4:
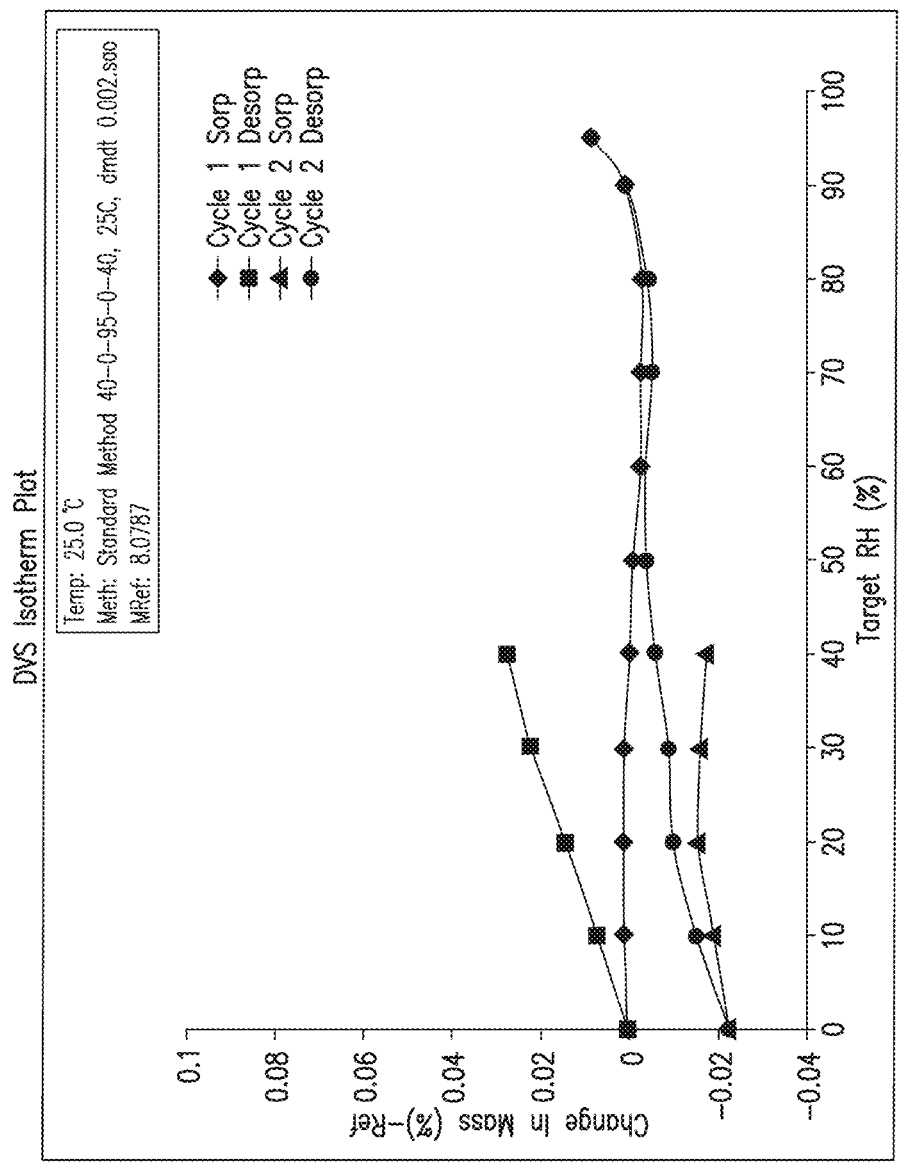
FIG. 4: illustrates a representative dynamic vapor sorption analysis (DVS) of crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention in the range of from 0 to 95% relative humidity. The x-axis displays the relative humidity in percent (%) measured at a temperature of (25.0±0.1) ° C., the y-axis displays the equilibrium mass change in weight percent (w-%). The sorption cycle is marked by triangles, whereas the desorption cycle is marked by squares. The values are displayed as uncorrected values.

In one embodiment, the present invention relates to a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Form A) characterized by showing a mass change of not more than 0.05 w-% based on the weight of the crystalline form, when measured with DVS as shown in FIG. 4 at a relative humidity in the range of from 0 to 95% and a temperature of about 25° C.

Figure 8:
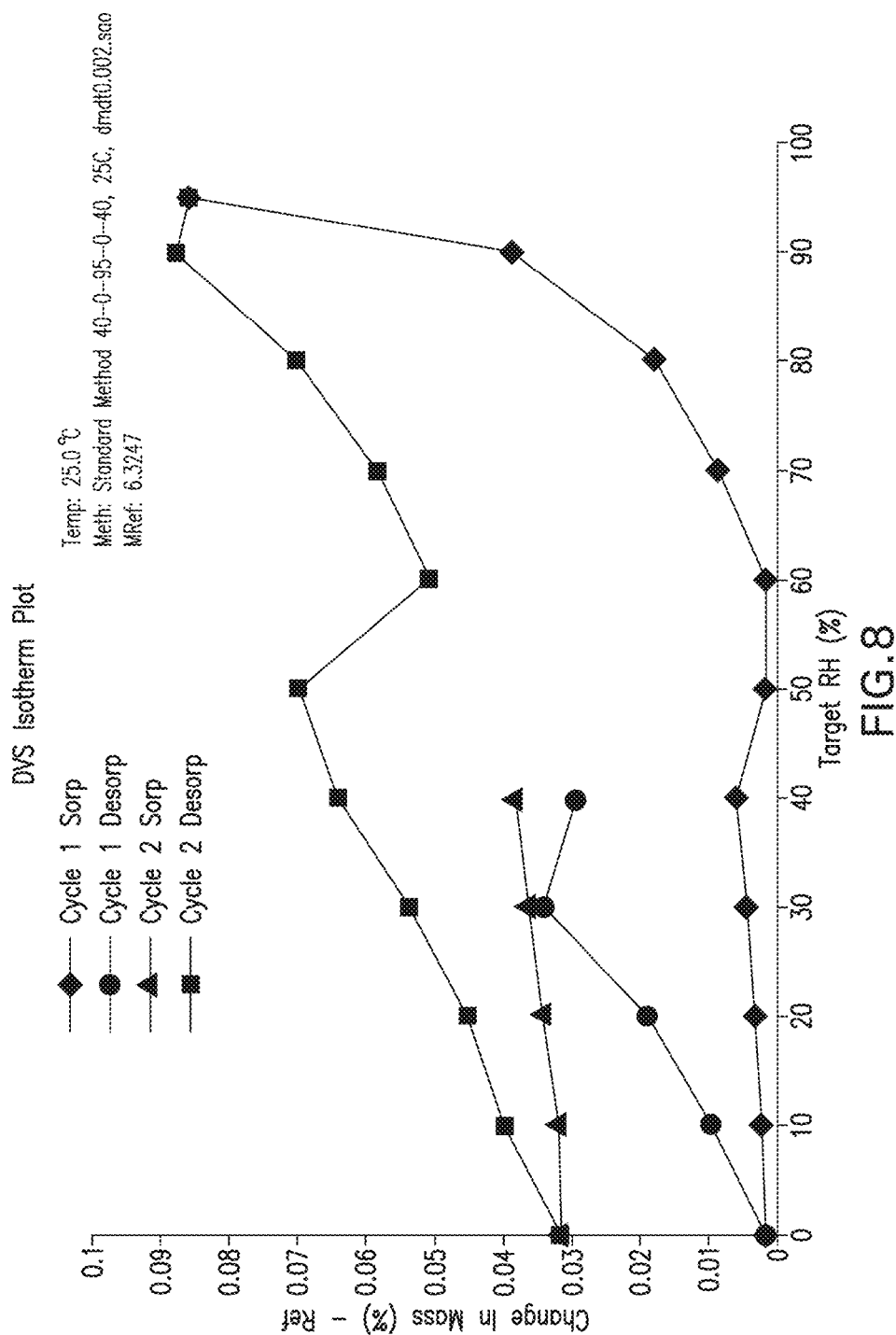
FIG. 8: illustrates a representative dynamic vapor sorption analysis (DVS) of crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate of the present invention in the range of from 0 to 95% relative humidity. The x-axis displays the relative humidity in percent (%) measured at a temperature of (25.0±0.1) ° C., the y-axis displays the equilibrium mass change in weight percent (w-%). The sorption cycle is marked by triangles, whereas the desorption cycle is marked by squares. The values are displayed as uncorrected values.

In another embodiment, the present invention relates to a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate] (Form A) characterized by showing a mass change of not more than 0.1 w-% based on the weight of the crystalline form, when measured with DVS as shown in FIG. 8 at a relative humidity in the range of from 0 to 95% and a temperature of about 25° C.

Exemplification of Further Embodiments

The following non-limiting example is illustrative for the disclosure and is not to be construed as to be in any way limiting for the scope of the invention.

Example 120: Fumarate salt of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline]

About 1107 mg of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] and 435 mg of fumaric acid were added into 8.5 mL of ethanol, heated to 50 C with magnetic stirring overnight; Cooled to r.t. and kept stirring for 3 hours; The suspension was then filtrated. About 1.2 g of white powder was obtained after drying at 50° C. under vacuum.

X-Ray Diffraction:

The X-ray powder diffraction (XRPD) patterns described herein were recorded on a Bruker D8 Advance diffractometer using CuKα radiation (wavelength 0.15406 nm). The XRPD pattern was recorded between 2° and 40° (2-theta).

One of ordinary skill in the art will appreciate that an XRPD pattern may be obtained with a measurement error that is dependent upon the measurement conditions employed. In particular, it is generally known that intensities in an XRPD pattern may fluctuate depending upon measurement conditions employed. It should be further understood that relative intensities may also vary depending upon experimental conditions and wavelength of X-ray radiation used. The agreement in the 2-theta-diffraction angles between specimen and reference is within 0.2° for the same crystal form and such degree of measurement error should be taken into account as pertaining to the aforementioned diffraction angles. Consequently, it is to be understood that the crystal forms of the instant invention are not limited to the crystal forms that provide X-ray diffraction patterns completely identical to the XRPD patterns depicted in the accompanying Figures disclosed herein. Any crystal forms that provide XRPD patterns substantially identical to those disclosed in the accompanying Figures fall within the scope of the present invention. The ability to ascertain substantial identities of XRPD patterns is within the purview of one of ordinary skill in the art.

A representative diffractogram of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] is displayed in FIG. 1 herein. The corresponding reflection list is provided in Table 1 below.

TABLE 1

XRPD reflection positions and corresponding relative intensities of crystalline form A of (S)-1'-chloro-8-(difluoromethoxy)-8', 8'-difluoro-6-(trifluoromethyl)-7',8'-dihydro-3H, 6'H-spiro[imidazo[1,2-a]pyridine-2,5'-isoquinoline] in the range of from 2 to 30° 2-Theta; a typical precision of the 2-Theta values is in the range of ± 0.2° 2-Theta, preferably of ± 0.1° 2-Theta. Differential Scanning Calorimetry (DSC):

| Index | Angle deg (2-theta) | d value Å | Rel. Intensity(%) | Relevant peaks |
|---|---|---|---|---|
| 1 | 9.7 | 9.10 | 7 (low) | 1 |
| 2 | 10.3 | 8.61 | 7 (low) | 8 |
| 3 | 13.4 | 6.62 | 5 (low) | 4 |
| 4 | 14.4 | 6.14 | 5 (low) | 9 |
| 5 | 18.4 | 4.82 | 26 (medium) | 2 |
| 6 | 19.4 | 4.56 | 100 (high) | 3 |
| 7 | 20.7 | 4.29 | 14 (medium) | 5 |
| 8 | 22.1 | 4.02 | 11 (low) | 7 |
| 9 | 24.2 | 3.67 | 18 (medium) | 6 |

The DSC instrument used to test the crystalline forms was a TA Discovery. The instrument was programmed to heat at 10° C. per minute in the temperature range between 30° C. and 300° C. under nitrogen flow at 50 mL/min.

A representative DSC curve of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] is displayed in FIG. 2 and shows a single endotherm with an onset temperature of about 162.5° C. and a peak temperature of about 163.9° C.

Thermogravimetric Method:

The TGA instruments used to test the crystalline forms was a TA Discovery. Samples of 2 to 10 milligrams were analyzed at a heating rate of 10° C. per minute in the temperature range between 30° C. and about 300° C.

A representative TGA curve of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] is displayed in FIG. 3 and shows a step from about 48 to 190° C. and a mass loss of not more than 0.4 w-% based on the weight of the crystalline form.

Dynamic Vapor Sorption (DVS) Data:

Dynamic vapor sorption was performed using a SMS Advantage system. Approximately 10 mg of sample was subjected to varying humidities between 0% RH and 95% RH at 25° C. Evaluation was performed using the system software.

FIG. 4 shows the equilibrium mass changes (delta m in weight % on the y-axis) of crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] during the sorption cycle (marked by triangles) from 0% to 40% RH, as well as during the desorption cycle (marked by squares) from 40 to 0% RH (on the x-axis). The mass difference between 0 and 95% RH is less than 0.05 weight % and no significant hysteresis between the sorption and desorption curve can be observed. Therefore, crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention can be assigned as being non-hygroscopic.

Characterization of Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline]

X-Ray Diffraction:

The X-ray powder diffraction (XRPD) patterns described herein were recorded on a Bruker D8 Advance diffractometer using CuKα radiation (wavelength 0.15406 nm). The XRPD pattern was recorded between 2° and 40° (2-theta).

A representative diffractogram of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate is displayed in FIG. 5 herein. The corresponding reflection list is provided in Table 2 below.

TABLE 2

XRPD reflection positions and corresponding relative intensities of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate in the range of from 2 to 30° 2-Theta; a typical precision of the 2-Theta values is in the range of ± 0.2° 2-Theta, preferably of ± 0.1° 2-Theta. Differential Scanning Calorimetry (DSC):

| Index | Angle deg (2-theta) | d value Å | Rel. Intensity(%) | Relevant peaks |
|---|---|---|---|---|
| 1 | 6.2 | 14.28 | 11 (low) | 2 |
| 2 | 10.9 | 8.11 | 62 (high) | 4 |
| 3 | 12.9 | 6.84 | 71 (high) | 7 |
| 4 | 16.1 | 5.50 | 43 (medium) | 8 |
| 5 | 18.5 | 4.79 | 23 (medium) | 5 |
| 6 | 20.9 | 4.25 | 66 (high) | 3 |
| 7 | 22.8 | 3.89 | 81 (high) | 6 |
| 8 | 24.9 | 3.59 | 100 (high) | 1 |

The DSC instrument used to test the crystalline forms was a TA Discovery. The instrument was programmed to heat at 10° C. per minute in the temperature range between 30° C. and 300° C. under nitrogen flow at 50 mL/min.

A representative DSC curve of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate is displayed in FIG. 6 and shows a single endotherm with an onset temperature of about 172.2° C. and a peak temperature of about 173.5° C.

Thermogravimetric Method:

The TGA instruments used to test the crystalline forms was a TA Discovery. Samples of 2 to 10 milligrams were analyzed at a heating rate of 10° C. per minute in the temperature range between 30° C. and about 300° C.

A representative TGA curve of crystalline form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate is displayed in FIG. 7 and shows a step from about 23 to 173° C. and a mass loss of not more than 0.2 w-% based on the weight of the crystalline form.

Dynamic Vapor Sorption (DVS) Data:

Dynamic vapor sorption was performed using a SMS Advantage system. Approximately 10 mg of sample was subjected to varying humidities between 0% RH and 95% RH at 25° C. Evaluation was performed using the system software.

FIG. 8 shows the equilibrium mass changes (delta m in weight % on the y-axis) of crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate during the sorption cycle (marked by triangles) from 0% to 40% RH, as well as during the desorption cycle (marked by squares) from 40 to 0% RH (on the x-axis). The mass difference between 0 and 95% RH is less than 0.1 weight % and no significant hysteresis between the sorption and desorption curve can be observed. Therefore, crystalline Form A of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] of the present invention can be assigned as being non-hygroscopic.

In Vitro SPA with the PAS-B Domain of HIF2α

The scintillation proximal assay (SPA) was based on a competition binding assay with the radio-ligand N-(3-chloro-5-fluorophenyl-4-t)-4-nitrobenzo[c][1,2,5]oxadiazol-7-t-5-amine (1.8 TBq/mmol, affinity of the non-labeled ligand, $IC_{50}$=82±18 nM, n=3). Assays were run using 384-well plates (781207/Greiner) in which one column was designated as the high signal control, and contained DMSO with no compound, and another column was designated as the low signal control, and contained no protein. Compounds (tested using a 14-point dose response with 3-fold compound dilutions from 100 µM to 60 pM) were pre-incubated for 30 min with HIF2α PAS-B domain (236-350, biotinylated on the N-terminus), before addition of the radio-ligand. Final concentrations in an assay volume of 60 µL were 5 nM HIF2α, and 25 nM radio-ligand. The assay buffer contained 50 mM Tris-HCl pH7 (Sigma), 20 mM NaCl (Fluka), 0.02% BSA (Sigma), 0.005% Triton X-100 (Pierce) and 1 mM DTT (Fluka). After a 30 min incubation period, 5 µL Streptavidin PVT SPA Beads (Perkin Elmer) at 1.2 mg/mL, diluted in the buffer, were added. After a 60 min incubation, plates were centrifuged and read on a Topcount NXT 384 (Packard). Duplicates were made using 2 different plates, and mean $IC_{50}$ values were determined using the Helios system based on the following equation: % inhibition=[(high control−sample)/(high control−low control)]× 100. The $IC_{50}$ values in the Tabulated HIF2α activities are the average from 1 to 10 independent experiments.

Purification of the HIF2α PAS-B Domain 236-350, Biotinylated on the N-Terminus

Human HIF2α (Uniprot Q99814) amino acids D236 N350 were expressed from plasmid pLAF727 (generated in-house) in E. coli Tuner (DE3) in the presence of plasmid pBirA (co-expression of biotin ligase) in Terrific Broth (TB) medium substituted with antibiotics, 200 μM biotin, 8 mg/mL L-arabinose, and 0.1 mM isopropyl β-D-1-thiogalactopyranoside for 18 hr at 20° C. Cells were harvested by centrifugation and deep-frozen until further processing. Cells were thawed and resuspended in Buffer A (50 mM $NaH_2PO_4$ pH 8.0, 300 mM NaCl, 20 mM imidazole, Benzonase® 25 U/mL (Novagen)) and incubated for 20 min at 4° C. Upon addition of 4-(2-aminoethyl)benzenesulfonyl fluoride (0.5 mM final) the cells were lysed with an Avestin homogenizer at about 20000 psi (5 bar nitrogen) and insoluble debris removed by centrifugation. Immobilized metal affinity chromatography was performed with a His-Trap HP 5 mL column (GE) with Buffer A and eluted with a gradient over 10 column volumes of Buffer A substituted with 300 mM imidazole. Eluted protein fractions were analyzed by Novex NuPage 4-12% PAGE and the affinity tag protein removed by HRV3C protease cleavage (produced in-house) during incubation for 18 hr at 4° C. In a final polishing step, the protein was loaded on a HiLoad Superdex 75 26/60 size-exclusion column pre-equilibrated with SEC-buffer (50 mM Tris-pH 7.4, 150 mM NaCl, 1 mM 3,3',3''-phosphanetriyltripropanoic acid (TCEP), 10% Glycerol). Positive fractions were determined by PAGE (Novex NuPage 4-12% BisTris) analysis. The correct mass was determined by RP LC-MS, and indicated complete biotinylation of the protein.

N-(3-chloro-5-fluorophenyl-4-t)-4-nitrobenzo[c][1,2,5]oxadiazol-7-t-5-amine

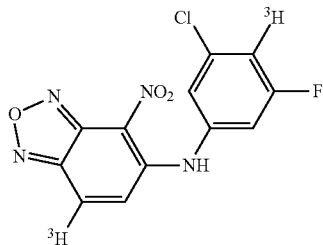 [SMILES: [3H]c1c(F)cc(Nc2cc([3H])c3nonc3c2[N+](=O)[O-])cc1Cl]

Step 1: 7-bromo-N-(4-bromo-3-chloro-5-fluorophenyl)-4-nitrobenzo[c][1,2,5]oxadiazol-5-amine 5,7-Dibromo-4-nitrobenzo[c][1,2,5]oxadiazole (prepared as described in *J. Med. Chem.* 1974, 17, 203-206, 420 mg, 1.2 mmol), 4-bromo-3-chloro-5-fluoroaniline (prepared as described in WO 2012/143599, 302 mg, 1.3 mmol) and DMF (620 μL) were combined at RT and heated at 90° C. under an argon atmosphere for 4 hr. MeOH (15 mL) was added to the cooled RM and the mixture stirred at RT for 15 min, filtered, washing with MeOH, to give an orange crystalline solid. The solid was then suspended in MeOH (6 mL) and refluxed for 2 hr with stirring, cooled to RT, filtered, washing with MeOH, to give the title compound after drying as an orange solid.

$^1$H NMR (400 MHz, DMSO-$d_6$) δ 11.52 (s, 1H), 7.85 (s, 1H), 7.65-7.62 (m, 1H), 7.58-7.54 (m, 1H).

Step 2: N-(3-chloro-5-fluorophenyl-4-t)-4-nitrobenzo[c][1,2,5]oxadiazol-7-t-5-amine 7-bromo-N-(4-bromo-3-chloro-5-fluorophenyl)-4-nitrobenzo[c][1,2,5]oxadiazol-5-amine (Step 1, 6.86 mg, 14.70 μmol) and Lindlar catalyst (20.63 mg) were suspended in DMF (0.7 mL) and (iPr)$_2$NEt 11.8 μL (8.74 mg; 67.6 μmol) was added. The dark red suspension was degassed three times at the high vacuum manifold and stirred under an atmosphere of tritium gas (9.0 Ci) for 2 hr at RT. The solvent was removed in vacuo, and labile tritium was exchanged by adding of ethanol (1 mL), stirring the solution, and removing the solvent again under vacuum. This process was repeated three times. Finally, the well dried solid was extracted with 5 ml of ethanol and the suspension was filtered through a 0.2 μm nylon membrane, obtaining a clear, dark red solution. The activity of the crude product was 281 mCi. The radiochemical purity was determined to 23% (HPLC 22). Purification of 250 mCi (9.25 GBq) was carried out by HPLC (RP-HPLC 6). The product containing fractions were treated with aq. $NaHCO_3$ (5%) and the volume was partially reduced using a rotary evaporator. The product was captured with a Phenomenex StrataX cartridge (3 mL, 100 mg), and then eluted with 10 mL of ethanol. The extract contained the title compound with an activity of 41.6 mCi and a radiochemical purity of >99%. The specific activity was determined to be 38.9 Ci/mmol.

Preparation of Compound Solutions for Cellular Assays

Stock solutions of compounds were prepared at a concentration of 10 mM in DMSO and stored at 4° C. Where necessary to afford a full dose-response curve, the stock solutions were pre-diluted in DMSO to 1,000-fold the desired reduced start concentration. On the day after cell seeding, eleven 2-fold serial dilutions of each compound were dispensed directly into the cell assay plates using either HP 300D non-contact Digital Dispenser (TECAN) or a ATS100 acoustic dispenser (EDC Biosystems).

Cellular iScript Assay for HIF2α

Compound-mediated modulation of the HIF2α-regulated expression of the endogenous target gene hEGLN3 (OMIM: 606426), as well as beta-actin (OMIM: 102630) as a housekeeping control, was assess in 786-O cells (RRID CVCL_1051) using a quantitative RT-PCR approach. In short, 786-O cells were maintained in growth medium composed of DMEM (GIBCO #11995-065), 2 mM L-Glutamine (BioConcept #5-10K50-H), 1× Penicillin/Streptomycin (BioConcept #4-01F00-H), 10% fetal calf serum (Gibco #A31608-01), 1 mM Sodium pyruvate (BioConcept #5-60F00-H). Cells were seeded at 1,000 cells/20 μL/well into white-wall, clear-bottom 384-well plates (Greiner #781098) and incubated over night at 37° C. prior to addition of serial compound dilutions as described above. Following incubation for 48 hours at 37° C., medium supernatant was discarded and the plate blotted dry by inverting on a tissue. The same procedure was repeated following one wash with 20 μL phosphate-buffered saline. Following addition of 25 μL/well iScript sample preparation reagent (BioRad #170-8899) using a 16-channel Matrix pipette, the plate was incubated for 2 min at room temperature. 20 μL lysate supernatant was then removed and transferred to a new 384 well plate (Costar #3656) and diluted 1:3 by adding 5 μL of the lysate to 10 μL $H_2O$ using a Bravo liquid handler (Agilent). 2 μL of the diluted lysate was added to the 8 μL of a mastermix containing 5 μL iTaq Universal Probes One-step kit (BioRad #172-5141), 0.25 μL iScript reverse transcription supermix (BioRad #1708840), 0.25 μL 40×HEX-ZEN-labeled TaqMan probe for beta-actin (IDT

Hs.PT.39a.22214847: Probe 5' HEX-TCA TCC ATG/ZEN/ GTG AGC TGG CGG-3' (SEQ ID NO: 2) Iowa Black FQ, Primer 1: ACA GAG CCT CGC CTT TG (SEQ ID NO: 3); Primer 2: CCT TGC ACA TGC CGG (SEQ ID NO: 4) AG), 0.25 µL, 40×FAM-ZEN-labeled TaqMan probe for hEGLN3 (IDT #Hs.PT.58.189348: Probe 5' 6-FAM-TTT GGC TTC/ ZEN/TGC CCT TTC TTC AGC-3' (SEQ ID NO: 5) Iowa Black FQ, Primer 1: CAC GGT CAG TCT TCA GTG AG (SEQ ID NO: 6); Primer 2: CGC AAC CAG ATA TGC TAT GAC T (SEQ ID NO: 7)), 2.25 µL RNase-free water, prelaid in a 384 well plate (ABI #4309849) using a 16-channel Matrix pipette. The plate was sealed with a PCR-compatible optical film (MicroAmp, ABI #4360954) and centrifuged (1500 rpm, 5 min, +4° C.) to collect all reagents in the bottom of the well and to remove bubbles. The plate content was amplified on a 7900HT thermal cycler (ABI) using the following conditions: Step 1: 50° C. for 10 min, Step 2: 95° C. for 3 min, Step 3 (40×): 95° C. for 15 s, 60° C. for 1 min. ROX (reaction volume 10 µL) was used as a passive reference. Data were collected with manual adjustment of the Ct threshold (beta-actin: 0.046, hEGLN3: 0.06) and were analyzed using the $2^{\wedge}(-\Delta\Delta Ct)$ method. Thus, for each sample, the following values were calculated: $2^{\wedge}(-Ct)a$ for beta-actin, $2^{\wedge}(-Ct)e$ for EGLN3, and $2^{\wedge}(-\Delta Ct)$ calculated as $(2^{\wedge}(-Ct)e/2^{\wedge}(-Ct)a)$. The mean $2^{\wedge}(-\Delta Ct)$ as well as the corresponding standard deviation was calculated for each sample. Taking the DMSO-treated sample as a reference, the $2^{\wedge}(-\Delta\Delta Ct)$ for each sample was calculated as follows: $2^{\wedge}(-\Delta\Delta Ct)=2^{\wedge}(-\Delta Ct)sample/(2^{\wedge}(-\Delta Ct)DMSO)$. After calculating differential expression as $2^{\wedge}(-\Delta\Delta Ct)$ for each sample, it was then expressed as a percentage (×100) to obtain a dose-response curve in % of DMSO control and IC50s were calculated using a four-parametric fit model.

In Vitro Cellular Hypoxia Response Element (HRE) Reporter Gene Assay (RGA) for HIF1α and HIF2α

The ability of compounds to inhibit HIF2α- and HIF1α-dependent transcription was assessed in 786-O-HRE-Luc and RCC4-HRE-Luc cells, respectively. The putative unselective inhibition of firefly luciferase activity or expression was assessed in 786-O-UB6-Luc and RCC4-UB6-Luc cells, respectively. The reporter lines were generated as follows: 786-O (RRID: CVCL_1051) and RCC4 (RRID: CVCL_0498) clear cell renal carcinoma cell lines were obtained from ATCC and Celeste Simon (University of Pennsylvania), respectively. Either cell line was transduced with a lentiviral vector in which the expression of a PEST-destabilized version of firefly-luciferase is under the control of either a minimal promoter coupled to four copies of a minimal hypoxia response element (HRE) sequence (pLenti 4×HRE Luc PEST), or a promoter from the house-keeping UBC gene (pLenti UB6 Luc PEST). In short, for the construction of the pLenti 4×HRE Luc PEST vector, 4×HRE DNA oligonucleotides were synthesized, annealed and cloned into pGL4.27 plasmid vector (Promega) predigested with NheI and HindIII restriction enzymes. The sequence of the two DNA oligonucleotides was as follows: NheI 4×HRE HindIII FWD: ctagcctgcacgtactgcacgtactgcacgtactgcacgtacgctcgcttcgaa (SEQ ID NO: 8); NheI 4×HRE HindIII REV agctttcgaagcgagcgtacgtgcagtacgtgcagtacgtgcagtacgtgcagg (SEQ ID NO: 9). The 4×HRE Luc PEST fragment was then PCRed from this plasmid with restriction enzyme sites NheI and XhoI at the two ends, and inserted into pLenti6/BLOCK iT DEST (Thermo Fisher Scientific) predigested with NheI and XhoI restriction enzymes. For the construction of the pLenti UB6 Luc PEST vector, the Luc PEST sequence was PCRed from pGL4.27 (Promega) using EcoRV and XhoI restriction enzymes at the two ends, and inserted into pLenti6/UBC/V5/DEST (Thermo Fisher Scientific) predigested with the same enzymes. 786-O and RCC4 cells (300,000 per well of a 6 well plate) were infected in the presence of 10 µg/ml polybrene with lentivirus harvested two days after transfection of HEK293-FT (ThermoFisher Scientific #R70007) cells (80% confluent in a 100 cm² dish) with a mix of 1.5 ml OptiMEM (ThermoFisher Scientific #31985062) containing 3 µg of the desired plasmids and 9 µl of ViralPower Packaging mix (ThermoFisher Scientific #K497500), and 1.5 ml OptiMEM containing 36 µl Lipofectamine 2000 (ThermoFisher Scientific #11668019). Successfully infected cells were selected using blasticidin (Gibco #A11139-03) at a final concentration of 5 µg/ml. The resulting stable cell lines were named 786-O pLenti 4×HRE Luc PEST (short: 786-O-HRE-Luc), 786-O pLenti UB6 Luc PEST (short: 786-O-UB6-Luc), RCC4 pLenti 4×HRE Luc PEST (short: RCC4-HRE-Luc) and RCC4 pLenti UB6 Luc PEST (short: RCC4-UB6-Luc). All 4 cell lines were maintained in growth medium composed of DMEM (GIBCO #11995-065), 2 mM L-Glutamine (BioConcept #5-10K50-H), 10% fetal calf serum (Gibco #A31608-01), 1× Penicillin/Streptomycin (BioConcept #4-01F00-H), 1 mM Sodium pyruvate (BioConcept #5-60F00-H) and 5 µg/ml blasticidin (Gibco #A11139-03) at 37° C. in a humidified 5% $CO_2$ incubator.

For the reporter gene assay, the individual cell lines were seeded at 2,500 cells/20 µL/well into white-wall, clear-bottom 384-well plates (Greiner #781098) and incubated over night at 37° C. prior to addition of serial compound dilutions as described above. Following incubation for 24 hours at 37° C., compound-mediated modulation of reporter-gene activity was quantified 5 min after addition of 20 µL, BrightGlo (Promega, Cat #E2620), by measuring luminescence intensity on a M1000 multi-mode plate-reader (TECAN) with Integration times of 100 ms. For data analysis, the assay background value determined in wells containing medium, but no cells, was subtracted from all data points. Dose-dependent compound effects were expressed as % of vehicle-treated control (luminescence signal produced by cells receiving DMSO only) and IC50s calculated using a four-parametric fit model. The concentration of DMSO was normalized to 0.1% in all wells.

| Tabulated in vitro HIF2α activities | | | |
|---|---|---|---|
| Example | HIF2α SPA $IC_{50}$ (nM) | HIF2α iScript $IC_{50}$ (nM) | HIF2α HRE RGA $IC_{50}$ (nM) |
| 1 | ≤3 | 65 | 232 |
| 2 | 12 | 152 | 1530 |
| 3 | 12 | 187 | >10000 |
| 4 | 9 | 155 | 699 |
| 5 | 9 | 138 | 328 |
| 6 | 8 | 84 | 250 |
| 7 | ≤3 | 32 | 82 |
| 8 | 14 | 198 | 271 |
| 9 | 15 | 173 | 2210 |
| 10 | 21 | 77 | 207 |
| 11 | ≤3 | 33 | 89 |
| 12 | 8 | 59 | 250 |
| 13 | 5 | 42 | 113 |
| 14 | 9 | 57 | 146 |
| 15 | 16 | 128 | 392 |
| 16 | ≤6 | 43 | 372 |
| 17 | 62 | 199 | 466 |
| 18 | 6 | 37 | 92 |
| 19 | 36 | 144 | 446 |
| 20 | 15 | 155 | 892 |

-continued

Tabulated in vitro HIF2α activities

| Example | HIF2α SPA IC$_{50}$ (nM) | HIF2α iScript IC$_{50}$ (nM) | HIF2α HRE RGA IC$_{50}$ (nM) |
|---|---|---|---|
| 21 | 36 | 121 | 1100 |
| 22 | 8 | 37 | 185 |
| 23 | 4 | 30 | 92 |
| 24 | 15 | 151 | 364 |
| 25 | 19 | 83 | 202 |
| 26 | ≤6 | 34 | 144 |
| 27 | 12 | 102 | 188 |
| 28 | 5 | 66 | 169 |
| 29 | 8 | 93 | 1310 |
| 30 | 27 | 129 | 1350 |
| 31 | 9 | 37 | 246 |
| 32 | 13 | 78 | 861 |
| 33 | 17 | 78 | 547 |
| 34 | 23 | 197 | 1430 |
| 35 | 9 | 83 | 267 |
| 36 | 6 | 73 | 147 |
| 37 | 25 | 89 | 308 |
| 38 | 12 | 84 | 322 |
| 39 | ≤6 | 49 | 251 |
| 40 | 6 | 50 | 190 |
| 41 | 11 | 54 | 283 |
| 42 | 8 | 72 | 96 |
| 43 | 10 | 59 | 180 |
| 44 | 13 | 65 | 112 |
| 45 | ≤10 | 85 | 313 |
| 46 | 13 | 50 | 68 |
| 47 | 11 | 82 | 694 |
| 48 | ≤10 | 63 | 974 |
| 49 | 12 | 173 | 979 |
| 50 | ≤10 | 61 | 153 |
| 51 | 9 | 81 | 509 |
| 52 | 11 | 87 | 416 |
| 53 | 14 | 184 | 839 |
| 54 | 33 | 85 | 317 |
| 55 | 9 | 115 | 7650 |
| 56 | 13 | 164 | 6660 |
| 57 | 12 | 62 | 196 |
| 58 | 8 | 173 | 183 |
| 59 | 12 | 55 | 73 |
| 60 | 6 | 27 | 65 |
| 61 | 17 | 51 | 143 |
| 62 | 13 | 102 | 484 |
| 63 | 11 | 197 | 465 |
| 64 | 10 | 51 | 236 |
| 65 | ≤3 | 30 | 114 |
| 66 | ≤8 | 47 | 385 |
| 67 | 15 | 57 | 107 |
| 68 | 11 | 111 | 670 |
| 69 | 9 | 44 | 273 |
| 70 | 20 | 96 | 1670 |
| 71 | 20 | 181 | n.d. |
| 72 | 7 | 84 | n.d. |
| 73 | ≤6 | 135 | 542 |
| 74 | ≤10 | 108 | 517 |
| 75 | 76 | 183 | n.d. |
| 76 | 49 | 175 | 777 |
| 77 | ≤3 | 103 | 600 |
| 78 | 8 | 161 | 4230 |
| 79 | 5 | 70 | n.d. |
| 80 | 11 | 106 | 2040 |
| 81 | ≤10 | 57 | 143 |
| 82 | ≤3 | 39 | 155 |
| 83 | 9 | 30 | 27 |
| 84 | 3 | 69 | 184 |
| 85 | 4 | 71 | 204 |
| 86 | 13 | 64 | 179 |
| 87 | n.d. | 159 | n.d. |
| 88 | ≤4 | 32 | 142 |
| 89 | ≤7 | 34 | 220 |
| 90 | 10 | 162 | n.d. |
| 91 | 5 | 30 | 262 |
| 92 | 29 | 153 | 626 |
| 93 | 12 | 178 | n.d. |
| 94 | 33 | 197 | 2260 |
| 95 | 23 | 181 | 271 |
| 96 | 32 | 199 | 518 |
| 97 | 11 | 57 | 193 |
| 98 | 17 | 104 | 120 |
| 99 | 10 | 71 | 286 |
| 100 | 4 | 63 | 106 |
| 101 | 15 | 149 | n.d. |
| 102 | 11 | 48 | 66 |
| 103 | 42 | 109 | 417 |
| 104 | ≤5 | 118 | 624 |
| 105 | 21 | 183 | 248 |
| 106 | 10 | 81 | 148 |
| 107 | 7 | 189 | 807 |
| 108 | 29 | 156 | 692 |
| 109 | 4 | 42 | 90 |
| 110 | n.d. | 35 | n.d. |
| 111 | 9 | 43 | 100 |
| 112 | 7 | 41 | 116 |
| 113 | 4 | 32 | n.d. |
| 114 | 42 | 84 | 356 |
| 115 | ≤3 | 30 | n.d. |
| 116 | 6 | 46 | n.d. |
| 117 | ≤4 | 24 | 281 |
| 118 | 16 | 161 | 1030 |
| 119 | 19 | 97 | 292 | n.d. = not determined

In Vivo HIF2α 786-O and SKRC-01 Tumor Growth Models

Animals and Maintenance Conditions:

Mice:

Experiments were performed in female nude Crl:NU (NCr)-Foxnlnu-Homozygous mice (Charles River, Germany). Animals were 6-9 weeks of age at time of application of the compound. Animals were housed under Optimized Hygienic Conditions in Makrolon type III cages (max. 5 animals per cage) with free access to food and water. They were allowed to adapt for at least 6 days before the experiment was started.

Rats:

Experiments were performed in female nude Rowett rats Hsd: RH-Foxlrnu (Harlan, The Netherlands). Animals were 6-9 weeks of age at time of application of the compound. Animals were housed under Optimized Hygienic Conditions in Makrolon type III cages (max. 2 animals per cage) with free access to food and water. They were allowed to adapt for at least 6 days before the experiment was started.

The rodent species used for the tumor growth models were selected based upon the pharmacokinetic profiles determined for each compound.

Cell line and cell culture: SKRC-01 cells were grown in 500 ml RPMI1640 Medium+5 ml L-Glutamine+50 ml FCS+5 ml Sodium Pyruvate+5 ml HEPES and incubated at 37° C. in a 5% $CO_2$ humidified atmosphere. Cells were harvested with trypsin-EDTA, re-suspended in culture medium (with additives) and counted with a Casy® system. Finally, cells were centrifuged and suspended in ice-cold Hanks' balanced salt solution (HBSS). Cell culture reagents were purchased from BioConcept (Allschwil, Switzerland).

Establishment of tumor xenografts in vivo: SKRC-01 tumors were established by subcutaneous injection of $5\times10^6$ cells in 150 µL HBSS (Sigma #H8264): Matrigel (50%: 50%) into the right flank of nude mice or rats. For the efficacy experiments, treatments were initiated when the mean tumor volumes were approx. 300 mm³ (21 days post tumor cells injection) in mice and approx. 350 mm³ (21 days post tumor cells injection) in rats.

Compound formulation and animal treatment: Compound A was prepared for dosing as homogenous suspensions in 10% Ethanol+30% PEG400+60% water containing 0.5% MC+0.5% Tween 80. Fresh suspensions were prepared once every 7 days and stored at 4° C. Compound A or vehicle were administered orally at a volume of 10 mL/kg.

Evaluation of antitumor activity: Tumor volumes were measured with calipers and determined according to the formula: length×diameter²×π/6. In addition to presenting changes of tumor volumes over the course of treatments, antitumor activity is expressed as T/C % (mean change of tumor volume of treated animals/mean change of tumor volume of control animals)×100. Regressions (%) were calculated according to the formula ((mean tumor volume at end of treatment−mean tumor volume at start of treatment)/mean tumor volume at start of treatment)×100. Body weights and tumor volumes were recorded two to three times a week.

Statistical analysis: Absolute values for primary tumor growth and body weight were used to make the statistical comparisons between groups (one way ANOVA followed by Dunnett's or Tukey's test for normally distributed data; ANOVA on Ranks for not normally distributed data followed by Dunnett's test for equal group size or Dunn's for unequal group size). The significant level was set at p<0.05. All statistical calculations were carried out using SigmaStat.

Evaluation of PD activity: For each tumor sample, tumor powder was prepared by pulverising frozen tissue using a CryoPrep according to the manufacturers instructions (Covaris, Woburn, Massachusetts, USA). An aliquot of 10 mg of tumor powder was transferred on dry ice to a pre-cooled Eppendorf tube and lysed in 700 µL of the RLT buffer supplied in the RNeasy mini kit (Qiagen, #74104 or #74106).

The lysate was first homogenized manually using a syringe and a 20 G or 21 G needle before being used for RNA extraction using the QiaShredder and RNeasy mini protocols (Qiagen, kit #79656 and kit #74104 or #74106 respectively). RNA concentration was measured using the NanoDrop spectrometer (BioTek, ND2000). One microgram of RNA was reverse transcribed with the high capacity cDNA reverse transcription kit (Life Technologies, kit #4368813) and 14 ng of resulting cDNA were used in single-plex TaqMan assay using the Fast Advanced Mastermix in a final volume of 10 µL per reaction. All reactions were done in triplicate in a MicroAmp Optical 384-well reaction plate (Life Technologies, #4309849) sealed with the corresponding optical film (Life Technologies, #4311971) on the ABI 7900HT cycler using the default cycling parameters and ROX as a passive reference.

Primers for the gene of interest, human CCND1 (Integrated DNA technologies, #Hs.PT.56a.3857509, Probe 5'-/56-FAM/TGCCAGGAG/ZEN/CAGATCGAAGCC/3IABkFQ/-3' (SEQ ID NO: 10), Primer 1: 5'-CCAGAGTGATCAAGTGTGACC-3' (SEQ ID NO: 11); Primer 2: 5'-CGCAGGCTTGACTCCAG-3' (SEQ ID NO: 12)) and for the normalizer gene, human beta-actin (ABI, kit #4326315E) were tested for their linear range and equivalent PCR-efficiency and were hence validated for the use of the 2^(−ΔΔCt) calculation method.

Data were collected with manual adjustment of the Ct threshold and they were analyzed using the 2^(−ΔΔCt) method.

Figure 9A:
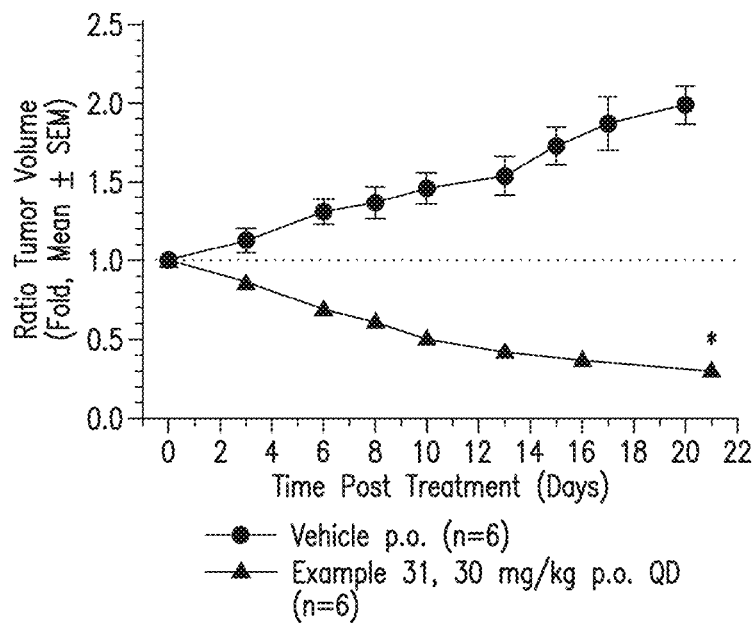
FIG. 9A: illustrates the effect of Example 31 on tumor growth in a 786-O mouse model, wherein *: p<0.05 vs. vehicle controls (ANOVA on ranks and post hoc Tukey test).
Figure 10A:
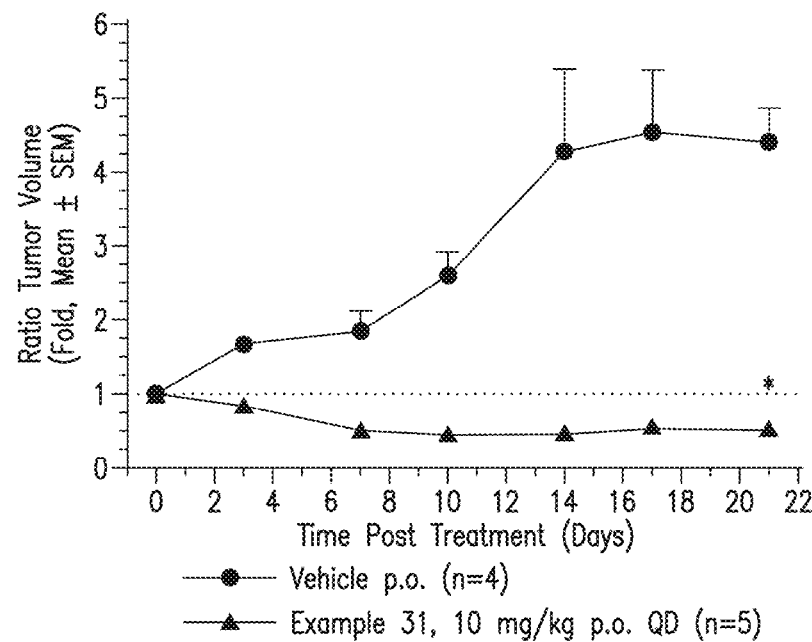
FIG. 10A: illustrates the effect of Example 31 on tumor growth in a SKRC-01 mouse model, wherein *: p<0.05 vs. vehicle controls (ANOVA on ranks and post hoc Tukey test).
Figure 10B:
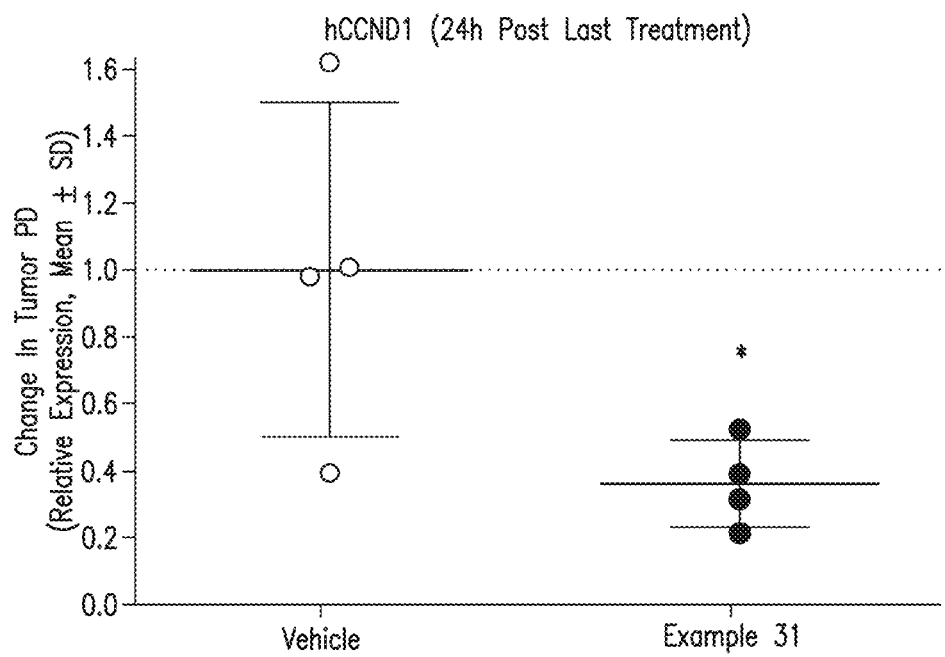
FIG. 10B: illustrates the effect of Example 31 on hCCND1 transcript levels in a SKRC-01 mouse model, wherein *: p<0.05 vs. vehicle controls (unpaired two tailed T-test).
Figure 11A:
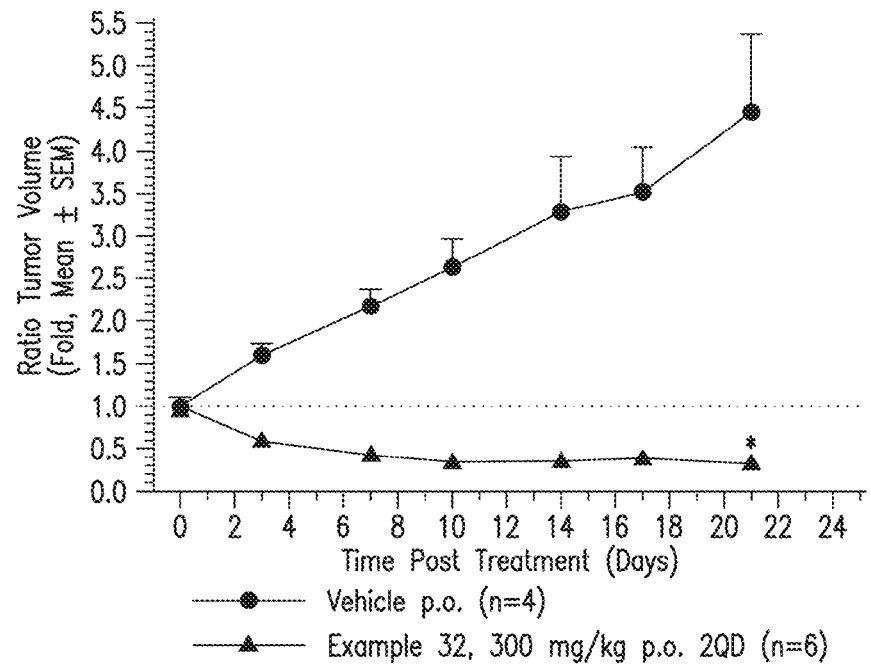
FIG. 11A: illustrates the effect of Example 32 on tumor growth in a SKRC-01 mouse model, wherein *: p<0.05 vs. vehicle controls (ANOVA on ranks and post hoc Dunn's test).
Figure 11B:
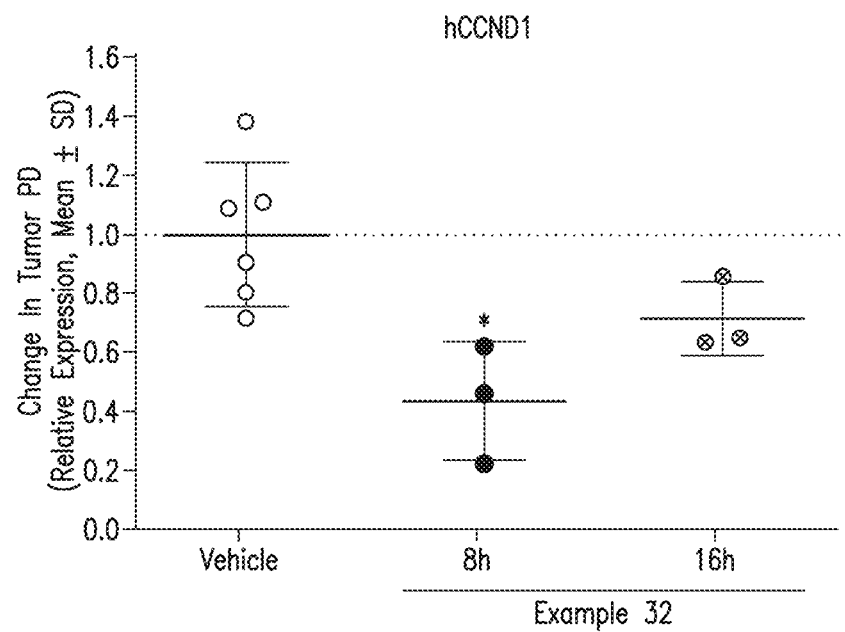
FIG. 11B: illustrates the effect of Example 32 on hCCND1 transcript levels in a SKRC-01 mouse model, wherein *: p<0.05 vs. vehicle controls (ANOVA on ranks and post hoc Dunn's test).

| | Ct Threshold values | |
|---|---|---|
| | CCND1 | β-actin |
| FIG. 9a | 0.3188 | 0.0268 |
| FIG. 10a | 0.0811 | 0.0312 |
| FIG. 11a | 0.1453 | 0.0482 |

The mean and standard deviation were calculated for each group of triplicates.

The ΔCt (delta Ct) for each sample was calculated as the difference between the Ct of the gene of interest (CCND1) and the reference gene (beta-actin). The standard deviation of this difference equals the square root of the sum of the squared standard deviation of the individual mean Ct.

The ΔΔCt (delta-delta Ct) is the difference between the ΔCt of the sample of interest (ex: treated sample) and the ΔCt of the reference samples (vehicle treated group). Same as previously, the standard deviation of this difference equals the square root of the sum of the squared standard deviation of the individual ΔCt. Differential expression was calculated as 2^(−ΔΔCt) for each sample.

The error of the 2^(−ΔΔCt) was calculated as a range depending on the standard deviation of the ΔΔCt-term (2^(x) is a strictly positive, growing function but nonlinear)

Results were then normalized setting the mean vehicle value to 1.0 for each gene of interest.

Example 121

Figure 9B:
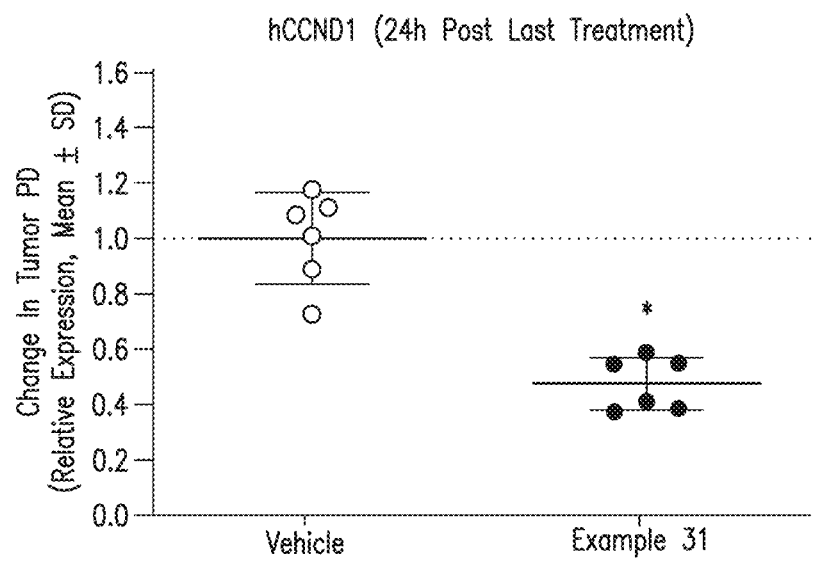
FIG. 9B: illustrates the effect of Example 31 on hCCNDI transcript levels in a 786-O mouse model, wherein *: p<0.05 vs. vehicle controls (unpaired two tailed T-test).

The anti-tumor activity of Example 31 was demonstrated in a 786-O mouse model (FIGS. 9a and 9b). Female nude mice bearing 786-O subcutaneous xenografts were treated with Example 31 at 30 mg/kg p.o. qd or vehicle control. Treatments started 34 days post tumor inoculation and lasted 21 days. Values are provided as mean±SEM with a sample size of n=6 mice per group. The initial tumor volume at day 0 was approximately 260 mm³.

Materials and Methods
Animals and Maintenance Conditions:
Mice:

Experiments were performed in female nude Crl:NU (NCr)-Foxnlnu-Homozygous mice (Charles River, Germany). Animals were 6-9 weeks of age at time of application of the compound. Animals were housed under Optimized Hygienic Conditions in Makrolon type III cages (max. 5 animals per cage) with free access to food and water. They were allowed to adapt for at least 6 days before the experiment was started.

Cell line and cell culture: 786-O and SKRC-01 cells were grown in 500 ml RPMI1640 Medium+5 ml L-Glutamine+50 ml FCS+5 ml Sodium Pyruvate+5 ml HEPES and incubated at 37° C. in a 5% CO₂ humidified atmosphere. Cells were harvested with trypsin-EDTA, re-suspended in culture medium (with additives) and counted with a Casy® system. Finally, cells were centrifuged and suspended in ice-cold Hanks' balanced salt solution (HBSS). Cell culture reagents were purchased from BioConcept (Allschwil, Switzerland).

Establishment of tumor xenografts in vivo: 786-O and SKRC-01 tumors were established by subcutaneous injection of 5×10⁶ cells in 150 µL HBSS (Sigma #H8264): Matrigel (50%:50%) into the right flank of nude mice or rats. For the efficacy experiments, treatments were initiated when the mean tumor volumes were approx. 300 mm³ (34 to 45 days post tumor cells injection).

Establishment of patient-derived ccRCC cancer tumors xenografts in vivo: Patient tumor samples from surgical resection were directly implanted subcutaneously in nude mice without any in vitro manipulations. A model is considered to be established after at least three consecutive passages in mice. Tumor xenografts (HKIX1169, HKIX1569, HKIX2207, HKIX2347, HKIX2597, HKIX2967, HKIX3629, HKIX3717, HKIX5510, HKIX5739, 28797-HX, 28799-HX, 28800-HX, 28805-HX, 28806-HX, 28807-HX, 28809-HX, 28814-HX, 28817-HX, 28836-HX, 28837-HX and 29158-HX) were grown subcutaneously in nude mice by s.c. implantation on the right flank of a matrigel embedded tumor fragment from a donor mice. For efficacy experiments, treatments were always initiated when the mean tumor volume in each group reached 200-400 mm$^3$ (around 20 to 85 days following cell inoculation).

Figure 12:
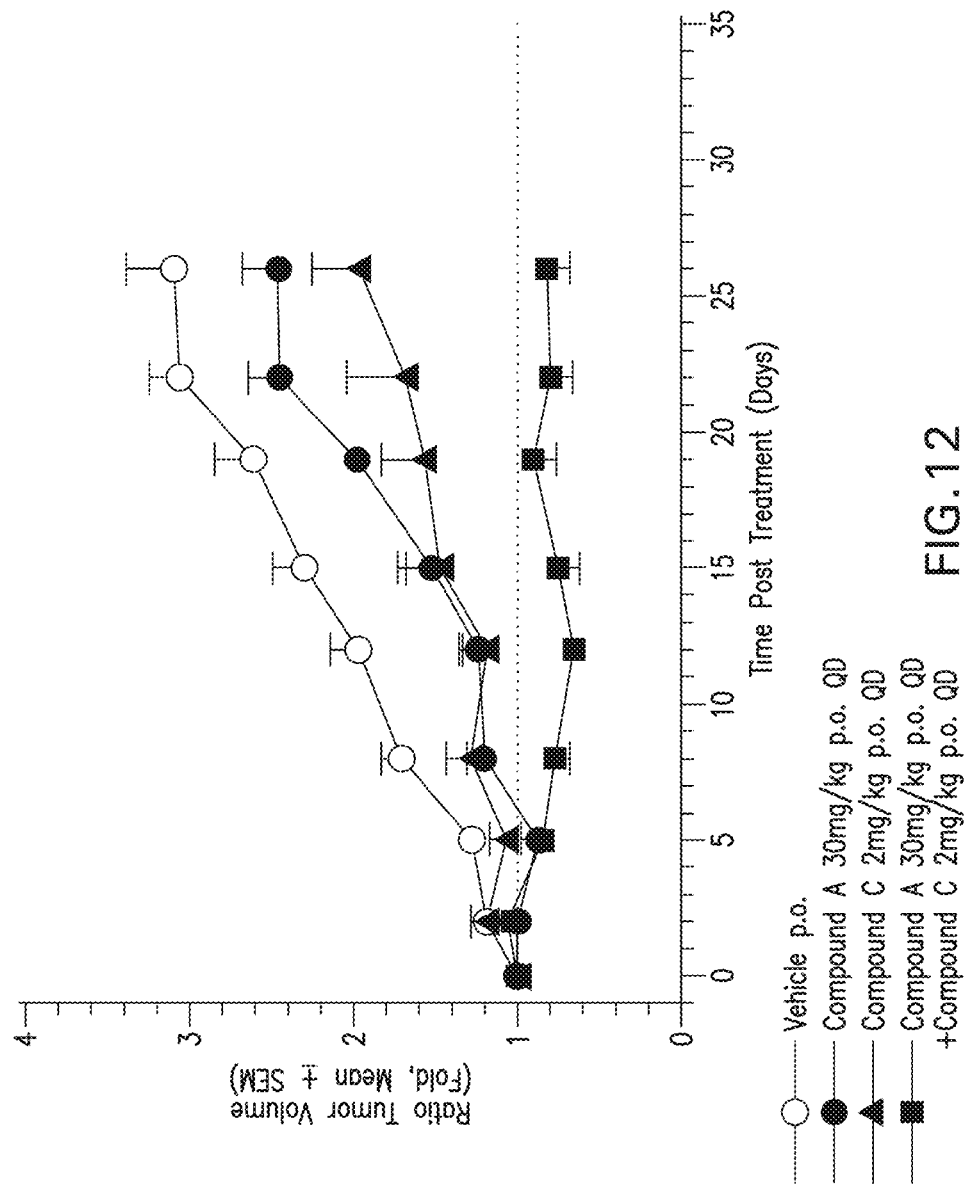
FIG. 12: illustrates Female nude mice bearing HKIX2207 subcutaneous xenografts that were treated with compound A at 30 mg/kg p.o. qd or compound C at 2 mg/kg p.o. qd or the combination or vehicle control. Treatments started 25 days post tumor inoculation and lasted 26 days. Values are mean±SEM; sample size, (n=5-6 mice per group). Initial tumor volume at day 0 was approximately 307 mm$^3$. The significant level for statistical analysis was set at p<0.05 vs. vehicle controls (ANOVA on ranks and post hoc Tukey test) and p<0.05 vs best single agent, one way analysis of variance (Tukey's Test).
Figure 13:
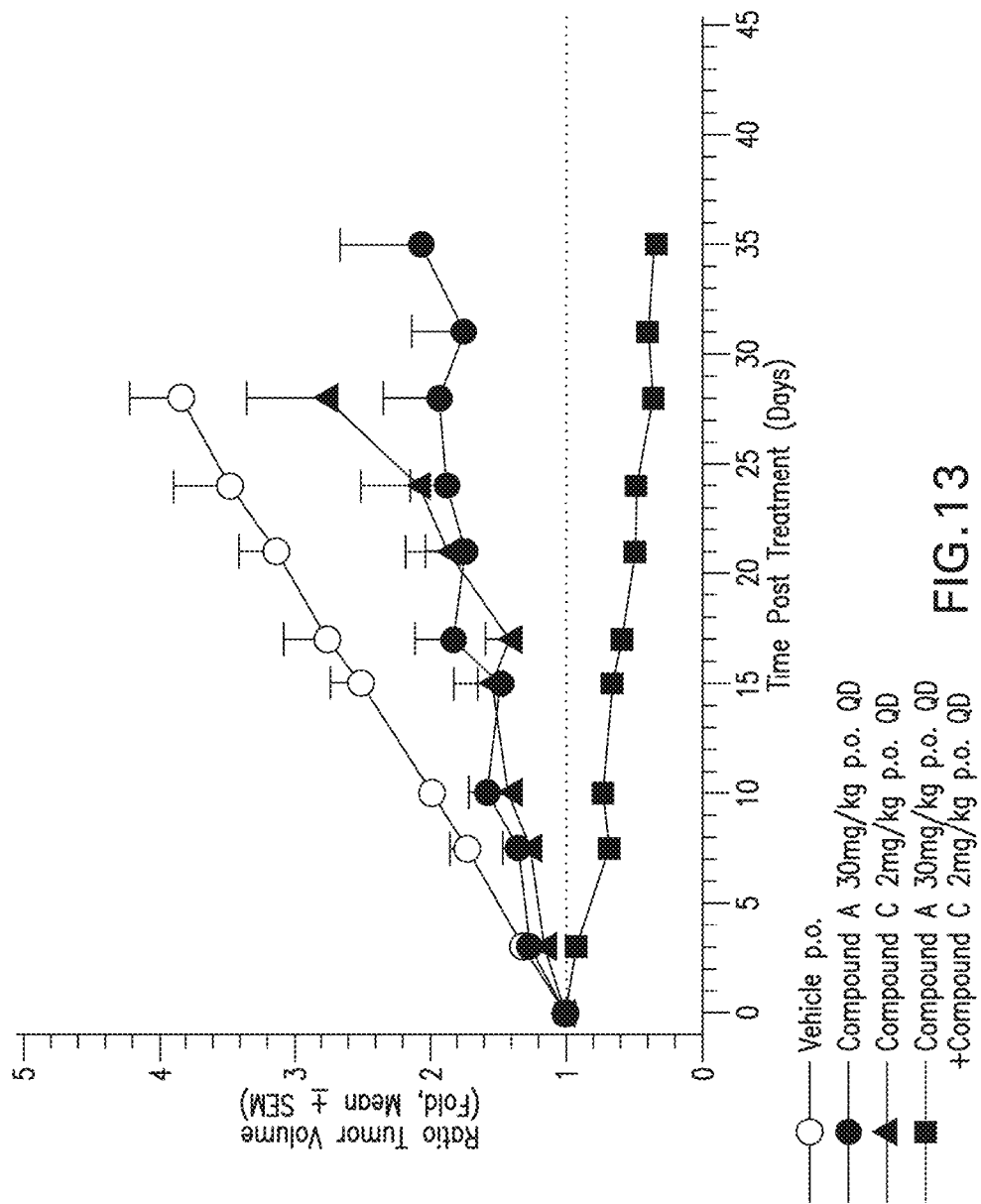
FIG. 13: illustrates Female nude mice bearing HKIX2967 subcutaneous xenografts were treated with compound A at 30 mg/kg p.o. qd or compound C at 2 mg/kg p.o. qd or the combination or vehicle control. Treatments started 20 days post tumor inoculation and lasted 35 days. Values are mean±SEM; sample size, (n=5-6 mice per group). Initial tumor volume at day 0 was approximately 283 mm$^3$. The significant level for statistical analysis was set at p<0.05 vs. vehicle controls (ANOVA on ranks and post hoc Tukey test) and p<0.05 vs best single agent, one way analysis of variance (Tukey's Test).
Figure 14:
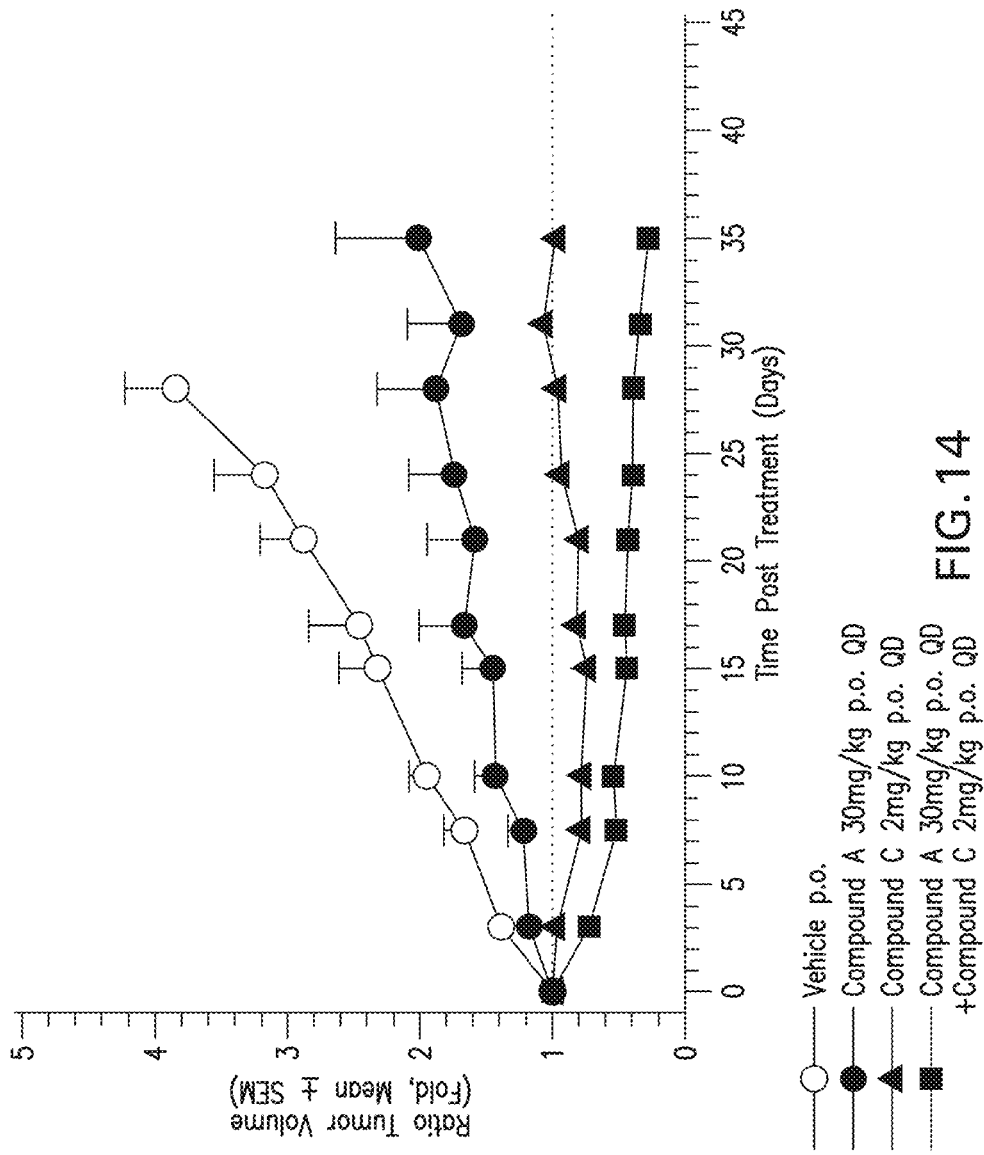
FIG. 14: illustrates Female nude mice bearing HKIX2967 subcutaneous xenografts that were treated with compound A at 30 mg/kg p.o. qd or compound C at 10 mg/kg p.o. qd or the combination or vehicle control. Treatments started 20 days post tumor inoculation and lasted 35 days. Values are mean±SEM; sample size, (n=5-6 mice per group). Initial tumor volume at day 0 was approximately 283 mm$^3$. The significant level for statistical analysis was set at p<0.05 vs. vehicle controls (ANOVA on ranks and post hoc Tukey test) and p<0.05 vs best single agent, one way analysis of variance (Tukey's Test).

Compound formulation and animal treatment: (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Compound A) were prepared for dosing as homogenous suspensions in 10% Ethanol+30% PEG400+60% water containing 0.5% MC+0.5% Tween 80. Everolimus (RAD001(Compound C)) is prepared as solution in water. Fresh suspensions or solution were prepared once every 7 days and stored at 4° C. (5)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] (Compound A) and everolimus (RAD001 (Compound C)) or vehicle were administered orally at a volume of 10 mL/kg. The results of experiments in the HKIX2207 and HKIX2967 are illustrated in FIGS. 12-14.

Evaluation of antitumor activity: Tumor volumes were measured with calipers and determined according to the formula: length×diameter$^2$×π/6. In addition to presenting changes of tumor volumes over the course of treatments, antitumor activity is expressed as T/C % (mean change of tumor volume of treated animals/mean change of tumor volume of control animals)×100. Regressions (%) were calculated according to the formula ((mean tumor volume at end of treatment−mean tumor volume at start of treatment)/mean tumor volume at start of treatment)×100. Body weights and tumor volumes were recorded two to three times a week.

Statistical analysis: Absolute values for primary tumor growth were used to make the statistical comparisons between groups (one way ANOVA followed by Dunnett's or Tukey's test for normally distributed data; ANOVA on Ranks for not normally distributed data followed by Dunnett's test for equal group size or Dunn's for unequal group size). The significant level was set at $p<0.05$. All statistical calculations were carried out using GraphPad Prism8.

The invention claimed is:

1. A compound of formula (I)

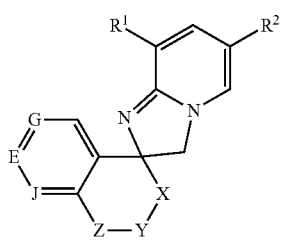

wherein
$R^1$ is F, Cl, Br, $OCH_3$, $OCH_2F$, $OCHF_2$, or $OCF_3$;
$R^2$ is F, CL, $CF_3$, or CN;
X is $(CH_2)_{1-2}$, CHF, CHD, $CD_2$ or $CF_2$;
Y is $(CH_2)_{0-2}$, CHF, CHD, $CD_2$, O, S, $OCH_2$ or $CF_2$;
Z is $CH_2$, $CD_2$, CHF, CDF, $CF_2$, CH(OH), CO, $CH(CH_3)$, O, or S,
wherein, when Y is O, $OCH_2$, or S, then Z is $CH_2$;
wherein, when Z is O, S, or $NCH_3$, then Y is $(CH_2)_{0-2}$, or $CF_2$;
wherein, when Z is CH(OH), then Y is CHF or $CF_2$;
J is $CR^J$;

wherein $R^J$ is H, F, Cl, Br, $CH_3$, $CD_3$, $CF_3$, $CHF_2$, $CDF_2$, $OCH_3$ or CN;
E is $CR^E$ or N;
wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD_3)F_2$, $CF_3$, cyclopropyl, $OCH_3$, $OCH_2CH_2OH$, $OCF_3$, $SCH_3$ or $SCHF_2$; and
G is CH or N;
in free form or in a pharmaceutically acceptable salt thereof.

2. The compound of formula (I) according to claim 1 or a pharmaceutically acceptable salt thereof, wherein
$R^1$ is F, Cl or $OCHF_2$;
$R^2$ is $CF_3$ or CN;
X is $CH_2$ or CHF;
Y is a $(CH_2)_{0-2}$ or CHF;
Z is CHF, CDF, $CF_2$, O, or S;
J is $CR^J$;
wherein $R^J$ is H, F, Cl, $CH_3$ or $CD_3$;
E is $CR^E$ or N;
wherein $R^E$ is H, F, Br, or $CF_3$; and
G is CH.

3. The compound of formula (I) according to claim 1 or a pharmaceutically acceptable salt thereof, wherein
$R^1$ is $OCHF_2$;
$R^2$ is $CF_3$;
X is $CH_2$ or CHF;

Y is (CH$_2$)$_{0-2}$;
Z is CF$_2$, or O;
J is CR$^J$;
wherein R$^J$ is H, F, Cl, CH$_3$ or CD$_3$;
E is CR$^E$ or N;
wherein R$^E$ is H, F, Br or CF$_3$; and
G is CH.

4. The compound of formula (I) according to claim 1 or a pharmaceutically acceptable salt thereof, wherein the stereochemistry is defined as shown in formula (Ia)

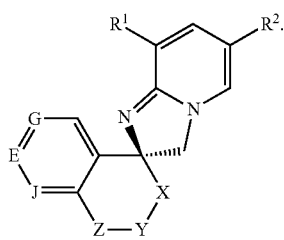

(Ia)

5. The compound of formula (I) according to claim 4 or a pharmaceutically acceptable salt thereof, wherein the stereochemistry is defined as shown in formula (Ib)

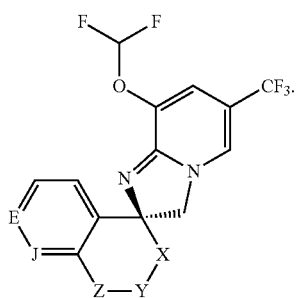

(Ib)

6. The compound according to claim 5, wherein
X is CH$_2$ or CHF;
Y is (CH$_2$)$_{0-2}$;
Z is O, S or CF$_2$;
E is CR$^E$ or N;
wherein R$^E$ is H, F, Br or CF$_3$; and
J is CR$^J$;
wherein R$^J$ is H, F, Cl, CH$_3$ or CD$_3$.

7. The compound of formula (I) according to claim 1 or a pharmaceutically acceptable salt thereof, which is selected from the group consisting of:
- (S)-5'-bromo-8-(difluoromethoxy)-4'-fluoro-6-(trifluoromethyl)-2',3'-dihydro-3H-spiro[imidazo[1,2-a]pyridine-2,1'-indene];
- (S)-8-(difluoromethoxy)-4',5'-difluoro-6-(trifluoromethyl)-2',3'-dihydro-3H-spiro[imidazo[1,2-a]pyridine-2,1'-indene];
- (S)-8'-(difluoromethoxy)-3,6'-bis(trifluoromethyl)-5,6-dihydro-3'H-spiro[cyclopenta[c]pyridine-7,2'-imidazo[1,2-a]pyridine];
- (S)-5'-bromo-8-(difluoromethoxy)-4'-fluoro-2',3'-dihydro-3H-spiro[imidazo[1,2-a]pyridine-2,1'-indene]-6-carbonitrile;
- (S)-5'-bromo-4'-fluoro-8-(fluoromethoxy)-6-(trifluoromethyl)-2',3'-dihydro-3H-spiro[imidazo[1,2-a]pyridine-2,1'-indene];
- (S)-8-(difluoromethoxy)-5',6-bis(trifluoromethyl)-2',3'-dihydro-3H-spiro[imidazo[1,2-a]pyridine-2,1'-indene];
- (S)-6'-bromo-8-(difluoromethoxy)-5'-fluoro-6-(trifluoromethyl)-3',4'-dihydro-2'H,3H-spiro[imidazo[1,2-a]pyridine-2,1'-naphthalene];
- (S)-6'-bromo-8-(difluoromethoxy)-5'-fluoro-6-(trifluoromethyl)-2'H,3H-spiro[imidazo[1,2-a]pyridine-2,1'-naphthalen]-4'(3'H)-one;
- (1'S,3'R)-6'-bromo-8-(difluoromethoxy)-3',5'-difluoro-6-(trifluoromethyl)-2'H,3H-spiro[imidazo[1,2-a]pyridine-2,1'-naphthalen]-4'(3'H)-one;
- (1'S,3'R,4'S)-6'-bromo-8-(difluoromethoxy)-3',5'-difluoro-6-(trifluoromethyl)-3',4'-dihydro-2'H,3H-spiro[imidazo[1,2-a]pyridine-2,1'-naphthalen]-4'-ol;
- (S)-6'-bromo-8-(difluoromethoxy)-6-(trifluoromethyl)-3',4'-dihydro-2'H,3H-spiro[imidazo[1,2-a]pyridine-2,1'-naphthalene];
- (S)-8-(difluoromethoxy)-6-(trifluoromethyl)-3',4'-dihydro-2'H,3H-spiro[imidazo[1,2-a]pyridine-2,1'-naphthalene];
- (S)-6'-bromo-8-(difluoromethoxy)-5'-fluoro-3',4'-dihydro-2'H,3H-spiro[imidazo[1,2-a]pyridine-2,1'-naphthalene]-6-carbonitrile;
- (S)-6'-bromo-8-(difluoromethoxy)-4',4',5'-trifluoro-6-(trifluoromethyl)-3',4'-dihydro-2'H,3H-spiro[imidazo[1,2-a]pyridine-2,1'-naphthalene];
- (S)-8-(difluoromethoxy)-4',4',5'-trifluoro-6-(trifluoromethyl)-3',4'-dihydro-2'H,3H-spiro[imidazo[1,2-a]pyridine-2,1'-naphthalene]-6'-carbonitrile;
- (S)-6'-bromo-8-chloro-5'-fluoro-6-(trifluoromethyl)-3',4'-dihydro-2'H,3H-spiro[imidazo[1,2-a]pyridine-2,1'-naphthalene];
- (S)-6'-bromo-8-(difluoromethoxy)-3',3',5'-trifluoro-6-(trifluoromethyl)-2'H,3H-spiro[imidazo[1,2-a]pyridine-2,1'-naphthalen]-4'(3'H)-one;
- (1'S,4'S)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol;
- (1'S,4'R)-6'-bromo-8-(difluoromethoxy)-3',3',5'-trifluoro-6-(trifluoromethyl)-3',4'-dihydro-2'H,3H-spiro[imidazo[1,2-a]pyridine-2,1'-naphthalen]-4'-ol;
- (1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one;
- (1'S,3'R)-8-(difluoromethoxy)-3',5'-difluoro-6-(trifluoromethyl)-2'H,3H-spiro[imidazo[1,2-a]pyridine-2,1'-naphthalen]-4'(3'H)-one;
- (S)-8-(difluoromethoxy)-5'-fluoro-6-(trifluoromethyl)-3',4'-dihydro-2'H,3H-spiro[imidazo[1,2-a]pyridine-2,1'-naphthalene]-6'-carbonitrile;
- (S)-8-(difluoromethoxy)-4',4',5'-trifluoro-6-(trifluoromethyl)-3',4'-dihydro-2'H,3H-spiro[imidazo[1,2-a]pyridine-2,1'-naphthalene];
- (2S,4'S)-6'-bromo-8-(difluoromethoxy)-4',5'-difluoro-3',4'-dihydro-2'H,3H-spiro[imidazo[1,2-a]pyridine-2,1'-naphthalene]-6-carbonitrile;
- (1'S,4'S)-8-(difluoromethoxy)-4',5'-difluoro-6-(trifluoromethyl)-3',4'-dihydro-2'H,3H-spiro[imidazo[1,2-a]pyridine-2,1'-naphthalene]-6'-carbonitrile;
- (S)-8-(difluoromethoxy)-5'-fluoro-3',4'-dihydro-2'H,3H-spiro[imidazo[1,2-a]pyridine-2,1'-naphthalene]-6-carbonitrile;
- d2-(S)-8-(difluoromethoxy)-5'-fluoro-3',4'-dihydro-2'H,3H-spiro[imidazo[1,2-a]pyridine-2,1'-naphthalene]-6-carbonitrile;

(S)-8-(difluoromethoxy)-5'-fluoro-6-(trifluoromethyl)-3',4'-dihydro-2'H,3H-spiro[imidazo[1,2-a]pyridine-2,1'-naphthalene];

(S)-5',6',8-trifluoro-6-(trifluoromethyl)-3',4'-dihydro-2'H,3H-spiro[imidazo[1,2-a]pyridine-2,1'-naphthalene];

(S)-1'-chloro-8',8'-difluoro-8-methoxy-6-(trifluoromethyl)-7',8'-dihydro-3H,6'H-spiro[imidazo[1,2-a]pyridine-2,5'-isoquinoline];

(S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-(methyl-d$_3$)-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-methoxy-6-(trifluoromethyl)-7',8'-dihydro-3H,6'H-spiro[imidazo[1,2-a]pyridine-2,5'-isoquinoline];

(S)-8-(difluoromethoxy)-6'-fluoro-3',4'-dihydro-2'H,3H-spiro[imidazo[1,2-a]pyridine-2,1'-naphthalene]-6-carbonitrile;

(S)-1'-chloro-8-(difluoromethoxy)-6-(trifluoromethyl)-7',8'-dihydro-3H,6'H-spiro[imidazo[1,2-a]pyridine-2,5'-isoquinoline];

(S)-3'-chloro-8-(difluoromethoxy)-6-(trifluoromethyl)-6',7'-dihydro-3H,5'H-spiro[imidazo[1,2-a]pyridine-2,8'-isoquinoline];

(S)-8-(difluoromethoxy)-6-(trifluoromethyl)-3',4'-dihydro-2'H,3H-spiro[imidazo[1,2-a]pyridine-2,1'-naphthalene]-6'-carbonitrile;

(S)-7-bromo-8'-(difluoromethoxy)-8-fluoro-6'-(trifluoromethyl)-3'H-spiro[chroman-4,2'-imidazo[1,2-a]pyridine];

(S)-8'-(difluoromethoxy)-8-fluoro-6',7-bis(trifloromethyl)-3'H-spiro[chroman-4,2'-imidazo[1,2-a]pyridine];

(S)-7-chloro-8'-(difluoromethoxy)-6'-(trifluoromethyl)-3'H-spiro[chroman-4,2'-imidazo[1,2-a]pyridine];

(S)-7-bromo-8-fluoro-8'-(fluoromethoxy)-6'-(trifluoromethyl)-3'H-spiro[chroman-4,2'-imidazo[1,2-a]pyridine];

(S)-7-chloro-8'-(difluoromethoxy)-8-fluoro-6'-(trifluoromethyl)-3'H-spiro[chroman-4,2'-imidazo[1,2-a]pyridine];

(S)-8'-(difluoromethoxy)-6',7-bis(trifluoromethyl)-3'H-spiro[chroman-4,2'-imidazo[1,2-a]pyridine];

(S)-8'-(difluoromethoxy)-7,8-difluoro-6'-(trifluoromethyl)-3'H-spiro[chroman-4,2'-imidazo[1,2-a]pyridine];

(S)-8'-(difluoromethoxy)-8-fluoro-7-methyl-6'-(trifluoromethyl)-3'H-spiro[chroman-4,2'-imidazo[1,2-a]pyridine];

(S)-8'-(difluoromethoxy)-8-fluoro-6'-(trifluoromethyl)-3'H-spiro[chroman-4,2'-imidazo[1,2-a]pyridine];

(S)-8-chloro-8'-(difluoromethoxy)-6'-(trifluoromethyl)-3'H-spiro[chroman-4,2'-imidazo[1,2-a]pyridine];

(S)-7-bromo-8'-(difluoromethoxy)-8-fluoro-3'H-spiro[chroman-4,2'-imidazo[1,2-a]pyridine]-6'-carbonitrile;

(S)-7-bromo-8'-(difluoromethoxy)-6'-(trifluoromethyl)-3'H-spiro[chroman-4,2'-imidazo[1,2-a]pyridine];

(S)-8'-(difluoromethoxy)-8-fluoro-7-iodo-3'H-spiro[chroman-4,2'-imidazo[1,2-a]pyridine]-6'-carbonitrile;

(S)-7-bromo-6'-chloro-8'-(difluoromethoxy)-8-fluoro-3'H-spiro[chroman-4,2'-imidazo[1,2-a]pyridine];

(S)-8'-chloro-6',7-bis(trifluoromethyl)-3'H-spiro[chroman-4,2'-imidazo[1,2-a]pyridine];

(S)-7,8'-bis(difluoromethoxy)-8-fluoro-6-(trifluoromethyl)-3H-spiro[chroman-4,2L imidazo[1,2-a]pyridine];

(S)-8'-(difluoromethoxy)-8-(difluoromethyl)-6'-(trifluoromethyl)-3'H-spiro[chroman-4,2'-imidazo[1,2-a]pyridine];

(S)-8'-chloro-8-(difluoromethoxy)-6-(trifluoromethyl)-2',3'-dihydro-3H-spiro[imidazo[1,2-a]pyridine-2,4'-pyrano[2,3-c]pyridine];

(2'S,3R)-7-bromo-8'-(difluoromethoxy)-3,8-difluoro-6'-(trifluoromethyl)-3'H-spiro[chroman-4,2'-imidazo[1,2-a]pyridine];

(2'S,3S)-7-bromo-8'-(difluoromethoxy)-3,8-difluoro-6'-(trifluoromethyl)-3'H-spiro[chroman-4,2'-imidazo[1,2-a]pyridine];

(2'S,3R)-7-bromo-8'-(difluoromethoxy)-3-fluoro-6'-(trifluoromethyl)-3'H-spiro[chroman-4,2'-imidazo[1,2-a]pyridine];

(2'S,3R)-8'-(difluoromethoxy)-3-fluoro-7-iodo-6'-(trifluoromethyl)-3'H-spiro[chroman-4,2'-imidazo[1,2-a]pyridine];

(2'S,3R)-8'-(difluoromethoxy)-3-fluoro-6',7-bis(trifluoromethyl)-3'H-spiro[chroman-4,2'-imidazo[1,2-a]pyridine];

(2'S,3R)-8'-(difluoromethoxy)-3,8-difluoro-6'-(trifluoromethyl)-3'H-spiro[chroman-4,2'-imidazo[1,2-a]pyridine];

(S)-8-(difluoromethoxy)-8'-fluoro-6-(trifluoromethyl)-3H-spiro[imidazo[1,2-a]pyridine-2,4'-isochroman];

(S)-7'-chloro-8-(difluoromethoxy)-8'-fluoro-3H-spiro[imidazo[1,2-a]pyridine-2,4'-thiochroman]-6-carbonitrile;

(S)-8-(difluoromethoxy)-8'-fluoro-6-(trifluoromethyl)-3H-spiro[imidazo[1,2-a]pyridine-2,4'-thiochroman];

(S)-8-(difluoromethoxy)-8'-fluoro-3H-spiro[imidazo[1,2-a]pyridine-2,4'-thiochroman]-6-carbonitrile;

(S)-8-(difluoromethoxy)-8'-fluoro-6,7'-bis(trifluoromethyl)-2',3'-dihydro-3H-spiro[imidazo[1,2-a]pyridine-2,4'-thiopyrano[3,2-c]pyridine];

(S)-8-(difluoromethoxy)-8'-fluoro-3H-spiro[imidazo[1,2-a]pyridine-2,4'-isothiochroman]-6-carbonitrile;

(S)-8'-(difluoromethoxy)-9-fluoro-6'-(trifluoromethyl)-3,4-dihydro-2H,3'H-spiro[benzo[b]oxepine-5,2'-imidazo[1,2-a]pyridine];

(S)-8-(difluoromethoxy)-1'-(difluoromethyl)-8',8'-difluoro-6-(trifluoromethyl)-7',8'-dihydro-3H,6'H-spiro[imidazo[1,2-a]pyridine-2,5'-isoquinoline];

(S)-5'-bromo-4',8-dichloro-6-(trifluoromethyl)-2',3'-dihydro-3H-spiro[imidazo[1,2-a]pyridine-2,1'-indene];

(S)-5'-bromo-8-(difluoromethoxy)-6-(trifluoromethyl)-2',3'-dihydro-3H-spiro[imidazo[1,2-a]pyridine-2,1'-indene];

(S)-8-(difluoromethoxy)-5'-iodo-2',3'-dihydro-3H-spiro[imidazo[1,2-a]pyridine-2,1'-indene]-6-carbonitrile;

(S)-8-(difluoromethoxy)-4'-fluoro-5',6-bis(trifluoromethyl)-2',3'-dihydro-3H-spiro[imidazo[1,2-a]pyridine-2,1'-indene];

(S)-8-(difluoromethoxy)-6-(trifluoromethyl)-2',3'-dihydro-3H-spiro[imidazo[1,2-a]pyridine-2,1'-indene];

(S)-5',8-difluoro-6'-methoxy-6-(trifluoromethyl)-3',4'-dihydro-2'H,3H-spiro[imidazo]1,2-alpyridine-2,1'-naphthalene];

(S)-8-fluoro-6,6'-bis(trifluoromethyl)-3',4'-dihydro-2'H,3H-spiro[imidazo[1,2-a]pyridine-2,1'-naphthalene];

rac-5',6',8-trifluoro-6-(trifluoromethyl)-3',4'-dihydro-2'H, 3H-spiro[imidazo[1,2-a]pyridine-2,1'-naphthalene];

(S)-8-chloro-5'-fluoro-6-(trifluoromethyl)-3',4'-dihydro-2'H,3H-spiro[imidazo[1,2-a]pyridine-2,1'-naphthalene];

(S)-6'-bromo-5'-fluoro-8-methoxy-6-(trifluoromethyl)-3',4'-dihydro-2'H,3H-spiro[imidazo[1,2-a]pyridine-2,1'-naphthalene];

rac-5'-bromo-8-(difluoromethoxy)-6-(trifluoromethyl)-3',4'-dihydro-2'H,3H-spiro[imidazo[1,2-a]pyridine-2,1'-naphthalene];

(S)-5'-chloro-8-(difluoromethoxy)-6'-fluoro-6-(trifluoromethyl)-3',4'-dihydro-2'H,3H-spiro[imidazo[1,2-a]pyridine-2,1'-naphthalene];

(2S,3'R,4'R)-6'-bromo-8-(difluoromethoxy)-3',4',5'-trifluoro-6-(trifluoromethyl)-3',4'-dihydro-2'H,3H-spiro[imidazo[1,2-a]pyridine-2,1'-naphthalene];

(S)-8-(difluoromethoxy)-5'-fluoro-6'-methoxy-6-(trifluoromethyl)-3',4'-dihydro-2'H,3H-spiro[imidazo[1,2-a]pyridine-2,1'-naphthalene];

(S)-8-(difluoromethoxy)-5',6'-difluoro-6-(trifluoromethyl)-3',4'-dihydro-2'H,3H-spiro[imidazo[1,2-a]pyridine-2,1'-naphthalene];

(S)-8-(difluoromethoxy)-6,6'-bis(trifluoromethyl)-3',4'-dihydro-2'H,3H-spiro[imidazo[1,2-a]pyridine-2,1'-naphthalene];

rac-8-(difluoromethoxy)-5',6-bis(trifluoromethyl)-3',4'-dihydro-2'H,3H-spiro[imidazo[1,2-a]pyridine-2,1'-naphthalene];

(S)-5'-chloro-8-(difluoromethoxy)-6-(trifluoromethyl)-3',4'-dihydro-2'H,3H-spiro[imidazo[1,2-a]pyridine-2,1'-naphthalene];

(S)-6'-bromo-6-chloro-8-(difluoromethoxy)-5'-fluoro-3',4'-dihydro-2'H,3H-spiro[imidazo[1,2-a]pyridine-2,1'-naphthalene];

(S)-6'-bromo-8-(difluoromethoxy)-6-(trifluoromethyl)-2',3'-dihydro-3H,4'H-spiro[imidazo[1,2-a]pyridine-2,1'-naphthalen]-4'-one;

(S)-8-(difluoromethoxy)-5',6'-difluoro-3',4'-dihydro-2'H,3H-spiro[imidazo[1,2-a]pyridine-2,1'-naphthalene]-6-carbonitrile;

(S)-6'-bromo-8-(difluoromethoxy)-4',4',5'-trifluoro-3',4'-dihydro-2'H,3H-spiro[imidazo[1,2-a]pyridine-2,1'-naphthalene]-6-carbonitrile;

rac-8-(difluoromethoxy)-6-(trifluoromethyl)-7',8'-dihydro-3H,6'H-spiro[imidazo[1,2-a]pyridine-2,5'-isoquinoline];

(S)-1'-chloro-8-(difluoromethoxy)-7',8'-dihydro-3H,6'H-spiro[imidazo[1,2-a]pyridine-2,5'-isoquinoline]-6-carbonitrile;

(S)-8-chloro-8'-(fluoromethoxy)-6'-(trifluoromethyl)-3'H-spiro[chromane-4,2'-imidazo[1,2-a]pyridine];

(S)-8-chloro-8'-(difluoromethoxy)-6'-(trifluoromethyl)-3'H-spiro[chromane-4,2'-imidazo[1,2-a]pyridine]-7-carbonitrile;

(3R,4S)-7-chloro-8'-(difluoromethoxy)-3,8-difluoro-6'-(trifluoromethyl)-3'H-spiro[chromane-4,2'-imidazo[1,2-a]pyridine];

(3R,4S)-8'-(difluoromethoxy)-3,7,8-trifluoro-6'-(trifluoromethyl)-3'H-spiro[chromane-4,2'-imidazo[1,2-a]pyridine];

(S)-8'-(difluoromethoxy)-8-fluoro-7-(methylthio)-6'-(trifluoromethyl)-3'H-spiro[chromane-4,2'-imidazo[1,2-a]pyridine];

(S)-7-bromo-8-chloro-8'-(difluoromethoxy)-6'-(trifluoromethyl)-3'H-spiro[chromane-4,2'-imidazo[1,2-a]pyridine];

rac-8'-(difluoromethoxy)-3,8-difluoro-6'-(trifluoromethyl)-3'H-spiro[chromane-4,2'-imidazo[1,2-a]pyridine];

(S)-7,8-dibromo-g-(difluoromethoxy)-6'-(trifluoromethyl)-3'H-spiro[chromane-4,2L imidazo[1,2-a]pyridine];

(S)-8'-(difluoromethoxy)-8-fluoro-7-methoxy-6'-(trifluoromethyl)-3'H-spiro[chromane-4,2'-imidazo[1,2-a]pyridine];

(S)-8'-(difluoromethoxy)-6',8-bis(trifluoromethyl)-3'H-spiro[chromane-4,2'-imidazo[1,2-a]pyridine];

(S)-8'-(difluoromethoxy)-8-fluoro-7-(trifluoromethoxy)-6'-(trifluoromethyl)-3'H-spiro[chromane-4,2'-imidazo[1,2-a]pyridine];

(S)-8'-(difluoromethoxy)-7-((difluoromethyl)thio)-8-fluoro-6'-(trifluoromethyl)-3'H-spiro[chromane-4,2'-imidazo[1,2-a]pyridine];

(S)-8-bromo-8'-(difluoromethoxy)-6'-(trifluoromethyl)-3'H-spiro[chromane-4,2'-imidazo[1,2-a]pyridine];

rac-8-(difluoromethoxy)-8'-fluoro-6,7'-bis(trifluoromethyl)-3H-spiro[imidazo[1,2-a]pyridine-2,4'-isochroman];

(2S)-8-(difluoromethoxy)-8'-fluoro-3H-spiro[imidazo[1,2-a]pyridine-2,4'-thiochromane]-6-carbonitrile-2',2',3'-d3;

(S)-7'-bromo-8-(difluoromethoxy)-8'-fluoro-3H-spiro[imidazo[1,2-a]pyridine-2,4'-thiochromane]-6-carbonitrile;

(S)-8-(difluoromethoxy)-8'-fluoro-6-(trifluoromethyl)-3H-spiro[imidazo[1,2-a]pyridine-2,4'-thiochromane]-7'-carbonitrile;

(S)-8-(difluoromethoxy)-7',8'-difluoro-3H-spiro[imidazo[1,2-a]pyridine-2,4'-thiochroman]-6-carbonitrile;

(S)-8-(difluoromethoxy)-7',8'-difluoro-6-(trifluoromethyl)-3H-spiro[imidazo[1,2-a]pyridine-2,4'-thiochromane];

(S)-8'-fluoro-8-(fluoromethoxy)-6,7'-bis(trifluoromethyl)-2',3'-dihydro-3H-spiro[imidazo[1,2-a]pyridine-2,4'-thiopyrano[3,2-c]pyridine];

(S)-8-(difluoromethoxy)-8'-fluoro-6-(trifluoromethyl)-3H-spiro[imidazo[1,2-a]pyridine-2,4'-isothiochromane];

(S)-8-(difluoromethoxy)-7'-fluoro-6-(trifluoromethyl)-3H-spiro[imidazo[1,2-a]pyridine-2,4'-isothiochromane];

(S)-8'-(difluoromethoxy)-8,9-difluoro-6'-(trifluoromethyl)-3,4-dihydro-2H,3'H-spiro[benzo[b]oxepine-5,2'-imidazo[1,2-a]pyridine];

rac-9-chloro-8'-(difluoromethoxy)-6'-(trifluoromethyl)-3,4-dihydro-2H,3'H-spiro[benzo[b]oxepine-5,2'-imidazo[1,2-a]pyridine]; and (S)-8-chloro-8'-(difluoromethoxy)-9-fluoro-6'-(trifluoromethyl)-3,4-dihydro-1H,3'H-spiro[benzo[c]oxepine-5,2'imidazo[1,2-a]pyridine].

8. The compound of formula (I) according to claim 1 or a pharmaceutically acceptable salt thereof, which is selected from the group consisting of:

(S)-8-(difluoromethoxy)-8'-fluoro-3H-spiro[imidazo[1,2-a]pyridine-2,4'-thiochroman]-6-carbonitrile;

(S)-8'-(difluoromethoxy)-9-fluoro-6'-(trifluoromethyl)-3,4-dihydro-2H,3'H-spiro[benzo[b]oxepine-5,2'-imidazo[1,2-a]pyridine];

(S)-8'-(difluoromethoxy)-6',7-bis(trifluoromethyl)-3'H-spiro[chroman-4,2'-imidazo[1,2-a]pyridine];

(S)-7-bromo-8'-(difluoromethoxy)-8-fluoro-6'-(trifluoromethyl)-3'H-spiro[chroman-4,2'-imidazo[1,2-a]pyridine];

(2'S,3R)-8'-(difluoromethoxy)-3,8-difluoro-6'-(trifluoromethyl)-3'H-spiro[chroman-4,2'-imidazo[1,2-a]pyridine];

(S)-8'-(difluoromethoxy)-7,8-difluoro-6'-(trifluoromethyl)-3'H-spiro[chroman-4,2'-imidazo[1,2-a]pyridine];

(S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline];

(S)-8-(difluoromethoxy)-8',8'-difluoro-1'-(methyl-d₃)-6-(trifluoromethyl)-7',8'-dihydro-3H,6'H-spiro[imidazo[1,2-a]pyridine-2,5'-isoquinoline]; and (S)-8-(difluoromethoxy)-8',8'-difluoro-1'-methyl-6-(trifluoromethyl)-7',8'-dihydro-3H,6'H-spiro[imidazo[1,2-a]pyridine-2,5'-isoquinoline].

9. A compound, or a pharmaceutically acceptable salt thereof, that is selected from the group consisting of:

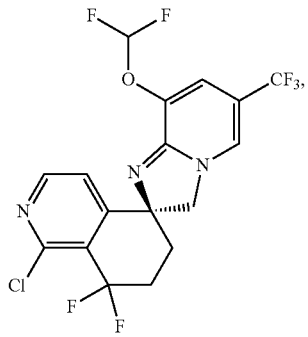 [SMILES: FC(F)OC1=CC(C(F)(F)F)=CN2C[C@@]3(CCC(F)(F)c4c3ccnc4Cl)N=C12]

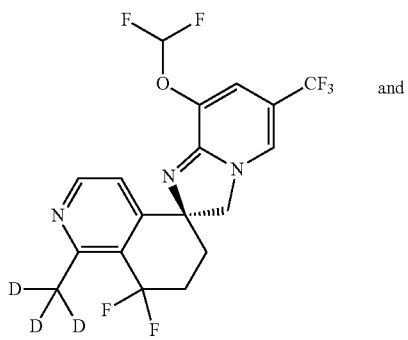
and

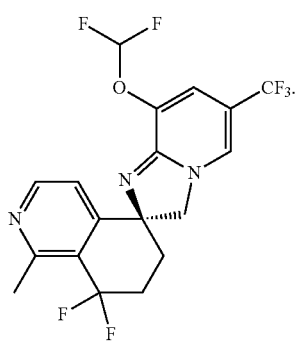

10. The compound of claim 9, or a pharmaceutically acceptable salt thereof, that is:

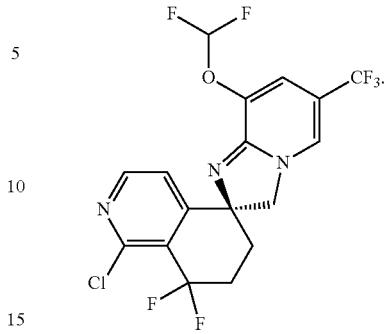

11. A pharmaceutical composition comprising a therapeutically effective amount of a compound according to claim 1 or a pharmaceutically acceptable salt thereof and one or more pharmaceutically acceptable carriers.

12. A combination comprising a therapeutically effective amount of a compound according to claim 1 or a pharmaceutically acceptable salt thereof and one or more therapeutically active agents.

13. The combination according to claim 12, wherein said therapeutic agent is selected from a mTOR inhibitor selected from Temsirolimus; Ridaforolimus; Everolimus (RAD001); Rapamycin; Simapimod; (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one; $N^2$-[1,4-dioxo-4-[[4-(4-oxo-8-phenyl-4H-1-benzopyran-2-yl)morpholinium-4-yl]methoxy]butyl]-L-arginylglycyl-L-$\alpha$-aspartylL-serine-; N-[4-[[[3-[(3,5-dimethoxyphenyl)amino]-2-quinoxalinyl]amino]sulfonyl]phenyl]-3-methoxy-4-methyl-benzamide; or (1r,4r)-4-(4-amino-5-(7-methoxy-1H-indol-2-yl)imidazo[1,5-f][1,2,4]triazin-7-yl)cyclohexanecarboxylic acid.

14. The combination according to claim 13, wherein said mTOR inhibitor is everolimus.

15. A method of modulating HIF2α activity in a subject, wherein the method comprises administering to the subject a therapeutically effective amount of the compound according to claim 1 or a pharmaceutically acceptable salt thereof.

16. A method of treating a disorder or disease which is a cancer, comprising administering to the subject a therapeutically effective amount of the compound according to claim 1 or a pharmaceutically acceptable salt thereof, wherein the cancer is selected from clear cell renal cell carcinoma, glioma, and renal cell carcinoma.

17. A crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] fumarate.

18. A crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form.

19. The crystalline form of claim 17 characterized by having a powder X-ray diffractogram comprising reflections at 2-Theta angles of (24.9±0.2)°, (6.2±0.2)° and (20.9±0.2)°, when measured at a temperature in the range of from 20 to 30° C. with Cu-Kalpha1,2 radiation having a wavelength of 0.15406 nm.

20. The crystalline form of claim 17 characterized by having a powder X-ray diffractogram comprising reflections at 2-Theta angles of (24.9±0.2)°, (6.2±0.2)°, (20.9±0.2)°, (10.9±0.2)° and (18.5±0.2)°, when measured at a temperature in the range of from 20 to 30° C. with Cu-Kalpha1,2 radiation having a wavelength of 0.15406 nm.

21. The crystalline form of claim 17 (-characterized by having a powder X-ray diffractogram comprising reflections at 2-Theta angles of (24.9±0.2)°, (6.2±0.2)°, (20.9±0.2)°, (10.9±0.2)°, (18.5±0.2)°, (22.8±0.2)°, (12.9±0.2)° and (16.1±0.2)°, when measured at a temperature in the range of from 20 to 30° C. with Cu-Kalpha1,2 radiation having a wavelength of 0.15406 nm.

22. The crystalline form according to claim 17 characterized by having a thermogravimetric analysis curve showing a mass loss of not more than 0.4 weight % based on the weight of the crystalline form, when heated from 10 to 250° C. at a rate of 10 K/min.

23. The crystalline form of claim 18 characterized by having a powder X-ray diffractogram comprising reflections at 2-Theta angles of (9.7±0.2)°, (18.4±0.2)° and (19.4±0.2)°, when measured at a temperature in the range of from 20 to 30° C. with Cu-Kalpha1,2 radiation having a wavelength of 0.15406 nm.

24. The crystalline form of claim 18 characterized by having a powder X-ray diffractogram comprising reflections at 2-Theta angles of (9.7±0.2)°, (18.4±0.2)°, (19.4±0.2)°, (13.4±0.2)° and (20.7±0.2)°, when measured at a temperature in the range of from 20 to 30° C. with Cu-Kalpha1,2 radiation having a wavelength of 0.15406 nm.

25. The crystalline form of claim 18 characterized by having a powder X-ray diffractogram comprising reflections at 2-Theta angles of (9.7±0.2)°, (18.4±0.2)°, (19.4±0.2)°, (13.4±0.2)°, (20.7±0.2)°, (24.2±0.2)°, (22.1±0.2)° and (10.3±0.2)°, when measured at a temperature in the range of from 20 to 30° C. with Cu-Kalpha1,2 radiation having a wavelength of 0.15406 nm.

26. The crystalline form according to claim 18 characterized by having a thermogravimetric analysis curve showing a mass loss of not more than 0.2 weight % based on the weight of the crystalline form, when heated from 10 to 250° C. at a rate of 10 K/min.

27. A pharmaceutical composition comprising a therapeutically effective amount of a crystalline form of (S)-1'-chloro-8-(difluoromethoxy)-8',8'-difluoro-6-(trifluoromethyl)-7',8'-dihydro-3H,6'H-spiro[imidazo[1,2-a]pyridine-2,5'-isoquinoline] free form or fumarate and one or more pharmaceutically acceptable carriers.

28. A method of treating a disorder or disease which is a cancer, comprising administering to the subject a therapeutically effective amount of the pharmaceutical composition of claim 27, wherein the cancer is selected from clear cell renal cell carcinoma, glioma, and renal cell carcinoma.

29. A process for producing the compound of formula (I)

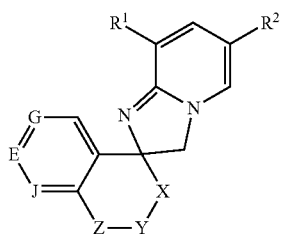

(I)

or a pharmaceutically acceptable salt thereof,
comprising cyclizing a compound of formula (II),

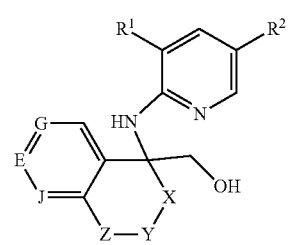

(II)

or a salt, solvate, stereoisomer, complex, co-crystal, ester, or oxazoline thereof;
wherein the compound of formula (II) is produced by a process
comprising the step of reacting the compound of formula (IV),

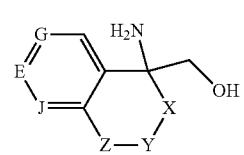

(IV)

or a salt, solvate, stereoisomer, complex, co-crystal, ester, or oxazoline thereof,
with a compound of formula (III)

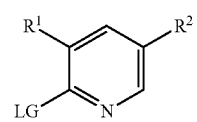

(III)

or a salt, solvate, stereoisomer, complex, co-crystal, ester, or oxazoline thereof,
wherein
$R^1$ is F, Cl, Br, $OCH_3$, $OCH_2F$, $OCHF_2$, or $OCF_3$;
$R^2$ is F, Cl, $CF_3$, or CN;
X is $(CH_2)_{1-2}$, CHF, CHD, $CD_2$ or $CF_2$;
Y is $(CH_2)_{0-2}$, CHF, CHD, $CD_2$, O, S, $OCH_2$, or $CF_2$;
Z is $CH_2$, $CD_2$, CHF, CDF, $CF_2$, CH(OH), CO, CH($CH_3$), O, or S,
wherein, when Y is O, $OCH_2$, or S, then Z is $CH_2$;
wherein, when Z is O, S, or $NCH_3$, then Y is $(CH_2)_{0-2}$, or $CF_2$;
wherein, when Z is CH(OH), then Y is CHF or $CF_2$;
J is $CR^J$;
wherein $R^J$ is H, F, Cl, Br, $CH_3$, $CD_3$, $CF_3$, $CHF_2$, $CDF_2$, $OCH_3$ or CN;
E is $CR^E$ or N;
wherein $R^E$ is H, F, Cl, Br, I, CN, $CH_3$, $CH_2CH_3$, $CH(CH_3)_2$, $CD_3$, $CHD_2$, $CH_2D$, $CHF_2$, $CDF_2$, $C(CH_3)F_2$, $C(CD3)F_2$, $CF_3$, cyclopropyl, $OCH_3$, $OCH_2CH_2OH$, $OCF_3$, $SCH_3$, $SCHF_2$,
G is CH or N; and
LG is a leaving group selected from F, Cl, or Br;
and the reaction of compound (III) and compound (IV) occurs in the presence of base,
to obtain the compound of formula (I) or a pharmaceutically acceptable salt thereof.

30. The process according to claim 29, wherein the compound of formula (II) is cyclised with reagents selected from SOCl$_2$ in toluene, toluene sulfonyl chloride, and methanesulfonyl chloride, in the presence of a base selected from pyridine and Et$_3$N to give a compound of formula (I).

* * * * *

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Gly Asp Ser
1

<210> SEQ ID NO 2
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 2
gtgagctggc gg                                                            12

<210> SEQ ID NO 3
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
acagagcctc gcctttg                                                       17

<210> SEQ ID NO 4
```

```
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ccttgcacat gccgg                                                    15

<210> SEQ ID NO 5
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
tgccctttct tcagc                                                    15

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
cacggtcagt cttcagtgag                                               20

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cgcaaccaga tatgctatga ct                                            22

<210> SEQ ID NO 8
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ctagcctgca cgtactgcac gtactgcacg tactgcacgt acgctcgctt cgaa         54

<210> SEQ ID NO 9
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
```

```
agctttcgaa gcgagcgtac gtgcagtacg tgcagtacgt gcagtacgtg cagg        54

<210> SEQ ID NO 10
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 10
cagatcgaag cc                                                      12

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ccagagtgat caagtgtgac c                                            21

<210> SEQ ID NO 12
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cgcaggcttg actccag                                                 17
```